United States Patent
Libermann et al.

(10) Patent No.: US 12,372,530 B2
(45) Date of Patent: Jul. 29, 2025

(54) MARKERS FOR THE DIAGNOSIS AND TREATMENT OF NON-ALCOHOLIC STEATOHEPATITIS (NASH) AND ADVANCED LIVER FIBROSIS

(71) Applicants: BETH ISRAEL DEACONESS MEDICAL CENTER, INC., Boston, MA (US); BOARD OF REGENTS OF THE UNIVERSITY OF NEBRASKA, Lincoln, NE (US)

(72) Inventors: Towia Aron Libermann, Chestnut Hill, MA (US); Michelle Lai, Brookline, MA (US); Nezam Hassan Afdhal, Charlestown, MA (US); Hasan Huseyin Otu, Lincoln, NE (US); Simon Thomas Dillon, Rockport, MA (US)

(73) Assignees: Beth Israel Deaconess Medical Center, Inc., Boston, MA (US); Board of Regents of the University of Nebraska, Lincoln, NE (US)

( * ) Notice: Subject to any disclaimer, the term of this patent is extended or adjusted under 35 U.S.C. 154(b) by 1192 days.

(21) Appl. No.: 16/764,305

(22) PCT Filed: Nov. 15, 2018

(86) PCT No.: PCT/US2018/061330
§ 371 (c)(1),
(2) Date: May 14, 2020

(87) PCT Pub. No.: WO2019/099706
PCT Pub. Date: May 23, 2019

(65) Prior Publication Data
US 2023/0194536 A1 Jun. 22, 2023

Related U.S. Application Data

(60) Provisional application No. 62/586,812, filed on Nov. 15, 2017.

(51) Int. Cl.
*G01N 33/576* (2006.01)
*G01N 33/50* (2006.01)

(52) U.S. Cl.
CPC ....... *G01N 33/576* (2013.01); *G01N 33/5008* (2013.01); *G01N 2333/47* (2013.01); *G01N 2500/10* (2013.01); *G01N 2800/085* (2013.01); *G01N 2800/50* (2013.01)

(58) Field of Classification Search
CPC ............ G01N 33/576; G01N 33/5008; G01N 2333/47; G01N 2800/085; G01N 2800/50
See application file for complete search history.

(56) References Cited

U.S. PATENT DOCUMENTS

| 9,486,433 B2 | 11/2016 | Mizuguchi et al. |
| 2014/0303018 A1* | 10/2014 | Nikrad ............... G01N 33/6893 435/7.4 |
| 2015/0247149 A1 | 9/2015 | Feldstein et al. |
| 2017/0227550 A1 | 8/2017 | Nikrad et al. |
| 2017/0335395 A1* | 11/2017 | Chen-Plotkin ......... G16B 40/30 |
| 2018/0170908 A1* | 6/2018 | Aspnes ..................... A61P 3/04 |
| 2018/0200228 A1* | 7/2018 | Glenn ..................... A61P 29/00 |
| 2020/0292553 A1* | 9/2020 | Kim ........................ G01N 33/68 |

FOREIGN PATENT DOCUMENTS

| WO | 2014/150198 A2 | 9/2014 |
| WO | 2017/139254 A1 | 8/2017 |

OTHER PUBLICATIONS

Bedossa et al., Biopsy and Noninvasive Methods to Assess Progression of Nonalcoholic Fatty Liver Disease. Gastroenterology. Jun. 2016;150(8):1811-1822.
Enomoto et al., Liver fibrosis markers of nonalcoholic steatohepatitis. World J Gastroenterol. Jun. 28, 2015;21(24):7427-35.
Yoshimura et al., Identification of novel noninvasive markers for diagnosing nonalcoholic steatohepatitis and related fibrosis by data mining. Hepatology. Feb. 2016;63(2):462-73.
International Search Report and Written Opinion for Application No. PCT/US2018/061330, dated Mar. 14, 2019, 15 pages.
International Preliminary Report on Patentability for Application No. PCT/US2018/061330, dated May 28, 2020, 11 pages.

* cited by examiner

*Primary Examiner* — Changhwa J Cheu
(74) *Attorney, Agent, or Firm* — McCarter & English, LLP; Thomas O. Hoover

(57) ABSTRACT

Methods for diagnosing non-alcoholic steatohepatitis (NASH) and NASH with or without advanced liver fibrosis in a subject are provided, such methods including the detection of levels of a variety of biomarkers diagnostic of NASH versus simple steatosis and NASH with advanced liver fibrosis versus NASH without advanced liver fibrosis. The invention also provides methods treating NASH (e.g., NASH with or without advanced liver fibrosis) by administering a biomarker or an agent that modulates a biomarker of NASH or fibrosis. Compositions in the form of kits and panels of reagents for detecting the biomarkers of the invention are also provided.

12 Claims, 19 Drawing Sheets

Performance of 152-protein NASH with Advanced Fibrosis Predictor on training set of AN (red) and ST controls (blue) (AN= NASH with Advanced Fibrosis, ST= Simple Steatosis) patient samples using L1OXV. 2D visualization of SVM solution. Support vectors are indicated by circles and the line (or plane) that best separates AN from ST.

Performance of 21-protein NASH with Advanced Fibrosis Predictor on training set of AN (red) and ST controls (blue) (AN= NASH with Advanced Fibrosis, ST= Simple Steatosis) patient samples using L1OXV. 2D visualization of SVM solution. Support vectors are indicated by circles and the line (or plane) that best separates AN from ST.

FIG. 5 Colorgram of hierarchical cluster of a 152 protein NASH with Advanced Fibrosis biomarker panel. 20 of 20 NASH with advanced fibrosis samples cluster together and 17 of 20 Simple Steatosis samples cluster together. Red = high expression; Blue = low expression.

Colorgram of hierarchical cluster of a 21-protein NASH with Advanced Fibrosis biomarker panel. 18 of 20 NASH with advanced fibrosis samples cluster together and 20 of 20 Simple Steatosis samples cluster together. Red = high expression; Blue = low expression.

Colorgram of hierarchical cluster of a 11-protein NASH with Advanced Fibrosis biomarker panel. 18 of 20 NASH with advanced fibrosis samples cluster together and 20 of 20 Simple Steatosis samples cluster together. Red = high expression; Blue = low expression.

Performance of 52-protein NASH without Advanced Fibrosis Predictor on training set of NN (red) and ST controls (blue) (NN= NASH without Advanced Fibrosis, ST= Simple Steatosis) patient samples using L1OXV. 2D visualization of SVM solution. Support vectors are indicated by circles and the line (or plane) that best separates NN from ST.

Performance of 20-protein NASH without Advanced Fibrosis Predictor on training set of NN (red) and ST controls (blue) (NN= NASH without Advanced Fibrosis, ST= Simple Steatosis) patient samples using L1OXV. 2D visualization of SVM solution. Support vectors are indicated by circles and the line (or plane) that best separates NN from ST.

Colorgram of hierarchical cluster of a 52 protein NASH without Advanced Fibrosis biomarker panel. 18 of 20 NASH without advanced fibrosis samples cluster together and 19 of 20 Simple Steatosis samples cluster together. Red = high expression; Blue = low Colorgram of hierarchical cluster of a 20-protein NASH without Advanced Fibrosis biomarker panel. 18 of 20 NASH without advanced fibrosis samples cluster together and 19 of 20 Simple Steatosis samples cluster together. Red = high expression; Blue = low Performance of 51-protein NASH Predictor on training set of NASH (blue) and ST controls (red) (NASH= NASH with and without Advanced Fibrosis, ST= Simple Steatosis) patient samples using L1OXV. 2D visualization of SVM solution. Support vectors are indicated by circles and the line (or plane) that best separates NASH from ST.

Colorgram of hierarchical cluster of a 51-protein NASH biomarker panel. 34 of 40 NASH samples cluster together and 17 of 20 Simple Steatosis samples cluster together. Red = high expression; Blue = low expression.

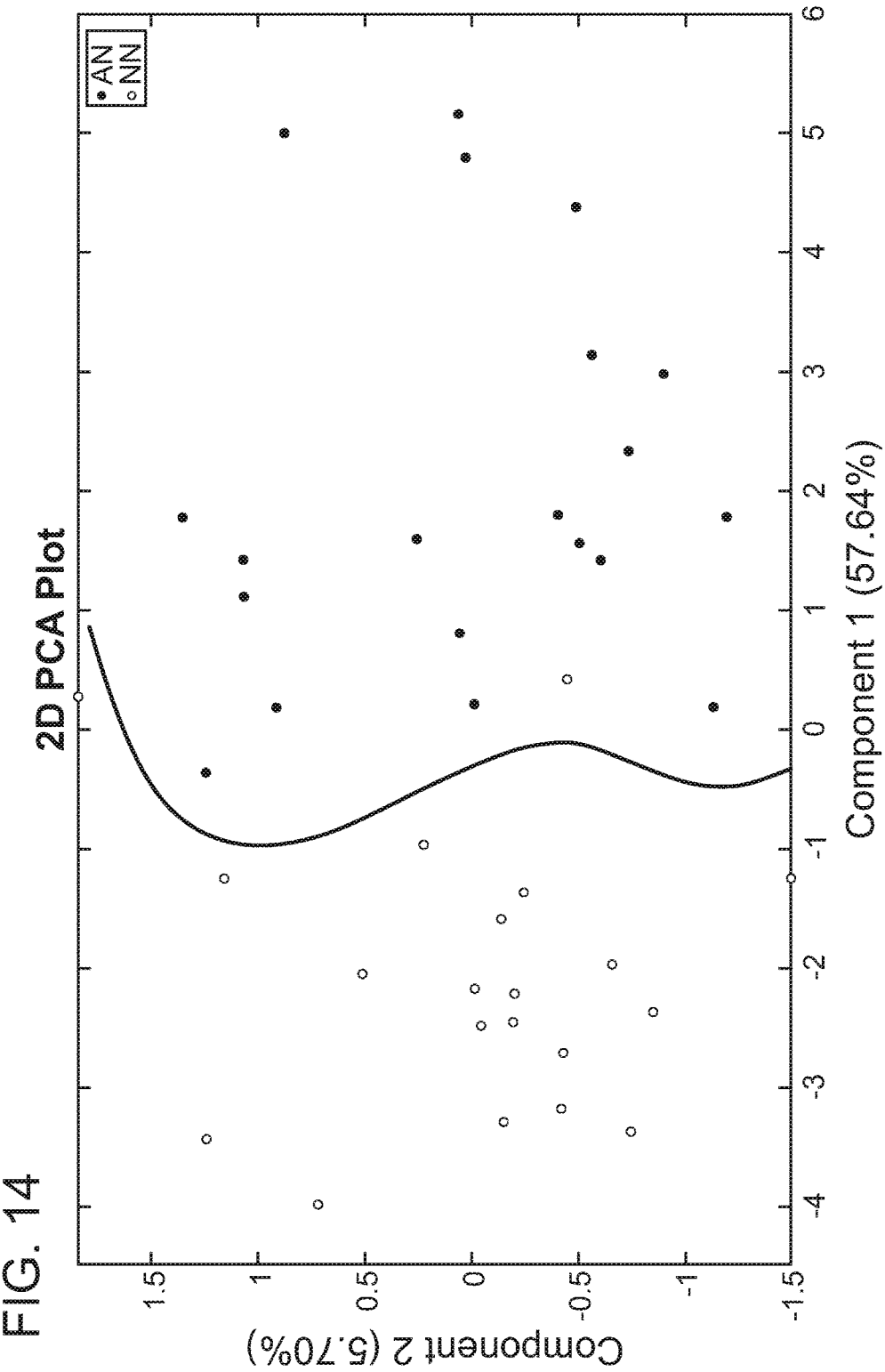

FIG. 14

2D PCA Plot

Performance of 61-protein Fibrosis Predictor on training set of NASH with Advanced Fibrosis (red) and NASH without Advanced Fibrosis (blue) (AN= NASH with Advanced Fibrosis, NN= NASH without Advanced Fibrosis) patient samples using L1OXV. 2D visualization of SVM solution. Support vectors are indicated by circles and the line (or plane) that best separates AN from NN.

61 proteins [AN vs NN] with Mann Whitney U BH corrected p-value <0.01

Colorgram of hierarchical cluster of a 61-protein Fibrosis biomarker panel. 19 of 20 NASH with Advanced fibrosis samples cluster together and 19 of 20 NASH without Advanced fibrosis samples cluster together. Red = high expression; Blue = low expression.

MARKERS FOR THE DIAGNOSIS AND TREATMENT OF NON-ALCOHOLIC STEATOHEPATITIS (NASH) AND ADVANCED LIVER FIBROSIS

This application is a 35 U.S.C. § 371 national stage filing of International Application No. PCT/US2018/061330, filed on Nov. 15, 2018, which in turn claims priority to U.S. Provisional Application No. 62/586,812, filed Nov. 15, 2017, the contents of each of which are incorporated herein by reference in their entirety.

GOVERNMENT SUPPORT

This invention was made with government support under Grant No. DK083439 awarded by the National Institutes of Health. The government has certain rights in the invention.

INCORPORATION BY REFERENCE

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

BACKGROUND

Non-alcoholic fatty liver disease (NAFLD) is the most common cause of liver disease worldwide, affecting about 20% of the general population. While prevalence of other liver diseases has been stable over the last 20 years, NAFLD has increased remarkably during this time period along with the prevalence of metabolic syndrome, obesity and diabetes. NAFLD currently impacts between 20-35% of the general population in many countries, with more than 65 million people just in the US being affected. With the current steadily rising prevalence of NAFLD and the only relatively accurate diagnosis being invasive and costly liver biopsy, diagnostic tools for disease assessment and monitoring are desperately needed.

NAFLD natural history depends on the severity of liver damage and population risk factors (e.g., obesity and diabetes). The disease spectrum ranges from a mild benign form with simple steatosis (NAFL) to a more severe form of NAFLD in 10-20% of these patients, non-alcoholic steatohepatitis (NASH).

NASH is characterized by steatosis, inflammation, and hepatocyte ballooning (apoptosis), leading to liver fibrosis. Because NASH has a more severe disease course in which patients are more susceptible to develop liver cirrhosis and hepatocellular carcinoma, identifying patients at risk for end stage liver disease is essential during evaluation and management. Patients with NASH have increased overall mortality, cardiovascular disease and liver-related complications as well as an increased risk for liver cancer as well as several other types of gastrointestinal cancers. Although some studies suggest that not only NASH, but also NAFL, can progress to liver fibrosis, the annual progression rate in patients with steatohepatitis in liver biopsy is higher than simple steatosis (1 stage of progression over 7.1 years versus 14.3 years, respectively). Moreover, while NASH with fibrosis stage F0-2 is being monitored, only more advanced fibrosis stages F3-4 are currently recommended to be treated. Nevertheless, except liver biopsy no non-invasive test is capapble to accurately diagnose the stage of fibrosis.

While some noninvasive methods of assessing liver fibrosis have been developed such as transient elastography, MR elastography, and serum fibrosis panels, there are no accepted and high accuracy non-invasive markers to distinguish NASH from NAFL. The most well-studied biomarker, cytokeratin-18 (CK18), was found to have poor inter-test kit reliability.

Currently, liver biopsy is the only way to distinguish between NAFL and NASH, between different stages of fibrosis or to assess improvement or resolution of NASH; however, it is invasive and expensive with known sampling variability and risks of complications such as bleeding, bile leaks and death in rare cases, as well as dependent on who evaluates the pathology. Repeated liver biopsies add to the cost as well as patient risk of these investigations and hinder recruitment into trials. Most importantly, liver biopsy can not be routinely used as a screening tool. Thus, non-invasive methods to distinguish between NAFL and NASH, to assess absence or presence of advanced liver fibrosis, and to predict and monitor treatment response are critically needed for diagnosis, clinical management, patient stratification, and development of effective therapies.

SUMMARY OF THE INVENTION

The present invention is based, at least in part, on the discovery that the markers in Tables 1-3, 7 and 9 are differentially expressed in non-alcoholic steatohepatitis (NASH), and that the markers in Tables 4-6, 8 and 10 are differentially expressed in advanced liver fibrosis. In particular, the invention is based on the surprising discovery that the markers in Tables 1-3, 7 and 9 are either elevated or depressed in the serum of patients with NASH and that the markers in Tables 4-6, 8 and 10 are either elevated or depressed in the serum of patients with advanced liver fibrosis, e.g., in patients having NASH.

Accordingly, the invention provides methods for diagnosing and/or monitoring (e.g., monitoring of disease progression or treatment) and/or prognosing a liver disease state, e.g., NASH or advanced liver fibrosis, in a subject, based on detecting one or more markers set forth in Tables 1-3, 7 and 9 or 4-6, 8 and 10. The markers of the invention may also be applicable to other related diseases and disorders such as liver fibrosis, hepatocellular cancer, primary biliary cirrhosis, primary sclerosing cholangitis, alcohol induced steatohepatitis, and transplant rejection in liver transplant patients or fibrosis of other organs.

The present invention also provides methods for treating or for adjusting treatment regimens, and for predicting and monitoring therapeutic response based on diagnostic information relating to the levels of the one or more markers selected from Tables 1-3, 7 and 9 and 4-6, 8 and 10 in the serum of a subject with NASH and/or advanced liver fibrosis. The invention further provides panels and kits for practicing the methods of the invention. Furthermore, the invention provides methods for treating NASH and fibrosis, e.g., advanced liver fibrosis, by administering a marker in Tables 1-10 or by modulating a marker in Tables 1-10. Furthermore, the invention provides methods for a referral pathway for patients that will rule in or rule out NASH or advanced fibrosis.

In one aspect, the present invention provides a method of diagnosing non-alcoholic steatohepatitis (NASH) in a subject, comprising detecting the level of a NASH marker in a biological sample from the subject, wherein the NASH marker comprises one or more markers selected from Tables 1-3, 7 and 9; and comparing the level of the NASH marker in the biological sample with a predetermined threshold value; wherein the level of the NASH marker above or below the predetermined threshold value indicates a diagnosis of NASH in the subject.

In another aspect, the present invention provides a method of determining whether a subject is at increased risk for developing non-alcoholic steatohepatitis (NASH), comprising detecting the level of a NASH marker in a biological sample from the subject, wherein the NASH marker comprises one or more markers selected from Tables 1-3, 7 and 9; and comparing the level of the NASH marker in the biological sample with a predetermined threshold value; wherein the level of the NASH marker above or below the predetermined threshold value indicates that the subject is at risk for developing NASH.

In one embodiment, the subject has or has been diagnosed with non-alcoholic fatty liver disease (NAFLD). In another embodiment, the one or more NASH markers distinguish between NASH and simple steatosis in the subject. In still another embodiment, the NASH is stage 1, 2, 3, or 4 NASH.

In one embodiment, the one or more NASH markers include one or more clinical variables selected from the group consisting of: gender, body mass index (BMI), age, albumin, alanine aminotransferase (ALT), aspartate aminotransferase (AST), platelet counts, diabetes, hypercholesterolemia, and hypertension.

In another embodiment, the NASH marker comprises a marker or a panel of markers selected from the following makers and panels of markers: THBS2, COLEC11, and GDF15; COLEC11, GDF15, albumin, and AST; SELE, COLEC11, BMI, ALT, albumin, and platelet count; SELE, THBS2, COLEC11 and GDF15; GDF15; COLEC11, GDF15, age, BMI, ALT, albumin, and platelet count; COLEC11, GDF15, age, and ALT, COLEC11, GDF15, BMI, ALT, albumin, and diabetes; COLEC11, GDF15, BMI, ALT, albumin, and platelet count; and COLEC11, GDF15, BMI, and ALT.

In one embodiment, the NASH marker comprises a panel of two markers, three markers, four markers, five markers, six markers, seven markers, eight markers, nine markers or ten markers selected from the panels of markers set forth in Tables 3, 7 and 9.

In another embodiment, the NASH marker comprises one or more markers selected from THBS2, BCL2A1, YES1, COLEC11, IGFBP7, N6AMT1, GDF15, C7, ITGA1 ITGB1, AKT2, SELE, ACY1, TGFB1, TIMP1, DCN, LTBP4, NAGK, IGFBP5, IL19, APOM, MMP7, ANGPT2, and POR.

In one embodiment, the NASH marker comprises one or more markers with an increased level when compared to the predetermined threshold value in the subject, and/or one or more markers with a decreased level when compared to the predetermined threshold value in the subject. In one embodiment, the NASH marker having an increased level when compared to the predetermined threshold value in the subject is selected from the group consisting of THBS2, YES1, COLEC11, IGFBP7, GDF15, C7, ITGA1 ITGB1, SELE, ACY1, TGFB1, TIMP1, DCN, LTBP4, NAGK, IL19, MMP7, ANGPT2, and POR. In another embodiment, the NASH marker having a decreased level when compared to the predetermined threshold value in the subject is selected from the group consisting of BCL2A1, N6AMT1, IGFBP5, APOM, and AKT2.

In one embodiment, the subject has a non-alcoholic fatty liver disease (NAFLD) comorbidity selected from obesity, abdominal obesity, metabolic syndrome, cardiovascular disease, and diabetes.

In another embodiment, the level of the NASH marker is detected by enzymatic analysis, mass spectrometry, NMR, immunoassay, ELISA, aptamers, nanopores, microfluidics, sequencing or any combination thereof, or by determining the level of its corresponding mRNA in the biological sample.

In one embodiment, the sample is selected from a serum sample, a plasma sample, a saliva sample, a tear sample, a urine sample, and a tissue sample.

In another embodiment, the diagnosis indicates the presence of NASH in the subject, or the subject is at risk for NASH, the subject is recommended for further validation by liver biopsy and/or imaging.

In one embodiment, the method indicates the presence of NASH in the subject, or the subject is at risk for NASH, the subject is treated with one or more therapeutic agents selected from stearoyl CoA desaturase-1 inhibitor, farnesoid X receptor agonist, CCR2 and CCR5 chemokine antagonist, PPAR alpha and delta agonist, caspase inhibitor, Galectin-3 inhibitor, acetyl CoA carboxylase inhibitor, PDE-5 inhibitor, deacetylase sirtuin stimulator, ileal sodium bile acid co-transporter inhibitor, lysyl oxidase-like 2 (LOXL2) inhibitor, ASK-1 inhibitor, DPP4 inhibitor, FGF21 agonist, ASBT inhibitor, niacin analogue, SGLT2 inhibitor, GLP1R agonist, HSP47 inhibitor, MAPK5 inhibitor, thyroid receptor β agonist, LTD receptor antagonist, semicarbazide sensitive amine oxidase inhibitor, and an immunomodulatory agent.

In another aspect, the present invention provides a method for monitoring the progression of NASH in a subject, the method comprising detecting the level of a NASH marker in a first biological sample obtained at a first time from the subject having NASH, wherein the NASH marker comprises one or more markers selected from Tables 1-3, 7 and 9; detecting the level of the NASH marker in a second biological sample obtained from the subject at a second time, wherein the second time is later than the first time; and comparing the level of the NASH marker in the second sample with the level of the NASH marker in the first sample; wherein a change in the level of the NASH marker is indicative of a change in NASH status in the subject.

In one embodiment, an increased or decreased level of the NASH marker in the second biological sample as compared to the first biological sample is indicative of progression of NASH in the subject.

In another embodiment, an increased, decreased, or equivalent level of the NASH marker in the second biological sample as compared to the first biological sample is indicative of non-progression of the NASH in the subject.

In another embodiment, the NASH marker comprises a panel of two markers, three markers, four markers, five markers, six markers, seven markers, eight markers, nine markers or ten markers selected from the panels of markers set forth in Tables 3, 7 and 9.

In another embodiment, the NASH marker comprises one or more markers selected from THBS2, BCL2A1, YES1, COLEC11, IGFBP7, N6AMT1, GDF15, C7, ITGA1 ITGB1, SELE, ACYL, TGFB1, TIMP1, DCN, LTBP4, NAGK, IGFBP5, IL19, APOM, MMP7, ANGPT2, AKT2, and POR.

In one embodiment, the NASH is stage 1, 2, 3, or 4 NASH. In another embodiment, the subject has or has been diagnosed as having non-alcoholic fatty liver disease (NAFLD) or NASH.

In one embodiment, the method further comprises using information resulting from the method to predict and/or manage the utilization of medical resources.

In another aspect, the present invention provides a method for identifying an agent that modulates NASH progression, comprising contacting a cell with a test compound, determining the expression and/or activity of a NASH marker, wherein the NASH marker comprises one or more markers selected from Tables 1-3, 7 and 9, and identifying a test compound as an agent that modulates NASH when the test compound modulates the activity and/or expression of the NASH marker. In another embodiment, the invention provides a compound identified by the methods described herein.

In another aspect, the present invention provides methods of treating or preventing NASH or inhibiting the progression of NASH, in a subject, comprising administering to the subject a modulator of one or more NASH marker, wherein the one or more NASH marker comprises one or more markers selected from Tables 1-3, 7 and 9.

In one embodiment, the modulator is an inhibitor of the at least one or more NASH markers. In another embodiment, the NASH marker is one or more markers selected from Tables 1-3, 7 and 9 which has an increased level of expression when compared to the predetermined threshold value in the subject. In another embodiment, the one or more NASH marker is selected from the group consisting of THBS2, YES1, COLEC11, IGFBP7, GDF15, C7, ITGA1 ITGB1, SELE, ACY1, TGFB1, TIMP1, DCN, LTBP4, NAGK, IL19, MMP7, ANGPT2, and POR. In another embodiment, the one or more NASH marker comprises at least one secreted, extracellular or transmembrane marker protein selected from Tables 1-3, 7 and 9. In one embodiment, the one or more NASH marker protein is a receptor, growth factor, cytokine, chemokine, extracellular matrix protein or enzyme. In one embodiment, the inhibitor is selected from an antibody, a small molecule, an aptamer, a peptide, a peptide mimetic, an RNA molecule and a DNA molecule.

In another embodiment, the modulator is an agonist of the at least one or more NASH markers. In one embodiment, wherein the NASH marker is one or more marker selected from Tables 1-3, 7 and 9 which has a decreased level of expression when compared to the predetermined threshold value in the subject. In another embodiment, the one or more NASH marker is selected from the group consisting of BCL2A1, N6AMT1, IGFBP5, APOM, and AKT2.

In one embodiment, the subject is a human.

In another aspect, the present invention provides a diagnostic tool comprising a plurality of isolated polynucleotides associated with NASH on a substrate, wherein said plurality of polynucleotides comprises at least two polynucleotides that specifically bind to at least two polynucleotides that encode proteins having at least 95% identity to one or more of the proteins selected from the group consisting of the markers set forth in Tables 1-3, 7 and 9. In one embodiment, the protein is selected from the group consisting of THBS2, BCL2A1, YES1, COLEC11, IGFBP7, N6AMT1, GDF15, C7, ITGA1 ITGB1, SELE, ACY1, TGFB1, TIMP1, DCN, LTBP4, NAGK, IGFBP5, IL19, APOM, MMP7, ANGPT2, and POR.

In another aspect, the present invention provides a kit for detecting a NASH marker in a biological sample from a subject having NASH, suspected of having NASH, or at risk for having NASH, comprising one or more reagents for measuring the level of the NASH marker in the biological sample from the subject, wherein the NASH marker comprises one or more markers selected from Tables 1-3, 7 and 9 and a set of instructions for measuring the level of the NASH marker. In one embodiment, the reagent is an antibody or an oligonucleotide that is complementary to the corresponding mRNA of the NASH marker.

In another aspect, the present invention provides a panel for use in a method of diagnosing whether a subject has NASH, determining whether a subject is at increased risk of developing NASH, predicting treatment response in a subject, or monitoring the treatment of NASH in a subject, the panel comprising one or more detection reagents, wherein each detection reagent is specific for the detection of a NASH marker, wherein the NASH marker comprises one or more markers selected from Tables 1-3, 7 and 9.

In one embodiment, the kit or panel comprises a set of instructions for obtaining diagnostic information based on a level of the NASH marker.

In one embodiment, the NASH marker comprises one or more markers with an increased level when compared to a predetermined threshold value, and/or one or more markers with a decreased level when compared to a predetermined threshold value.

In another aspect, the present invention provides a method of diagnosing whether a subject has advanced liver fibrosis, comprising detecting the level of a fibrosis marker in a biological sample from the subject, wherein the fibrosis marker comprises one or more markers selected from Tables 4-6, 8 and 10; and comparing the level of the fibrosis marker in the biological sample with a predetermined threshold value; wherein the level of the fibrosis marker above or below the predetermined threshold value indicates a diagnosis of advanced liver fibrosis in the subject or stage 0, 1, 2, 3, or 4 fibrosis.

In another aspect, the present invention provides a method of determining whether a subject is at increased risk for developing advanced liver fibrosis, comprising detecting the level of a fibrosis marker in a biological sample from the subject, wherein the fibrosis marker comprises one or more markers selected from Tables 4-6, 8 and 10; and comparing the level of the fibrosis marker in the biological sample with a predetermined threshold value; wherein the level of the fibrosis marker above or below the predetermined threshold value indicates that the subject is at risk for developing advanced liver fibrosis.

In one embodiment, the subject has or has been diagnosed as having non-alcoholic fatty liver disease (NAFLD) or NASH.

In one embodiment, the one or more NASH markers include one or more clinical variables selected from the group consisting of: gender, body mass index (BMI), age, albumin, alanine aminotransferase (ALT), aspartate aminotransferase (AST), platelet counts, diabetes, hypercholesterolemia, and hypertension.

In another embodiment, the fibrosis marker comprises a marker or a panel of markers selected from the following makers and panels of markers: SELE, COLEC11, GDF15, and BMI; SELE and COLEC11; SELE, COLEC11 and GDF15; SELE, THBS2 and COLEC11; THBS2 and COLEC11; SELE, COLEC11, age and BMI; SELE, COLEC11, GDF15, BMI and albumin; SELE, COLEC11, BMI, ALT, and albumin; SELE, COLEC11, BMI, and ALT; SELE, COLEC11, age, BMI and albumin.

In another embodiment, the fibrosis marker comprises a panel of two markers, three markers, four markers, five markers, six markers, seven markers, eight markers, nine markers or ten markers selected from the panels of markers set forth in Tables 6, 8 and 10.

In another embodiment, the fibrosis marker comprises one or more markers selected from SELE, IGFBP7, IGFBP5, C7, COLEC11, DCN, CCL21, IL1R2, THBS2, NAGK, LTBP4, TIMP1, CD163, PRSS22, A2M, MMP7, CHRDL1, ROBO2, TIE1, LAMA1 LAMB1 LAMC1, and PRL.

In one embodiment, the fibrosis marker comprises one or more markers with an increased level when compared to the predetermined threshold value in the subject, and/or one or more markers with a decreased level when compared to the predetermined threshold value in the subject.

In one embodiment, the one or more fibrosis marker having an increased level when compared to the predetermined threshold value in the subject is selected from the group consisting of SELE, IGFBP7, THBS2, C7, COLEC11, DCN, NAGK, CCL21, IL1R2, LTBP4, TIMP1, CD163, PRSS22, A2M, MMP7, CHRDL1, ROBO2, TIE1, LAMA1 LAMB1 LAMC1. In another embodiment, the one or more fibrosis marker having a decreased level when compared to the predetermined threshold value in the subject comprises IGFBP5 and PRL.

In one embodiment, the subject has an NAFLD comorbidity selected from obesity, abdominal obesity, metabolic syndrome, cardiovascular disease, and diabetes.

In another embodiment, the level of the fibrosis marker is detected by enzymatic analysis, mass spectrometry, NMR, microfluidics, immunoassay, ELISA, aptamers, nanopores, sequencing or any combination thereof, or by determining the level of its corresponding mRNA in the biological sample.

In one embodiment, the sample is selected from a serum sample, a plasma sample, a saliva sample, a tear sample, a urine sample and a tissue sample.

In one embodiment, when the diagnosis indicates the presence of advanced liver fibrosis in the subject, or the subject is at risk for advanced liver fibrosis, the subject is recommended for further validation by liver biopsy and/or imaging.

In another embodiment, when the method indicates the presence of advanced liver fibrosis in the subject, or the subject is at risk for advanced liver fibrosis, the subject is treated with one or more therapeutic agents selected from stearoyl CoA desaturase-1 inhibitor, farnesoid X receptor agonist, CCR2 and CCR5 chemokine antagonist, PPAR alpha and delta agonist, caspase inhibitor, galectin-3 inhibitor, acetyl CoA carboxylase inhibitor, PDE-5 inhibitor, deacetylase sirtuin stimulator, ileal sodium bile acid co-transporter inhibitor, lysyl oxidase-like 2 (LOXL2) inhibitor, ASK-1 inhibitor, DPP4 inhibitor, FGF21 agonist, ASBT inhibitor, niacin analogue, SGLT2 inhibitor, GLP1R agonist, HSP47 inhibitor, MAPK5 inhibitor, thyroid receptor β agonist, LTD receptor antagonist, semicarbazide sensitive amine oxidase inhibitor, and an immunomodulatory agent.

In another aspect, the present invention provides a method for monitoring the progression of liver fibrosis in a subject, the method comprising detecting the level of a fibrosis marker in a first biological sample obtained at a first time from the subject having liver fibrosis, wherein the fibrosis marker comprises one or more markers selected from Tables 4-6, 8 and 10; detecting the level of the fibrosis marker in a second biological sample obtained from the subject at a second time, wherein the second time is later than the first time; and comparing the level of the liver fibrosis marker in the second sample with the level of the fibrosis marker in the first sample; wherein a change in the level of the fibrosis marker is indicative of a change in liver fibrosis status in the subject.

In one embodiment, an increased or decreased level of the fibrosis marker in the second biological sample as compared to the first biological sample is indicative of progression of liver fibrosis in the subject. In another embodiment, an increased, decreased, or equivalent level of the fibrosis marker in the second biological sample as compared to the first biological sample is indicative of non-progression or regression of the liver fibrosis in the subject.

In one embodiment, the fibrosis marker comprises a panel of two markers, three markers, four markers, five markers, six markers, seven markers, eight markers, nine markers or ten markers selected from the panels of markers set forth in Tables 6, 8 and 10. In another embodiment, the fibrosis marker comprises one or more markers selected from SELE, IGFBP7, IGFBP5, C7, COLEC11, DCN, CCL21, IL1R2, THBS2, NAGK, LTBP4, TIMP1, CD163, PRSS22, A2M, MMP7, CHRDL1, ROBO2, TIE1, LAMA1 LAMB1 LAMC1, and PRL.

In one embodiment, the subject has or has been diagnosed with non-alcoholic fatty liver disease (NAFLD) or NASH.

In another embodiment, the method further comprises using information resulting from the method to predict and/or manage the utilization of medical resources.

In another aspect, the present invention provides a method for identifying an agent that modulates liver fibrosis progression, comprising contacting a cell with a test compound, and determining the expression and/or activity of a fibrosis marker, wherein the fibrosis marker comprises one or more markers selected from Tables 4-6, 8 and 10, and identifying a test compound as an agent that modulates liver fibrosis progression, when the test compound modulates the activity and/or expression of the fibrosis marker.

In another aspect, the present invention provides a compound identified by the methods of the invention.

In still another aspect, the present invention provides a method of treating or preventing advanced liver fibrosis or inhibiting the progression of liver fibrosis, in a subject, comprising administering to the subject a modulator of one or more fibrosis marker, wherein the one or more fibrosis marker comprises one or more markers selected from Tables 4-6, 8 and 10.

In one embodiment, the modulator is an inhibitor of the one or more fibrosis marker. In one embodiment, the one or more fibrosis marker is selected from the group consisting of SELE, IGFBP7, THBS2, C7, COLEC11, DCN, NAGK, CCL21, IL1R2, LTBP4, TIMP1, CD163, PRSS22, A2M, MMP7, CHRDL1, ROBO2, TIE1, LAMA1 LAMB1 LAMC1. In another embodiment, the one or more fibrosis marker comprises at least one secreted, extracellular or transmembrane marker protein selected from Tables 4-6, 8 and 10. In another embodiment, the one or more fibrosis marker protein is a receptor, growth factor, cytokine, chemokine, extracellular matrix protein or enzyme. In still another embodiment, the inhibitor is selected from an antibody, a small molecule, an aptamer, a peptide, a peptide mimetic, an RNA molecule and a DNA molecule.

In another embodiment, the modulator is an agonist of the at least one or more fibrosis markers. In one embodiment, the fibrosis marker is one or more marker selected from Tables 4-6, 8 and 10 which has a decreased level of expression when compared to the predetermined threshold value in the subject. In another embodiment, the one or more fibrosis marker is selected from the group consisting of IGFBP5 and PRL.

In one embodiment, the subject is a human.

In another aspect, the present invention provides a diagnostic tool comprising a plurality of isolated polynucleotides associated with advanced liver fibrosis on a substrate, wherein said plurality of polynucleotides comprises at least two polynucleotides that specifically bind to at least two polynucleotides that encode proteins having at least 95% identity to the proteins selected from the markers set forth in Tables 4-6, 8 and 10. In one embodiment, the markers are selected from the group consisting of SELE, IGFBP7, IGFBP5, C7, COLEC11, DCN, CCL21, IL1R2, THBS2, NAGK, LTBP4, TIMP1, CD163, PRSS22, A2M, MMP7, CHRDL1, ROBO2, TIE1, LAMA1 LAMB1 LAMC1, and PRL.

In another aspect, the present invention provides a kit for detecting a fibrosis marker in a biological sample from a subject having, suspected of having, or at risk for having advanced liver fibrosis, comprising one or more reagents for measuring the level of the fibrosis marker in the biological sample from the subject, wherein the fibrosis marker comprises one or more markers selected from Tables 4-6, 8 and 10 and a set of instructions for measuring the level of the fibrosis marker.

In one embodiment, the reagent is an antibody or an oligonucleotide that is complementary to the corresponding mRNA of the fibrosis marker.

In another aspect, the present invention provides a panel for use in a method of diagnosing whether a subject has liver fibrosis, determining whether a subject is at increased risk of developing liver fibrosis, predicting treatment response in a subject, or monitoring the treatment of advanced liver fibrosis, the panel comprising one or more detection reagents, wherein each detection reagent is specific for the detection of a fibrosis marker, wherein the fibrosis marker comprises one or more markers selected from Tables 4-6, 8 and 10.

In one embodiment, a kit or panel comprises a set of instructions for obtaining diagnostic information based on a level of the fibrosis marker.

In one embodiment, the fibrosis marker comprises one or more markers with an increased level when compared to a predetermined threshold value, and/or one or more markers with a decreased level when compared to a predetermined threshold value.

Where applicable or not specifically disclaimed, any one of the embodiments described herein are contemplated to be able to combine with any other one or more embodiments, even though the embodiments are described under different aspects of the invention.

These and other embodiments are disclosed or are obvious from and encompassed by, the following Detailed Description.

BRIEF DESCRIPTION OF THE DRAWINGS

FIG. 14 depicts the performance of a set of 61 protein markers for NASH with advanced liver fibrosis (AN) versus NASH without advanced liver fibrosis (NN) tested by Leave-One-Out Cross Validation (L1OXV). 2D visualization of support vector machine (SVM) solution. Support vectors are indicated by circles and the line (or plane) that best separates AN from NN.

DETAILED DESCRIPTION OF THE INVENTION

A. Overview

Figure 1:
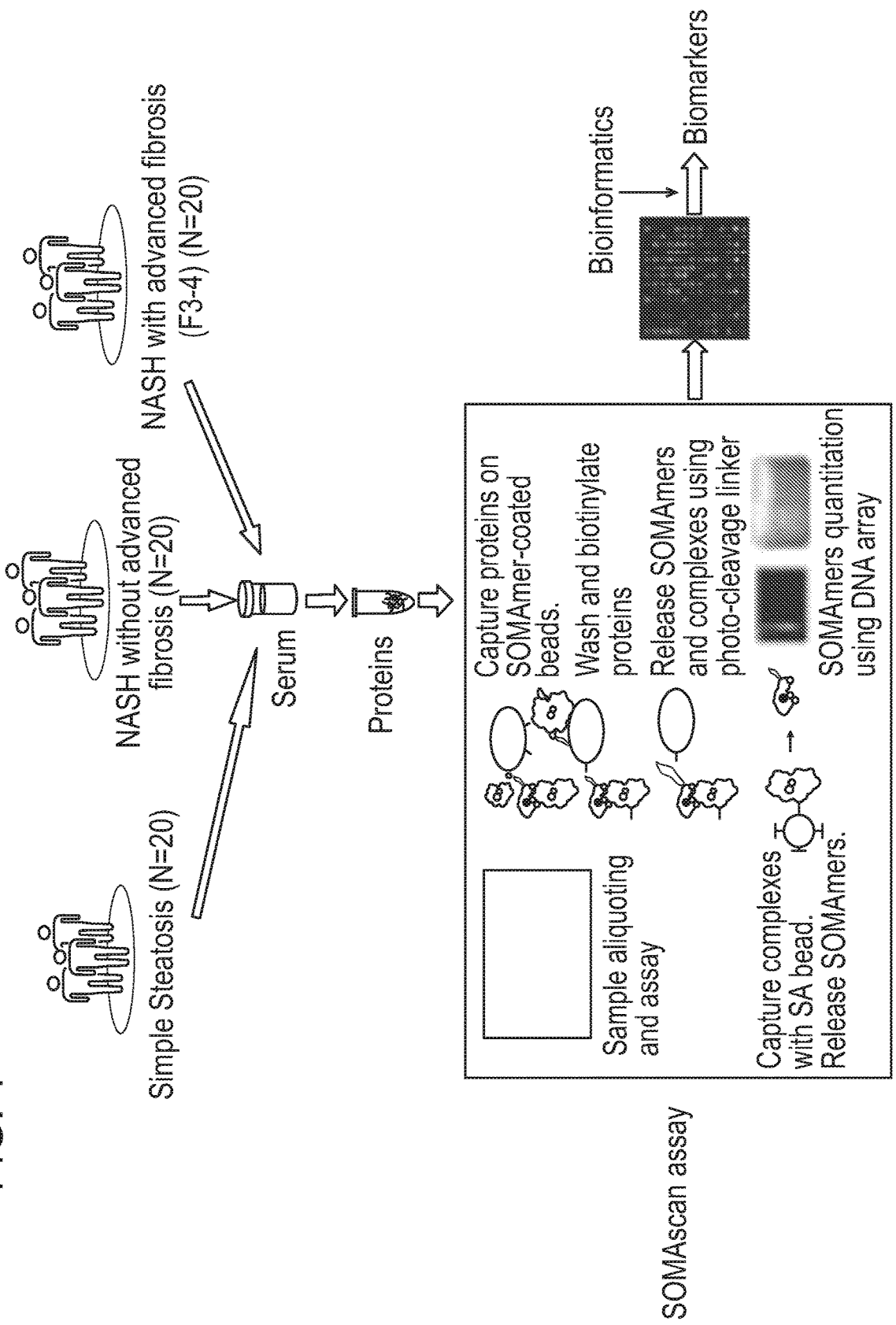
FIG. 1 is a diagram depicting the overall study design.

There remains a need for non-invasive, efficient, accurate, and rapid molecular prognosis, prediction, and diagnosis means for distinguishing NAFL (simple steatosis) from NASH and to assess the presence or absence of advanced liver fibrosis. The development of molecular tests for the accurate prognosis, i.e., prediction of one's risk for the development of NASH or advanced liver fibrosis and detection of NASH or advanced liver fibrosis will also lead to improved management and development of appropriate therapies, and an overall improved outcome. Thus, there remains a need to provide an improved prognostic and/or diagnostic test for the prediction or detection of NASH, and for the assessment of liver fibrosis, which is less invasive and more accurate than current non-invasive tests or scoring systems and can replace or complement or triage to liver biopsy. The present invention addresses this need by providing the use of biomarkers, i.e., one or more markers selected from Tables 1-3, 7 and 9 for the accurate and reliable diagnosis and prognosis of NASH, e.g., distinguishing between NAFL (simple steatosis) and NASH. The present invention also addresses this need by providing the use of biomarkers, i.e., one or more markers selected from Tables 4-6, 8 and 10 for the accurate and reliable diagnosis, prognosis and assessment of the presence or absence of advanced liver fibrosis, e.g., advanced liver fibrosis in NASH and for the staging of fibrosis from 0 to 4.

As presently described herein, the invention at hand is based, at least in part, on the discovery that the one or more markers selected from Tables 1-3, 7 and 9 are differentially expressed in NASH, and one or more markers selected from Tables 4-6, 8 and 10 are differentially expressed in advanced liver fibrosis, and serve as useful biomarkers of NASH and advanced liver fibrosis, respectively. In particular, the invention is based on the surprising discovery that the markers in Tables 1-3, 7 and 9 are differentially expressed, e.g., either increased or decreased as compared to a control, in the serum of patients with NASH, and the surprising discovery that the markers in Tables 4-6, 8 and 10 are differentially expressed, e.g., either increased or decreased as compared to a control, in the serum of patients with advanced liver fibrosis, and are thus useful in the diagnosis, prediction, and/or prognosis of NASH and in the diagnosis, prediction, and/or prognosis of advanced liver fibrosis.

Accordingly, the invention provides methods for diagnosing and/or monitoring (e.g., monitoring of disease progression or treatment) and/or prognosing a liver disease state, e.g., NASH or advanced liver fibrosis, in a subject. The markers of the invention may also be applicable to other related diseases and disorders such as liver fibrosis, primary biliary cirrhosis, primary sclerosing cholangitis, alcohol induced steatohepatitis, hepatocellular cancer, and transplant rejection in liver transplant patients or fibrosis of other organs.

In one embodiment, these one or more markers selected from Tables 1-3, 7 and 9 can serve as useful diagnostic biomarkers to detect the presence ("ruling in") or absence ("ruling out") of non-alcoholic fatty liver disease (NAFLD), e.g., NASH, in a subject. In one embodiment, where the subject has NAFLD, the one or markers can be used to distinguish between simple steatosis and NASH in a subject. In another embodiment, these one or more markers selected from Tables 1-3, 7 and 9 can serve to monitor NAFLD, e.g., NASH progression, remission and progression towards cirrhosis and hepatocellular cancer. In another embodiment, these one or more markers selected from Tables 1-3, 7 and 9 can serve as useful prognostic biomarkers, serving to inform on the likely risk for development or progression of NAFLD, e.g., NASH in a subject with or without treatment. In still another embodiment, these one or more markers selected from Tables 1-3, 7 and 9 can serve as useful predictive biomarkers for helping to monitor and assess the likely response of NAFLD, e.g., NASH to a particular treatment. Accordingly, the invention provides methods that use the one or more markers selected from Tables 1-3, 7 and 9 in the diagnosis of NAFLD, e.g., NASH (e.g., detecting the presence of NAFLD, e.g., NASH in a subject), in the monitoring of NAFLD, e.g., NASH (e.g., monitoring, progression, remission and progression towards cirrhosis and hepatocellular cancer), in the prognosis of NAFLD, e.g., NASH (e.g., prediction of the risk for development of NASH, or the course or outcome of NAFLD, e.g., NASH with or without treatment), and in the assessment of therapies intended to treat NAFLD, e.g., NASH (e.g., the one or more markers selected from Tables 1-3, 7 and 9 as a theranostic marker).

In one embodiment, these one or more markers selected from Tables 4-6, 8 and 10 can serve as useful diagnostic biomarkers to detect advanced liver fibrosis in a subject. In one embodiment, the one or more markers can be used to distinguish between NASH with advanced liver fibrosis and NASH without advanced liver fibrosis in a subject. In another embodiment, these one or more markers selected from Tables 4-6, 8 and 10 can serve as useful prognostic biomarkers, serving to inform on the likely risk for development or progression of advanced liver fibrosis in a subject with or without treatment. In still another embodiment, these one or more markers selected from Tables 4-6, 8 and 10 can serve as useful predictive biomarkers for helping to assess the likely response of advanced liver fibrosis to a particular treatment. Accordingly, the invention provides methods that use the one or more markers selected from Tables 4-6, 8 and 10 in the diagnosis of advanced liver fibrosis (e.g., prediction of the presence of advanced liver fibrosis in a subject), in the prognosis of advanced liver fibrosis (e.g., prediction of the risk for development of advanced liver fibrosis, or the course or outcome of advanced liver fibrosis with or without treatment), and in the assessment of therapies intended to treat advanced liver fibrosis (e.g., the one or more markers selected from Tables 4-6, 8 and 10 as a theranostic marker). In one embodiment, the subject has non-alcoholic fatty liver disease (NAFLD). In another embodiment, the subject has NASH.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

B. Definitions

Unless defined otherwise, all technical and scientific terms used herein have the meaning commonly understood by a person skilled in the art to which this invention belongs. The following references, the entire disclosures of which are incorporated herein by reference, provide one of skill with a general definition of many of the terms (unless defined otherwise herein) used in this invention: Singleton et al., Dictionary of Microbiology and Molecular Biology ($2^{nd}$ ed. 1994); The Cambridge Dictionary of Science and Technology (Walker ed., 1988); The Glossary of Genetics, $5^{th}$ Ed., R. Rieger et al. (eds.), Springer Verlag (1991); and Hale & Marham, the Harper Collins Dictionary of Biology (1991). Generally, the procedures of molecular biology methods described or inherent herein and the like are common methods used in the art. Such standard techniques can be found in reference manuals such as for example Sambrook et al., (2000, Molecular Cloning—A Laboratory Manual, Third Edition, Cold Spring Harbor Laboratories); and Ausubel et al., (1994, Current Protocols in Molecular Biology, John Wiley & Sons, New-York).

The following terms may have meanings ascribed to them below, unless specified otherwise. However, it should be understood that other meanings that are known or understood by those having ordinary skill in the art are also possible, and within the scope of the present invention. All publications, patent applications, patents, and other references mentioned herein are incorporated by reference in their entirety. In the case of conflict, the present specification, including definitions, will control. In addition, the materials, methods, and examples are illustrative only and not intended to be limiting.

As used herein, the singular forms "a", "and", and "the" include plural references unless the context clearly dictates otherwise. All technical and scientific terms used herein have the same meaning.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

As used herein, the term "amplification" refers to any known in vitro procedure for obtaining multiple copies ("amplicons") of a target nucleic acid sequence or its complement or fragments thereof. In vitro amplification refers to production of an amplified nucleic acid that may contain less than the complete target region sequence or its complement. Known in vitro amplification methods include, e.g., transcription-mediated amplification, replicase-mediated amplification, polymerase chain reaction (PCR) amplification, ligase chain reaction (LCR) amplification and strand-displacement amplification (SDA including multiple strand-displacement amplification method (MSDA)). Replicase-mediated amplification uses self-replicating RNA molecules, and a replicase such as Q-β-replicase (e.g., Kramer et al., U.S. Pat. No. 4,786,600). PCR amplification is well known and uses DNA polymerase, primers and thermal cycling to synthesize multiple copies of the two complementary strands of DNA or cDNA (e.g., Mullis et al., U.S. Pat. Nos. 4,683,195, 4,683,202, and 4,800,159). LCR amplification uses at least four separate oligonucleotides to amplify a target and its complementary strand by using multiple cycles of hybridization, ligation, and denaturation (e.g., EP Pat. App. Pub. No. 0 320 308). SDA is a method in which a primer contains a recognition site for a restriction endonuclease that permits the endonuclease to nick one strand of a hemimodified DNA duplex that includes the target sequence, followed by amplification in a series of primer extension and strand displacement steps (e.g., Walker et al., U.S. Pat. No. 5,422,252). Two other known strand-displacement amplification methods do not require endonuclease nicking (Dattagupta et al., U.S. Pat. Nos. 6,087,133 and 6,124,120 (MSDA)). Those skilled in the art will understand that the oligonucleotide primer sequences of the present invention may be readily used in any in vitro amplification method based on primer extension by a polymerase. (see generally Kwoh et al., 1990, Am. Biotechnol. Lab. 8:14-25 and (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 2000, Molecular Cloning—A Laboratory Manual, Third Edition, CSH Laboratories). As commonly known in the art, the oligos are designed to bind to a complementary sequence under selected conditions.

As used herein, the term "antigen" refers to a molecule, e.g., a peptide, polypeptide, protein, fragment, or other biological moiety, which elicits an antibody response in a subject, or is recognized and bound by an antibody.

As used herein, the term "marker" is a biological molecule, or a panel of biological molecules, whose altered level in a biological sample as compared to its level in normal or healthy or control biological sample is associated with a disease state, such as NASH or advanced liver fibrosis, including disease in an early stage, e.g., prior to the detection of one or more symptoms associated with the disease. In a preferred embodiment, the marker is detected in a blood sample, e.g., serum or plasma. In one embodiment, the marker is detected in serum. In one embodiment, the marker is detected in plasma. In certain embodiments, the serum or plasma can be further processed to remove abundant blood proteins (e.g., albumin) or proteins that are not marker proteins prior to analysis. Examples of biomarkers include, for example, polypeptides, peptides, polypeptide fragments, proteins, polynucleotides, RNA or RNA fragments, or microRNA (miRNAs).

A "marker", as used herein, also includes a characteristic or clinical variable that is associated with a disease state, such as NASH or fibrosis, including advanced liver fibrosis. These markers include characteristics or clinical variables can be objectively measured and evaluated as indicators of normal processes, pathogenic processes, or pharmacologic responses to a therapeutic intervention, including, in particular, NASH or advanced liver fibrosis. The association between clinical variable markers and a disease state, such as NASH or fibrosis, including advanced liver fibrosis, may be known or understood by one of ordinary skill in the art. Examples of clinical variable markers associated with NASH or advanced liver fibrosis include, but are not limited to, gender, body mass index (BMI), age, albumin, alanine aminotransferase (ALT), aspartate aminotransferase (AST), platelet count, diabetes, hypercholesterolemia, and hypertension. In one embodiment, any one or more clinical variable markers is used in combination with any one or more biological molecule markers as set forth herein in the methods of the invention.

The clinical variables are incorporated into the modeling of the predictors in the same way as the protein markers, with gender, diabetes, hypercholesterolemia, and hypertension being used as binary variables, and age, BMI, ALT, AST, albumin, and platelet counts as continuous variables. Various noninvasive NASH and fibrosis tests have been developed and are known in the art which include different combinations of the aforementioned clinical variables as well as some other variables in their scoring algorithm such as FIB-4, BAAT, BARD, ELF, FibroTest, FibroScan (see, e.g., Cheah M C, et al. J Clin Transl Hepatol. 2017 Sep. 28; 5(3):261-271; Vilar-Gomez E, Chalasani N. J Hepatol. 2018 February; 68(2):305-315; Tsai E, Lee T P. Clin Liver Dis. 2018 February; 22(1):73-92; Golabi P, et al. Expert Rev Gastroenterol Hepatol. 2016; 10(1):63-71; Castera L. Semin Liver Dis. 2015 August; 35(3):291-303; Mansoor S, Collyer E, Alkhouri N. Curr Gastroenterol Rep. 2015 June; 17(6):23; Sumida Y, Nakajima A, Itoh Y. World J Gastroenterol. 2014 Jan. 14; 20(2):475-85; and Festi D, et al. Aliment Pharmacol Ther. 2013 February; 37(4):392-400, the contents of which are incorporated herein by reference).

With respect to age as a clinical variable, there is no age cut-off and age can be used as a continuous variable. Gender is a binary (male versus female) variable. BMI can be used either as a continuous variable or as three classes: lean (BMI<25), overweight (BMI 25-30), obese (BMI>30). AST, ALT, albumin, and platelet counts are also used as continuous variables. Diabetes, hypercholesterolemia and hypertension are used as a binary, i.e., absent or present, variable. Hypercholesterolemia is defined as total cholesterol levels above 240 mg/dL. Platelet counts between 150,000-450,000 per microliter are considered normal.

As used herein, the term "NASH marker" is a "marker" as set forth above, which is associated with NASH, e.g., wherein the marker is associated with NASH versus simple steatosis. As used herein, a NASH marker includes one or more of the markers set forth in Tables 1-3, 7 and 9, including one or more of the sets or panels of markers set forth in Tables 3, 7 and 9.

As used herein, the term "fibrosis marker" or "advanced liver fibrosis marker", used interchangeably herein, is a "marker" as set forth above, which is associated with advanced liver fibrosis, e.g., NASH with advanced liver fibrosis. As used herein, a fibrosis marker includes one or more of the markers set forth in Tables 4-6, 8 and 10, including one or more of the sets or panels of markers set forth in Tables 6, 8 and 10.

Preferably, a marker of the present invention is modulated (e.g., increased or decreased level) in a biological sample from a subject or a group of subjects having a first phenotype (e.g., having a disease) as compared to a biological sample from a subject or group of subjects having a second phenotype (e.g., not having the disease or having a precursor of the disease, e.g., a control). A biomarker may be differentially present at any level, but is generally present at a level that is increased relative to normal or control levels by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased relative to normal or control levels by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker is preferably differentially present at a level that is statistically significant (e.g., a p-value less than 0.05 and/or a q-value of less than 0.10 as determined using either Welch's T-test or Wilcoxon's rank-sum Test).

As used herein, the term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control sample" or "control," as used herein, refers to any clinically relevant comparative sample, including, for example, a sample from a healthy subject not afflicted with NAFLD, e.g., NASH, or a sample from a subject from an earlier time point, e.g., prior to treatment. In one embodiment, a control sample can also refer to a sample from a subject having simple steatosis. In another embodiment, a control sample can refer to a sample from a subject having NASH without advanced liver fibrosis. In one embodiment, a control sample can have an NAFLD comorbidity selected from obesity, abdominal obesity, metabolic syndrome, cardiovascular disease, and diabetes. A control sample can be a purified sample, protein, and/or nucleic acid provided with a kit. Such control samples can be diluted, for example, in a dilution series to allow for quantitative measurement of levels of analytes, e.g., markers, in test samples. A control sample may include a sample derived from one or more subjects. A control sample may also be a sample made at an earlier time point from the subject to be assessed. For example, the control sample could be a sample taken from the subject to be assessed before the onset of NASH or NASH with advanced liver fibrosis, at an earlier stage of disease, e.g., simple steatosis, or before the administration of treatment or of a portion of treatment. The control sample may also be a sample from an animal model, or from a tissue or cell line derived from the animal model of NASH or advanced liver fibrosis. The level of activity or expression of one or more markers (e.g., 1, 2, 3, 4, 5, 6, 7, 8, or 9 or more markers) in a control sample consists of a group of measurements that may be determined, e.g., based on any appropriate statistical measurement, such as, for example, measures of central tendency including average, median, or modal values. In one embodiment, "different from a control" is preferably statistically significantly different from a control.

As used herein, "changed, altered, increased or decreased as compared to a control" sample or subject is understood as having a level of the analyte or diagnostic or therapeutic indicator (e.g., marker) to be detected at a level that is statistically different, e.g., increased or decreased, as compared to a sample from a normal, untreated, or abnormal state control sample. Changed as compared to control can also include a difference in the rate of change of the level of one or more markers obtained in a series of at least two subject samples obtained over time. Determination of statistical significance is within the ability of those skilled in the art and can include any acceptable means for determining and/or measuring statistical significance, such as, for example, the number of standard deviations from the mean that constitute a positive or negative result, an increase in the detected level of a biomarker in a sample (e.g., a NASH or advanced liver fibrosis sample) versus a control or healthy sample, wherein the increase is above some threshold value, or a decrease in the detected level of a biomarker in a sample (e.g., a NASH or advanced liver fibrosis sample) versus a control or healthy sample, wherein the decrease is below some threshold value. The threshold value can be determined by any suitable means by measuring the biomarker levels in a plurality of tissues or samples known to have a disease, e.g., NASH or advanced liver fibrosis, and comparing those levels to a normal sample or control sample and calculating a statistically significant threshold value.

The term "control level" refers to an accepted or predetermined level of a marker in a subject sample. A control level can be a range of values. Marker levels can be compared to a single control value, to a range of control values, to the upper level of normal, or to the lower level of normal as appropriate for the assay.

In one embodiment, the control is a standardized control, such as, for example, a control which is predetermined using an average of the levels of expression of one or more markers from a population of subjects having no NASH, a population of subjects having simple steatosis, or a population of subjects having NASH without advanced liver fibrosis.

It is understood that a combination of marker levels may be most useful to distinguish between NASH and/or advanced liver fibrosis, possibly in combination with other diagnostic methods. Further, marker levels in biological samples can be compared to more than one control sample (e.g., normal, abnormal, from the same subject, from a population control). Marker levels can be used in combination with other signs or symptoms of NASH or advanced liver fibrosis to provide a diagnosis for the subject.

A control can also be a sample from a subject at an earlier time point, e.g., a baseline level prior to suspected presence of disease, before the diagnosis of a disease, before the treatment with a specific agent or intervention. In certain embodiments, a change in the level of the marker in a subject can be more significant than the absolute level of a marker, e.g., as compared to control.

As used herein, "detecting", "detection", "determining", and the like are understood to refer to an assay performed for identification of one or more markers selected from Tables 1-3, 7 and 9 or Tables 4-6, 8 and 10. The amount of marker expression or activity detected in the sample can be none or below the level of detection of the assay or method.

As used herein, the term "DNA" or "RNA" molecule or sequence (as well as sometimes the term "oligonucleotide") refers to a molecule comprised generally of the deoxyribonucleotides adenine (A), guanine (G), thymine (T) and/or cytosine (C). In "RNA", T is replaced by uracil (U).

The terms "disorders", "diseases", and "abnormal state" are used inclusively and refer to any deviation from the normal structure or function of any part, organ, or system of the body (or any combination thereof). A specific disease is manifested by characteristic symptoms and signs, including biological, chemical, and physical changes, and is often associated with a variety of other factors including, but not limited to, demographic, environmental, employment, genetic, and medically historical factors. An early stage disease state includes a state wherein one or more physical symptoms are not yet detectable. Certain characteristic signs, symptoms, and related factors can be quantitated through a variety of methods to yield important diagnostic information. As used herein the disorder, disease, or abnormal state is an abnormal liver state, including simple steatosis.

As used herein, a sample obtained at an "earlier time point" is a sample that was obtained at a sufficient time in the past such that clinically relevant information could be obtained in the sample from the earlier time point as compared to the later time point. In certain embodiments, an earlier time point is at least four weeks earlier. In certain embodiments, an earlier time point is at least six weeks earlier. In certain embodiments, an earlier time point is at least two months earlier. In certain embodiments, an earlier time point is at least three months earlier. In certain embodiments, an earlier time point is at least six months earlier. In certain embodiments, an earlier time point is at least nine months earlier. In certain embodiments, an earlier time point is at least one year earlier. Multiple subject samples (e.g., 3, 4, 5, 6, 7, or more) can be obtained at regular or irregular intervals over time and analyzed for trends in changes in marker levels. Appropriate intervals for testing for a particular subject can be determined by one of skill in the art based on ordinary considerations.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, or protein, or both.

As used herein, "fold change ratio" or "FC ratio" refers to a change, e.g., increase or decrease, of the expression or level of a marker, e.g., one or more marker selected from Tables 1-3, 7 and 9 or Tables 4-6, 8 and 10. In some embodiments, the FC ratio is greater than 1, which indicates an up-regulation or increase in the expression or level of the marker. In other embodiments, the FC ratio is less than 1, indicating a down-regulation or decrease in the expression or level of the marker. FC ratio can also be calculated and expressed as a Log unit. When the FC ratio is expressed as a Log FC value, a Log FC value greater than 0 is equivalent to an FC ratio greater than 1, indicating an up-regulation or increase in the expression or level of the marker. Alternatively, a Log FC value less than 0 is equivalent to an FC ratio less than 1, indicating a down-regulation or decrease in the expression or level of the marker. The FC for the markers disclosed herein are set forth in Table 1 and Table 4.

A "higher level of expression", "higher level", "increased level," and the like of a marker refers to an expression level in a test sample that is greater than the standard error of the assay employed to assess expression, and is preferably at least 25% more, at least 50% more, at least 75% more, at least two, at least three, at least four, at least five, at least six, at least seven, at least eight, at least nine, or at least ten times the expression level of the marker in a control sample and preferably, the average expression level of the marker or markers in several control samples.

As used herein, the term "hybridization," as in "nucleic acid hybridization," refers generally to the hybridization of two single-stranded nucleic acid molecules having complementary base sequences, which under appropriate conditions will form a thermodynamically favored double-stranded structure. Examples of hybridization conditions can be found in the two laboratory manuals referred above (Sambrook et al., 2000, supra and Ausubel et al., 1994, supra, or further in Higgins and Hames (Eds.) "Nucleic acid hybridization, a practical approach" IRL Press Oxford, Washington D.C., (1985)) and are commonly known in the art. In the case of a hybridization to a nitrocellulose filter (or other such support like nylon), as for example in the well-known Southern blotting procedure, a nitrocellulose filter can be incubated overnight at a temperature representative of the desired stringency condition (60-65° C. for high stringency, 50-60° C. for moderate stringency and 40-45° C. for low stringency conditions) with a labeled probe in a solution containing high salt (6×SSC or 5×SSPE), 5×Denhardt's solution, 0.5% SDS, and 100 µg/ml denatured carrier DNA (e.g., salmon sperm DNA). The non-specifically binding probe can then be washed off the filter by several washes in 0.2×SSC/0.1% SDS at a temperature which is selected in view of the desired stringency: room temperature (low stringency), 42° C. (moderate stringency) or 65° C. (high stringency). The salt and SDS concentration of the washing solutions may also be adjusted to accommodate for the desired stringency. The selected temperature and salt concentration is based on the melting temperature (Tm) of the DNA hybrid. Of course, RNA-DNA hybrids can also be formed and detected. In such cases, the conditions of hybridization and washing can be adapted according to well-known methods by the person of ordinary skill Stringent conditions will be preferably used (Sambrook et al., 2000, supra). Other protocols or commercially available hybridization kits (e.g., ExpressHyb® from BD Biosciences Clonetech) using different annealing and washing solutions can also be used as well known in the art. As is well known, the length of the probe and the composition of the nucleic acid to be determined constitute further parameters of the hybridization conditions. Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Hybridizing nucleic acid molecules also comprise fragments of the above described molecules. Furthermore, nucleic acid molecules which hybridize with any of the aforementioned nucleic acid molecules also include complementary fragments, derivatives and allelic variants of these molecules. Additionally, a hybridization complex refers to a complex between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed).

As used herein, the term "identical" or "percent identity" in the context of two or more nucleic acid or amino acid sequences, refers to two or more sequences or subsequences that are the same, or that have a specified percentage of amino acid residues or nucleotides that are the same (e.g., 60% or 65% identity, preferably, 70-95% identity, more preferably at least 95% identity), when compared and aligned for maximum correspondence over a window of comparison, or over a designated region as measured using a sequence comparison algorithm as known in the art, or by manual alignment and visual inspection. Sequences having, for example, 60% to 95% or greater sequence identity are considered to be substantially identical. Such a definition also applies to the complement of a test sequence. Preferably the described identity exists over a region that is at least about 15 to 25 amino acids or nucleotides in length, more preferably, over a region that is about 50 to 100 amino acids or nucleotides in length. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art. Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations. Also available to those having skill in this art are the BLAST and BLAST 2.0 algorithms (Altschul Nucl. Acids Res. 25 (1977), 3389-3402). The BLASTN program for nucleic acid sequences uses as defaults a word length (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff Proc. Natl. Acad. Sci., USA, 89, (1989), 10915) uses alignments (B) of 50, expectation (E) of 10, M=5, N=4, and a comparison of both strands. Moreover, the present invention also relates to nucleic acid molecules the sequence of which is degenerate in comparison with the sequence of an above-described hybridizing molecule. When used in accordance with the present invention the term "being degenerate as a result of the genetic code" means that due to the redundancy of the genetic code different nucleotide sequences code for the same amino acid. The present invention also relates to nucleic acid molecules which comprise one or more mutations or deletions, and to nucleic acid molecules which hybridize to one of the herein described nucleic acid molecules, which show (a) mutation(s) or (a) deletion(s).

The term "including" is used herein to mean, and is used interchangeably with, the phrase "including but not limited to."

A subject at "increased risk for developing NASH" may or may not develop NASH. In one embodiment, identification of a subject at increased risk for developing NASH ("rule in") should be monitored for additional signs or symptoms of NASH. In one embodiment, identification of a subject at low or no risk for developing NASH ("rule out") does not have to be monitored for additional signs or symptoms of NASH. The methods provided herein for identifying a subject with increased risk for developing NASH can be used in combination with assessment of other known risk factors or signs of NASH or advanced liver fibrosis including, but not limited to the presence of simple steatosis, obesity, abdominal obesity, metabolic syndrome, cardiovascular disease, diabetes, age, and other factors known in the art.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein, a "label" refers to a molecular moiety or compound that can be detected or can lead to a detectable signal. A label is joined, directly or indirectly, to a molecule, such as an antibody, a nucleic acid probe or the protein/antigen or nucleic acid to be detected (e.g., an amplified sequence). Direct labeling can occur through bonds or interactions that link the label to the nucleic acid (e.g., covalent bonds or non-covalent interactions), whereas indirect labeling can occur through the use of a "linker" or bridging moiety, such as oligonucleotide(s) or small molecule carbon chains, which is either directly or indirectly labeled. Bridging moieties may amplify a detectable signal. Labels can include any detectable moiety (e.g., a radionuclide, ligand such as biotin or avidin, enzyme or enzyme substrate, reactive group, chromophore such as a dye or colored particle, luminescent compound including a bioluminescent, phosphorescent or chemiluminescent compound, and fluorescent compound). Preferably, the label on a labeled probe is detectable in a homogeneous assay system, i.e., in a mixture, the bound label exhibits a detectable change compared to an unbound label.

The terms "level of expression of a gene", "gene expression level", "level of a marker", and the like refer to the level of mRNA, as well as pre-mRNA nascent transcript(s), transcript processing intermediates, mature mRNA(s) and degradation products, or the level of protein, encoded by the gene in the cell. The "level" of one or more biomarkers means the absolute or relative amount or concentration of the biomarker in the sample.

A "lower level of expression" or "lower level" or "decreased level" of a marker refers to an expression level in a test sample that is less than 90%, 85%, 80%, 75%, 70%, 65%, 60%, 55%, 50%, 45%, 40%, 35%, 30%, 25%, 20%, 15%, or 10% of the expression level of the marker in a control sample and preferably, the average expression level of the marker in several control samples.

The term "modulation" refers to upregulation (i.e., activation or stimulation), down-regulation (i.e., inhibition or suppression) of a response (e.g., level of a marker), or the two in combination or apart. A "modulator" is a compound or molecule that modulates, and may be, e.g., an agonist, antagonist, activator, stimulator, suppressor, or inhibitor.

The term "agonist" refers to any modulator that increases the expression and/or activity of a marker of the invention, and includes a protein or nucleic acid marker itself, wherein the marker is a marker set forth in Tables 1-10 and has decreased expression or activity as compared to a control or a predetermined threshold level.

The terms "non-alcoholic fatty liver disease" or "NAFLD" refers to liver disease characterized by the accumulation of fat in the liver cells (steatosis). Steatosis is broadly understood to describe a process involving the abnormal retention of lipids within the liver, which accumulation inhibits the normal liver functions. Liver biopsy enables analysis and scoring of steatosis in a patient, with scores ranging from 0-3. Steatosis is traditionally graded with a score of 1 indicating the presence of fat droplets in less than 33% of hepatocytes, a score of 2 indicating fat droplets observed in 33-66% of hepatocytes, and a score of 3 indicating observation of fat droplets in greater than 66% of hepatocytes. (See Kleinen et al., Design and Validation of a Histological Scoring System for Nonalcoholic Fatty Liver Disease, Hepatology, Vol. 41, No. 6, 2005, pp. 1313-1321, the contents of which are hereby incorporated by reference herein). NAFLD comorbidity includes, but it not limited to, obesity, abdominal obesity, metabolic syndrome, cardiovascular disease, and diabetes.

The term "simple steatosis" refers to the hepatic steatosis in the absence of significant inflammation and hepatocellular damage.

The term "NASH" or "non-alcoholic steatohepatitis" refers to a more severe form of NAFLD than simple steatosis. NASH is characterized by steatosis, inflammation, and hepatocyte ballooning (apoptosis). Patients with NASH are more susceptible to develop liver cirrhosis and hepatocellular carcinoma, and have increased overall mortality, cardiovascular diseases and liver-related complications. In NASH, fat accumulation is associated with liver cell inflammation and different degrees of scarring. Cirrhosis occurs when the liver sustains substantial damage and the liver cells are gradually replaced by scar tissue, which results in the inability of the liver to work properly. NASH can progress to liver fibrosis, which is the excessive accumulation of extracellular matrix proteins including collagen that occurs in most types of chronic liver diseases. NASH can be characterized based on stage 1, 2, 3, or 4. Evaluation and staging of fatty liver disease, including NASH and liver fibrosis, is described in Dyson et al., *Frontline Gastroenterology*, 2014; 5:211-218, the contents of which are hereby incorporated by reference herein).

The term "advanced liver fibrosis" or "advanced fibrosis" refers to liver fibrosis that can result in cirrhosis, liver failure, and portal hypertension and often requires liver transplantation. Fibrosis can be evaluated upon liver biopsy and scored based on the The Metavir Score (F0-F4). As used herein, "advanced liver fibrosis" refers to fibrosis with a score of F3 or F4. A fibrosis score of F0, F1, or F2 refers to non-advanced fibrosis. Advanced fibrosis may also be defined as F2, F3, and F4. (see Rockey et al. *Hepatology, AASLD Position Paper*, March, 2009, pp. 1017-1044, the contents of which are hereby incorporated by reference herein). Fibrosis can also affect other organs of the body other than the liver.

As used herein, "nucleic acid molecule" or "polynucleotides", refers to a polymer of nucleotides. Non-limiting examples thereof include DNA (e.g., genomic DNA, cDNA), RNA molecules (e.g., mRNA) and chimeras thereof. The nucleic acid molecule can be obtained by cloning techniques or synthesized. DNA can be double-stranded or single-stranded (coding strand or non-coding strand [antisense]). Conventional ribonucleic acid (RNA) and deoxyribonucleic acid (DNA) are included in the term "nucleic acid" and polynucleotides as are analogs thereof. A nucleic acid backbone may comprise a variety of linkages known in the art, including one or more of sugar-phosphodiester linkages, peptide-nucleic acid bonds (referred to as "peptide nucleic acids" (PNA); Hydig-Hielsen et al., PCT Intl Pub. No. WO 95/32305), phosphorothioate linkages, methylphosphonate linkages or combinations thereof. Sugar moieties of the nucleic acid may be ribose or deoxyribose, or similar compounds having known substitutions, e.g., 2' methoxy substitutions (containing a 2'-O-methylribofuranosyl moiety; see PCT No. WO 98/02582) and/or 2' halide substitutions. Nitrogenous bases may be conventional bases (A, G, C, T, U), known analogs thereof (e.g., inosine or others; see The Biochemistry of the Nucleic Acids 5-36, Adams et al., ed., 11th ed., 1992), or known derivatives of purine or pyrimidine bases (see, Cook, PCT Int'l Pub. No. WO 93/13121) or "abasic" residues in which the backbone includes no nitrogenous base for one or more residues (Arnold et al., U.S. Pat. No. 5,585,481). A nucleic acid may comprise only conventional sugars, bases and linkages, as found in RNA and DNA, or may include both conventional components and substitutions (e.g., conventional bases linked via a methoxy backbone, or a nucleic acid including conventional bases and one or more base analogs). An "isolated nucleic acid molecule", as is generally understood and used herein, refers to a polymer of nucleotides, and includes, but should not limited to DNA and RNA. The "isolated" nucleic acid molecule is purified from its natural in vivo state, obtained by cloning or chemically synthesized.

As used herein, the term "obtaining" is understood herein as manufacturing, purchasing, or otherwise coming into possession of.

As used herein, "oligonucleotides" or "oligos" define a molecule having two or more nucleotides (ribo or deoxyribonucleotides). The size of the oligo will be dictated by the particular situation and ultimately on the particular use thereof and adapted accordingly by the person of ordinary skill. An oligonucleotide can be synthesized chemically or derived by cloning according to well-known methods. While they are usually in a single-stranded form, they can be in a double-stranded form and even contain a "regulatory region". They can contain natural rare or synthetic nucleotides. They can be designed to enhance a chosen criteria like stability for example. Chimeras of deoxyribonucleotides and ribonucleotides may also be within the scope of the present invention.

As used herein, "one or more" is understood as each value 1, 2, 3, 4, 5, 6, 7, 8, 9, 10, and any value greater than 10.

The term "or" is used inclusively herein to mean, and is used interchangeably with, the term "and/or," unless context clearly indicates otherwise.

As used herein, "patient" or "subject" can mean either a human or non-human animal, preferably a mammal. By "subject" is meant any animal, including horses, dogs, cats, pigs, goats, rabbits, hamsters, monkeys, guinea pigs, rats, mice, lizards, snakes, sheep, cattle, fish, and birds. A human subject may be referred to as a patient. It should be noted that clinical observations described herein were made with human subjects and, in at least some embodiments, the subjects are human.

As used herein, "preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). Prevention does not require that the disease or condition never occurs in the subject. Prevention includes delaying the onset or severity of the disease or condition.

As used herein, a "predetermined threshold value" or "threshold value" of a biomarker refers to the level of the biomarker (e.g., the expression level or quantity (e.g., ng/ml) in a biological sample) in a corresponding control sample or group of control samples obtained from normal or healthy subjects, or subjects not having the condition to be tested. For example, a control sample can include a sample from a normal subject, a subject that does not have NASH, a subject that has simple steatosis, or a subject that has NASH without advanced liver fibrosis. The predetermined threshold value may be determined prior to or concurrently with measurement of marker levels in a biological sample. The control sample may be from the same subject at a previous time or from different subjects.

As used herein, a "probe" is meant to include a nucleic acid oligomer or oligonucleotide that hybridizes specifically to a target sequence in a nucleic acid or its complement, under conditions that promote hybridization, thereby allowing detection of the target sequence or its amplified nucleic acid. Detection may either be direct (i.e., resulting from a probe hybridizing directly to the target or amplified sequence) or indirect (i.e., resulting from a probe hybridizing to an intermediate molecular structure that links the probe to the target or amplified sequence). A probe's "target" generally refers to a sequence within an amplified nucleic acid sequence (i.e., a subset of the amplified sequence) that hybridizes specifically to at least a portion of the probe sequence by standard hydrogen bonding or "base pairing." Sequences that are "sufficiently complementary" allow stable hybridization of a probe sequence to a target sequence, even if the two sequences are not completely complementary. A probe may be labeled or unlabeled. A probe can be produced by molecular cloning of a specific DNA sequence or it can also be synthesized. Numerous primers and probes which can be designed and used in the context of the present invention can be readily determined by a person of ordinary skill in the art to which the present invention pertains.

As used herein, the terminology "prognosis" is defined herein as the prediction of the degree of severity of NASH or fibrosis and of its evolution as well as the prospect of recovery as anticipated from usual course of the disease.

As used herein, "prophylactic" or "therapeutic" treatment refers to administration to the subject of one or more agents or interventions to provide the desired clinical effect. If it is administered prior to clinical manifestation of the unwanted condition (e.g., disease or other unwanted state of the host animal) then the treatment is prophylactic, i.e., it protects the host against developing at least one sign or symptom of the unwanted condition, whereas if administered after manifestation of the unwanted condition, the treatment is therapeutic (i.e., it is intended to diminish, ameliorate, or maintain at least one sign or symptom of the existing unwanted condition or side effects therefrom).

As used herein, a "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype. For example, a "NASH-positive reference level" of a biomarker means a level of a biomarker that is indicative of a positive diagnosis of NASH in a subject, and a "NASH-negative reference level" of a biomarker means a level of a biomarker that is indicative of a negative diagnosis of NASH in a subject. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, e.g., diabetes or obesity, phenotype, or lack thereof in a certain age group). Such reference levels may also be tailored to specific techniques that are used to measure levels of biomarkers in biological samples (e.g., LC-MS, GC-MS, etc.), where the levels of biomarkers may differ based on the specific technique that is used.

As used herein, "sample" or "biological sample" includes a specimen or culture obtained from any source. Biological samples can be obtained from blood (including any blood product, such as whole blood, plasma, serum, or specific types of cells of the blood), urine, saliva, seminal fluid, and the like. In one embodiment, the biological sample is from blood, e.g., serum.

As use herein, the phrase "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabeled A) in a reaction containing labeled "A" and the antibody will reduce the amount of labeled A bound to the antibody.

The phrase "specific identification" is understood as detection of a marker of interest with sufficiently low background of the assay and cross-reactivity of the reagents used such that the detection method is diagnostically useful. In certain embodiments, reagents for specific identification of a marker bind to only one isoform of the marker. In certain embodiments, reagents for specific identification of a marker bind to more than one isoform of the marker. In certain embodiments, reagents for specific identification of a marker bind to all known isoforms of the marker.

The term "such as" is used herein to mean, and is used interchangeably, with the phrase "such as but not limited to."

The terms "test compound" and "candidate compound" refer to any chemical entity, pharmaceutical, drug, and the like that is a candidate for use to treat or prevent a disease, illness, sickness, or disorder of bodily function (e.g., NASH or advanced liver fibrosis). Test compounds comprise both known and potential therapeutic compounds. A test compound can be determined to be therapeutic by screening using the screening methods of the present invention. In some embodiments of the present invention, test compounds include antisense compounds.

The term "therapeutic effect" refers to a local or systemic effect in animals, particularly mammals, and more particularly humans caused by a pharmacologically active substance. The term thus means any substance intended for use in the diagnosis, cure, mitigation, treatment, or prevention of disease, or in the enhancement of desirable physical or mental development and conditions in an animal or human. As used herein, "therapeutically effective amount" means the amount of a compound that, when administered to a patient for treating a disease, is sufficient to effect such treatment for the disease, e.g., the amount of such a substance that produces some desired local or systemic effect at a reasonable benefit/risk ratio applicable to any treatment, e.g., is sufficient to ameliorate at least one sign or symptom of the disease, e.g., to prevent progression of the disease or condition, e.g., prevent or treat NASH, steatosis, inflammation, apoptosis, fibrosis, cirrhosis, or hepatocellular carcinoma. When administered for preventing a disease, the amount is sufficient to avoid or delay onset of the disease. The "therapeutically effective amount" will vary depending on the compound, its therapeutic index, solubility, the disease and its severity and the age, weight, etc., of the patient to be treated, and the like. For example, certain compounds discovered by the methods of the present invention may be administered in a sufficient amount to produce a reasonable benefit/risk ratio applicable to such treatment. Administration of a therapeutically effective amount of a compound may require the administration of more than one dose of the compound.

A "transcribed polynucleotide" or "nucleotide transcript" is a polynucleotide (e.g. an mRNA, hnRNA, a cDNA, or an analog of such RNA or cDNA) which is complementary to or having a high percentage of identity (e.g., at least 80% identity) with all or a portion of a mature mRNA made by transcription of a marker of the invention and normal post-transcriptional processing (e.g. splicing), if any, of the RNA transcript, and reverse transcription of the RNA transcript.

As used herein, "treatment," particularly "active treatment," refers to performing an intervention to treat NASH or advanced liver fibrosis in a subject, e.g., reduce at least one of steatosis, inflammation, apoptosis, or fibrosis, by administration of one or more of a therapeutic agent, e.g., stearoyl CoA desaturase-1 inhibitor, farnesoid X receptor agonist, CCR2 and CCR5 chemokine antagonist, PPAR alpha and delta agonist, caspase inhibitor, galectin-3 inhibitor, acetyl CoA carboxylase inhibitor, PDE-5 inhibitor, deacetylase sirtuin stimulator, ileal sodium bile acid co-transporter inhibitor, lysyl oxidase-like 2 (LOXL2) inhibitor, ASK-1 inhibitor, DPP4 inhibitor, FGF21 agonist, ASBT inhibitor, niacin analogue, SGLT2 inhibitor, GLP1R agonist, HSP47 inhibitor, MAPK5 inhibitor, thyroid receptor β agonist, LTD receptor antagonist, semicarbazide sensitive amine oxidase inhibitor, and an immunomodulatory agent, or any combination thereof appropriate for treatment of the subject.

The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Reference will now be made in detail to exemplary embodiments of the invention. While the invention will be described in conjunction with the exemplary embodiments, it will be understood that it is not intended to limit the invention to those embodiments. To the contrary, it is intended to cover alternatives, modifications, and equivalents as may be included within the spirit and scope of the invention as defined by the appended claims.

Exemplary compositions and methods of the present invention are described in more detail in the following sections: (C) Biomarkers of the invention; (D) Samples; (E) Detection and/or measurement of the biomarkers of the invention; (F) Isolated biomarkers; (G) Applications of biomarkers of the invention; (H) Therapeutics; (I) Drug screening; and (J) Kits/panels.

C. Biomarkers of the Invention

The present invention is based, at least in part, on the discovery that the markers (hereinafter "biomarkers", "markers" or "markers of the invention") in Tables 1-3, 7 and 9 are differentially regulated in NASH versus simple steatosis. The present invention is also based, at least in part, on the discovery that the markers in Tables 4-6, 8 and 10 are differentially regulated in NASH with advanced liver fibrosis versus NASH without advanced liver fibrosis. In particular, the invention is based on the surprising discovery that the markers described herein are either elevated or depressed in the serum of patients with NASH (Tables 1-3, 7 and 9) or are either elevated or depressed in the serum of patients with NASH with advanced liver fibrosis (Tables 4-6, 8 and 10).

Accordingly, the invention provides methods for predicting prognosing, diagnosing and/or monitoring (e.g., monitoring of disease progression or treatment) and/or predicting or prognosing NASH or advanced liver fibrosis, in a subject. Specifically, the markers of the invention, e.g., one or more markers selected from Tables 1-3, 7 and 9, are diagnostic and/or indicative and/or predicative of NASH. Specifically, the markers of the invention, e.g., one or more markers selected from Tables 4-6, 8 and 10, are diagnostic and/or indicative and/or predicative of advanced liver fibrosis, e.g., F3-4.

Accordingly, the invention provides methods for diagnosing and/or monitoring (e.g., monitoring of disease progression or treatment) and/or predicting and/or prognosing NASH or advanced liver fibrosis, in a subject.

The invention also provides methods for treating or for adjusting treatment regimens based on diagnostic information relating to the levels of one or more of the markers in Tables 1-3, 7 and 9 or 4-6, 8 and 10 in the serum of a subject with NASH or advanced liver fibrosis. The invention further provides panels and kits for practicing the methods of the invention.

The present invention provides new markers and combinations of markers for use in diagnosing and/or predicting and/or prognosing NASH and new markers and combinations of markers for use in diagnosing and/or predicting and/or prognosing advanced liver fibrosis (e.g., NASH with advanced liver fibrosis). These markers are particularly useful in screening for the presence or absence of NASH or advanced liver fibrosis, in assessing whether a subject is afflicted with NASH or advanced liver fibrosis, identifying a composition for treating simple steatosis, NASH or advanced liver fibrosis, assessing the efficacy of a compound for preventing or treating NASH or advanced liver fibrosis, monitoring the progression of NASH or advanced liver fibrosis, monitoring NASH progression, remission and progression towards cirrhosis and hepatocellular cancer, and prognosing whether a subject is predisposed to developing an NASH or advanced liver fibrosis. The markers of the invention may also be applicable to other related diseases and disorders such as hepatocellular cancer, primary biliary cirrhosis, primary sclerosing cholangitis, alcohol induced steatohepatitis, hepatitis, liver fibrosis and transplant rejection in liver transplant patients or fibrosis of other organs.

The markers of the invention include, but are not limited to, one or more NASH markers selected from Tables 1-3, 7 and 9 and one or more fibrosis markers selected from Tables 4-6, 8 and 10. The markers of the invention, or panels of markers of the invention, also include one or more clinical variables that are predictive of NASH or advanced fibrosis, such as, but not limited to gender, BMI, age, albumin, ALT, AST, platelet count, diabetes, hypercholesterolemia, and hypertension.

In one embodiment, the NASH markers used in the methods of the invention include a marker or a panel or set of markers as set forth in Tables 3, 7 and 9. Tables 3, 7 and 9 includes markers for NASH based on average accuracy, sensitivity and specificity. In one embodiment, NASH markers used in the methods of the invention include a marker or panel of markers set forth in Tables 3, 7 and 9, having an average accuracy of about 75%, 77%, 80%, 81%, 82%, 83%, 84%, 85%, 86%, 87%, 88%, 89%, 90%, 91%, 92%, 93%, 94%, 95%, 96%, 97%, 98% 99% or greater. In another embodiment, NASH markers used in the methods of the invention include a marker or panel of markers set forth in Tables 3, 7 and 9, having an average sensitivity of about 75%, 77%, 80%, 81%, 82%, 83%, 84%, 85%, 86%, 87%, 88%, 89%, 90%, 91%, 92%, 93%, 94%, 95%, 96%, 97%, 98% 99% or greater. In another embodiment, NASH markers used in the methods of the invention include a marker or panel of markers set forth in Tables 3, 7 and 9, having an average specificity of about 75%, 77%, 80%, 81%, 82%, 83%, 84%, 85%, 86%, 87%, 88%, 89%, 90%, 91%, 92%, 93%, 94%, 95%, 96%, 97%, 98% 99% or greater.

In another embodiment, the fibrosis markers used in the methods of the invention include a marker or a panel or set of markers as set forth in Tables 6, 8 and 10. Tables 6, 8 and 10 includes markers for advanced liver fibrosis based on average accuracy, sensitivity and specificity. In one embodiment, advanced liver fibrosis markers used in the methods of the invention include a marker or panel of markers set forth in Tables 6, 8 and 10, having an average accuracy of about 75%, 77%, 80%, 81%, 82%, 83%, 84%, 85%, 86%, 87%, 88%, 89%, 90%, 91%, 92%, 93%, 94%, 95%, 96%, 97%, 98% 99% or greater. In another embodiment, advanced liver fibrosis markers used in the methods of the invention include a marker or panel of markers set forth in Tables 6, 8 and 10, having an average sensitivity of about 75%, 77%, 80%, 81%, 82%, 83%, 84%, 85%, 86%, 87%, 88%, 89%, 90%, 91%, 92%, 93%, 94%, 95%, 96%, 97%, 98% 99% or greater. In another embodiment, advanced liver fibrosis markers used in the methods of the invention include a marker or panel of markers set forth in Tables 6, 8 and 10, having an average specificity of about 75%, 77%, 80%, 81%, 82%, 83%, 84%, 85%, 86%, 87%, 88%, 89%, 90%, 91%, 92%, 93%, 94%, 95%, 96%, 97%, 98% 99% or greater.

In some embodiments of the present invention, other biomarkers can be used in connection with the methods of the present invention. As used herein, the term "one or more biomarkers" is intended to mean that one or more (e.g., 1, 2, 3, 4, 5, 6, 7, 8, 9, 10, 11, 12, 13, 14, 15, 16, 17, 18, 19, 20, or more) markers selected from Tables 1-3, 7 and 9 or Tables 4-6, 8 and 10, are assayed, optionally in combination with another NASH or advanced liver fibrosis marker, and, in various embodiments, more than one other biomarker may be assayed, such as one or more biomarkers from Tables 1-3, 7 and 9 or Tables 4-6, 8 and 10 may be assayed.

In some embodiments, the NASH markers, which are predictive of NASH versus simple steatosis, comprise THBS2, COLEC11 and GDF15. In other embodiments, the NASH markers comprise COLEC11, GDF15, albumin and AST. In some embodiments, the NASH markers comprise SELE, COLEC11, BMI, ALT, albumin and platelet count. In other embodiments, the NASH markers comprise SELE, THBS2, COLEC11 and GDF15. In some embodiments, the NASH marker comprises GDF15. In other embodiments, the NASH markers comprise COLEC11, GDF15, age, BMI, ALT, albumin, and platelet count. In some embodiments, the NASH markers comprise COLEC11, GDF15, age and ALT. In other embodiments, the NASH markers comprise COLEC11, GDF15, BMI, ALT, albumin and diabetes. In some embodiments, the NASH markers comprise COLEC11, GDF15, BMI, ALT, albumin and platelet count. In other embodiments, the NASH markers comprise COLEC11, GDF15, BMI and ALT.

In some embodiments, the fibrosis markers, which are predictive of advanced fibrosis versus non-advanced fibrosis, comprise SELE, COLEC11, GDF15 and BMI. In other embodiments, the fibrosis markers comprise SELE and COLEC11. In some embodiments, the fibrosis markers comprise SELE, COLEC11 and GDF15. In other embodiments, the fibrosis markers comprise SELE, THBS2 and COLEC11. In some embodiments, the fibrosis markers comprise THBS2 and COLEC11. In other embodiments, the fibrosis markers comprise SELE, COLEC11, age and BMI. In some embodiments, the fibrosis markers comprise SELE, COLEC11, GDF15, BMI and albumin. In other embodiments, the fibrosis markers comprise SELE, COLEC11, BMI, ALT and albumin. In some embodiments, the fibrosis markers comprise SELE, COLEC11, BMI and ALT. In other embodiments, the fibrosis markers comprise SELE, COLEC11, age, BMI and albumin.

Methods, kits, and panels provided herein include any combination of e.g., 1, 2, 3, 4, 5, 6, 7, 8, 9, 10, 11, 12, 13, 14, 15, 16, 17, 18, 19, 20, or more markers selected from Tables 1-3, 7 and 9 or Tables 4-6, 8 and 10, and in particular panels selected from Tables 3, 7 and 9 or Tables 6, 8 and 10. Any one marker or any combination of more than one marker selected from Tables 1-3, 7 and 9 or Tables 4-6, 8 and 10 can be used in combination with another NASH or fibrosis marker.

The markers of the invention are meant to encompass any measurable characteristic that reflects in a quantitative or qualitative manner the physiological state of an organism, e.g., whether the organism has NASH or whether the organism has advanced liver fibrosis. The physiological state of an organism is inclusive of any disease or non-disease state, e.g., a subject having NASH or advanced liver fibrosis or a subject who is otherwise healthy. Said another way, the markers of the invention include characteristics that can be objectively measured and evaluated as indicators of normal processes, pathogenic processes, or pharmacologic responses to a therapeutic intervention, including, in particular, NASH or advanced liver fibrosis. Examples of markers include, for example, polypeptides, peptides, polypeptide fragments, proteins, polynucleotides, RNA or RNA fragments, microRNA (miRNAs), and other bodily metabolites that are diagnostic and/or indicative and/or predictive of NASH or advanced liver fibrosis, including one or more of the markers of Tables 1-3, 7 and 9 or Tables 4-6, 8 and 10.

The markers of the invention, e.g., one or more markers selected from Tables 1-3, 7 and 9, are diagnostic and/or indicative and/or predictive of NASH in a subject, or NASH versus simple steatosis in a subject.

The markers of the invention, e.g., one or more markers selected from Tables 4-6, 8 and 10, are diagnostic and/or indicative and/or predictive of advanced liver fibrosis in a subject, e.g., advanced liver fibrosis in a subject having NASH.

In one aspect, the present invention relates to using, measuring, detecting, and the like of one or more of the markers in Tables 1-3, 7 and 9 or Tables 4-6, 8 and 10 for diagnosis of the presence of NASH or advanced liver fibrosis in a subject.

In another aspect, the present invention relates to using, measuring, detecting, and the like of one or more of the markers in Tables 1-3, 7 and 9 or Tables 4-6, 8 and 10 alone, or together with one or more additional markers of NASH or advanced liver fibrosis. Other markers that may be used in combination with the one or more markers in Tables 1-3, 7 and 9 or 4-6, 8 and 10 include any measurable clinical variable or characteristic described herein that reflects in a quantitative or qualitative manner the physiological state of an organism, e.g., whether the organism has NASH or advanced liver fibrosis. The physiological state of an organism is inclusive of any disease or non-disease state, e.g., a subject having NASH or advanced liver fibrosis or a subject who is otherwise healthy. The markers of the invention that may be used in combination with the markers in Tables 1-3, 7 and 9 or Tables 4-6, 8 and 10 include characteristics or clinical variables that can be objectively measured and evaluated as indicators of normal processes, pathogenic processes, or pharmacologic responses to a therapeutic intervention, including, in particular, NASH or advanced liver fibrosis. Such combination markers can be clinical variables (e.g., performance status, gender, body mass index (BMI), age, albumin, alanine aminotransferase (ALT), aspartate aminotransferase (AST), platelet counts, diabetes, hypercholesterolemia, and hypertension), imaging-based measures such as ultrasound-based elastography, liver biopsy, or genetic or other molecular determinants. In other embodiments, the present invention also involves the analysis and consideration of any clinical and/or patient-related health data, for example, data obtained from an Electronic Medical Record (e.g., collection of electronic health information about individual patients or populations relating to various types of data, such as, demographics, medical history, medication and allergies, immunization status, laboratory test results, radiology images, vital signs, personal statistics like age and weight, and billing information).

The present invention also contemplates the use of particular combinations of the markers of Tables 1-3, 7 and 9 or Tables 4-6, 8 and 10. In one embodiment, the invention contemplates marker sets with at least two (2) members, which may include any two of the markers in Tables 1-3, 7 and 9 or Tables 4-6, 8 and 10. In another embodiment, the invention contemplates marker sets with at least three (3) members, which may include any three of the markers in Tables 1-3, 7 and 9 or Tables 4-6, 8 and 10. In another embodiment, the invention contemplates marker sets with at least four (4) members, which may include any four of the markers in Tables 1-3, 7 and 9 or Tables 4-6, 8 and 10. In another embodiment, the invention contemplates marker sets with at least five (5) members, which may include any five of the markers in Tables 1-3, 7 and 9 or Tables 4-6, 8 and 10. In another embodiment, the invention contemplates marker sets with at least six (6) members, which may include any six of the markers in Tables 1-3, 7 and 9 or Tables 4-6, 8 and 10. In another embodiment, the invention contemplates marker sets with at least seven (7) members, which may include any seven of the markers in Tables 1-3, 7 and 9 or Tables 4-6, 8 and 10. In another embodiment, the invention contemplates marker sets with at least eight (8) members, which may include any eight of the markers in Tables 1-3, 7 and 9 or Tables 4-6, 8 and 10. In another embodiment, the invention contemplates marker sets with at least nine (9) members, which may include any nine of the markers in Tables 1-3, 7 and 9 or Tables 4-6, 8 and 10. In another embodiment, the invention contemplates marker sets with at least ten (10) members, which may include any ten of the markers in Tables 1-3, 7 and 9 or Tables 4-6, 8 and 10. In another embodiment, the invention contemplates marker sets with at least eleven (11) members, which may include any ten of the markers in Tables 1-3, 7 and 9 or Tables 4-6, 8 and 10. In another embodiment, the invention contemplates marker sets with at least twelve (12) members, which may include any ten of the markers in Tables 1-3, 7 and 9 or Tables 4-6, 8 and 10. In other embodiments, the invention contemplates a marker set comprising at least 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90, 100, 110, or 120 of the markers listed in Tables 1-3, 7 and 9 or Tables 4-6, 8 and 10.

In one embodiment, markers used in the methods of the invention which are diagnostic and/or indicative and/or predictive of NASH comprise one or more of THBS2, BCL2A1, YES1, COLEC11, IGFBP7, N6AMT1, GDF15, C7, ITGA1 ITGB1, SELE, ACY1, TGFB1, TIMP1, DCN, LTBP4, NAGK, IGFBP5, IL19, APOM, MMP7, ANGPT2, AKT2, and POR. In one embodiment, one or more of THBS2, YES1, COLEC11, IGFBP7, GDF15, C7, ITGA1 ITGB1, SELE, ACY1, TGFB1, TIMP1, DCN, LTBP4, NAGK, IL19, MMP7, ANGPT2, and POR are increased in a subject having NASH. In one embodiment, one or more of BCL2A1, N6AMT1, IGFBP5, AKT2 and APOM are decreased in a subject having NASH.

In one embodiment, markers used in the methods of the invention which are diagnostic and/or indicative and/or predictive of advanced liver fibrosis comprise one or more of GDF15, SELE, IGFBP7, IGFBP5, C7, COLEC11, DCN, CCL21, IL1R2, THBS2, NAGK, LTBP4, TIMP1, CD163, PRSS22, A2M, MMP7, CHRDL1, ROBO2, TIE1, LAMA1 LAMB1 LAMC1, and PRL. In one embodiment, one or more of GDF15, SELE, IGFBP7, THBS2, C7, COLEC11, DCN, NAGK, CCL21, IL1R2, LTBP4, TIMP1, CD163, PRSS22, A2M, MMP7, CHRDL1, ROBO2, TIE1, LAMA1 LAMB1 LAMC1 are increased in a subject having advanced liver fibrosis. In one embodiment, one or both of IGFBP5 and PRL are decreased in a subject having advanced liver fibrosis.

In certain embodiments, the markers in Tables 1-3, 7 and 9 or Tables 4-6, 8 and 10 may be used in combination with at least one other marker, or more preferably, with at least two other markers, or still more preferably, with at least three other markers, or even more preferably with at least four other markers. Still further, the markers in Tables 1-3, 7 and 9 or Tables 4-6, 8 and 10 in certain embodiments, may be used in combination with at least five other markers, or at least six other markers, or at least seven other markers, or at least eight other markers, or at least nine other markers, or at least ten other markers, or at least eleven other markers, or at least twelve other markers, or at least thirteen other markers, or at least fourteen other markers, or at least fifteen other markers, or at least sixteen other markers, or at least seventeen other markers, or at least eighteen other markers, or at least nineteen other markers, or at least twenty other markers. Further, the markers in Tables 1-3, 7 and 9 or Tables 4-6, 8 and 10 may be used in combination with a multitude of other markers, including, for example, with between about 20-50 other markers, or between 50-100, or between 100-500, or between 500-1000, or between 1000-10,000 or markers or more.

In certain embodiments, the level of the marker, e.g., a NASH marker, is increased when compared to the predetermined threshold value in the subject. In some embodiments, the marker, e.g., a NASH marker, is selected from the group consisting of THBS2, YES1, COLEC11, IGFBP7, GDF15, C7, ITGA1 ITGB1, SELE, ACY1, TGFB1, TIMP1, DCN, LTBP4, NAGK, IL19, MMP7, ANGPT2, and POR. In other embodiments, the marker, e.g., a NASH marker, comprises one or more markers selected from Table 1, wherein the one or more markers have an FC ratio greater than 1, or a Log FC value greater than 0.

In other embodiments, the level of the marker, e.g., a NASH marker, is decreased when compared to the predetermined threshold value in the subject. In some embodiments, the marker, e.g., a NASH marker, is selected from the group consisting of BCL2A1, N6AMT1, IGFBP5, AKT2 and APOM. In other embodiments, the marker, e.g., a NASH marker, comprises one or more markers selected from Table 1, wherein the one or more markers have an FC ratio greater than 1, or a Log FC value greater than 0.

In certain embodiments, the level of the marker, e.g., a fibrosis marker, is increased when compared to the predetermined threshold value in the subject. In some embodiments, the marker, e.g., a fibrosis marker, is selected from the group consisting of GDF15, SELE, IGFBP7, THBS2, C7, COLEC11, DCN, NAGK, CCL21, IL1R2, LTBP4, TIMP1, CD163, PRSS22, A2M, MMP7, CHRDL1, ROBO2, TIE1, LAMA1 LAMB1 LAMC1. In other embodiments, the marker, e.g., a fibrosis marker, comprises one or more markers selected from Table 4, wherein the one or more markers have an FC ratio greater than 1, or a Log FC value greater than 0.

In other embodiments, the level of the marker, e.g., a fibrosis marker, is decreased when compared to the predetermined threshold value in the subject. In some embodiments, the marker, e.g., a fibrosis marker, is selected from the group consisting of IGFBP5 and PRL. In other embodiments, the marker, e.g., a fibrosis marker, comprises one or more markers selected from Table 4, wherein the one or more markers have an FC ratio greater than 1, or a Log FC value greater than 0.

In certain embodiments, the marker comprises one or more markers with an increased level when compared to the predetermined threshold value in the subject, and/or one or more markers with a decreased level when compared to the predetermined threshold value in the subject.

In a particular embodiment, a NASH or advanced liver fibrosis profile or diagnostic signature is determined on the basis of the combination of the markers in Tables 1-3, 7 and 9 or Tables 4-6, 8 and 10 together with one or more additional markers of NASH or advanced liver fibrosis. Other markers that may be used in combination with the markers in Tables 1-3, 7 and 9 or Tables 4-6, 8 and 10 include any measurable characteristic or clinical variable that reflects in a quantitative or qualitative manner the physiological state of an organism, e.g., whether the organism has NASH or advanced liver fibrosis. The physiological state of an organism is inclusive of any disease or non-disease state, e.g., a subject having NASH or advanced liver fibrosis or a subject who is otherwise healthy. Said another way, the markers of the invention that may be used in combination with the markers in Tables 1-3, 7 and 9 or Tables 4-6, 8 and 10 include clinical variables or characteristics that can be objectively measured and evaluated as indicators of normal processes, pathogenic processes, or pharmacologic responses to a therapeutic intervention, including, in particular, NASH or advanced liver fibrosis. Such combination markers can be clinical variables (e.g., performance status, gender, body mass index (BMI), age, albumin, alanine aminotransferase (ALT), aspartate aminotransferase (AST), platelet counts, diabetes, hypercholesterolemia, and hypertension), imaging-based measures, liver biopsy, or genetic or other molecular determinants. In other embodiments, the present invention also involves the analysis and consideration of any clinical and/or patient-related health data, for example, data obtained from an Electronic Medical Record (e.g., collection of electronic health information about individual patients or populations relating to various types of data, such as, demographics, medical history, medication and allergies, immunization status, laboratory test results, biopsy results, vital signs, personal statistics like age and weight, and billing information). Any one or more protein marker of the invention may be combined with any one or more clinical variable. For example, panels of markers used for the diagnosis of NASH versus simple steatosis include those listed in Tables 7 and 9. Panels of markers used for the diagnosis of advanced fibrosis versus non-advanced fibrosis include those listed in Tables 8 and 10.

In certain embodiments, the diagnostic signature is obtained by (1) detecting the level of at least one of the markers in Tables 1-3, 7 and 9 or Tables 4-6, 8 and 10 in a biological sample, (2) comparing the level of the at least one marker in Tables 1-3, 7 and 9 or Tables 4-6, 8 and 10 to the levels of the same marker from a control sample, and (3) determining if the at least one marker in Tables 1-3, 7 and 9 or Tables 4-6, 8 and 10 is above or below a certain threshold level. If the at least one marker in Tables 1-3, 7 and 9 or Tables 4-6, 8 and 10 is above or below the threshold level, then the diagnostic signature is indicative of NASH or advanced liver fibrosis in the biological sample. In certain embodiments, the diagnostic signature can be determined based on an algorithm or computer program that predicts whether the biological sample is from a subject with NASH or advanced liver fibrosis based on the level of the at least one marker in Tables 1-3, 7 and 9 or Tables 4-6, 8 and 10.

In certain other embodiments, the diagnostic signature is obtained by (1) detecting the level of at least two markers in Tables 1-3, 7 and 9 or Tables 4-6, 8 and 10 in a biological sample, (2) comparing the levels of the at least two markers in Tables 1-3, 7 and 9 or Tables 4-6, 8 and 10 to the levels of the same markers from a control sample, and (3) determining if the at least two markers in Tables 1-3, 7 and 9 or Tables 4-6, 8 and 10 detected in the biological sample are above or below a certain threshold level. If the at least two markers in Tables 1-3, 7 and 9 or Tables 4-6, 8 and 10 are above or below the threshold level, then the diagnostic signature is indicative of NASH or advanced liver fibrosis in the biological sample. In certain embodiments, the diagnostic signature can be determined based on an algorithm or computer program that predicts whether the biological sample is from a subject with NASH or advanced liver fibrosis based on the levels of the at least two markers in Tables 1-3, 7 and 9 or Tables 4-6, 8 and 10.

In certain other embodiments, the diagnostic signature is obtained by (1) detecting the level of at least three markers in Tables 1-3, 7 and 9 or Tables 4-6, 8 and 10 in a biological sample, (2) comparing the levels of the at least three markers in Tables 1-3, 7 and 9 or Tables 4-6, 8 and 10 to the levels of the same markers from a control sample, and (3) determining if the at least three markers in Tables 1-3, 7 and 9 or Tables 4-6, 8 and 10 detected in the biological sample are above or below a certain threshold level. If the at least three markers in Tables 1-3, 7 and 9 or Tables 4-6, 8 and 10 are above or below the threshold level, then the diagnostic signature is indicative of NASH or advanced liver fibrosis in the biological sample. In certain embodiments, the diagnostic signature can be determined based on an algorithm or computer program that predicts whether the biological sample is from a subject with NASH or advanced liver fibrosis based on the levels of the at least three markers in Tables 1-3, 7 and 9 or Tables 4-6, 8 and 10.

In certain other embodiments, the diagnostic signature is obtained by (1) detecting the level of at least four markers in Tables 1-3, 7 and 9 or Tables 4-6, 8 and 10 in a biological sample, (2) comparing the levels of the at least four markers in Tables 1-3, 7 and 9 or Tables 4-6, 8 and 10 to the levels of the same markers from a control sample, and (3) determining if the at least four markers in Tables 1-3, 7 and 9 or Tables 4-6, 8 and 10 detected in the biological sample are above or below a certain threshold level. If the at least four markers in Tables 1-3, 7 and 9 or Tables 4-6, 8 and 10 are above or below the threshold level, then the diagnostic signature is indicative of NASH or advanced liver fibrosis in the biological sample. In certain embodiments, the diagnostic signature can be determined based on an algorithm or computer program that predicts whether the biological sample is from a subject with NASH or advanced liver fibrosis based on the levels of the at least four markers in Tables 1-3, 7 and 9 or Tables 4-6, 8 and 10.

In certain other embodiments, the diagnostic signature is obtained by (1) detecting the level of at least five markers in Tables 1-3, 7 and 9 or Tables 4-6, 8 and 10 in a biological sample, (2) comparing the levels of the at least five markers in Tables 1-3, 7 and 9 or Tables 4-6, 8 and 10 to the levels of the same markers from a control sample, and (3) determining if the at least five markers in Tables 1-3, 7 and 9 or Tables 4-6, 8 and 10 detected in the biological sample are above or below a certain threshold level. If the at least five markers in Tables 1-3, 7 and 9 or Tables 4-6, 8 and 10 are above or below the threshold level, then the diagnostic signature is indicative of NASH or advanced liver fibrosis in the biological sample. In certain embodiments, the diagnostic signature can be determined based on an algorithm or computer program that predicts whether the biological sample is from a subject with NASH or advanced liver fibrosis based on the levels of the at least five markers in Tables 1-3, 7 and 9 or Tables 4-6, 8 and 10.

In certain other embodiments, the diagnostic signature is obtained by (1) detecting the level of at least six markers in Tables 1-3, 7 and 9 or Tables 4-6, 8 and 10 in a biological sample, (2) comparing the levels of the at least six markers in Tables 1-3, 7 and 9 or Tables 4-6, 8 and 10 to the levels of the same markers from a control sample, and (3) determining if the at least six markers in Tables 1-3, 7 and 9 or Tables 4-6, 8 and 10 detected in the biological sample are above or below a certain threshold level. If the at least six markers in Tables 1-3, 7 and 9 or Tables 4-6, 8 and 10 are above or below the threshold level, then the diagnostic signature is indicative of NASH or advanced liver fibrosis in the biological sample. In certain embodiments, the diagnostic signature can be determined based on an algorithm or computer program that predicts whether the biological sample is from a subject with NASH or advanced liver fibrosis based on the levels of the at least six markers in Tables 1-3, 7 and 9 or Tables 4-6, 8 and 10.

In certain other embodiments, the diagnostic signature is obtained by (1) detecting the level of at least seven markers in Tables 1-3, 7 and 9 or Tables 4-6, 8 and 10 in a biological sample, (2) comparing the levels of the at least seven markers in Tables 1-3, 7 and 9 or Tables 4-6, 8 and 10 to the levels of the same markers from a control sample, and (3) determining if the at least seven markers in Tables 1-3, 7 and 9 or Tables 4-6, 8 and 10 detected in the biological sample are above or below a certain threshold level. If the at least seven markers in Tables 1-3, 7 and 9 or Tables 4-6, 8 and 10 are above or below the threshold level, then the diagnostic signature is indicative of NASH or advanced liver fibrosis in the biological sample. In certain embodiments, the diagnostic signature can be determined based on an algorithm or computer program that predicts whether the biological sample is from a subject with NASH or advanced liver fibrosis based on the levels of the at least seven markers in Tables 1-3, 7 and 9 or Tables 4-6, 8 and 10.

In certain other embodiments, the diagnostic signature is obtained by (1) detecting the level of at least eight markers in Tables 1-3, 7 and 9 or Tables 4-6, 8 and 10 in a biological sample, (2) comparing the levels of the at least eight markers in Tables 1-3, 7 and 9 or Tables 4-6, 8 and 10 to the levels of the same markers from a control sample, and (3) determining if the at least eight markers in Tables 1-3, 7 and 9 or Tables 4-6, 8 and 10 detected in the biological sample are above or below a certain threshold level. If the at least eight markers in Tables 1-3, 7 and 9 or Tables 4-6, 8 and 10 are above or below the threshold level, then the diagnostic signature is indicative of NASH or advanced liver fibrosis in the biological sample. In certain embodiments, the diagnostic signature can be determined based on an algorithm or computer program that predicts whether the biological sample is from a subject with NASH or advanced liver fibrosis based on the levels of the at least eight markers in Tables 1-3, 7 and 9 or Tables 4-6, 8 and 10.

In certain other embodiments, the diagnostic signature is obtained by (1) detecting the level of at least nine markers in Tables 1-3, 7 and 9 or Tables 4-6, 8 and 10 in a biological sample, (2) comparing the levels of the at least nine markers in Tables 1-3, 7 and 9 or Tables 4-6, 8 and 10 to the levels of the same markers from a control sample, and (3) determining if the at least nine markers in Tables 1-3, 7 and 9 or Tables 4-6, 8 and 10 detected in the biological sample are above or below a certain threshold level. If the at least nine markers in Tables 1-3, 7 and 9 or Tables 4-6, 8 and 10 are above or below the threshold level, then the diagnostic signature is indicative of NASH or advanced liver fibrosis in the biological sample. In certain embodiments, the diagnostic signature can be determined based on an algorithm or computer program that predicts whether the biological sample is from a subject with NASH or advanced liver fibrosis based on the levels of the at least nine markers in Tables 1-3, 7 and 9 or Tables 4-6, 8 and 10.

In certain other embodiments, the diagnostic signature is obtained by (1) detecting the level of at least ten markers in Tables 1-3, 7 and 9 or Tables 4-6, 8 and 10 in a biological sample, (2) comparing the levels of the at least ten markers in Tables 1-3, 7 and 9 or Tables 4-6, 8 and 10 to the levels of the same markers from a control sample, and (3) determining if the at least ten markers in Tables 1-3, 7 and 9 or Tables 4-6, 8 and 10 detected in the biological sample are above or below a certain threshold level. If the at least ten markers in Tables 1-3, 7 and 9 or Tables 4-6, 8 and 10 are above or below the threshold level, then the diagnostic signature is indicative of NASH or advanced liver fibrosis in the biological sample. In certain embodiments, the diagnostic signature can be determined based on an algorithm or computer program that predicts whether the biological sample is from a subject with NASH or advanced liver fibrosis based on the levels of the at least ten markers in Tables 1-3, 7 and 9 or Tables 4-6, 8 and 10.

In certain embodiments, the level of the marker, e.g., a NASH or advanced liver fibrosis marker, is increased when compared to the predetermined threshold value in the subject. In other embodiments, the level of the marker, e.g., a NASH or advanced liver fibrosis marker, is decreased when compared to the predetermined threshold value in the subject.

In accordance with various embodiments, algorithms may be employed to predict whether or not a biological sample is likely to be diseased, e.g., have NASH or advanced liver fibrosis. The skilled artisan will appreciate that an algorithm can be any computation, formula, statistical survey, nomogram, look-up Tables, decision tree method, or computer program which processes a set of input variables (e.g., number of markers (n) which have been detected at a level exceeding some threshold level, or number of markers (n) which have been detected at a level below some threshold level) through a number of well-defined successive steps to eventually produce a score or "output," e.g., a diagnosis of NASH or advanced liver fibrosis. Any suitable algorithm—whether computer-based or manual-based (e.g., look-up Tables)—is contemplated herein.

In certain embodiments, an algorithm of the invention is used to predict whether a biological sample is from a subject that has NASH or advanced liver fibrosis by producing a score on the basis of the detected level of at least 1, 2, 3, 4, 5, 6, 7, 8, 9, 10, 11, 12, 13, 14, 15, 20, 30, 40, 50, 60, 70, or 80 of the markers in Tables 1-3, 7 and 9 or Tables 4-6, 8 and 10 in the sample, wherein if the score is above or below a certain threshold score, then the biological sample is from a subject that has NASH or advanced liver fibrosis.

Moreover, a NASH or advanced liver fibrosis profile or signature may be obtained by detecting at least one of the markers in Tables 1-3, 7 and 9 or Tables 4-6, 8 and 10 in combination with at least one other marker, or more preferably, with at least two other markers, or still more preferably, with at least three other markers, or even more preferably with at least four other markers. Still further, the markers in Tables 1-3, 7 and 9 or Tables 4-6, 8 and 10 in certain embodiments, may be used in combination with at least five other markers, or at least six other markers, or at least seven other markers, or at least eight other markers, or at least nine other markers, or at least ten other markers, or at least eleven other markers, or at least twelve other markers, or at least thirteen other markers, or at least fourteen other markers, or at least fifteen other markers, or at least sixteen other markers, or at least seventeen other markers, or at least eighteen other markers, or at least nineteen other markers, or at least twenty other markers. Further still, the markers in Tables 1-3, 7 and 9 or Tables 4-6, 8 and 10 may be used in combination with a multitude of other markers, including, for example, with between about 20-50 other markers, or between 50-100, or between 100-500, or between 500-1000, or between 1000-10,000 or markers or more.

In certain embodiments, the markers of the invention can include variant sequences. More particularly, certain binding agents/reagents used for detecting certain of the markers of the invention can bind and/or identify variants of these certain markers of the invention. As used herein, the term "variant" encompasses nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 80%, 85%, 90%, 95%, 96%, 97%, 98% or 99% identity to a sequence disclosed herein. The percentage identity is determined by aligning the two sequences to be compared as described below, determining the number of identical residues in the aligned portion, dividing that number by the total number of residues in the inventive (queried) sequence, and multiplying the result by 100.

In addition to exhibiting the recited level of sequence identity, variants of the disclosed protein markers are preferably themselves expressed in subjects with NASH or advanced liver fibrosis at levels that are higher or lower than the levels of expression in normal, healthy individuals.

Variant sequences generally differ from the specifically identified sequence only by conservative substitutions, deletions or modifications. As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptide and polynucleotide sequences may be aligned, and percentages of identical amino acids or nucleotides in a specified region may be determined against another polypeptide or polynucleotide sequence, using computer algorithms that are publicly available. The percentage identity of a polynucleotide or polypeptide sequence is determined by aligning polynucleotide and polypeptide sequences using appropriate algorithms, such as BLASTN or BLASTP, respectively, set to default parameters; identifying the number of identical nucleic or amino acids over the aligned portions; dividing the number of identical nucleic or amino acids by the total number of nucleic or amino acids of the polynucleotide or polypeptide of the present invention; and then multiplying by 100 to determine the percentage identity.

Two exemplary algorithms for aligning and identifying the identity of polynucleotide sequences are the BLASTN and FASTA algorithms. The alignment and identity of polypeptide sequences may be examined using the BLASTP algorithm. BLASTX and FASTX algorithms compare nucleotide query sequences translated in all reading frames against polypeptide sequences. The FASTA and FASTX algorithms are described in Pearson and Lipman, Proc. Natl. Acad. Sci. USA 85:2444-2448, 1988; and in Pearson, Methods in Enzymol. 183:63-98, 1990. The FASTA software package is available from the University of Virginia, Charlottesville, Va. 22906-9025. The FASTA algorithm, set to the default parameters described in the documentation and distributed with the algorithm, may be used in the determination of polynucleotide variants. The readme files for FASTA and FASTX Version 2.0x that are distributed with the algorithms describe the use of the algorithms and describe the default parameters.

The BLASTN software is available on the NCBI anonymous FTP server and is available from the National Center for Biotechnology Information (NCBI), National Library of Medicine, Building 38A, Room 8N805, Bethesda, Md. 20894. The BLASTN algorithm Version 2.0.6 [Sep. 10, 1998] and Version 2.0.11 [Jan. 20, 2000] set to the default parameters described in the documentation and distributed with the algorithm, is preferred for use in the determination of variants according to the present invention. The use of the BLAST family of algorithms, including BLASTN, is described at NCBI's website and in the publication of Altschul, et al., "Gapped BLAST and PSI-BLAST: a new generation of protein database search programs," Nucleic Acids Res. 25:3389-3402, 1997.

In an alternative embodiment, variant polypeptides are encoded by polynucleotide sequences that hybridize to a disclosed polynucleotide under stringent conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone. An example of "stringent conditions" is prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The invention provides for the use of various combinations and sub-combinations of markers. It is understood that any single marker or combination of the markers provided herein can be used in the invention unless clearly indicated otherwise.

D. Samples

The present invention may be practiced with any suitable biological sample that potentially contains, expresses, includes, a detectable disease biomarker. For example, the biological sample may be obtained from sources that include whole blood, serum, plasma, urine, tears, saliva, diseased and/or healthy organ tissue, for example, biopsy of liver. Preferably, the biological sample is serum, plasma or urine.

Any commercial device or system for isolating and/or obtaining blood or other biological products, and/or for processing said materials prior to conducting a detection reaction is contemplated.

In certain embodiments, the present invention relates to detecting biomarker nucleic acid molecules (e.g., mRNA encoding the protein markers of Tables 1-3 or 4-6). In such embodiments, RNA can be extracted from a biological sample before analysis. Methods of RNA extraction are well known in the art (see, for example, J. Sambrook et al., "Molecular Cloning: A Laboratory Manual", 1989, $2^{nd}$ Ed., Cold Spring Harbour Laboratory Press: New York). Most methods of RNA isolation from bodily fluids or tissues are based on the disruption of the tissue in the presence of protein denaturants to quickly and effectively inactivate RNases. Generally, RNA isolation reagents comprise, among other components, guanidinium thiocyanate and/or beta-mercaptoethanol, which are known to act as RNase inhibitors. Isolated total RNA is then further purified from the protein contaminants and concentrated by selective ethanol precipitations, phenol/chloroform extractions followed by isopropanol precipitation (see, for example, P. Chomczynski and N. Sacchi, Anal. Biochem., 1987, 162: 156-159) or cesium chloride, lithium chloride or cesium trifluoroacetate gradient centrifugations.

Numerous different and versatile kits can be used to extract RNA (i.e., total RNA or mRNA) from bodily fluids or tissues and are commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Gaithersburg, Md.), and Giagen, Inc. (Valencia, Calif.). User Guides that describe in great detail the protocol to be followed are usually included in all these kits. Sensitivity, processing time and cost may be different from one kit to another. One of ordinary skill in the art can easily select the kit(s) most appropriate for a particular situation.

In certain embodiments, after extraction, mRNA is amplified, and transcribed into cDNA, which can then serve as template for multiple rounds of transcription by the appropriate RNA polymerase. Amplification methods are well known in the art (see, for example, A. R. Kimmel and S. L. Berger, Methods Enzymol. 1987, 152: 307-316; J. Sambrook et al., "Molecular Cloning: A Laboratory Manual", 1989, 2.sup.nd Ed., Cold Spring Harbour Laboratory Press: New York; "Short Protocols in Molecular Biology", F. M. Ausubel (Ed.), 2002, 5.sup.th Ed., John Wiley & Sons; U.S. Pat. Nos. 4,683,195; 4,683,202 and 4,800,159). Reverse transcription reactions may be carried out using non-specific primers, such as an anchored oligo-dT primer, or random sequence primers, or using a target-specific primer complementary to the RNA for each genetic probe being monitored, or using thermostable DNA polymerases (such as avian myeloblastosis virus reverse transcriptase or Moloney murine leukemia virus reverse transcriptase).

In certain embodiments, the RNA isolated from the tissue, blood or urine sample (for example, after amplification and/or conversion to cDNA or cRNA) is labeled with a detectable agent before being analyzed. The role of a detectable agent is to facilitate detection of RNA or to allow visualization of hybridized nucleic acid fragments (e.g., nucleic acid fragments hybridized to genetic probes in an array-based assay). Preferably, the detectable agent is selected such that it generates a signal which can be measured and whose intensity is related to the amount of labeled nucleic acids present in the sample being analyzed. In array-based analysis methods, the detectable agent is also preferably selected such that it generates a localized signal, thereby allowing spatial resolution of the signal from each spot on the array.

Methods for labeling nucleic acid molecules are well-known in the art. For a review of labeling protocols, label detection techniques and recent developments in the field, see, for example, L. J. Kricka, Ann. Clin. Biochem. 2002, 39: 114-129; R. P. van Gijlswijk et al., Expert Rev. Mol. Diagn. 2001, 1: 81-91; and S. Joos et al., J. Biotechnol. 1994, 35: 135-153. Standard nucleic acid labeling methods include: incorporation of radioactive agents, direct attachment of fluorescent dyes (see, for example, L. M. Smith et al., Nucl. Acids Res. 1985, 13: 2399-2412) or of enzymes (see, for example, B. A. Connoly and P. Rider, Nucl. Acids. Res. 1985, 13: 4485-4502); chemical modifications of nucleic acid fragments making them detectable immunochemically or by other affinity reactions (see, for example, T. R. Broker et al., Nucl. Acids Res. 1978, 5: 363-384; E. A. Bayer et al., Methods of Biochem. Analysis, 1980, 26: 1-45; R. Langer et al., Proc. Natl. Acad. Sci. USA, 1981, 78: 6633-6637; R. W. Richardson et al., Nucl. Acids Res. 1983, 11: 6167-6184; D. J. Brigati et al., Virol. 1983, 126: 32-50; P. Tchen et al., Proc. Natl Acad. Sci. USA, 1984, 81: 3466-3470; J. E. Landegent et al., Exp. Cell Res. 1984, 15: 61-72; and A. H. Hopman et al., Exp. Cell Res. 1987, 169: 357-368); and enzyme-mediated labeling methods, such as random priming, nick translation, PCR and tailing with terminal transferase (for a review on enzymatic labeling, see, for example, J. Temsamani and S. Agrawal, Mol. Biotechnol. 1996, 5: 223-232).

Any of a wide variety of detectable agents can be used in the practice of the present invention. Suitable detectable agents include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

However, in some embodiments, the expression levels are determined by detecting the expression of a gene product (e.g., protein) thereby eliminating the need to obtain a genetic sample (e.g., RNA) from the tissue sample.

In still other embodiments, the present invention relates to preparing a prediction model for NASH or advanced liver fibrosis by preparing a model for NASH or advanced liver fibrosis based on measuring the biomarkers of the invention in known control samples. More particularly, the present invention relates in some embodiments to preparing a predictive model by evaluating the biomarkers of the invention, i.e., the markers of Tables 1-3, 7 and 9 or Tables 4-6, 8 and 10.

The invention further relates to the preparation of a model for NASH or advanced liver fibrosis or NASH or advanced liver fibrosis relapse by evaluating the biomarkers of the invention in known samples of NASH or advanced liver fibrosis. More particularly, the present invention relates to a NASH or advanced liver fibrosis model for diagnosing and/or monitoring and/or prognosing NASH or advanced liver fibrosis or NASH or advanced liver fibrosis relapse using the biomarkers of the invention, i.e., the markers of Tables 1-3, 7 and 9 or Tables 4-6, 8 and 10.

E. Detection and/or Measurement of Biomarkers

The present invention contemplates any suitable means, techniques, and/or procedures for detecting and/or measuring the biomarkers of the invention. The skilled artisan will appreciate that the methodologies employed to measure the biomarkers of the invention will depend at least on the type of biomarker being detected or measured and the source of the biological sample.

1. Detection of Protein Markers

The present invention contemplates any suitable method for detecting polypeptide biomarkers of the invention, i.e., the proteins of Tables 1-10. In certain embodiments, the detection method is an immunodetection method involving an antibody that specifically binds to one or more of the proteins of Tables 1-10. The steps of various useful immunodetection methods have been described in the scientific literature, such as, e.g., Nakamura et al. (1987), which is incorporated herein by reference.

In general, the immunobinding methods include obtaining a sample suspected of containing a biomarker protein, peptide or antibody, and contacting the sample with an antibody or protein or peptide in accordance with the present invention, as the case may be, under conditions effective to allow the formation of immunocomplexes.

The immunobinding methods include methods for detecting or quantifying the amount of a reactive component in a sample, which methods require the detection or quantitation of any immune complexes formed during the binding process.

In terms of biomarker detection, the biological sample analyzed may be any sample that is suspected of containing one or more proteins of Tables 1-10. The biological sample may be, for example, a serum sample, a plasma sample, a saliva sample, and/or a urine sample.

Contacting the chosen biological sample with the protein under conditions effective and for a period of time sufficient to allow the formation of immune complexes (primary immune complexes). Generally, complex formation is a matter of simply adding the composition to the biological sample and incubating the mixture for a period of time long enough for the antibodies to form immune complexes with, i.e., to bind to, any antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The protein employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

The immunodetection methods of the present invention have evident utility in the diagnosis of conditions such as NASH or advanced liver fibrosis. Here, a biological or clinical sample suspected of containing either the encoded protein or peptide or corresponding antibody is used. However, these embodiments also have applications to non-clinical samples, such as in the tittering of antigen or antibody samples, in the selection of hybridomas, and the like.

The present invention, in particular, contemplates the use of ELISAs as a type of immunodetection assay. It is contemplated that the biomarker proteins or peptides of the invention will find utility as immunogens in ELISA assays in diagnosis and prognostic monitoring of NASH or advanced liver fibrosis. Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and Western blotting, dot blotting, FACS analyses, immune PCR, aptamers, mass spectrometry and the like also may be used.

In one exemplary ELISA, antibodies binding to the biomarkers of the invention are immobilized onto a selected surface exhibiting protein affinity, such as a well in a polystyrene microtiter plate. Then, a test composition suspected of containing the NASH or advanced liver fibrosis marker antigen, such as a clinical sample, is added to the wells. After binding and washing to remove non-specifically bound immunecomplexes, the bound antigen may be detected. Detection is generally achieved by the addition of a second antibody specific for the target protein, that is linked to a detectable label. This type of ELISA is a simple "sandwich ELISA." Detection also may be achieved by the addition of a second antibody, followed by the addition of a third antibody that has binding affinity for the second antibody, with the third antibody being linked to a detectable label.

In another exemplary ELISA, the samples suspected of containing the NASH or advanced liver fibrosis marker antigen are immobilized onto the well surface and then contacted with the anti-biomarker antibodies of the invention. After binding and washing to remove non-specifically bound immunecomplexes, the bound antigen is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Irrespective of the format employed, ELISAs have certain features in common, such as coating, incubating or binding, washing to remove non-specifically bound species, and detecting the bound immunecomplexes. These are described as follows.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control and/or clinical or biological sample to be tested under conditions effective to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand.

The phrase "under conditions effective to allow immunecomplex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 h, at temperatures preferably on the order of 25 to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immunecomplex with a urease, glucose oxidase, alkaline phosphatase or hydrogen peroxidase-conjugated antibody for a period of time and under conditions that favor the development of further immunecomplex formation (e.g., incubation for 2 h at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple. Quantitation is then achieved by measuring the degree of color generation, e.g., using a visible spectra spectrophotometer.

The protein biomarkers of the invention can also be measured, quantitated, detected, and otherwise analyzed using protein mass spectrometry methods and instrumentation. Protein mass spectrometry refers to the application of mass spectrometry to the study of proteins. Although not intending to be limiting, two approaches are typically used for characterizing proteins using mass spectrometry. In the first, intact proteins are ionized and then introduced to a mass analyzer. This approach is referred to as "top-down" strategy of protein analysis. The two primary methods for ionization of whole proteins are electrospray ionization (ESI) and matrix-assisted laser desorption/ionization (MALDI). In the second approach, proteins are enzymatically digested into smaller peptides using a protease such as trypsin. Subsequently these peptides are introduced into the mass spectrometer and identified by peptide mass fingerprinting or tandem mass spectrometry. Hence, this latter approach (also called "bottom-up" proteomics) uses identification at the peptide level to infer the existence of proteins.

Whole protein mass analysis of the biomarkers of the invention can be conducted using time-of-flight (TOF) MS, or Fourier transform ion cyclotron resonance (FT-ICR). These two types of instruments are useful because of their wide mass range, and in the case of FT-ICR, its high mass accuracy. The most widely used instruments for peptide mass analysis are the MALDI time-of-flight instruments as they permit the acquisition of peptide mass fingerprints (PMFs) at high pace (1 PMF can be analyzed in approx. 10 sec). Multiple stage quadrupole-time-of-flight and the quadrupole ion trap also find use in this application.

The protein biomarkers of the invention can also be measured in complex mixtures of proteins and molecules that co-exist in a biological medium or sample, however, fractionation of the sample may be required and is contemplated herein. It will be appreciated that ionization of complex mixtures of proteins can result in situation where the more abundant proteins have a tendency to "drown" or suppress signals from less abundant proteins in the same sample. In addition, the mass spectrum from a complex mixture can be difficult to interpret because of the overwhelming number of mixture components. Fractionation can be used to first separate any complex mixture of proteins prior to mass spectrometry analysis. Two methods are widely used to fractionate proteins, or their peptide products from an enzymatic digestion. The first method fractionates whole proteins and is called two-dimensional gel electrophoresis. The second method, high performance liquid chromatography (LC or HPLC) is used to fractionate peptides after enzymatic digestion. In some situations, it may be desirable to combine both of these techniques. Any other suitable methods known in the art for fractionating protein mixtures are also contemplated herein.

Gel spots identified on a 2D Gel are usually attributable to one protein. If the identity of the protein is desired, usually the method of in-gel digestion is applied, where the protein spot of interest is excised, and digested proteolytically. The peptide masses resulting from the digestion can be determined by mass spectrometry using peptide mass fingerprinting. If this information does not allow unequivocal identification of the protein, its peptides can be subject to tandem mass spectrometry for de novo sequencing.

Characterization of protein mixtures using HPLC/MS may also be referred to in the art as "shotgun proteomics" and MuDPIT (Multi-Dimensional Protein Identification Technology). A peptide mixture that results from digestion of a protein mixture is fractionated by one or two steps of liquid chromatography (LC). The eluent from the chromatography stage can be either directly introduced to the mass spectrometer through electrospray ionization, or laid down on a series of small spots for later mass analysis using MALDI.

The protein biomarkers of the present invention can be identified using MS using a variety of techniques, all of which are contemplated herein. Peptide mass fingerprinting uses the masses of proteolytic peptides as input to a search of a database of predicted masses that would arise from digestion of a list of known proteins. If a protein sequence in the reference list gives rise to a significant number of predicted masses that match the experimental values, there is some evidence that this protein was present in the original sample. It will be further appreciated that the development of methods and instrumentation for automated, data-dependent electrospray ionization (ESI) tandem mass spectrometry (MS/MS) in conjunction with microcapillary liquid chromatography (LC) and database searching has significantly increased the sensitivity and speed of the identification of gel-separated proteins. Microcapillary LC-MS/MS has been used successfully for the large-scale identification of individual proteins directly from mixtures without gel electrophoretic separation (Link et al., 1999; Opitek et al., 1997).

Several recent methods allow for the quantitation of proteins by mass spectrometry. For example, stable (e.g., non-radioactive) heavier isotopes of carbon ($^{13}C$) or nitrogen ($^{15}N$) can be incorporated into one sample while the other one can be labeled with corresponding light isotopes (e.g. $^{12}C$ and $^{14}N$). The two samples are mixed before the analysis. Peptides derived from the different samples can be distinguished due to their mass difference. The ratio of their peak intensities corresponds to the relative abundance ratio of the peptides (and proteins). The most popular methods for isotope labeling are SILAC (stable isotope labeling by amino acids in cell culture), trypsin-catalyzed $^{18}O$ labeling, ICAT (isotope coded affinity tagging), iTRAQ (isobaric tags for relative and absolute quantitation). "Semi-quantitative" mass spectrometry can be performed without labeling of samples. Typically, this is done with MALDI analysis (in linear mode). The peak intensity, or the peak area, from individual molecules (typically proteins) is here correlated to the amount of protein in the sample. However, the individual signal depends on the primary structure of the protein, on the complexity of the sample, and on the settings of the instrument. Other types of "label-free" quantitative mass spectrometry, uses the spectral counts (or peptide counts) of digested proteins as a means for determining relative protein amounts.

In one embodiment, any one or more of the protein markers of the invention can be identified and quantified from a complex biological sample using mass spectroscopy in accordance with the following exemplary method, which is not intended to limit the invention or the use of other mass spectrometry-based methods.

In the first step of this embodiment, (A) a biological sample, e.g., a biological sample suspected of having NASH or advanced liver fibrosis, which comprises a complex mixture of protein (including at least one biomarker of interest) is fragmented and labeled with a stable isotope X. (B) Next, a known amount of an internal standard is added to the biological sample, wherein the internal standard is prepared by fragmenting a standard protein that is identical to the at least one target biomarker of interest, and labeled with a stable isotope Y. (C) This sample obtained is then introduced in an LC-MS/MS device, and multiple reaction monitoring (MRM) analysis is performed using MRM transitions selected for the internal standard to obtain an MRM chromatogram. (D) The MRM chromatogram is then viewed to identify a target peptide biomarker derived from the biological sample that shows the same retention time as a peptide derived from the internal standard (an internal standard peptide), and quantifying the target protein biomarker in the test sample by comparing the peak area of the internal standard peptide with the peak area of the target peptide biomarker.

Any suitable biological sample may be used as a starting point for LC-MS/MS/MRM analysis, including biological samples derived blood, urine, saliva, hair, cells, cell tissues, biopsy materials, and treated products thereof; and protein-containing samples prepared by gene recombination techniques.

Each of the above steps (A) to (D) is described further below.

Step (A) (Fragmentation and Labeling). In step (A), the target protein biomarker is fragmented to a collection of peptides, which is subsequently labeled with a stable isotope X. To fragment the target protein, for example, methods of digesting the target protein with a proteolytic enzyme (protease) such as trypsin, and chemical cleavage methods, such as a method using cyanogen bromide, can be used. Digestion by protease is preferable. It is known that a given mole quantity of protein produces the same mole quantity for each tryptic peptide cleavage product if the proteolytic digest is allowed to proceed to completion. Thus, determining the mole quantity of tryptic peptide to a given protein allows determination of the mole quantity of the original protein in the sample. Absolute quantification of the target protein can be accomplished by determining the absolute amount of the target protein-derived peptides contained in the protease digestion (collection of peptides). Accordingly, in order to allow the proteolytic digest to proceed to completion, reduction and alkylation treatments are preferably performed before protease digestion with trypsin to reduce and alkylate the disulfide bonds contained in the target protein.

Subsequently, the obtained digest (collection of peptides, comprising peptides of the target biomarker in the biological sample) is subjected to labeling with a stable isotope X.

Examples of stable isotopes X include $^1$H and $^2$H for hydrogen atoms, $^{12}$C and $^{13}$C for carbon atoms, and $^{14}$N and $^{15}$N for nitrogen atoms. Any isotope can be suitably selected therefrom. Labeling by a stable isotope X can be performed by reacting the digest (collection of peptides) with a reagent containing the stable isotope. Preferable examples of such reagents that are commercially available include mTRAQ (registered trademark) (produced by Applied Biosystems), which is an amine-specific stable isotope reagent kit. mTRAQ is composed of 2 or 3 types of reagents (mTRAQ-light and mTRAQ-heavy; or mTRAQ-D0, mTRAQ-D4, and mTRAQ-D8) that have a constant mass difference therebetween as a result of isotope-labeling, and that are bound to the N-terminus of a peptide or the primary amine of a lysine residue.

Step (B) (Addition of the Internal Standard). In step (B), a known amount of an internal standard is added to the sample obtained in step (A). The internal standard used herein is a digest (collection of peptides) obtained by fragmenting a protein (standard protein) consisting of the same amino acid sequence as the target protein (target biomarker) to be measured, and labeling the obtained digest (collection of peptides) with a stable isotope Y. The fragmentation treatment can be performed in the same manner as above for the target protein. Labeling with a stable isotope Y can also be performed in the same manner as above for the target protein. However, the stable isotope Y used herein must be an isotope that has a mass different from that of the stable isotope X used for labeling the target protein digest. For example, in the case of using the aforementioned mTRAQ (registered trademark) (produced by Applied Biosystems), when mTRAQ-light is used to label a target protein digest, mTRAQ-heavy should be used to label a standard protein digest.

Step (C) (LC-MS/MS and MRM Analysis). In step (C), the sample obtained in step (B) is first placed in an LC-MS/MS device, and then multiple reaction monitoring (MRM) analysis is performed using MRM transitions selected for the internal standard. By LC (liquid chromatography) using the LC-MS/MS device, the sample (collection of peptides labeled with a stable isotope) obtained in step (B) is separated first by one-dimensional or multi-dimensional high-performance liquid chromatography. Specific examples of such liquid chromatography include cation exchange chromatography, in which separation is conducted by utilizing electric charge difference between peptides; and reversed-phase chromatography, in which separation is conducted by utilizing hydrophobicity difference between peptides. Both of these methods may be used in combination.

Subsequently, each of the separated peptides is subjected to tandem mass spectrometry by using a tandem mass spectrometer (MS/MS spectrometer) comprising two mass spectrometers connected in series. The use of such a mass spectrometer enables the detection of several fmol levels of a target protein. Furthermore, MS/MS analysis enables the analysis of internal sequence information on peptides, thus enabling identification without false positives. Other types of MS analyzers may also be used, including magnetic sector mass spectrometers (Sector MS), quadrupole mass spectrometers (QMS), time-of-flight mass spectrometers (TOFMS), and Fourier transform ion cyclotron resonance mass spectrometers (FT-ICRMS), and combinations of these analyzers.

Subsequently, the obtained data are put through a search engine to perform a spectral assignment and to list the peptides experimentally detected for each protein. The detected peptides are preferably grouped for each protein, and preferably at least three fragments having an m/z value larger than that of the precursor ion and at least three fragments with an m/z value of, preferably, 500 or more are selected from each MS/MS spectrum in descending order of signal strength on the spectrum. From these, two or more fragments are selected in descending order of strength, and the average of the strength is defined as the expected sensitivity of the MRR transitions. When a plurality of peptides is detected from one protein, at least two peptides with the highest sensitivity are selected as standard peptides using the expected sensitivity as an index.

Step (D) (Quantification of the Target Protein in the Test Sample). Step (D) comprises identifying, in the MRM chromatogram detected in step (C), a peptide derived from the target protein (a target biomarker of interest) that shows the same retention time as a peptide derived from the internal standard (an internal standard peptide), and quantifying the target protein in the test sample by comparing the peak area of the internal standard peptide with the peak area of the target peptide. The target protein can be quantified by utilizing a calibration curve of the standard protein prepared beforehand.

The calibration curve can be prepared by the following method. First, a recombinant protein consisting of an amino acid sequence that is identical to that of the target biomarker protein is digested with a protease such as trypsin, as described above. Subsequently, precursor-fragment transition selection standards (PFTS) of a known concentration are individually labeled with two different types of stable isotopes (i.e., one is labeled with a stable isomer used to label an internal standard peptide (labeled with IS), whereas the other is labeled with a stable isomer used to label a target peptide (labeled with T). A plurality of samples are produced by blending a certain amount of the IS-labeled PTFS with various concentrations of the T-labeled PTFS. These samples are placed in the aforementioned LC-MS/MS device to perform MRM analysis. The area ratio of the T-labeled PTFS to the IS-labeled PTFS (T-labeled PTFS/IS-labeled PTFS) on the obtained MRM chromatogram is plotted against the amount of the T-labeled PTFS to prepare a calibration curve. The absolute amount of the target protein contained in the test sample can be calculated by reference to the calibration curve.

In another embodiment, the marker proteins of the invention may be detected using an aptamer as the binding partner. Aptamers are a class of peptide or nucleic acid molecules that represents an alternative to antibodies in term of molecular recognition. As used herein, "aptamers" are oligonucleotide or peptide molecules that bind to a specific target molecule (see e.g., Bock L C et al., Nature 355(6360): 5646(1992); Hoppe-Seyler F, Butz K "Peptide aptamers: powerful new tools for molecular medicine". J Mol Med. 78(8):42630(2000); Cohen B A, Colas P, Brent R. "An artificial cell-cycle inhibitor isolated from a combinatorial library". Proc Natl Acad Sci USA. 95(24): 142727(1998)). Aptamers are oligonucleotide or oligopeptide sequences with the capacity to recognize virtually any class of target molecules with high affinity and specificity. Such ligands may be isolated through Systematic Evolution of Ligands by Exponential enrichment (SELEX) of a random sequence library, as described in WO2012098219 and references cited therein. The random sequence library is obtainable by combinatorial chemical synthesis of DNA. In this library, each member is a linear oligomer, eventually chemically modified, of a unique sequence. Possible modifications, uses and advantages of this class of molecules have been indicated and described in WO2012098219, and references cited therein. Aptamers, may be labelled with a detectable molecule or substance, such as a fluorescent molecule, a radioactive molecule or any others labels known in the art. Labels are known in the art that generally provide (either directly or indirectly) a signal.

2. Detection of Nucleic Acids Corresponding to Protein Markers

In certain embodiments, the invention involves the detection of nucleic acid biomarkers, e.g., the corresponding genes or mRNA of the protein markers of the invention, e.g., Tables 1-6.

In various embodiments, the diagnostic/prognostic methods of the present invention generally involve the determination of expression levels of a set of genes in a biological sample. Determination of gene expression levels in the practice of the inventive methods may be performed by any suitable method. For example, determination of gene expression levels may be performed by detecting the expression of mRNA expressed from the genes of interest and/or by detecting the expression of a polypeptide encoded by the genes.

For detecting nucleic acids encoding biomarkers of the invention, any suitable method can be used, including, but not limited to, Southern blot analysis, Northern blot analysis, polymerase chain reaction (PCR) (see, for example, U.S. Pat. Nos. 4,683,195; 4,683,202, and 6,040,166; "PCR Protocols: A Guide to Methods and Applications", Innis et al. (Eds), 1990, Academic Press: New York), reverse transcriptase PCR (RT-PCT), anchored PCR, competitive PCR (see, for example, U.S. Pat. No. 5,747,251), rapid amplification of cDNA ends (RACE) (see, for example, "Gene Cloning and Analysis: Current Innovations, 1997, pp. 99-115); ligase chain reaction (LCR) (see, for example, EP 01 320 308), one-sided PCR (Ohara et al., Proc. Natl. Acad. Sci., 1989, 86: 5673-5677), in situ hybridization, Taqman-based assays (Holland et al., Proc. Natl. Acad. Sci., 1991, 88: 7276-7280), differential display (see, for example, Liang et al., Nucl. Acid. Res., 1993, 21: 3269-3275) and other RNA fingerprinting techniques, nucleic acid sequence based amplification (NASBA) and other transcription based amplification systems (see, for example, U.S. Pat. Nos. 5,409,818 and 5,554,527), Qbeta Replicase, Strand Displacement Amplification (SDA), Repair Chain Reaction (RCR), nuclease protection assays, subtraction-based methods, Rapid-Scan®, etc.

In other embodiments, gene expression levels of biomarkers of interest may be determined by amplifying complementary DNA (cDNA) or complementary RNA (cRNA) produced from mRNA and analyzing it using a microarray. A number of different array configurations and methods of their production are known to those skilled in the art (see, for example, U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637). Microarray technology allows for the measurement of the steady-state mRNA level of a large number of genes simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., Science, 1995, 270: 467-470; M. Schena et al., Proc. Natl. Acad. Sci. USA 1996, 93: 10614-10619; J. J. Chen et al., Genomics, 1998, 51: 313-324; U.S. Pat. Nos. 5,143,854; 5,445,934; 5,807,522; 5,837,832; 6,040,138; 6,045,996; 6,284,460; and 6,607,885).

Nucleic acid used as a template for amplification can be isolated from cells contained in the biological sample, according to standard methodologies. (Sambrook et al., 1989) The nucleic acid may be genomic DNA or fractionated or whole cell RNA. Where RNA is used, it may be desired to convert the RNA to a complementary cDNA. In one embodiment, the RNA is whole cell RNA and is used directly as the template for amplification.

Pairs of primers that selectively hybridize to nucleic acids corresponding to any of the NASH or advanced liver fibrosis biomarker nucleotide sequences identified herein are contacted with the isolated nucleic acid under conditions that permit selective hybridization. Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced. Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology; Bellus, 1994). Following detection, one may compare the results seen in a given patient with a statistically significant reference group of normal patients and NASH patients. In this way, it is possible to correlate the amount of nucleic acid detected with various clinical states.

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences may be employed. Primers may be provided in double-stranded or single-stranded form, although the single-stranded form is preferred.

A number of template dependent processes are available to amplify the nucleic acid sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety.

In PCR, two primer sequences are prepared which are complementary to regions on opposite complementary strands of the target nucleic acid sequence. An excess of deoxynucleoside triphosphates are added to a reaction mixture along with a DNA polymerase, e.g., Taq polymerase. If the target nucleic acid sequence is present in a sample, the primers will bind to the target nucleic acid and the polymerase will cause the primers to be extended along the target nucleic acid sequence by adding on nucleotides. By raising and lowering the temperature of the reaction mixture, the extended primers will dissociate from the target nucleic acid to form reaction products, excess primers will bind to the target nucleic acid and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641 filed Dec. 21, 1990. Polymerase chain reaction methodologies are well known in the art.

Another method for amplification is the ligase chain reaction ("LCR"), disclosed in European Application No. 320 308, incorporated herein by reference in its entirely. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, also may be used as still another amplification method in the present invention. In this method, a replicative sequence of RNA which has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'[α-thio]-triphosphates in one strand of a restriction site also may be useful in the amplification of nucleic acids in the present invention. Walker et al. (1992), incorporated herein by reference in its entirety.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases may be added as biotinylated derivatives for easy detection. A similar approach is used in SDA. Target specific sequences also may be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated.

Still other amplification methods described in GB Application No. 2 202 328, and in PCT Application No. PCT/US89/01025, each of which is incorporated herein by reference in its entirety, may be used in accordance with the present invention. In the former application, "modified" primers are used in a PCR like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other contemplated nucleic acid amplification procedures include transcription-based amplification systems (TAS), including nucleic acid sequence based amplification (NASBA) and 3SR. Kwoh et al. (1989); Gingeras et al., PCT Application WO 88/10315, incorporated herein by reference in their entirety. In NASBA, the nucleic acids may be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate target specific sequences.

Davey et al., European Application No. 329 822 (incorporated herein by reference in its entirely) disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase 1), resulting in a double-stranded DNA ("dsDNA") molecule, having a sequence identical to that of the original RNA between the primers and having additionally, at one end, a promoter sequence. This promoter sequence may be used by the appropriate RNA polymerase to make many RNA copies of the DNA. These copies may then re-enter the cycle leading to very swift amplification. With proper choice of enzymes, this amplification may be done isothermally without addition of enzymes at each cycle. Because of the cyclical nature of this process, the starting sequence may be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR." Frohman (1990) and Ohara et al. (1989), each herein incorporated by reference in their entirety.

Methods based on ligation of two (or more) oligonucleotides in the presence of nucleic acid having the sequence of the resulting "di-oligonucleotide", thereby amplifying the di-oligonucleotide, also may be used in the amplification step of the present invention. Wu et al. (1989), incorporated herein by reference in its entirety.

Oligonucleotide probes or primers of the present invention may be of any suitable length, depending on the particular assay format and the particular needs and targeted sequences employed. In a preferred embodiment, the oligonucleotide probes or primers are at least 10 nucleotides in length (preferably, 10, 11, 12, 13, 14, 15, 16, 17, 18, 19, 20, 21, 22, 23, 24, 25, 26, 27, 28, 29, 30, 31, 32 . . . ) and they may be adapted to be especially suited for a chosen nucleic acid amplification system and/or hybridization system used. Longer probes and primers are also within the scope of the present invention as well known in the art. Primers having more than 30, more than 40, more than 50 nucleotides and probes having more than 100, more than 200, more than 300, more than 500 more than 800 and more than 1000 nucleotides in length are also covered by the present invention. Of course, longer primers have the disadvantage of being more expensive and thus, primers having between 12 and 30 nucleotides in length are usually designed and used in the art. As well known in the art, probes ranging from 10 to more than 2000 nucleotides in length can be used in the methods of the present invention. As for the % of identity described above, non-specifically described sizes of probes and primers (e.g., 16, 17, 31, 24, 39, 350, 450, 550, 900, 1240 nucleotides, . . . ) are also within the scope of the present invention.

In other embodiments, the detection means can utilize a hybridization technique, e.g., where a specific primer or probe is selected to anneal to a target biomarker of interest and thereafter detection of selective hybridization is made. As commonly known in the art, the oligonucleotide probes and primers can be designed by taking into consideration the melting point of hybridization thereof with its targeted sequence (see below and in Sambrook et al., 1989, Molecular Cloning—A Laboratory Manual, 2nd Edition, CSH Laboratories; Ausubel et al., 1994, in Current Protocols in Molecular Biology, John Wiley & Sons Inc., N.Y.).

To enable hybridization to occur under the assay conditions of the present invention, oligonucleotide primers and probes should comprise an oligonucleotide sequence that has at least 70% (at least 71%, 72%, 73%, 74%), preferably at least 75% (75%, 76%, 77%, 78%, 79%, 80%, 81%, 82%, 83%, 84%, 85%, 86%, 87%, 88%, 89%) and more preferably at least 90% (90%, 91%, 92%, 93%, 94%, 95%, 96%, 97%, 98%, 99%, 100%) identity to a portion of a marker of the invention. Probes and primers of the present invention are those that hybridize under stringent hybridization conditions and those that hybridize to biomarker homologs of the invention under at least moderately stringent conditions. In certain embodiments probes and primers of the present invention have complete sequence identity to the biomarkers of the invention. It should be understood that other probes and primers could be easily designed and used in the present invention based on the biomarkers of the invention disclosed herein by using methods of computer alignment and sequence analysis known in the art (cf. Molecular Cloning: A Laboratory Manual, Third Edition, edited by Cold Spring Harbor Laboratory, 2000).

In one embodiment, immune-polymerase chain reaction (immuno-PCR) can be utilized for detection and quantification of the markers of the invention Immuno-PCR utilizes oligonucleotides bound to antibodies. In particular, a streptavidin-protein A chimera that possesses tight and specific binding affinity both for biotin and immunobulin G is used to attach a biotinylated DNA specifically to antigen-monoclonal antibody complexes that have been immobilized on microtiter plate wells. Then a segment of the attached DNA is amplified by PCR. Analysis of the PCR products by gel electrophoresis after staining allow detection of antigen molecules. (see Malou et al., Trends Microbiol. 2011 June; 19(6):295-302; Sano, T., Smith, C. L., Cantor, C. R. Science (1992)).

rPCR, microarrys or sequencing to can be used to detect and/or quantitatively measure the markers of the invention.

3. Antibodies and Labels

In some embodiments, the invention provides methods and compositions that include labels for the highly sensitive detection and quantitation of the markers of the invention. One skilled in the art will recognize that many strategies can be used for labeling target molecules to enable their detection or discrimination in a mixture of particles. The labels may be attached by any known means, including methods that utilize non-specific or specific interactions of label and target. Labels may provide a detectable signal or affect the mobility of the particle in an electric field. In addition, labeling can be accomplished directly or through binding partners.

In some embodiments, the label comprises a binding partner that binds to the biomarker of interest, where the binding partner is attached to a fluorescent moiety. The compositions and methods of the invention may utilize highly fluorescent moieties, e.g., a moiety capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. Moieties suitable for the compositions and methods of the invention are described in more detail below.

In some embodiments, the invention provides a label for detecting a biological molecule comprising a binding partner for the biological molecule that is attached to a fluorescent moiety, wherein the fluorescent moiety is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. In some embodiments, the moiety comprises a plurality of fluorescent entities, e.g., about 2 to 4, 2 to 5, 2 to 6, 2 to 7, 2 to 8, 2 to 9, 2 to 10, or about 3 to 5, 3 to 6, 3 to 7, 3 to 8, 3 to 9, or 3 to 10 fluorescent entities. In some embodiments, the moiety comprises about 2 to 4 fluorescent entities. In some embodiments, the biological molecule is a protein or a small molecule. In some embodiments, the biological molecule is a protein. The fluorescent entities can be fluorescent dye molecules. In some embodiments, the fluorescent dye molecules comprise at least one substituted indolium ring system in which the substituent on the 3-carbon of the indolium ring contains a chemically reactive group or a conjugated substance. In some embodiments, the dye molecules are Alexa Fluor molecules selected from the group consisting of Alexa Fluor 488, Alexa Fluor 532, Alexa Fluor 647, Alexa Fluor 680 or Alexa Fluor 700. In some embodiments, the dye molecules are Alexa Fluor molecules selected from the group consisting of Alexa Fluor 488, Alexa Fluor 532, Alexa Fluor 680 or Alexa Fluor 700. In some embodiments, the dye molecules are Alexa Fluor 647 dye molecules. In some embodiments, the dye molecules comprise a first type and a second type of dye molecules, e.g., two different Alexa Fluor molecules, e.g., where the first type and second type of dye molecules have different emission spectra. The ratio of the number of first type to second type of dye molecule can be, e.g., 4 to 1, 3 to 1, 2 to 1, 1 to 1, 1 to 2, 1 to 3 or 1 to 4. The binding partner can be, e.g., an antibody.

In some embodiments, the invention provides a label for the detection of a biological marker of the invention, wherein the label comprises a binding partner for the marker and a fluorescent moiety, wherein the fluorescent moiety is capable of emitting at least about 200 photons when simulated by a laser emitting light at the excitation wavelength of the moiety, wherein the laser is focused on a spot not less than about 5 microns in diameter that contains the moiety, and wherein the total energy directed at the spot by the laser is no more than about 3 microJoules. In some embodiments, the fluorescent moiety comprises a fluorescent molecule. In some embodiments, the fluorescent moiety comprises a plurality of fluorescent molecules, e.g., about 2 to 10, 2 to 8, 2 to 6, 2 to 4, 3 to 10, 3 to 8, or 3 to 6 fluorescent molecules. In some embodiments, the label comprises about 2 to 4 fluorescent molecules. In some embodiments, the fluorescent dye molecules comprise at least one substituted indolium ring system in which the substituent on the 3-carbon of the indolium ring contains a chemically reactive group or a conjugated substance. In some embodiments, the fluorescent molecules are selected from the group consisting of Alexa Fluor 488, Alexa Fluor 532, Alexa Fluor 647, Alexa Fluor 680 or Alexa Fluor 700. In some embodiments, the fluorescent molecules are selected from the group consisting of Alexa Fluor 488, Alexa Fluor 532, Alexa Fluor 680 or Alexa Fluor 700. In some embodiments, the fluorescent molecules are Alexa Fluor 647 molecules. In some embodiments, the binding partner comprises an antibody. In some embodiments, the antibody is a monoclonal antibody. In other embodiments, the antibody is a polyclonal antibody.

The term "antibody," as used herein, is a broad term and is used in its ordinary sense, including, without limitation, to refer to naturally occurring antibodies as well as non-naturally occurring antibodies, including, for example, single chain antibodies, chimeric, bifunctional and humanized antibodies, as well as antigen-binding fragments thereof. An "antigen-binding fragment" of an antibody refers to the part of the antibody that participates in antigen binding. The antigen binding site is formed by amino acid residues of the N-terminal variable ("V") regions of the heavy ("H") and light ("L") chains. It will be appreciated that the choice of epitope or region of the molecule to which the antibody is raised will determine its specificity, e.g., for various forms of the molecule, if present, or for total (e.g., all, or substantially all of the molecule).

Methods for producing antibodies are well-established. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)). Monoclonal and polyclonal antibodies to molecules, e.g., proteins, and markers also commercially available (R and D Systems, Minneapolis, Minn.; HyTest, HyTest Ltd., Turku Finland; Abcam Inc., Cambridge, Mass., USA; Life Diagnostics, Inc., West Chester, Pa., USA; Fitzgerald Industries International, Inc., Concord, Mass. 01742-3049 USA; BiosPacific, Emeryville, Calif.).

In some embodiments, the antibody is a polyclonal antibody. In other embodiments, the antibody is a monoclonal antibody.

Antibodies may be prepared by any of a variety of techniques known to those of ordinary skill in the art (see, for example, Harlow and Lane, Antibodies: A Laboratory Manual, Cold Spring Harbor Laboratory, 1988). In general, antibodies can be produced by cell culture techniques, including the generation of monoclonal antibodies as described herein, or via transfection of antibody genes into suitable bacterial or mammalian cell hosts, in order to allow for the production of recombinant antibodies.

Monoclonal antibodies may be prepared using hybridoma methods, such as the technique of Kohler and Milstein (Eur. J. Immunol. 6:511-519, 1976), and improvements thereto. These methods involve the preparation of immortal cell lines capable of producing antibodies having the desired specificity. Monoclonal antibodies may also be made by recombinant DNA methods, such as those described in U.S. Pat. No. 4,816,567. DNA encoding antibodies employed in the disclosed methods may be isolated and sequenced using conventional procedures. Recombinant antibodies, antibody fragments, and/or fusions thereof, can be expressed in vitro or in prokaryotic cells (e.g. bacteria) or eukaryotic cells (e.g. yeast, insect or mammalian cells) and further purified as necessary using well known methods.

More particularly, monoclonal antibodies (MAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified expressed protein, polypeptide or peptide. The immunizing composition is administered in a manner effective to stimulate antibody producing cells. The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60-61), but mice are preferred, with the BALB/c mouse being most preferred as this is most routinely used and generally gives a higher percentage of stable fusions.

The animals are injected with antigen as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals. Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of the animal with the highest antibody titer will be removed and the spleen lymphocytes obtained by homogenizing the spleen with a syringe.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

The selected hybridomas would then be serially diluted and cloned into individual antibody-producing cell lines, which clones may then be propagated indefinitely to provide MAbs. The cell lines may be exploited for MAb production in two basic ways. A sample of the hybridoma may be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, may then be tapped to provide MAbs in high concentration. The individual cell lines also may be cultured in vitro, where the MAbs are naturally secreted into the culture medium from which they may be readily obtained in high concentrations. MAbs produced by either means may be further purified, if desired, using filtration, centrifugation and various chromatographic methods such as HPLC or affinity chromatography.

Large amounts of the monoclonal antibodies of the present invention also may be obtained by multiplying hybridoma cells in vivo. Cell clones are injected into mammals which are histocompatible with the parent cells, e.g., syngeneic mice, to cause growth of antibody-producing tumors. Optionally, the animals are primed with a hydrocarbon, especially oils such as pristane (tetramethylpentadecane) prior to injection.

In accordance with the present invention, fragments of the monoclonal antibody of the invention may be obtained from the monoclonal antibody produced as described above, by methods which include digestion with enzymes such as pepsin or papain and/or cleavage of disulfide bonds by chemical reduction. Alternatively, monoclonal antibody fragments encompassed by the present invention may be synthesized using an automated peptide synthesizer.

Antibodies may also be derived from a recombinant antibody library that is based on amino acid sequences that have been designed in silico and encoded by polynucleotides that are synthetically generated. Methods for designing and obtaining in silico-created sequences are known in the art (Knappik et al., J. Mol. Biol. 296:254:57-86, 2000; Krebs et al., J. Immunol. Methods 254:67-84, 2001; U.S. Pat. No. 6,300,064).

Digestion of antibodies to produce antigen-binding fragments thereof can be performed using techniques well known in the art. For example, the proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab').sub.2" fragment, which comprises both antigen-binding sites. "Fv" fragments can be produced by preferential proteolytic cleavage of an IgM, IgG or IgA immunoglobulin molecule, but are more commonly derived using recombinant techniques known in the art. The Fv fragment includes a non-covalent V.sub.H::V.sub.L heterodimer including an antigen-binding site which retains much of the antigen recognition and binding capabilities of the native antibody molecule (Inbar et al., Proc. Natl. Acad. Sci. USA 69:2659-2662 (1972); Hochman et al., Biochem. 15:2706-2710 (1976); and Ehrlich et al., Biochem. 19:4091-4096 (1980)).

Antibody fragments that specifically bind to the protein biomarkers disclosed herein can also be isolated from a library of scFvs using known techniques, such as those described in U.S. Pat. No. 5,885,793.

A wide variety of expression systems are available in the art for the production of antibody fragments, including Fab fragments, scFv, VL and VHs. For example, expression systems of both prokaryotic and eukaryotic origin may be used for the large-scale production of antibody fragments. Particularly advantageous are expression systems that permit the secretion of large amounts of antibody fragments into the culture medium. Eukaryotic expression systems for large-scale production of antibody fragments and antibody fusion proteins have been described that are based on mammalian cells, insect cells, plants, transgenic animals, and lower eukaryotes. For example, the cost-effective, large-scale production of antibody fragments can be achieved in yeast fermentation systems. Large-scale fermentation of these organisms is well known in the art and is currently used for bulk production of several recombinant proteins.

Antibodies that bind to the protein biomarkers employed in the present methods are, in some cases, available commercially or can be obtained without undue experimentation.

In still other embodiments, particularly where oligonucleotides are used as binding partners to detect and hybridize to mRNA biomarkers or other nucleic acid based biomarkers, the binding partners (e.g., oligonucleotides) can comprise a label, e.g., a fluorescent moiety or dye. In addition, any binding partner of the invention, e.g., an antibody, can also be labeled with a fluorescent moiety. The fluorescence of the moiety will be sufficient to allow detection in a single molecule detector, such as the single molecule detectors described herein. A "fluorescent moiety," as that term is used herein, includes one or more fluorescent entities whose total fluorescence is such that the moiety may be detected in the single molecule detectors described herein. Thus, a fluorescent moiety may comprise a single entity (e.g., a Quantum Dot or fluorescent molecule) or a plurality of entities (e.g., a plurality of fluorescent molecules). It will be appreciated that when "moiety," as that term is used herein, refers to a group of fluorescent entities, e.g., a plurality of fluorescent dye molecules, each individual entity may be attached to the binding partner separately or the entities may be attached together, as long as the entities as a group provide sufficient fluorescence to be detected.

Typically, the fluorescence of the moiety involves a combination of quantum efficiency and lack of photobleaching sufficient that the moiety is detectable above background levels in a single molecule detector, with the consistency necessary for the desired limit of detection, accuracy, and precision of the assay. For example, in some embodiments, the fluorescence of the fluorescent moiety is such that it allows detection and/or quantitation of a molecule, e.g., a marker, at a limit of detection of less than about 10, 5, 4, 3, 2, 1, 0.1, 0.01, 0.001, 0.00001, or 0.000001 pg/ml and with a coefficient of variation of less than about 20, 15, 14, 13, 12, 11, 10, 9, 8, 7, 6, 5, 4, 3, 2, 1% or less, e.g., about 10% or less, in the instruments described herein. In some embodiments, the fluorescence of the fluorescent moiety is such that it allows detection and/or quantitation of a molecule, e.g., a marker, at a limit of detection of less than about 5, 1, 0.5, 0.1, 0.05, 0.01, 0.005, 0.001 pg/ml and with a coefficient of variation of less than about 10%, in the instruments described herein. "Limit of detection," or LoD, as those terms are used herein, includes the lowest concentration at which one can identify a sample as containing a molecule of the substance of interest, e.g., the first non-zero value. It can be defined by the variability of zeros and the slope of the standard curve. For example, the limit of detection of an assay may be determined by running a standard curve, determining the standard curve zero value, and adding 2 standard deviations to that value. A concentration of the substance of interest that produces a signal equal to this value is the "lower limit of detection" concentration.

Furthermore, the moiety has properties that are consistent with its use in the assay of choice. In some embodiments, the assay is an immunoassay, where the fluorescent moiety is attached to an antibody; the moiety must have properties such that it does not aggregate with other antibodies or proteins, or experiences no more aggregation than is consistent with the required accuracy and precision of the assay. In some embodiments, fluorescent moieties that are preferred are fluorescent moieties, e.g., dye molecules that have a combination of 1) high absorption coefficient; 2) high quantum yield; 3) high photostability (low photobleaching); and 4) compatibility with labeling the molecule of interest (e.g., protein) so that it may be analyzed using the analyzers and systems of the invention (e.g., does not cause precipitation of the protein of interest, or precipitation of a protein to which the moiety has been attached).

Any suitable fluorescent moiety may be used. Examples include, but are not limited to, Alexa Fluor dyes (Molecular Probes, Eugene, Oreg.). The Alexa Fluor dyes are disclosed in U.S. Pat. Nos. 6,977,305; 6,974,874; 6,130,101; and 6,974,305 which are herein incorporated by reference in their entirety. Some embodiments of the invention utilize a dye chosen from the group consisting of Alexa Fluor 647, Alexa Fluor 488, Alexa Fluor 532, Alexa Fluor 555, Alexa Fluor 610, Alexa Fluor 680, Alexa Fluor 700, and Alexa Fluor 750. Some embodiments of the invention utilize a dye chosen from the group consisting of Alexa Fluor 488, Alexa Fluor 532, Alexa Fluor 647, Alexa Fluor 700 and Alexa Fluor 750. Some embodiments of the invention utilize a dye chosen from the group consisting of Alexa Fluor 488, Alexa Fluor 532, Alexa Fluor 555, Alexa Fluor 610, Alexa Fluor 680, Alexa Fluor 700, and Alexa Fluor 750. Some embodiments of the invention utilize the Alexa Fluor 647 molecule, which has an absorption maximum between about 650 and 660 nm and an emission maximum between about 660 and 670 nm. The Alexa Fluor 647 dye is used alone or in combination with other Alexa Fluor dyes.

In some embodiments, the fluorescent label moiety that is used to detect a biomarker in a sample using the analyzer systems of the invention is a quantum dot. Quantum dots (QDs), also known as semiconductor nanocrystals or artificial atoms, are semiconductor crystals that contain anywhere between 100 to 1,000 electrons and range from 2-10 nm. Some QDs can be between 10-20 nm in diameter. QDs have high quantum yields, which makes them particularly useful for optical applications. QDs are fluorophores that fluoresce by forming excitons, which are similar to the excited state of traditional fluorophores, but have much longer lifetimes of up to 200 nanoseconds. This property provides QDs with low photobleaching. The energy level of QDs can be controlled by changing the size and shape of the QD, and the depth of the QDs' potential. One optical feature of small excitonic QDs is coloration, which is determined by the size of the dot. The larger the dot, the redder, or more towards the red end of the spectrum the fluorescence. The smaller the dot, the bluer or more towards the blue end it is. The bandgap energy that determines the energy and hence the color of the fluoresced light is inversely proportional to the square of the size of the QD. Larger QDs have more energy levels which are more closely spaced, thus allowing the QD to absorb photons containing less energy, i.e., those closer to the red end of the spectrum. Because the emission frequency of a dot is dependent on the bandgap, it is possible to control the output wavelength of a dot with extreme precision. In some embodiments the protein that is detected with the single molecule analyzer system is labeled with a QD. In some embodiments, the single molecule analyzer is used to detect a protein labeled with one QD and using a filter to allow for the detection of different proteins at different wavelengths.

F. Isolated Biomarkers

1. Isolated Polypeptide Biomarkers

One aspect of the invention pertains to isolated marker proteins and biologically active portions thereof, as well as polypeptide fragments suitable for use as immunogens to raise antibodies directed against a marker protein or a fragment thereof. In one embodiment, the native marker protein can be isolated by an appropriate purification scheme using standard protein purification techniques. In another embodiment, a protein or peptide comprising the whole or a segment of the marker protein is produced by recombinant DNA techniques. Alternative to recombinant expression, such protein or peptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a marker protein include polypeptides comprising amino acid sequences sufficiently identical to or derived from the amino acid sequence of the marker protein, which include fewer amino acids than the full length protein, and exhibit at least one activity of the corresponding full-length protein. Typically, biologically active portions comprise a domain or motif with at least one activity of the corresponding full-length protein. A biologically active portion of a marker protein of the invention can be a polypeptide which is, for example, 10, 25, 50, 100 or more amino acids in length. Moreover, other biologically active portions, in which other regions of the marker protein are deleted, can be prepared by recombinant techniques and evaluated for one or more of the functional activities of the native form of the marker protein.

Preferred marker proteins are encoded by nucleotide sequences provided in the sequence listing. Other useful proteins are substantially identical (e.g., at least about 40%, preferably 50%, 60%, 70%, 80%, 90%, 91%, 92%, 93%, 94%, 95%, 96%, 97%, 98% or 99%) to one of these sequences and retain the functional activity of the corresponding naturally-occurring marker protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. Preferably, the percent identity between the two sequences is calculated using a global alignment. Alternatively, the percent identity between the two sequences is calculated using a local alignment. The percent identity between the two sequences is a function of the number of identical positions shared by the sequences (i.e., % identity=# of identical positions/total # of positions (e.g., overlapping positions)×100). In one embodiment the two sequences are the same length. In another embodiment, the two sequences are not the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the BLASTN and BLASTX programs of Altschul, et al. (1990) *J. Mol. Biol.* 215:403-410. BLAST nucleotide searches can be performed with the BLASTN program, score=100, wordlength=12 to obtain nucleotide sequences homologous to a nucleic acid molecules of the invention. BLAST protein searches can be performed with the BLASTP program, score=50, wordlength=3 to obtain amino acid sequences homologous to a protein molecules of the invention. To obtain gapped alignments for comparison purposes, a newer version of the BLAST algorithm called Gapped BLAST can be utilized as described in Altschul et al. (1997) *Nucleic Acids Res.* 25:3389-3402, which is able to perform gapped local alignments for the programs BLASTN, BLASTP and BLASTX. Alternatively, PSI-Blast can be used to perform an iterated search which detects distant relationships between molecules. When utilizing BLAST, Gapped BLAST, and PSI-Blast programs, the default parameters of the respective programs (e.g., BLASTX and BLASTN) can be used. See the NCBI website. Another preferred, non-limiting example of a mathematical algorithm utilized for the comparison of sequences is the algorithm of Myers and Miller, (1988) *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

Another aspect of the invention pertains to antibodies directed against a protein of the invention. In preferred embodiments, the antibodies specifically bind a marker protein or a fragment thereof. The terms "antibody" and "antibodies" as used interchangeably herein refer to immunoglobulin molecules as well as fragments and derivatives thereof that comprise an immunologically active portion of an immunoglobulin molecule, (i.e., such a portion contains an antigen binding site which specifically binds an antigen, such as a marker protein, e.g., an epitope of a marker protein). An antibody which specifically binds to a protein of the invention is an antibody which binds the protein, but does not substantially bind other molecules in a sample, e.g., a biological sample, which naturally contains the protein. Examples of an immunologically active portion of an immunoglobulin molecule include, but are not limited to, single-chain antibodies (scAb), F(ab) and F(ab')$_2$ fragments.

An isolated protein of the invention or a fragment thereof can be used as an immunogen to generate antibodies. The full-length protein can be used or, alternatively, the invention provides antigenic peptide fragments for use as immunogens. The antigenic peptide of a protein of the invention comprises at least 8 (preferably 10, 15, 20, or 30 or more) amino acid residues of the amino acid sequence of one of the proteins of the invention, and encompasses at least one epitope of the protein such that an antibody raised against the peptide forms a specific immune complex with the protein. Preferred epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions. In preferred embodiments, an isolated marker protein or fragment thereof is used as an immunogen.

The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope. Preferred polyclonal and monoclonal antibody compositions are ones that have been selected for antibodies directed against a protein of the invention. Particularly preferred polyclonal and monoclonal antibody preparations are ones that contain only antibodies directed against a marker protein or fragment thereof. Methods of making polyclonal, monoclonal, and recombinant antibody and antibody fragments are well known in the art.

2. Isolated Nucleic Acid Biomarkers

One aspect of the invention pertains to isolated nucleic acid molecules which encode a marker protein or a portion thereof. Isolated nucleic acids of the invention also include nucleic acid molecules sufficient for use as hybridization probes to identify marker nucleic acid molecules, and fragments of marker nucleic acid molecules, e.g., those suitable for use as PCR primers for the amplification of a specific product or mutation of marker nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. In one embodiment, an "isolated" nucleic acid molecule (preferably a protein-encoding sequences) is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. In another embodiment, an "isolated" nucleic acid molecule, such as a cDNA molecule, can be substantially free of other cellular material, or culture medium when produced by recombinant techniques, or substantially free of chemical precursors or other chemicals when chemically synthesized. A nucleic acid molecule that is substantially free of cellular material includes preparations having less than about 30%, 20%, 10%, or 5% of heterologous nucleic acid (also referred to herein as a "contaminating nucleic acid").

A nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual*, 2nd ed., Cold Spring Harbor Laboratory Press, Cold Spring Harbor, NY, 1989).

A nucleic acid molecule of the invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, nucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which has a nucleotide sequence complementary to the nucleotide sequence of a marker nucleic acid or to the nucleotide sequence of a nucleic acid encoding a marker protein. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence, wherein the full length nucleic acid sequence comprises a marker nucleic acid or which encodes a marker protein. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 15, more preferably at least about 25, 50, 75, 100, 125, 150, 175, 200, 250, 300, 350, or 400 or more consecutive nucleotides of a nucleic acid of the invention.

Probes based on the sequence of a nucleic acid molecule of the invention can be used to detect transcripts or genomic sequences corresponding to one or more markers of the invention. In certain embodiments, the probes hybridize to nucleic acid sequences that traverse splice junctions. The probe comprises a label group attached thereto, e.g., a radioisotope, a fluorescent compound, an enzyme, or an enzyme co-factor. Such probes can be used as part of a diagnostic test kit or panel for identifying cells or tissues which express or mis-express the protein, such as by measuring levels of a nucleic acid molecule encoding the protein in a sample of cells from a subject, e.g., detecting mRNA levels or determining whether a gene encoding the protein or its translational control sequences have been mutated or deleted.

The invention further encompasses nucleic acid molecules that differ, due to degeneracy of the genetic code, from the nucleotide sequence of nucleic acids encoding a marker protein, and thus encode the same protein.

It will be appreciated by those skilled in the art that DNA sequence polymorphisms that lead to changes in the amino acid sequence can exist within a population (e.g., the human population). An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

As used herein, the phrase "allelic variant" refers to a nucleotide sequence which occurs at a given locus or to a polypeptide encoded by the nucleotide sequence.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, an isolated nucleic acid molecule of the invention is at least 15, 20, 25, 30, 40, 60, 80, 100, 150, 200, 250, 300, 350, 400, 450, 550, 650, 700, 800, 900, 1000, 1200, 1400, 1600, 1800, 2000, 2200, 2400, 2600, 2800, 3000, 3500, 4000, 4500, or more nucleotides in length and hybridizes under stringent conditions to a marker nucleic acid or to a nucleic acid encoding a marker protein. As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

G. Biomarker Applications

The invention provides methods for diagnosing NASH or advanced liver fibrosis, in a subject. The invention further provides methods for prognosing or monitoring progression or monitoring response of NASH or advanced liver fibrosis, to a therapeutic treatment.

In one aspect, the present invention constitutes an application of diagnostic information obtainable by the methods of the invention in connection with analyzing, detecting, and/or measuring the NASH or advanced liver fibrosis biomarkers of the present invention, i.e., the markers of Tables 1-3, 7 and 9 or 4-6, 8 and 10, respectively, which goes well beyond the discovered correlation between NASH or advanced liver fibrosis and the biomarkers of the invention.

For example, when executing the methods of the invention for detecting and/or measuring an protein biomarker of the present invention, as described herein, one may contact a biological sample with a detection reagent, e.g., a monoclonal antibody, which selectively binds to the biomarker of interest, forming a protein-protein complex, which is then further detected either directly (if the antibody comprises a label) or indirectly (if a secondary detection reagent is used, e.g., a secondary antibody, which in turn is labeled). Thus, the method of the invention transforms the polypeptide markers of the invention to a protein-protein complex that comprises either a detectable primary antibody or a primary and further secondary antibody. Forming such protein-protein complexes is required in order to identify the presence of the biomarker of interest and necessarily changes the physical characteristics and properties of the biomarker of interest as a result of conducting the methods of the invention.

The same principal applies when conducting the methods of the invention for detecting nucleic acids that correspond to the protein biomarkers of the invention. In particular, when amplification methods are used, the process results in the formation of a new population of amplicons, i.e., molecules that are newly synthesized and which were not present in the original biological sample, thereby physically transforming the biological sample. Similarly, when hybridization probes are used to detect a target biomarker, a physical new species of molecules is in effect created by the hybridization of the probes (optionally comprising a label) to the target biomarker mRNA (or other nucleic acid), which is then detected. Such polynucleotide products are effectively newly created or formed as a consequence of carrying out the method of the invention.

The invention provides, in one embodiment, methods for diagnosing NASH or advanced liver fibrosis. The methods of the present invention can be practiced in conjunction with any other method used by the skilled practitioner to prognose the occurrence or recurrence of NASH or advanced liver fibrosis and/or the survival of a subject being treated for NASH or advanced liver fibrosis. The diagnostic and prognostic methods provided herein can be used to determine if additional and/or more invasive tests such as liver biopsy and/or imaging, or monitoring should be performed on a subject. It is understood that a disease as complex as NASH is rarely diagnosed using a single test. Therefore, it is understood that the diagnostic, prognostic, and monitoring methods provided herein are typically used in conjunction with other methods known in the art. For example, the methods of the invention may be performed in conjunction with a morphological or cytological analysis of the sample obtained from the subject, imaging analysis, and/or physical exam. Cytological methods would include immunohistochemical or immunofluorescence detection (and quantitation if appropriate) of any other molecular marker either by itself, in conjunction with other markers. Other methods would include detection of other markers by in situ PCR, or by extracting tissue and quantitating other markers by real time PCR. PCR is defined as polymerase chain reaction.

Methods for assessing NASH and/or advanced liver fibrosis progression during any other therapeutic approach useful for treating NASH and/or advanced liver fibrosis in a subject are also provided. In these methods the amount of marker in a pair of samples (a first sample obtained from the subject at an earlier time point or prior to the treatment regimen and a second sample obtained from the subject at a later time point, e.g., at a later time point when the subject has undergone at least a portion of the treatment regimen) is assessed. It is understood that the methods of the invention include obtaining and analyzing more than two samples (e.g., 3, 4, 5, 6, 7, 8, 9, or more samples) at regular or irregular intervals for assessment of marker levels. Pairwise comparisons can be made between consecutive or non-consecutive subject samples. Trends of marker levels and rates of change of marker levels can be analyzed for any two or more consecutive or non-consecutive subject samples.

The methods of the invention may also be used to select a compound that is capable of modulating, i.e., decreasing, NASH or advanced liver fibrosis. In this method, a sample is contacted with a test compound, and the ability of the test compound to modulate the expression and/or activity of a marker in the invention in the sample is determined, thereby selecting a compound that is capable of modulating NASH or advanced liver fibrosis.

Using the methods described herein, a variety of molecules, may be screened in order to identify molecules which modulate, e.g., increase or decrease the expression and/or activity of a marker of the invention. Compounds so identified can be provided to a subject in order to inhibit the progression of NASH or advanced liver fibrosis, or to treat NASH or advanced liver fibrosis in the subject.

The present invention pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining the level of expression of one or more marker proteins or nucleic acids, in order to determine whether an individual is at risk of developing a disease or disorder, such as, without limitation, NASH or advanced liver fibrosis. Such assays can be used for prognostic or predictive purposes to thereby prophylactically treat an individual prior to the onset of the disorder.

Yet another aspect of the invention pertains to monitoring the influence of agents (e.g., drugs or other therapeutic compounds) on the expression or activity of a biomarker of the invention in clinical trials. These and other applications are described in further detail in the following sections.

1. Diagnostic Assays

An exemplary method for detecting the presence or absence or change of expression level of a marker protein or a corresponding nucleic acid in a biological sample involves obtaining a biological sample from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo.

Methods provided herein for detecting the presence, absence, change of expression level of a marker protein or corresponding nucleic acid in a biological sample include obtaining a biological sample from a subject that may or may not contain the marker protein or nucleic acid to be detected, contacting the sample with a marker-specific binding agent (i.e., one or more marker-specific binding agents) that is capable of forming a complex with the marker protein or nucleic acid to be detected, and contacting the sample with a detection reagent for detection of the marker—marker-specific binding agent complex, if formed. It is understood that the methods provided herein for detecting an expression level of a marker in a biological sample includes the steps to perform the assay. In certain embodiments of the detection methods, the level of the marker protein or nucleic acid in the sample is none or below the threshold for detection.

The methods include formation of either a transient or stable complex between the marker and the marker-specific binding agent. The methods require that the complex, if formed, be formed for sufficient time to allow a detection reagent to bind the complex and produce a detectable signal (e.g., fluorescent signal, a signal from a product of an enzymatic reaction, e.g., a peroxidase reaction, a phosphatase reaction, a beta-galactosidase reaction, or a polymerase reaction).

In certain embodiments, all markers are detected using the same method. In certain embodiments, all markers are detected using the same biological sample (e.g., same body fluid or tissue). In certain embodiments, different markers are detected using various methods. In certain embodiments, markers are detected in different biological samples.

2. Protein Detection

In certain embodiments of the invention, the marker to be detected is a protein. Proteins are detected using a number of assays in which a complex between the marker protein to be detected and the marker specific binding agent would not occur naturally, for example, because one of the components is not a naturally occurring compound or the marker for detection and the marker specific binding agent are not from the same organism (e.g., human marker proteins detected using marker-specific binding antibodies from mouse, rat, or goat). In a preferred embodiment of the invention, the marker protein for detection is a human marker protein. In certain detection assays, the human markers for detection are bound by marker-specific, non-human antibodies, thus, the complex would not be formed in nature. The complex of the marker protein can be detected directly, e.g., by use of a labeled marker-specific antibody that binds directly to the marker, or by binding a further component to the marker—marker-specific antibody complex, or an aptamer. In certain embodiments, the further component is a second marker-specific antibody capable of binding the marker at the same time as the first marker-specific antibody. In certain embodiments, the further component is a secondary antibody that binds to a marker-specific antibody, wherein the secondary antibody preferably linked to a detectable label (e.g., fluorescent label, enzymatic label, biotin). When the secondary antibody is linked to an enzymatic detectable label (e.g., a peroxidase, a phosphatase, a beta-galactosidase), the secondary antibody is detected by contacting the enzymatic detectable label with an appropriate substrate to produce a colorimetric, fluorescent, or other detectable, preferably quantitatively detectable, product. Antibodies for use in the methods of the invention can be polyclonal, however, in a preferred embodiment monoclonal antibodies are used. An intact antibody, or a fragment or derivative thereof (e.g., Fab or $F(ab')_2$) can be used in the methods of the invention. Such strategies of marker protein detection are used, for example, in ELISA, RIA, western blot, and immunofluorescence assay methods.

In certain detection assays, the marker present in the biological sample for detection is an enzyme and the detection reagent is an enzyme substrate. For example, the enzyme can be a protease and the substrate can be any protein that includes an appropriate protease cleavage site. Alternatively, the enzyme can be a kinase and the substrate can be any substrate for the kinase. In preferred embodiments, the substrate which forms a complex with the marker enzyme to be detected is not the substrate for the enzyme in a human subject.

In certain embodiments, the marker—marker-specific binding agent (e.g., antibody or aptamer) complex is attached to a solid support for detection of the marker. The complex can be formed on the substrate or formed prior to capture on the substrate. For example, in an ELISA, RIA, immunoprecipitation assay, western blot, immunofluorescence assay, in gel enzymatic assay the marker for detection is attached to a solid support, either directly or indirectly. In an ELISA, RIA, or immunofluorescence assay, the marker is typically attached indirectly to a solid support through an antibody or binding protein. In a western blot or immunofluorescence assay, the marker is typically attached directly to the solid support. For in-gel enzyme assays, the marker is resolved in a gel, typically an acrylamide gel, in which a substrate for the enzyme is integrated.

3. Nucleic Acid Detection

In certain embodiments of the invention, the marker is a nucleic acid corresponding to a marker protein. Nucleic acids are detected using a number of assays in which a complex between the marker nucleic acid to be detected and a marker-specific probe would not occur naturally, for example, because one of the components is not a naturally occurring compound. In certain embodiments, the analyte comprises a nucleic acid and the probe comprises one or more synthetic single stranded nucleic acid molecules, e.g., a DNA molecule, a DNA-RNA hybrid, a PNA, or a modified nucleic acid molecule (modified oligonucleotide) containing one or more artificial bases, sugars, or backbone moieties. In certain embodiments, the synthetic nucleic acid is a single stranded is a DNA molecule that includes a fluorescent label. In certain embodiments, the synthetic nucleic acid is a single stranded oligonucleotide molecule of about 12 to about 50 nucleotides in length. In certain embodiments, the nucleic acid to be detected is an mRNA and the complex formed is an mRNA hybridized to a single stranded DNA molecule that is complementary to the mRNA. In certain embodiments, an RNA is detected by generation of a DNA molecule (i.e., a cDNA molecule) first from the RNA template using the single stranded DNA that hybridizes to the RNA as a primer, e.g., a general poly-T primer to transcribe poly-A RNA. The cDNA can then be used as a template for an amplification reaction, e.g., PCR, primer extension assay, using a marker-specific probe. In certain embodiments, a labeled single stranded DNA can be hybridized to the RNA present in the sample for detection of the RNA by fluorescence in situ hybridization (FISH) or for detection of the RNA by northern blot.

For example, in vitro techniques for detection of mRNA include northern hybridizations, in situ hybridizations, and rtPCR. In vitro techniques for detection of genomic DNA include Southern hybridizations. Techniques for detection of mRNA include PCR, northern hybridizations and in situ hybridizations. Methods include both qualitative and quantitative methods.

A general principle of such diagnostic, prognostic, and monitoring assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways known in the art, e.g., ELISA assay, PCR, FISH.

4. Detection of Expression Levels

Marker levels can be detected based on the absolute expression level or a normalized or relative expression level. Detection of absolute marker levels may be preferable when monitoring the treatment of a subject or in determining if there is a change in the NASH or advanced liver fibrosis status of a subject. For example, the expression level of one or more markers can be monitored in a subject undergoing treatment for NASH or advanced liver fibrosis, e.g., at regular intervals, such a monthly intervals. A modulation in the level of one or more markers can be monitored over time to observe trends in changes in marker levels. Expression levels of the biomarkers of the invention in the subject may be higher than the expression level of those markers in a normal sample, but may be lower than the prior expression level, thus indicating a benefit of the treatment regimen for the subject. Similarly, rates of change of marker levels can be important in a subject who is not subject to active treatment for NASH or advanced liver fibrosis. Changes, or not, in marker levels may be more relevant to treatment decisions for the subject than marker levels present in the population.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., normal sample, or between samples from different sources.

Alternatively, the expression level can be provided as a relative expression level as compared to an appropriate control, e.g., population control, earlier time point control, etc. Preferably, the samples used in the baseline determination will be from a normal sample. The choice of the cell source is dependent on the use of the relative expression level. In addition, as more data is accumulated, the mean expression value can be revised, providing improved relative expression values based on accumulated data.

5. Diagnostic, Prognostic, Monitoring and and Treatment Methods

The invention provides methods for diagnosing the presence of NASH or advanced liver fibrosis in a subject, comprising (a) detecting the level of a NASH or advanced liver fibrosis marker in a biological sample from the subject, wherein the NASH or advanced liver fibrosis marker comprises one or more markers selected from Tables 1-3, 7 and 9 or 4-6, 8 and 10, respectively; and (b) comparing the level of the NASH or advanced liver fibrosis marker in the biological sample with a predetermined threshold value; wherein the level of the NASH or advanced liver fibrosis marker above or below the predetermined threshold value indicates a diagnosis that NASH or advanced liver fibrosis is present in the subject.

In another aspect, the invention provides methods for diagnosing the presence of NASH or advanced liver fibrosis in a subject, comprising: (a) contacting a biological sample with one or more reagents that selectively bind to a NASH or advanced liver fibrosis marker in the biological sample from the subject, wherein the NASH or advanced liver fibrosis marker comprises one or more markers selected from Tables 1-3, 7 and 9 or 4-6, 8 and 10, respectively; (b) allowing a complex to form between the one or more reagents and the NASH or advanced liver fibrosis marker; (c) detecting the level of the complex; and (d) comparing the level of the complex with a predetermined threshold value; wherein the level of the complex above or below the predetermined threshold value indicates a diagnosis that NASH or advanced liver fibrosis is present in the subject.

In still another aspect, the invention provides methods for identifying a subject as being at an increased risk for developing NASH or advanced liver fibrosis, comprising (a) detecting the level of a NASH or advanced liver fibrosis marker in a biological sample from the subject, wherein the NASH or advanced liver fibrosis marker comprises one or more markers selected from Tables 1-3, 7 and 9 or 4-6, 8 and 10, respectively; and (b) comparing the level of the NASH or advanced liver fibrosis marker in the biological sample with a predetermined threshold value; wherein the level of the NASH or advanced liver fibrosis marker above or below the predetermined threshold value indicates that the subject is being at an increased risk for developing NASH or advanced liver fibrosis.

In still another aspect, the invention provides methods for identifying a subject as being at an increased risk for developing NASH or advanced liver fibrosis, comprising: (a) contacting a biological sample with one or more reagents that selectively bind to a NASH or advanced liver fibrosis marker in the biological sample from the subject, wherein the NASH or advanced liver fibrosis marker comprises one or more markers selected from Tables 1-3, 7 and 9 or 4-6, 8 and 10, respectively; (b) allowing a complex to form between the one or more reagents and the NASH or advanced liver fibrosis marker; (c) detecting the level of the complex; and (d) comparing the level of the complex with a predetermined threshold value; wherein the level of the complex above or below the predetermined threshold value that the subject is being at an increased risk for developing NASH or advanced liver fibrosis.

The invention provides methods for monitoring NASH or advanced liver fibrosis in a subject, the method comprising: (1) detecting the level of a NASH or advanced liver fibrosis marker in a first biological sample obtained at a first time from the subject having NASH or advanced liver fibrosis, wherein the NASH or advanced liver fibrosis marker comprises one or more markers selected from Tables 1-3, 7 and 9 or 4-6, 8 and 10, respectively; (2) detecting the level of the NASH or advanced liver fibrosis marker in a second biological sample obtained from the subject at a second time, wherein the second time is later than the first time; and (3) comparing the level of the NASH or advanced liver fibrosis marker in the second sample with the level of the NASH or advanced liver fibrosis marker in the first sample; wherein a change in the level of the NASH or advanced liver fibrosis marker is indicative of a change in NASH or advanced liver fibrosis status in the subject.

The invention also provides methods for treating NASH or advanced liver fibrosis in a subject, comprising administering to the subject a modulator of a NASH or advanced liver fibrosis marker, wherein the NASH or advanced liver fibrosis marker comprises one or more markers selected from Tables 1-3, 7 and 9 or 4-6, 8 and 10, respectively.

In certain embodiments of the diagnostic, prognostic, monitoring, and treatment methods provided herein, one or more marker, e.g., NASH or advanced liver fibrosis markers, is two or more markers. In certain embodiments of the diagnostic, prognostic, monitoring, and treatment methods provided herein, one or more marker, e.g., NASH or advanced liver fibrosis markers, is three or more markers. In certain embodiments of the diagnostic, prognostic, monitoring, and treatment methods provided herein, one or more marker, e.g., NASH or advanced liver fibrosis markers, is four or more markers. In certain embodiments of the diagnostic, prognostic, monitoring, and treatment methods provided herein, one or more marker, e.g., NASH or advanced liver fibrosis markers, is five or more markers. In certain embodiments of the diagnostic, prognostic, monitoring, and treatment methods provided herein, one or more marker, e.g., NASH or advanced liver fibrosis markers, is six or more markers. In certain embodiments of the diagnostic, prognostic, monitoring, and treatment methods provided herein, one or more marker, e.g., NASH or advanced liver fibrosis markers, is seven or more markers. In certain embodiments of the diagnostic, prognostic, monitoring, and treatment methods provided herein, one or more marker, e.g., NASH or advanced liver fibrosis markers, is eight or more markers. In certain embodiments of the diagnostic, prognostic, monitoring, and treatment methods provided herein, one or more marker, e.g., NASH or advanced liver fibrosis markers, is nine or more markers. In certain embodiments of the diagnostic, prognostic, monitoring, and treatment methods provided herein, one or more marker, e.g., NASH or advanced liver fibrosis markers, is ten or more markers.

In certain embodiments of the diagnostic methods provided herein, an increase or decrease in the level of one or more NASH or advanced liver fibrosis markers selected from Tables 1-3, 7 and 9 or 4-6, 8 and 10 in the biological sample as compared to the level of the one or more markers in a normal control sample is an indication that the subject is afflicted with NASH or advanced liver fibrosis. In certain embodiments of the diagnostic methods provided herein, no increase or decrease in the detected expression level of one or more NASH or advanced liver fibrosis markers selected from Tables 1-3, 7 and 9 or 4-6, 8 and 10 in the biological sample as compared to the expression level of the one or more markers in a normal control sample is an indication that the subject is not afflicted with NASH or advanced liver fibrosis or not predisposed to developing NASH or advanced liver fibrosis.

In certain embodiments of the diagnostic methods provided herein, an increase or decrease in the level of one or more NASH or advanced liver fibrosis markers selected from Tables 1-3, 7 and 9 or 4-6, 8 and 10 in the biological sample as compared to the level of the one or more markers in a normal control sample is an indication that the subject is predisposed to developing NASH or advanced liver fibrosis.

In certain embodiments of the monitoring methods provided herein, no increase or decrease in the detected level of one or more NASH or advanced liver fibrosis markers selected from Tables 1-3, 7 and 9 or 4-6, 8 and 10 in the second sample as compared to the level of the one or more markers in the first sample is an indication that the therapy is efficacious for treating NASH or advanced liver fibrosis in the subject. In certain embodiments of the monitoring methods provided herein, wherein an increased or decreased expression level of one or more NASH or advanced liver fibrosis markers selected from Tables 1-3, 7 and 9 or 4-6, 8 and 10 in the second sample as compared to the expression level in the first sample is an indication that the therapy is not efficacious in the treatment of NASH or advanced liver fibrosis.

In certain embodiments the monitoring methods provided herein further comprise comparing the level of the one or more markers selected from Tables 1-3, 7 and 9 or 4-6, 8 and 10 in the first sample or the level of the one or more NASH or advanced liver fibrosis markers selected from Tables 1-3, 7 and 9 or 4-6, 8 and 10 in the second sample with the level of the one or more markers in a control sample.

In certain embodiments of the monitoring methods provided herein, an increase or decrease in the level of the one or more NASH or advanced liver fibrosis markers selected from Tables 1-3, 7 and 9 or 4-6, 8 and 10 in the second sample as compared to the level of the one or more markers in the first sample is an indication for selection of active treatment of NASH or advanced liver fibrosis in the subject. In certain embodiments of the monitoring methods provided herein, no increase or decrease in the detected level of the one or more NASH or advanced liver fibrosis markers selected from Tables 1-3, 7 and 9 or 4-6, 8 and 10 in the second sample as compared to the level of the one or more markers in the first sample is an indication against selection of active treatment of NASH or advanced liver fibrosis in the subject.

In certain embodiments of the monitoring methods provided herein, modulation of the level of the one or more NASH or advanced liver fibrosis markers selected from Tables 1-3, 7 and 9 or 4-6, 8 and 10 in the second sample as compared to the level of the corresponding marker(s) in the first sample is indicative of a change in NASH or advanced liver fibrosis status in response to treatment of the NASH or advanced liver fibrosis in the subject. In certain embodiments of the monitoring methods provided herein, the methods further comprise comparing the level of the one or more NASH or advanced liver fibrosis markers selected from Tables 1-3, 7 and 9 or 4-6, 8 and 10 in the second sample to the level of the corresponding markers in a normal control sample.

In any of the aforementioned embodiments, the methods may also include a step of determining whether a subject having NASH or advanced liver fibrosis or who is being treated for NASH or advanced liver fibrosis is responsive to a particular treatment. Such a step can include, for example, measuring the level of the one or more NASH or advanced liver fibrosis markers selected from Tables 1-3, 7 and 9 or 4-6, 8 and 10 prior to administering an anti-NASH or advanced liver fibrosis treatment, and measuring the level of the one or more NASH or advanced liver fibrosis markers selected from Tables 1-3, 7 and 9 or 4-6, 8 and 10 after administering the anti-NASH or advanced liver fibrosis treatment, and comparing the expression level before and after treatment. Determining that the NASH or advanced liver fibrosis is responsive to the treatment if the expression level of the one or more markers is higher or lower than before treatment as compared to after treatment. The method may further include the step of adjusting the treatment to a higher dose in order to increase the responsiveness to the treatment, or adjusting the treatment to a lower dose in order to descrease the responsiveness to the treatment.

In any of the aforementioned embodiments, the methods may also include a step of determining whether a subject having NASH or advanced liver fibrosis or who is being treated for NASH or advanced liver fibrosis is not responsive to a particular treatment. Such a step can include, for example, measuring the level of the one or more NASH or advanced liver fibrosis markers selected from Tables 1-3, 7 and 9 or 4-6, 8 and 10 prior to administering an anti-NASH or advanced liver fibrosis treatment, and measuring the level of the one or more NASH or advanced liver fibrosis markers selected from Tables 1-3, 7 and 9 or 4-6, 8 and 10 after administering the anti-NASH or advanced liver fibrosis treatment, and comparing the expression level before and after treatment. Determining that the NASH or advanced liver fibrosis is not responsive to the treatment if the expression level of the one or more markers is higher or lower than before treatment as compared to after treatment. The method may further include the step of adjusting the treatment to a higher dose in order to increase the responsiveness to the treatment.

In certain embodiments, the level of the marker, e.g., a NASH marker, is increased when compared to the predetermined threshold value in the subject. In some embodiments, the marker, e.g., a NASH marker, is selected from the group consisting of THBS2, YES1, COLEC11, IGFBP7, GDF15, C7, ITGA1 ITGB1, SELE, ACY1, TGFB1, TIMP1, DCN, LTBP4, NAGK, IL19, MMP7, ANGPT2, and POR. In other embodiments, the marker, e.g., a NASH marker, comprises one or more markers selected from Table 1, wherein the one or more markers have an FC ratio greater than 1, or a Log FC value greater than 0.

In other embodiments, the level of the marker, e.g., a NASH marker, is decreased when compared to the predetermined threshold value in the subject. In some embodiments, the marker, e.g., a NASH marker, is selected from the group consisting of BCL2A1, N6AMT1, IGFBP5, AKT2 and APOM. In other embodiments, the marker, e.g., a NASH marker, comprises one or more markers selected from Table 1, wherein the one or more markers have an FC ratio greater than 1, or a Log FC value greater than 0.

In certain embodiments, the level of the marker, e.g., a fibrosis marker, is increased when compared to the predetermined threshold value in the subject. In some embodiments, the marker, e.g., a fibrosis marker, is selected from the group consisting of SELE, IGFBP7, THBS2, C7, COLEC11, DCN, NAGK, CCL21, IL1R2, LTBP4, TIMP1, CD163, PRSS22, A2M, MMP7, CHRDL1, ROBO2, TIE1, LAMA1 LAMB1 LAMC1. In other embodiments, the marker, e.g., a fibrosis marker, comprises one or more markers selected from Table 4, wherein the one or more markers have an FC ratio greater than 1, or a Log FC value greater than 0.

In other embodiments, the level of the marker, e.g., a fibrosis marker, is decreased when compared to the predetermined threshold value in the subject. In some embodiments, the marker, e.g., a fibrosis marker, is selected from the group consisting of IGFBP5 and PRL. In other embodiments, the marker, e.g., a fibrosis marker, comprises one or more markers selected from Table 4, wherein the one or more markers have an FC ratio greater than 1, or a Log FC value greater than 0.

In certain embodiments the diagnostic and monitoring methods provided herein further comprise comparing the detected level of the one or more NASH or advanced liver fibrosis markers in the biological samples with one or more control samples wherein the control sample is one or more of a sample from the same subject at an earlier time point than the biological sample, a sample from a subject with simple steatosis, or a sample from a subject with NASH without advanced liver fibrosis.

In other embodiments, the present invention also involves the analysis and consideration of any clinical and/or patient-related health data, for example, data obtained from an Electronic Medical Record (e.g., collection of electronic health information about individual patients or populations relating to various types of data, such as, demographics, medical history, medication and allergies, immunization status, laboratory test results, radiology images, biopsy results, vital signs, personal statistics like age and weight, and billing information).

In certain embodiments the diagnostic and monitoring methods provided herein further comprise selecting a subject for having or being suspected of having NASH or advanced liver fibrosis. In one embodiment, if, following the diagnostic methods of the invention, the subject has NASH or is suspected of having NASH, the subject can be subjected to further diagnostic methods, including liver biopsy or imaging of the liver. If, based on the diagnostic methods of the invention, the subject is found not to have NASH, no further diagnostic methods may be performed, or the subject can be monitored for further disease progression.

In another embodiment, if, following the diagnostic methods of the invention, the selected subject has advanced fibrosis or is suspected of having advanced fibrosis, the subject can be subjected to further diagnostic methods, including liver biopsy or imaging of the liver. If, based on the diagnostic methods of the invention, the subject is found not to have advanced fibrosis, no further diagnostic methods may be performed, or the subject can be monitored for further disease progression.

In certain embodiments the diagnostic and monitoring methods provided herein further comprising obtaining a biological sample from a subject suspected of having or being at risk of having NASH or advanced liver fibrosis.

In certain embodiments the diagnostic and monitoring methods provided herein further comprising selecting a treatment regimen for the subject based on the level of the one or more NASH or advanced liver fibrosis markers selected from Tables 1-3, 7 and 9 or 4-6, 8 and 10.

In certain embodiments the diagnostic and monitoring methods provided herein further comprising treating the subject with a regimen including one or more treatments selected from the group consisting of stearoyl CoA desaturase-1 inhibitor, farnesoid X receptor agonist, CCR2 and CCR5 chemokine antagonist, PPAR alpha and delta agonist, caspase inhibitor, Galectin-3 inhibitor, acetyl CoA carboxylase inhibitor, PDE-5 inhibitor, deacetylase sirtuin stimulator, ileal sodium bile acid co-transporter inhibitor, lysyl oxidase-like 2 (LOXL2) inhibitor, ASK-1 inhibitor, DPP4 inhibitor, FGF21 agonist, ASBT inhibitor, niacin analogue, SGLT2 inhibitor, GLP1R agonist, HSP47 inhibitor, MAPK5 inhibitor, thyroid receptor β agonist, LTD receptor antagonist, semicarbazide sensitive amine oxidase inhibitor, and an immunomodulatory agent.

In certain embodiments the diagnostic and monitoring methods provided herein further comprise selecting the one or more specific treatment regimens for the subject based on the results of the diagnostic and monitoring methods provided herein. In one embodiment, a treatment regimen known to be effective against NASH or advanced liver fibrosis having the biomarker signature detected in the subject/sample is selected for the subject. In certain embodiments, the treatment method is started, changed, revised, or maintained based on the results from the diagnostic or prognostic methods of the invention, e.g., when it is determined that the subject is responding to the treatment regimen, or when it is determined that the subject is not responding to the treatment regimen, or when it is determined that the subject is insufficiently responding to the treatment regimen. In certain embodiments, the treatment method is changed based on the results from the diagnostic or prognostic methods.

In certain other embodiments the diagnostic and monitoring methods provided herein further comprise introducing one or more specific treatment regimens for the subject based on the results of the diagnostic and monitoring methods provided herein. In one embodiment, a treatment regimen known to be effective against NASH or advanced liver fibrosis is selected for the subject. In certain embodiments, the treatment method is started, change, revised, or maintained based on the results from the diagnostic or prognostic methods of the invention, e.g., when it is determined that the subject is responding to the treatment regimen, or when it is determined that the subject is not responding to the treatment regimen, or when it is determined that the subject is insufficiently responding to the treatment regimen. In certain embodiments, the treatment method is changed based on the results from the diagnostic or prognostic methods.

In yet other embodiments the diagnostic and monitoring methods provided herein further comprise the step of administering a therapeutically effective amount of an anti-NASH or anti-fibrosis therapy based on the results of the diagnostic and monitoring methods provided herein. In one embodiment, a treatment regimen known to be effective against NASH or advanced liver fibrosis is selected for the subject. In certain embodiments, the treatment method is administered based on the results from the diagnostic or prognostic methods of the invention, e.g., when it is determined that the subject expresses one or more biomarkers of the invention (i.e., the one or more NASH or advanced liver fibrosis markers selected from Tables 1-3, 7 and 9 or 4-6, 8 and 10) above or below some threshold level that is indicative of NASH or advanced liver fibrosis.

In certain embodiments, treatments for NASH or advanced liver fibrosis include one or more of stearoyl CoA desaturase-1 inhibitor, farnesoid X receptor agonist, CCR2 and CCR5 chemokine antagonist, PPAR alpha and delta agonist, caspase inhibitor, Galectin-3 inhibitor, acetyl CoA carboxylase inhibitor, PDE-5 inhibitor, deacetylase sirtuin stimulator, ileal sodium bile acid co-transporter inhibitor, lysyl oxidase-like 2 (LOXL2) inhibitor, ASK-1 inhibitor, DPP4 inhibitor, FGF21 agonist, ASBT inhibitor, niacin analogue, SGLT2 inhibitor, GLP1R agonist, HSP47 inhibitor, MAPK5 inhibitor, thyroid receptor β agonist, LTD receptor antagonist, semicarbazide sensitive amine oxidase inhibitor, and an immunomodulatory agent, based on the results of a method of the present invention for an interval prior to performing a subsequent diagnostic, prognostic, or monitoring method provided herein.

In certain embodiments of the diagnostic and monitoring methods provided herein, the method further comprises isolating a component of the biological sample.

In certain embodiments of the diagnostic and monitoring methods provided herein, the method further comprises labeling a component of the biological sample.

In certain embodiments of the diagnostic and monitoring methods provided herein, the method further comprises amplifying a component of a biological sample.

In certain embodiments of the diagnostic and monitoring methods provided herein, the method comprises forming a complex with a probe and a component of a biological sample. In certain embodiments, forming a complex with a probe comprises forming a complex with at least one non-naturally occurring reagent. In certain embodiments of the diagnostic and monitoring methods provided herein, the method comprises processing the biological sample. In certain embodiments of the diagnostic and monitoring methods provided herein, the method of detecting a level of at least two markers comprises a panel of markers. In certain embodiments of the diagnostic and monitoring methods provided herein, the method of detecting a level comprises attaching the marker to be detected to a solid surface.

In certain embodiments, the method further comprising obtaining a third sample obtained from the subject at a third time (e.g., wherein the subject has not been actively treated), detecting a level of a NASH or advanced liver fibrosis marker in the third sample, wherein the NASH or advanced liver fibrosis markers comprises one or more markers selected from Tables 1-3, 7 and 9 or 4-6, 8 and 10, respectively, and comparing the level the NASH or advanced liver fibrosis marker in the third sample with the level of the NASH or advanced liver fibrosis marker in the first sample and/or the one or more markers in the second sample.

In certain embodiments, an increased or decreased level of the NASH or advanced liver fibrosis marker in the second sample as compared to the level of the NASH or advanced liver fibrosis marker in the first sample is an indication that the therapy is not efficacious in the treatment of NASH or advanced liver fibrosis, wherein the NASH or advanced liver fibrosis markers comprises one or more markers selected from Tables 1-3, 7 and 9 or 4-6, 8 and 10, respectively.

In certain embodiments, an increased or decreased level the NASH or advanced liver fibrosis marker in the second sample as compared to the NASH or advanced liver fibrosis marker in the first sample is an indication for selecting active treatment for NASH or advanced liver fibrosis, wherein the NASH or advanced liver fibrosis markers comprises one or more markers selected from Tables 1-3, 7 and 9 or 4-6, 8 and 10, respectively.

6. Monitoring Clinical Trials

Monitoring the influence of agents (e.g., drug compounds) on the level of a marker of the invention can be applied not only in basic drug screening or monitoring the treatment of a single subject, but also in clinical trials. For example, the effectiveness of an agent to affect marker expression can be monitored in clinical trials of subjects receiving treatment for NAFLD or NASH or fibrosis. In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate) comprising the steps of (i) obtaining a pre-administration sample from a subject prior to administration of the agent; (ii) detecting the level of one or more selected markers of the invention in the pre-administration sample; (iii) obtaining one or more post-administration samples from the subject; (iv) detecting the level of the marker(s) in the post-administration samples; (v) comparing the level of the marker(s) in the pre-administration sample with the level of the marker(s) in the post-administration sample or samples; and (vi) altering the administration of the agent to the subject accordingly. For example, increased expression of the marker during the course of treatment may indicate ineffective dosage and the desirability of increasing the dosage. Conversely, decreased expression of the marker may indicate efficacious treatment and no need to change dosage.

H. Treatment/Therapeutics

The present invention provides methods for treating disease states, e.g., NASH in a subject, e.g., a human, using one or more (e.g., 1, 2, 3, 4, 5, 6, 7, 8, 9 or more) markers selected from Tables 1-3, 7 and 9.

The present invention provides methods for treating disease states, e.g., advanced liver fibrosis in a subject, e.g., a human, using one or more (e.g., 1, 2, 3, 4, 5, 6, 7, 8, 9 or more) markers selected from Tables 4-6, 8 and 10.

The present invention also provides methods for treating or preventing NASH or advanced liver fibrosis with a therapeutic, e.g., a modulator, that modulates (e.g., reduces, or increases) the level of expression or activity of one or more (e.g., 1, 2, 3, 4, 5, 6, 7, 8, 9 or more) markers selected from Tables 1-3, 7 and 9 or 4-6, 8 and 10.

In certain embodiments, the modulator is an inhibitor that decreases the level or activity of the marker, e.g., a NASH marker of Tables 1-3, 7 and 9, whose expression level is increased in a subject having NASH. In some embodiments, the NASH marker is selected from the group consisting of THBS2, YES1, COLEC11, IGFBP7, GDF15, C7, ITGA1 ITGB1, SELE, ACYL, TGFB1, TIMP1, DCN, LTBP4, NAGK, IL19, MMP7, ANGPT2, and POR. In other embodiments, the NASH marker comprises one or more markers selected from Table 1, wherein the one or more markers have an FC ratio greater than 1, or a Log FC value greater than 0.

In other embodiments, the modulator is an agonist that increases the level or activity of the marker, e.g., a NASH marker of Tables 1-3, 7 and 9, whose expression level is decreased in a subject having NASH. In some embodiments, the NASH marker is selected from the group consisting of BCL2A1, N6AMT1, IGFBP5, AKT2 and APOM. In other embodiments, the NASH marker comprises one or more markers selected from Table 1, wherein the one or more markers have an FC ratio greater than 1, or a Log FC value greater than 0.

In certain embodiments, the modulator is an inhibitor that decreases the level or activity of the marker, e.g., an advanced liver fibrosis marker of Tables 4-6, 8 and 10, whose expression level is increased in a subject having advanced liver fibrosis. In some embodiments, the advanced liver fibrosis marker is selected from the group consisting of GDF15, SELE, IGFBP7, THBS2, C7, COLEC11, DCN, NAGK, CCL21, IL1R2, LTBP4, TIMP1, CD163, PRSS22, A2M, MMP7, CHRDL1, ROBO2, TIE1, LAMA1 LAMB1 LAMC1. In other embodiments, the advanced liver fibrosis marker comprises one or more markers selected from Table 4, wherein the one or more markers have an FC ratio greater than 1, or a Log FC value greater than 0.

In other embodiments, the modulator is an agonist that increases the level or activity of the marker, e.g., an advanced liver fibrosis marker of Tables 4-6, 8 and 10, whose expression level is decreased in a subject having advanced liver fibrosis. In some embodiments, the NASH or advanced liver fibrosis marker is selected from the group consisting of IGFBP5 and PRL. In other embodiments, the NASH or advanced liver fibrosis marker comprises one or more markers selected from Table 4, wherein the one or more markers have an FC ratio greater than 1, or a Log FC value greater than 0.

In certain embodiments, the NASH marker protein or the fibrosis marker protein to be modulated comprises at least one secreted, extracellular or transmembrane marker protein selected from Tables 1-3 or Tables 4-6, respectively. In one embodiment, the one or more NASH marker protein or fibrosis marker protein to be modulated is a receptor, growth factor, cytokine, chemokine, extracellular matrix protein or enzyme selected from Tables 1-3 or Tables 4-6, respectively.

1. Nucleic Acid Therapeutics

Nucleic acid therapeutics are well known in the art. Nucleic acid therapeutics include both single stranded and double stranded (i.e., nucleic acid therapeutics having a complementary region of at least 15 nucleotides in length that may be one or two nucleic acid strands) nucleic acids that are complementary to a target sequence in a cell. Nucleic acid therapeutics can be delivered to a cell in culture, e.g., by adding the nucleic acid to culture media either alone or with an agent to promote uptake of the nucleic acid into the cell. Nucleic acid therapeutics can be delivered to a cell in a subject, i.e., in vivo, by any route of administration. The specific formulation will depend on the route of administration.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

Sequences can be "fully complementary" with respect to each when there is base-pairing of the nucleotides of the first nucleotide sequence with the nucleotides of the second nucleotide sequence over the entire length of the first and second nucleotide sequences. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs as is common in double stranded nucleic acid therapeutics, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary," "fully complementary", and "substantially complementary" herein may be used with respect to the base matching between the sense strand and the antisense strand of a dsRNA, or between an antisense nucleic acid or the antisense strand of dsRNA and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest, including a 5' UTR, an open reading frame (ORF), or a 3' UTR. For example, a polynucleotide is complementary to at least a part of the mRNA corresponding to the protein markers of Tables 1-6.

Nucleic acid therapeutics typically include chemical modifications to improve their stability and to modulate their pharmacokinetic and pharmacodynamic properties. For example, the modifications on the nucleotides can include, but are not limited to, LNA, HNA, CeNA, 2'-hydroxyl, and combinations thereof.

Nucleic acid therapeutics may further comprise at least one phosphorothioate or methylphosphonate internucleotide linkage. The phosphorothioate or methylphosphonate internucleotide linkage modification may occur on any nucleotide of the sense strand or antisense strand or both (in nucleic acid therapeutics including a sense strand) in any position of the strand. For instance, the internucleotide linkage modification may occur on every nucleotide on the sense strand or antisense strand; each internucleotide linkage modification may occur in an alternating pattern on the sense strand or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

A. Single Stranded Therapeutics

Antisense nucleic acid therapeutic agent single stranded nucleic acid therapeutics, typically about 16 to 30 nucleotides in length and are complementary to a target nucleic acid sequence in the target cell, either in culture or in an organism.

Patents directed to antisense nucleic acids, chemical modifications, and therapeutic uses are provided, for example, in U.S. Pat. No. 5,898,031 related to chemically modified RNA-containing therapeutic compounds, and U.S. Pat. No. 6,107,094 related methods of using these compounds as therapeutic agent. U.S. Pat. No. 7,432,250 related to methods of treating patients by administering single-stranded chemically modified RNA-like compounds; and U.S. Pat. No. 7,432,249 related to pharmaceutical compositions containing single-stranded chemically modified RNA-like compounds. U.S. Pat. No. 7,629,321 is related to methods of cleaving target mRNA using a single-stranded oligonucleotide having a plurality RNA nucleosides and at least one chemical modification. Each of the patents listed in the paragraph are incorporated herein by reference.

B. Double Stranded Therapeutics

In many embodiments, the duplex region is 15-30 nucleotide pairs in length. In some embodiments, the duplex region is 17-23 nucleotide pairs in length, 17-25 nucleotide pairs in length, 23-27 nucleotide pairs in length, 19-21 nucleotide pairs in length, or 21-23 nucleotide pairs in length.

In certain embodiments, each strand has 15-30 nucleotides.

The RNAi agents that are used in the methods of the invention include agents with chemical modifications as disclosed, for example, in Publications WO 2009/073809 and WO/2012/037254, the entire contents of each of which are incorporated herein by reference.

Nucleic acid therapeutic agents for use in the methods of the invention also include double stranded nucleic acid therapeutics. An "RNAi agent," "double stranded RNAi agent," double-stranded RNA (dsRNA) molecule, also referred to as "dsRNA agent," "dsRNA", "siRNA", "iRNA agent," as used interchangeably herein, refers to a complex of ribonucleic acid molecules, having a duplex structure comprising two anti-parallel and substantially complementary, as defined below, nucleic acid strands. As used herein, an RNAi agent can also include dsiRNA (see, e.g., US Patent publication 20070104688, incorporated herein by reference). In general, the majority of nucleotides of each strand are ribonucleotides, but as described herein, each or both strands can also include one or more non-ribonucleotides, e.g., a deoxyribonucleotide and/or a modified oligonucleotide. In addition, as used in this specification, an "RNAi agent" may include ribonucleotides with chemical modifications; an RNAi agent may include substantial modifications at multiple nucleotides. Such modifications may include all types of modifications disclosed herein or known in the art. Any such modifications, as used in a siRNA type molecule, are encompassed by "RNAi agent" for the purposes of this specification and claims. The RNAi agents that are used in the methods of the invention include agents with chemical modifications as disclosed, for example, in U.S. Provisional Application No. 61/561,710, filed on Nov. 18, 2011, International Application No. PCT/US2011/051597, filed on Sep. 15, 2010, and PCT Publication WO 2009/073809, the entire contents of each of which are incorporated herein by reference. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi agent may comprise one or more nucleotide overhangs. The term "siRNA" is also used herein to refer to an RNAi agent as described above.

In another aspect, the agent is a single-stranded antisense RNA molecule. An antisense RNA molecule is complementary to a sequence within the target mRNA. Antisense RNA can inhibit translation in a stoichiometric manner by base pairing to the mRNA and physically obstructing the translation machinery, see Dias, N. et al., (2002) *Mol Cancer Ther* 1:347-355. The antisense RNA molecule may have about 15-30 nucleotides that are complementary to the target mRNA. For example, the antisense RNA molecule may have a sequence of at least 15, 16, 17, 18, 19, 20 or more contiguous nucleotides complementary to the mRNA sequences corresponding to the protein markers of Tables 1-6.

The term "antisense strand" refers to the strand of a double stranded RNAi agent which includes a region that is substantially complementary to a target sequence (e.g., a human TTR mRNA). As used herein, the term "region complementary to part of an mRNA encoding transthyretin" refers to a region on the antisense strand that is substantially complementary to part of a TTR mRNA sequence. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

The invention also includes molecular beacon nucleic acids having at least one region which is complementary to a nucleic acid of the invention, such that the molecular beacon is useful for quantitating the presence of the nucleic acid of the invention in a sample. A "molecular beacon" nucleic acid is a nucleic acid comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid are not annealed with one another, fluorescence of the fluorophore is quenched to a lesser degree. Molecular beacon nucleic acids are described, for example, in U.S. Pat. No. 5,876,930.

I. Drug Screening

As noted above, sets of markers whose expression levels correlate with one or more selected disease characteristics (e.g., NASH or advanced liver fibrosis progression) are attractive targets for identification of new therapeutic agents via screens to detect compounds or entities that inhibit or enhance expression of these biomarker genes and/or their products. Accordingly, the present invention provides methods for the identification of compounds potentially useful for modulating NASH or advanced liver fibrosis progression. In particular, the present invention provides methods for the identification of agents or compounds potentially useful for modulating NASH or advanced liver fibrosis progression wherein the agents or compounds modulate (e.g., increase or decrease) the expression and/or activity of one or more of the markers selected from Tables 1-3, 7 and 9 or 4-6, 8 and 10.

Such assays typically comprise a reaction between a marker of the invention and one or more assay components. The other components may be either the test compound itself, or a combination of test compounds and a natural binding partner of a marker of the invention. Compounds identified via assays such as those described herein may be useful, for example, for modulating, e.g., inhibiting, ameliorating, treating, or preventing the disease. Compounds identified for modulating the expression level of one or more of the markers selected from Tables 1-3, 7 and 9 or 4-6, 8 and 10 are preferably further tested for activity useful in the treatment NASH or advanced liver fibrosis.

The test compounds used in the screening assays of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

The screening methods of the invention comprise contacting a sample from a subject having NASH or NASH with advanced liver fibrosis, with a test compound and determining the ability of the test compound to modulate the expression and/or activity of one or more of the markers selected from Tables 1-3, 7 and 9 or 4-6, 8 and 10.

In another embodiment, the invention provides assays for screening candidate or test compounds which are substrates of a marker of the invention or biologically active portions thereof. In yet another embodiment, the invention provides assays for screening candidate or test compounds which bind to a marker of the invention or biologically active portions thereof. Determining the ability of the test compound to directly bind to a marker can be accomplished, for example, by any method known in the art.

This invention further pertains to novel agents identified by the above-described screening assays. Accordingly, it is within the scope of this invention to further use an agent identified as described herein in an appropriate animal model. For example, an agent capable of modulating the expression and/or activity of a marker of the invention identified as described herein can be used in an animal model to determine the efficacy, toxicity, or side effects of treatment (e.g., of NASH or advanced liver fibrosis) with such an agent. Alternatively, an agent identified as described herein can be used in an animal model to determine the mechanism of action of such an agent. Furthermore, this invention pertains to uses of novel agents identified by the above-described screening assays for treatment as described above.

In certain embodiments, the screening methods are performed using cells contained in a plurality of wells of a multi-well assay plate. Such assay plates are commercially available, for example, from Stratagene Corp. (La Jolla, Calif.) and Corning Inc. (Acton, Mass.) and include, for example, 48-well, 96-well, 384-well and 1536-well plates.

Reproducibility of the results may be tested by performing the analysis more than once with the same concentration of the same candidate compound (for example, by incubating cells in more than one well of an assay plate). Additionally, since candidate compounds may be effective at varying concentrations depending on the nature of the compound and the nature of its mechanism(s) of action, varying concentrations of the candidate compound may be tested. Generally, candidate compound concentrations from 1 fM to about 10 mM are used for screening. Preferred screening concentrations are generally between about 10 pM and about 100 µM.

The screening methods of the invention will provide "hits" or "leads," i.e., compounds that possess a desired but not optimized biological activity. Lead optimization performed on these compounds to fulfill all physicochemical, pharmacokinetic, and toxicologic factors required for clinical usefulness may provide improved drug candidates. The present invention also encompasses these improved drug candidates and their use as therapeutics for modulating NASH or advanced liver fibrosis progression.

J. Kits/Panels

The invention also provides compositions and kits for diagnosing, prognosing, or monitoring a disease or disorder, recurrence of a disorder, or survival of a subject being treated for NASH or advanced liver fibrosis. These kits may include one or more of the following: a reagent that specifically binds to a marker of the invention, and a set of instructions for measuring the level of the marker.

The invention also encompasses kits for detecting the presence of a marker protein or nucleic acid in a biological sample. Such kits can be used to determine if a subject has, or is at risk for developing, NASH or advanced liver fibrosis. For example, the kit can comprise a labeled compound or agent capable of detecting a marker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for use of the kit for practicing any of the methods provided herein or interpreting the results obtained using the kit based on the teachings provided herein. The kits can also include reagents for detection of a control protein in the sample not related to NASH or advanced liver fibrosis, e.g., actin for tissue samples, albumin in blood or blood derived samples for normalization of the amount of the marker present in the sample. The kit can also include the purified marker for detection for use as a control or for quantitation of the assay performed with the kit.

Kits include a panel of reagents for use in a method to diagnose NASH or advanced liver fibrosis in a subject (or to identify a subject predisposed to developing NASH or advanced liver fibrosis, etc.), the panel comprising at least two detection reagents, wherein each detection reagent is specific for one NASH or advanced liver fibrosis-specific protein, wherein said NASH or advanced liver fibrosis-specific proteins are selected from the NASH or advanced liver fibrosis-specific protein sets provided herein.

For antibody-based kits, the kit can comprise, for example: (1) a first antibody (e.g., attached to a solid support) which binds to a first marker protein; and, optionally, (2) a second, different antibody which binds to either the first marker protein or the first antibody and is conjugated to a detectable label. In certain embodiments, the kit includes (1) a second antibody (e.g., attached to a solid support) which binds to a second marker protein; and, optionally, (2) a second, different antibody which binds to either the second marker protein or the second antibody and is conjugated to a detectable label. The first and second marker proteins are different. In an embodiment, the first and second markers are markers of the invention, e.g., one or more of the markers selected from Tables 1-3, 7 and 9 or Tables 4-6, 8 and 10. In certain embodiments, the kit comprises a third antibody which binds to a third marker protein which is different from the first and second marker proteins, and a second different antibody that binds to either the third marker protein or the antibody that binds the third marker protein wherein the third marker protein is different from the first and second marker proteins.

For oligonucleotide-based kits, the kit can comprise, for example: (1) an oligonucleotide, e.g., a detectably labeled oligonucleotide, which hybridizes to a nucleic acid sequence encoding a marker protein or (2) a pair of primers useful for amplifying a marker nucleic acid molecule. In certain embodiments, the kit can further include, for example: (1) an oligonucleotide, e.g., a second detectably labeled oligonucleotide, which hybridizes to a nucleic acid sequence encoding a second marker protein or (2) a pair of primers useful for amplifying the second marker nucleic acid molecule. The first and second markers are different. In an embodiment, the first and second markers are markers of the invention, e.g., one or more of the markers selected from Tables 1-3, 7 and 9 or Tables 4-6, 8 and 10. In certain embodiments, the kit can further include, for example: (1) an oligonucleotide, e.g., a third detectably labeled oligonucleotide, which hybridizes to a nucleic acid sequence encoding a third marker protein or (2) a pair of primers useful for amplifying the third marker nucleic acid molecule wherein the third marker is different from the first and second markers. In certain embodiments, the kit includes a third primer specific for each nucleic acid marker to allow for detection using quantitative PCR methods.

For chromatography methods, the kit can include markers, including labeled markers, to permit detection and identification of one or more markers of the invention, e.g., one or more of the markers selected from Tables 1-3, 7 and 9 or Tables 4-6, 8 and 10 by chromatography. In certain embodiments, kits for chromatography methods include compounds for derivatization of one or more markers of the invention. In certain embodiments, kits for chromatography methods include columns for resolving the markers of the method.

Kits of the present invention can also include aptamers or modified oligonucleotides as reagents for detection of the one or more markers of the invention. In one embodiment, the aptamer or modified oligonucleotide reagents are used alone for detection of the one or more markers. In another embodiment, the aptamer or modified oligonucleotide can be used in combination with one or more antibodies for detection of the one or more markers of the invention.

Reagents specific for detection of a marker of the invention, e.g., one or more of the markers selected from Tables 1-3, 7 and 9 or Tables 4-6, 8 and 10, allow for detection and quantitation of the marker in a complex mixture, e.g., serum sample. In certain embodiments, the reagents are species specific. In certain embodiments, the reagents are not species specific. In certain embodiments, the reagents are isoform specific. In certain embodiments, the reagents are not isoform specific.

In certain embodiments, the kits for the diagnosis, monitoring, or characterization of NASH or advanced liver fibrosis comprise at least one reagent specific for the detection of the level of one or more of the markers selected from Tables 1-3, 7 and 9 or Tables 4-6, 8 and 10. In certain embodiments, the kits further comprise instructions for the diagnosis, monitoring, or characterization of NASH or advanced liver fibrosis based on the level of the at least one marker selected from Tables 1-3, 7 and 9 or Tables 4-6, 8 and 10.

In certain embodiments, the kits can also comprise, e.g., a buffering agents, a preservative, a protein stabilizing agent, reaction buffers. The kit can further comprise components necessary for detecting the detectable label (e.g., an enzyme or a substrate). The kit can also contain a control sample or a series of control samples which can be assayed and compared to the test sample. The controls can be control serum samples or control samples of purified proteins or nucleic acids, as appropriate, with known levels of target markers. Each component of the kit can be enclosed within an individual container and all of the various containers can be within a single package, along with instructions for interpreting the results of the assays performed using the kit.

The kits of the invention may optionally comprise additional components useful for performing the methods of the invention.

The invention further provides panels of reagents for detection of one or more NASH or advanced liver fibrosis marker in a subject sample and at least one control reagent. In certain embodiments, the NASH or advanced liver fibrosis marker comprises at least two or more markers. For example, a panel for detection of NASH may comprise reagents for detection of one or more NASH panels of markers set forth in Tables 3, 7 and 9. Also for example, a panel for detection of advanced liver fibrosis may comprise reagents for detection of one or more fibrosis panels of markers set forth in Tables 6, 8 and 10.

In certain embodiments, the control reagent is to detect the marker for detection in the biological sample wherein the panel is provided with a control sample containing the marker for use as a positive control and optionally to quantitate the amount of marker present in the biological sample. In certain embodiments, the panel includes a detection reagent for a maker not related to NASH or advanced liver fibrosis that is known to be present or absent in the biological sample to provide a positive or negative control, respectively. The panel can be provided with reagents for detection of a control protein in the sample not related to NASH or advanced liver fibrosis, e.g., actin for tissue samples, albumin in blood or blood derived samples for normalization of the amount of the marker present in the sample. The panel can be provided with a purified marker for detection for use as a control or for quantitation of the assay performed with the panel.

In certain embodiments, the level of the marker, e.g., a NASH marker, in the panel is increased when compared to a control or a predetermined threshold value. In some embodiments, the marker, e.g., a NASH marker, in the panel, is selected from the group consisting of THBS2, YES1, COLEC11, IGFBP7, GDF15, C7, ITGA1 ITGB1, SELE, ACYL, TGFB1, TIMP1, DCN, LTBP4, NAGK, IL19, MMP7, ANGPT2, and POR. In other embodiments, the marker, e.g., a NASH marker, comprises one or more markers selected from Table 1, wherein the one or more markers have an FC ratio greater than 1, or a Log FC value greater than 0.

In other embodiments, the level of the marker, e.g., a NASH marker in the panel, is decreased when compared to a control or a predetermined threshold value. In some embodiments, the marker, e.g., a NASH marker, in the panel is selected from the group consisting of BCL2A1, N6AMT1, IGFBP5, AKT2 and APOM. In other embodiments, the marker, e.g., a NASH marker, comprises one or more markers selected from Table 1, wherein the one or more markers have an FC ratio greater than 1, or a Log FC value greater than 0.

In certain embodiments, the level of the marker, e.g., a fibrosis marker in the panel, is increased when compared to a control or a predetermined threshold value. In some embodiments, the marker, e.g., a fibrosis marker, is selected from the group consisting of GDF15, SELE, IGFBP7, THBS2, C7, COLEC11, DCN, NAGK, CCL21, IL1R2, LTBP4, TIMP1, CD163, PRSS22, A2M, MMP7, CHRDL1, ROBO2, TIE1, LAMA1 LAMB1 LAMC1. In other embodiments, the marker, e.g., a fibrosis marker in the panel, comprises one or more markers selected from Table 4, wherein the one or more markers have an FC ratio greater than 1, or a Log FC value greater than 0.

In other embodiments, the level of the marker, e.g., a fibrosis marker in the panel, is decreased when compared to to control or a predetermined threshold value. In some embodiments, the marker, e.g., a fibrosis marker, is selected from the group consisting of IGFBP5 and PRL In other embodiments, the marker, e.g., a fibrosis marker, comprises one or more markers selected from Table 4, wherein the one or more markers have an FC ratio greater than 1, or a Log FC value greater than 0.

In some embodiments, the panel comprises one or more NASH or advanced liver fibrosis markers with an increased level when compared to a control or a predetermined threshold value, and/or one or more NASH or advanced liver fibrosis markers with a decreased level when compared to a control or a predetermined threshold value.

In a preferred embodiment, the panel includes reagents for detection of two or more markers of the invention (e.g., 2, 3, 4, 5, 6, 7, 8, 9), preferably in conjunction with a control reagent. In the panel, each marker is detected by a reagent specific for that marker. In certain embodiments, the panel includes replicate wells, spots, or portions to allow for analysis of various dilutions (e.g., serial dilutions) of biological samples and control samples. In a preferred embodiment, the panel allows for quantitative detection of one or more markers of the invention.

In certain embodiments, the panel is a protein chip for detection of one or more markers. In certain embodiments, the panel is an ELISA plate for detection of one or more markers. In certain embodiments, the panel is a plate for quantitative PCR for detection of one or more markers.

In certain embodiments, the panel of detection reagents is provided on a single device including a detection reagent for one or more markers of the invention and at least one control sample. In certain embodiments, the panel of detection reagents is provided on a single device including a detection reagent for two or more markers of the invention and at least one control sample. In certain embodiments, multiple panels for the detection of different markers of the invention are provided with at least one uniform control sample to facilitate comparison of results between panels.

EXAMPLES

This invention is further illustrated by the following examples which should not be construed as limiting. The contents of all references, GenBank Accession and Gene numbers, and published patents and patent applications cited throughout the application are hereby incorporated by reference. Those skilled in the art will recognize that the invention may be practiced with variations on the disclosed structures, materials, compositions and methods, and such variations are regarded as within the ambit of the invention.

Example 1: Quantitative Proteomics Strategy Identifies Panels of New Candidate Biomarkers for NASH And for Advanced Liver Fibrosis in Serum In order to identify new biomarkers for NASH and for advanced liver fibrosis, the proteome in serum from 20 simple steatosis, 20 NASH without advanced liver fibrosis, and 20 NASH with advanced liver fibrosis patients were evaluated using technology from Somalogics, SOMAscan. FIG. 1 shows the overall study design.

SOMAscan (SomaLogic) is a highly multiplexed, sensitive, and quantitative proteomic tool for biomarker discovery that uses SOMAmers (Slow Off-rate Modified Aptamers), modified DNA aptamers, which are oligonucleotides that bind with high specificity and high affinity to preselected proteins. SOMAscan simultaneously quantifies 1310 human proteins in 65 µl of serum by transforming each individual protein concentration into a corresponding SOMAmer concentration, which is then quantified using a DNA microarray readout. Key advantages of SOMAscan are a median lower limit of detection (LLOD) of 40 fM (<1 pg/ml), an exceptional dynamic range of >8 logs, and excellent reproducibility (median coefficient of variation [CV]<5%). SOMAscan's depth of coverage, with a particular focus on proteins found in blood, offers unprecedented power for biomarker discovery with a >10,000-fold greater dynamic range than other proteomic technologies. SOMAscan is particularly well-suited for studying NASH, because it provides a more complete picture of multiple pathways. SOMAscan is the only multiplex system for inflammation that can simultaneously quantify all complement system components, acute phase proteins, cytokines and chemokines in 65 µl of serum.

Serum for protein biomarkers in patients entering evaluation for simple steatosis or NASH were evaluated. All patients in this cohort underwent a detailed baseline evaluation and were assessed for NASH and fibrosis by liver biopsy. Serum was collected from all participants prior to diagnosis. Various clinical and laboratory evaluations were performed which can be incorporated into development of a risk score that combines clinical variables with the NASH and the advanced liver fibrosis predictors to generate a highly proprietary diagnostic algorithm. The primary goal was to examine novel serum protein biomarkers for NASH and advanced liver fibrosis and NASH- or advanced liver fibrosis-specific perturbations that provide insights into pathophysiological pathways underlying NASH and advanced liver fibrosis development and progression, as well as identify novel drivers of NASH and advanced liver fibrosis for discovery of new biologics or other kinds of drugs targeting such key causal proteins.

Applying this SOMAscan assay to the 60 samples across 1310 proteins, multiple proteins that are differentially expressed between simple steatosis and NASH, NASH without advanced liver fibrosis and NASH with advanced liver fibrosis were identified. Several biomarker panels that accurately separated simple steatosis from NASH and NASH without advanced liver fibrosis from NASH with advanced liver fibrosis were generated when analyzed by hierarchical clustering, principal component analysis or using various biomarker selection algorithms taking into account False Discovery Rate (FDR) and other criteria such as support vector machines (SVM) or other machine learning approaches. Multiple biomarker panels for this differential serum protein expression analysis were generated. The ratio of top upregulated to top downregulated protein were also analyzed to determine whether such a ratio analysis would accurately discriminate between simple steatosis and NASH or NASH without advanced liver fibrosis and NASH with advanced liver fibrosis. Indeed, using the ratio of 2 or a few more proteins resulted in very high sensitivity, specificity, and accuracy. As demonstrated herein, the SOMAscan analysis confirmed that this is a powerful tool to discover novel, low abundance, high accuracy biomarkers and new pathways for NASH and fibrosis.

The strategy to test the diagnostic performance of candidate biomarkers involves development of prediction models that can be tested by Leave-One-Out Crossvalidation (L1OXV) on the training set and then later on with independent validation sets. Mann Whitney U test with Benjamini-Hochberg (BH) correction was used in this study. The support vector machine (SVM) algorithm was applied to the SOMAscan data to develop markers for NASH with advanced liver fibrosis versus simple steatosis, NASH without advanced liver fibrosis versus simple steatosis, NASH with and without advanced liver fibrosis versus simple steatosis, and NASH without advanced liver fibrosis versus NASH with advanced liver fibrosis. The following notation: NASH with Advanced liver fibrosis (AN, n=20); NASH without Advanced liver fibrosis (NN, n=20); Simple Steatosis (ST, n=20), was used.

Simple Steatosis Versus NASH with Advanced Liver Fibrosis

Figure 2:
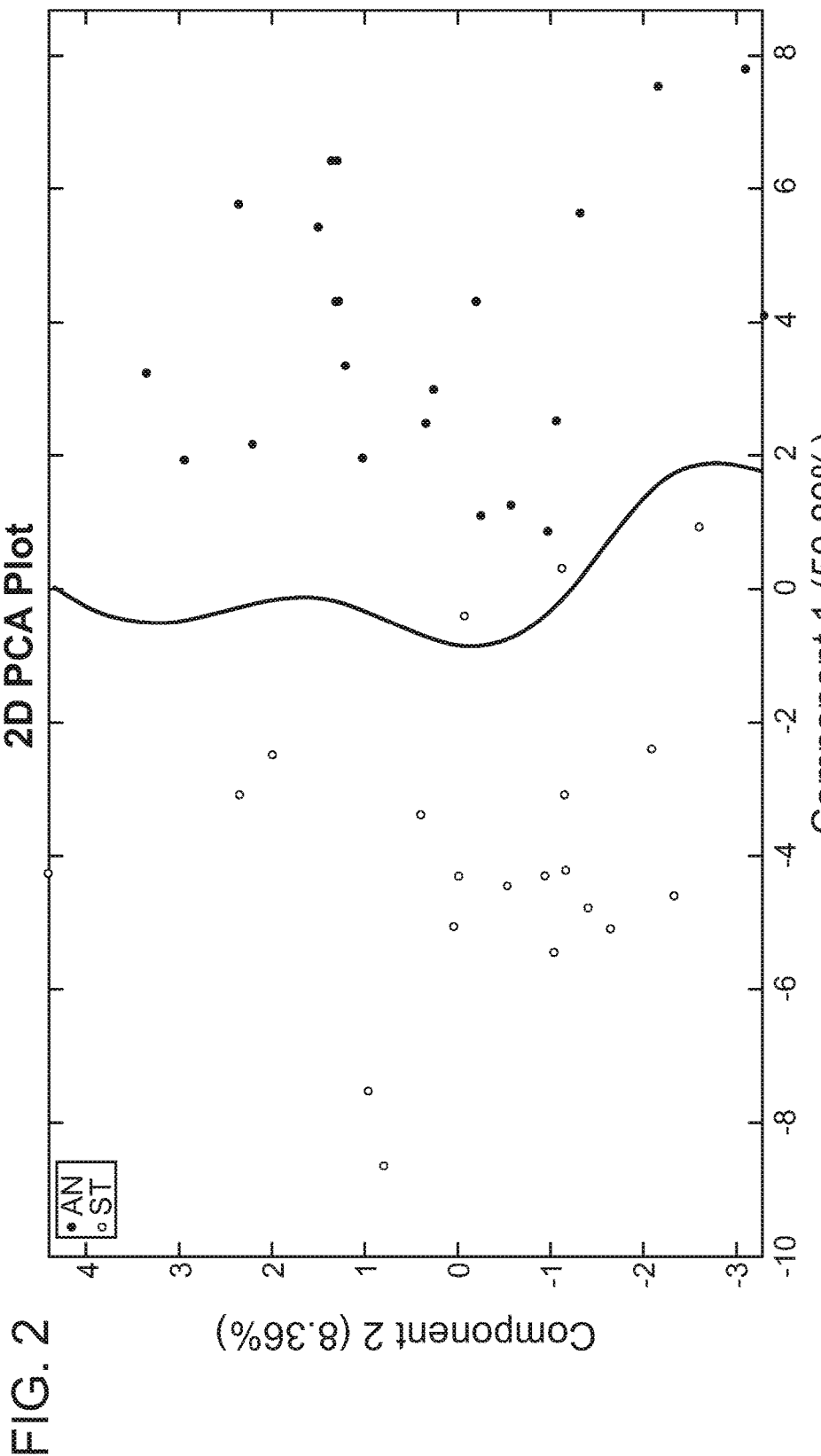
FIG. 2 depicts the performance of a set of 152 protein markers for NASH with advanced liver fibrosis (AN) versus simple steatosis (ST) tested by Leave-One-Out Cross Validation (L1OXV). 2D visualization of support vector machine (SVM) solution. Support vectors are indicated by circles and the line (or plane) that best separates AN from ST.

A L1 OXV prediction accuracy of 92.5% was achieved for predicting Simple Steatosis versus NASH with advanced liver fibrosis with BH corrected Mann Whitney U p-value <0.01 using a 152-protein NASH with Advanced liver fibrosis Predictor (FIG. 2).

Figure 3:
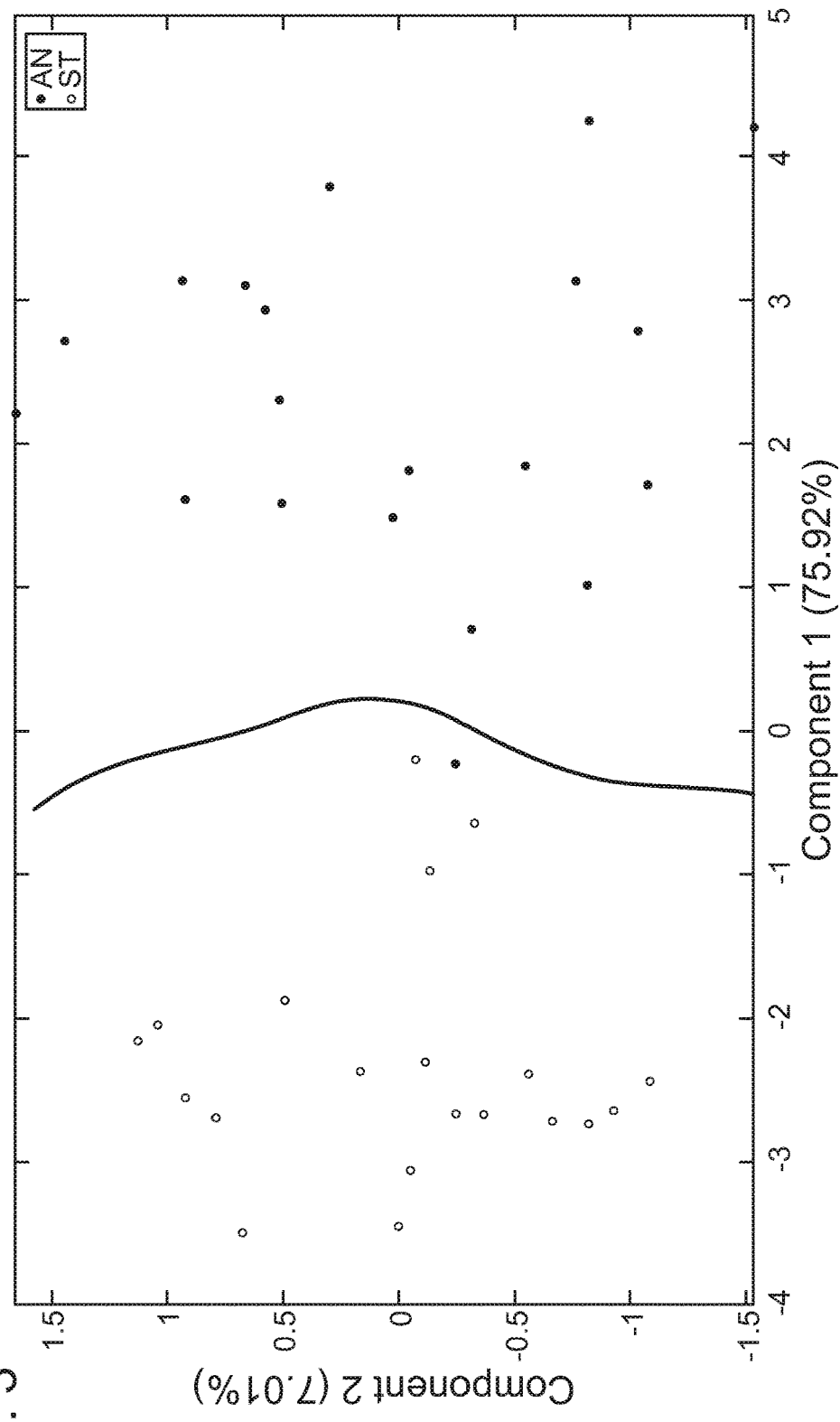
FIG. 3 depicts the performance of a set of 21 protein markers for NASH with advanced liver fibrosis (AN) versus simple steatosis (ST) tested by Leave-One-Out Cross Validation (L1OXV). 2D visualization of support vector machine (SVM) solution. Support vectors are indicated by circles and the line (or plane) that best separates AN from ST.
Figure 4:
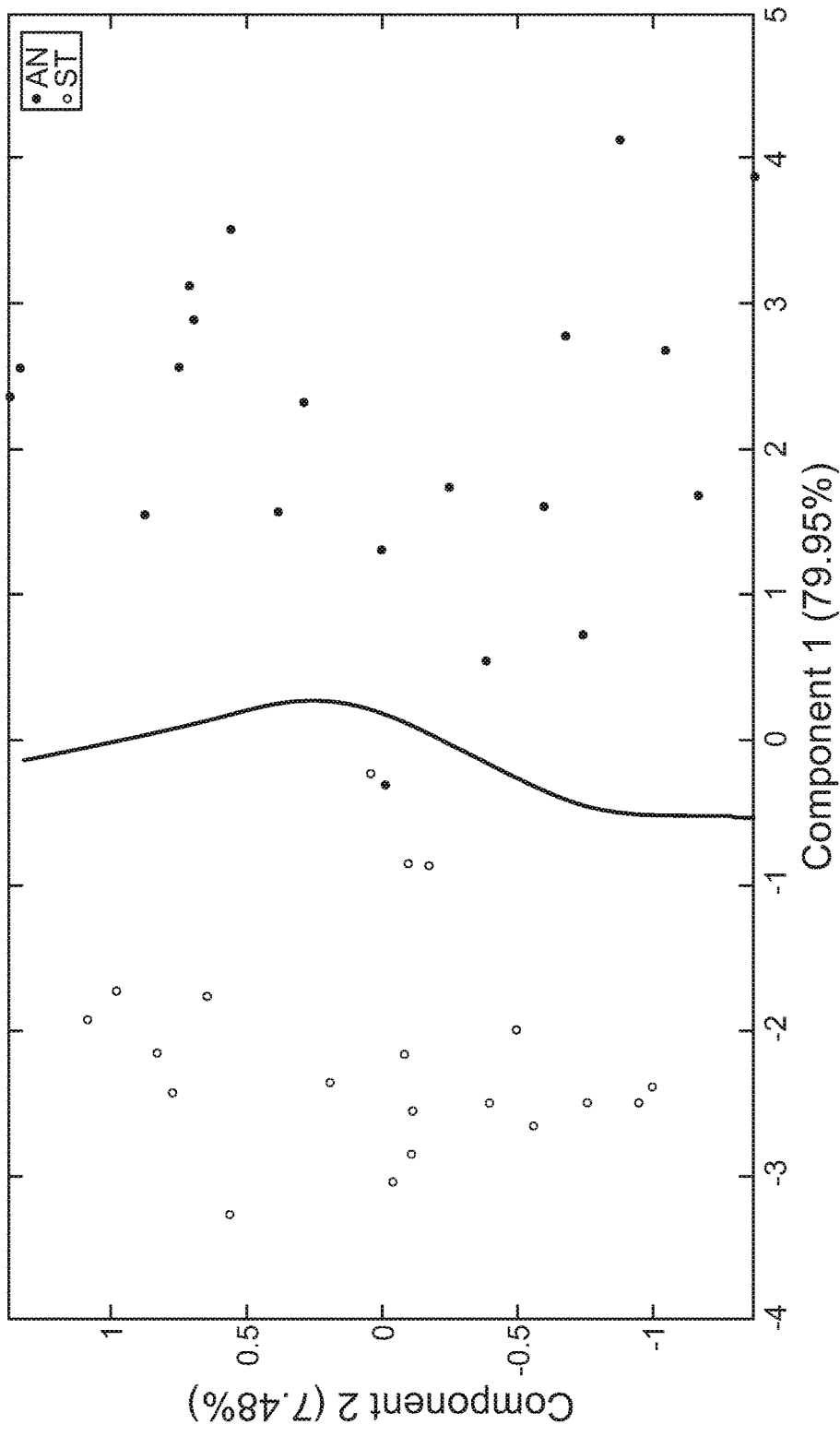
FIG. 4 depicts the performance of a set of 11 protein markers for NASH with advanced liver fibrosis (AN) versus simple steatosis (ST) tested by Leave-One-Out Cross Validation (L1OXV). 2D visualization of support vector machine (SVM) solution. Support vectors are indicated by circles and the line (or plane) that best separates AN from ST.

A L1 OXV prediction accuracy of 95% was achieved for predicting Simple Steatosis versus NASH with advanced liver fibrosis with BH corrected Mann Whitney U p-value <0.01 using a 21-protein or a 11-protein NASH with Advanced liver fibrosis Predictor (FIGS. 3 and 4).

Figure 5:
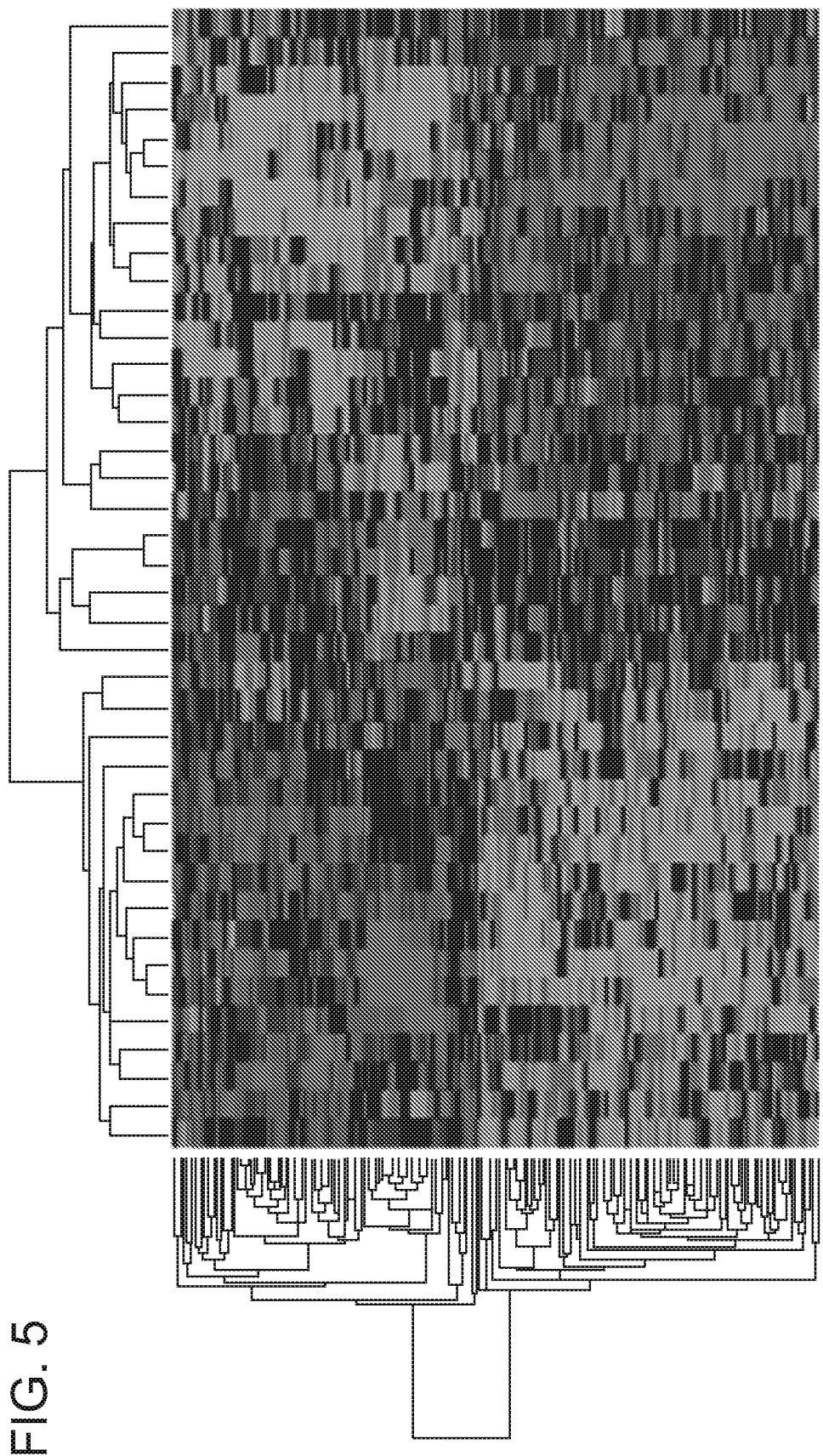
FIG. 5 is a colorgram depicting the hierarchical cluster of a 152-protein NASH with advanced liver fibrosis biomarker panel. 20 of 20 NASH with advanced liver fibrosis samples cluster together and 17 of 20 simple steatosis samples cluster together.
Figure 6:
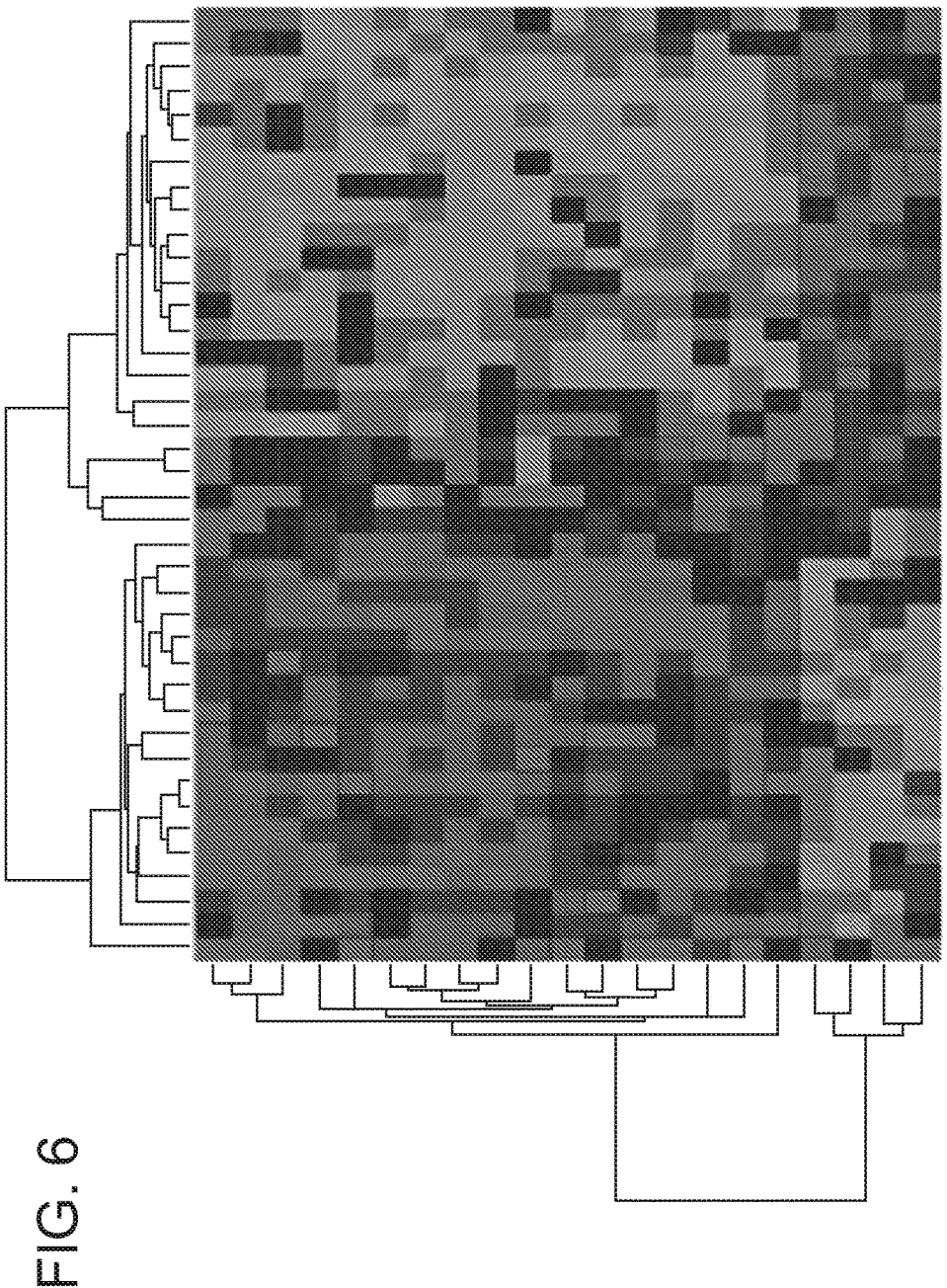
FIG. 6 is a colorgram depicting the hierarchical cluster of a 21-protein NASH with advanced liver fibrosis biomarker panel. 18 of 20 NASH with advanced liver fibrosis samples cluster together and 20 of 20 simple steatosis samples cluster together.
Figure 7:
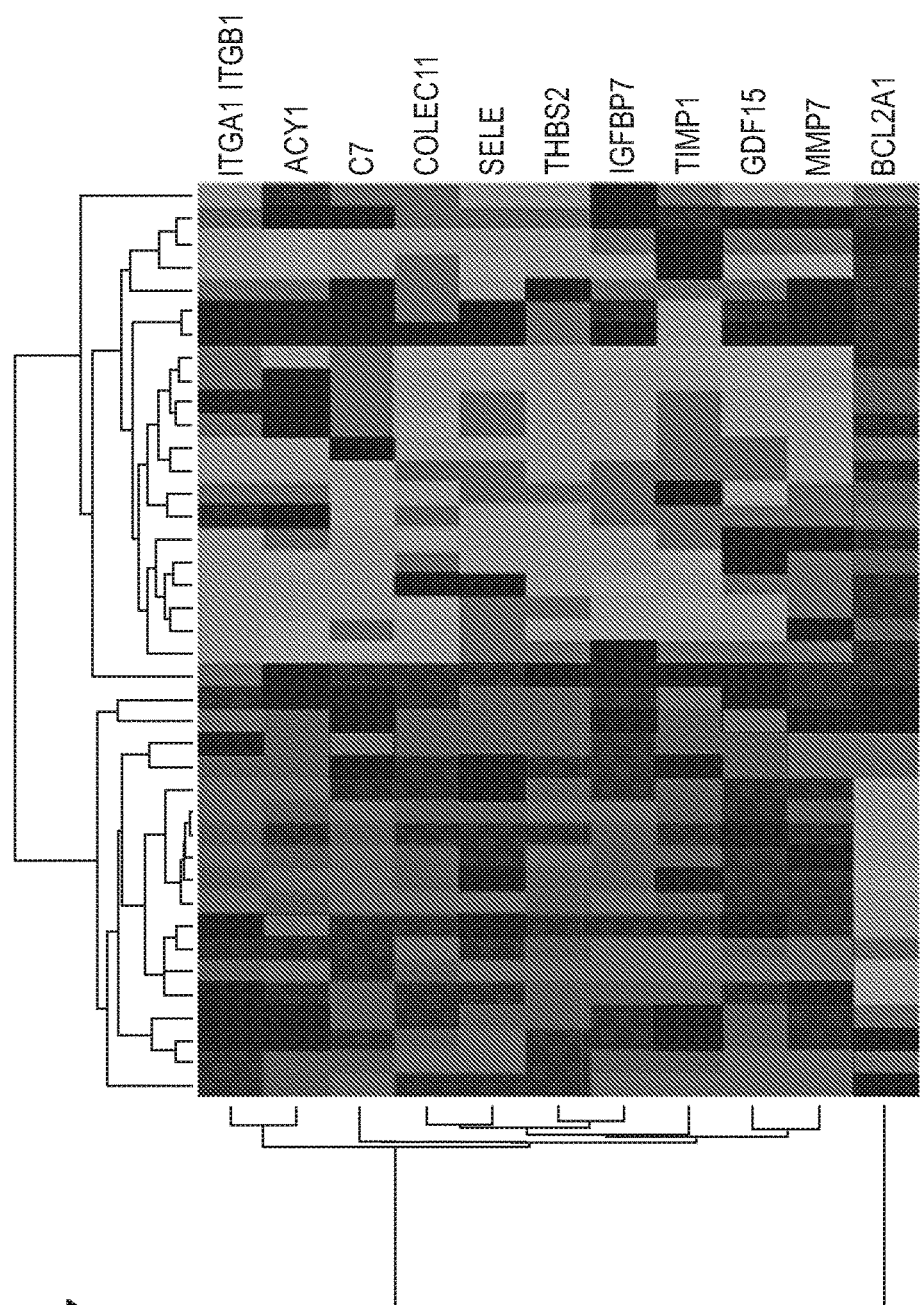
FIG. 7 is a colorgram depicting the hierarchical cluster of a 11-protein NASH with advanced liver fibrosis biomarker panel. 18 of 20 NASH with advanced liver fibrosis samples cluster together and 20 of 20 simple steatosis samples cluster together.

FIGS. 5-7 show the hierarchical clustering of the 152-protein, 21-protein, and 11-protein NASH with Advanced liver fibrosis Predictors, respectively. Using 152-protein predictors, 20 of 20 NASH with advanced liver fibrosis samples cluster together and 17 of 20 Simple Steatosis samples cluster together. Using 21-protein and 11-protein markers, 18 of 20 NASH with advanced liver fibrosis samples cluster together and 20 of 20 Simple Steatosis samples cluster together.

Simple Steatosis Versus NASH without Advanced Liver Fibrosis

Figure 8:
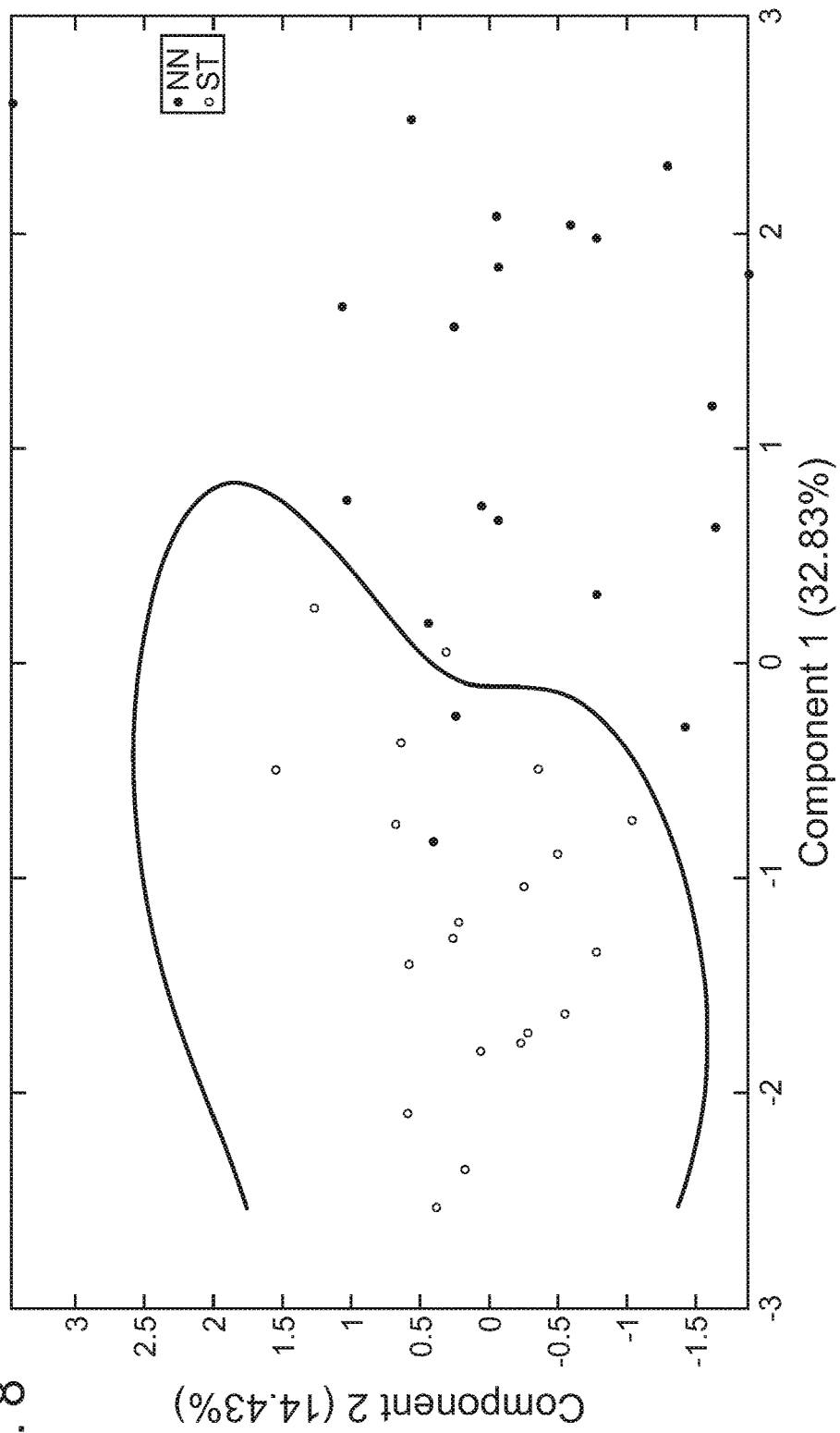
FIG. 8 depicts the performance of a set of 52 protein markers for NASH without advanced liver fibrosis (NN) versus simple steatosis (ST) tested by Leave-One-Out Cross Validation (L1OXV). 2D visualization of support vector machine (SVM) solution. Support vectors are indicated by circles and the line (or plane) that best separates NN from ST.

A L1 OXV prediction accuracy of 90% was achieved for predicting Simple Steatosis versus NASH without advanced liver fibrosis using a 52-protein NASH without Advanced liver fibrosis Predictor (FIG. 8).

Figure 9:
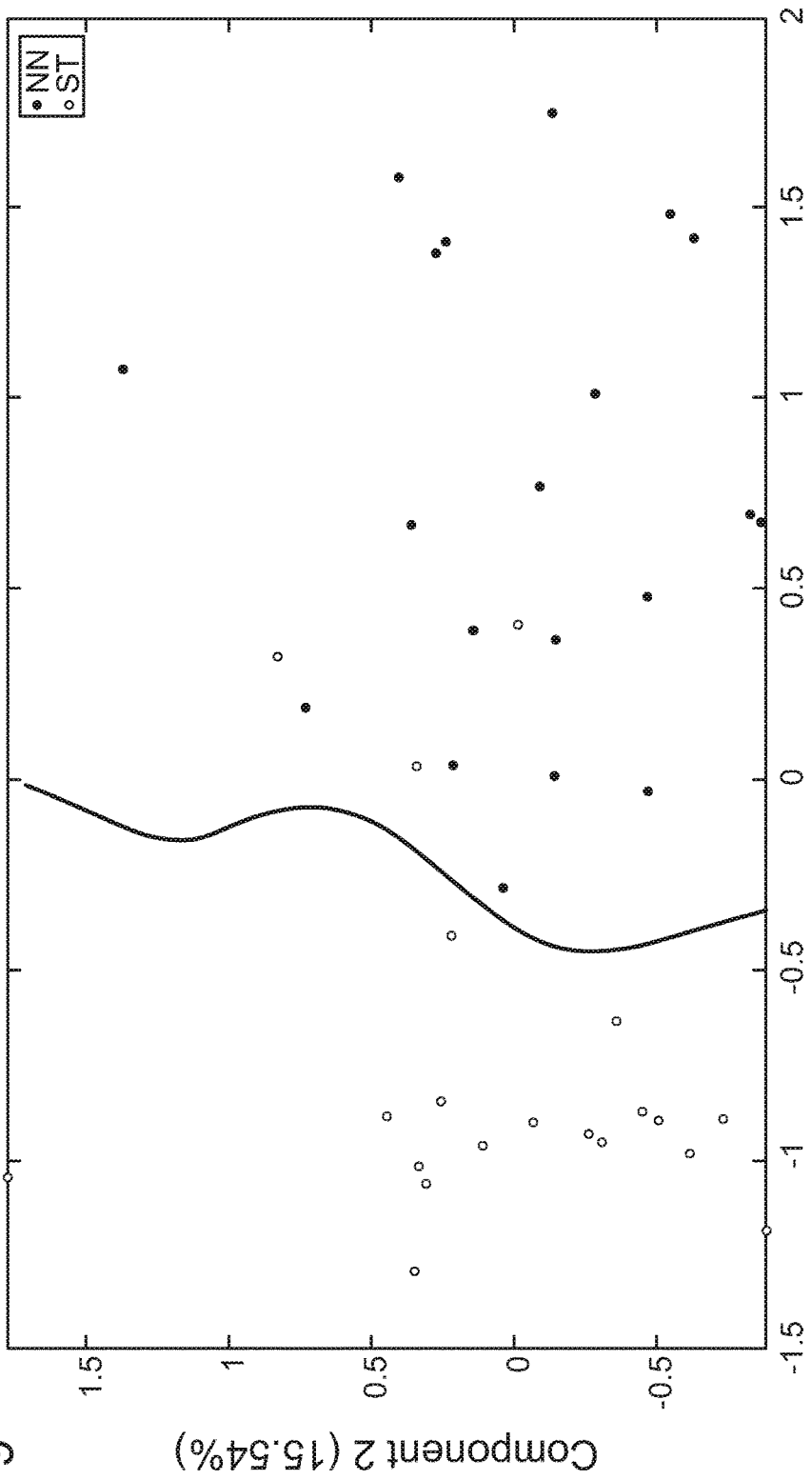
FIG. 9 depicts the performance of a set of 20 protein markers for NASH without advanced liver fibrosis (NN) versus simple steatosis (ST) tested by Leave-One-Out Cross Validation (L1OXV). 2D visualization of support vector machine (SVM) solution. Support vectors are indicated by circles and the line (or plane) that best separates NN from ST.

A L1 OXV prediction accuracy of 82.5% was achieved for predicting Simple Steatosis versus NASH without advanced liver fibrosis with BH corrected Mann Whitney U p-value <0.01 using a 20-protein NASH without Advanced liver fibrosis Predictor (FIG. 9).

Figure 10:
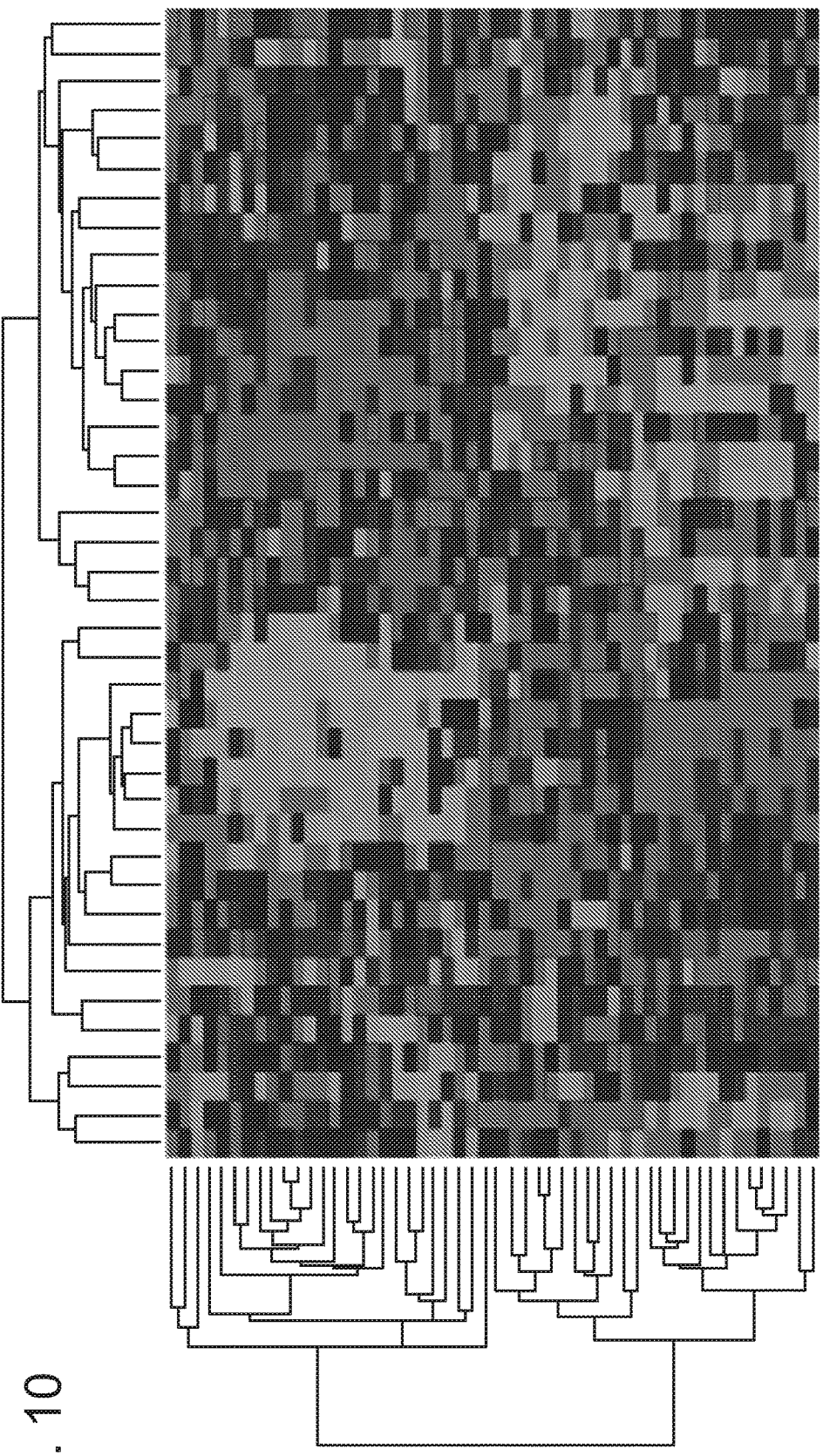
FIG. 10 is a colorgram depicting the hierarchical cluster of a 52-protein NASH without advanced liver fibrosis biomarker panel. 18 of 20 NASH without advanced liver fibrosis samples cluster together and 19 of 20 simple steatosis samples cluster together.
Figure 11:
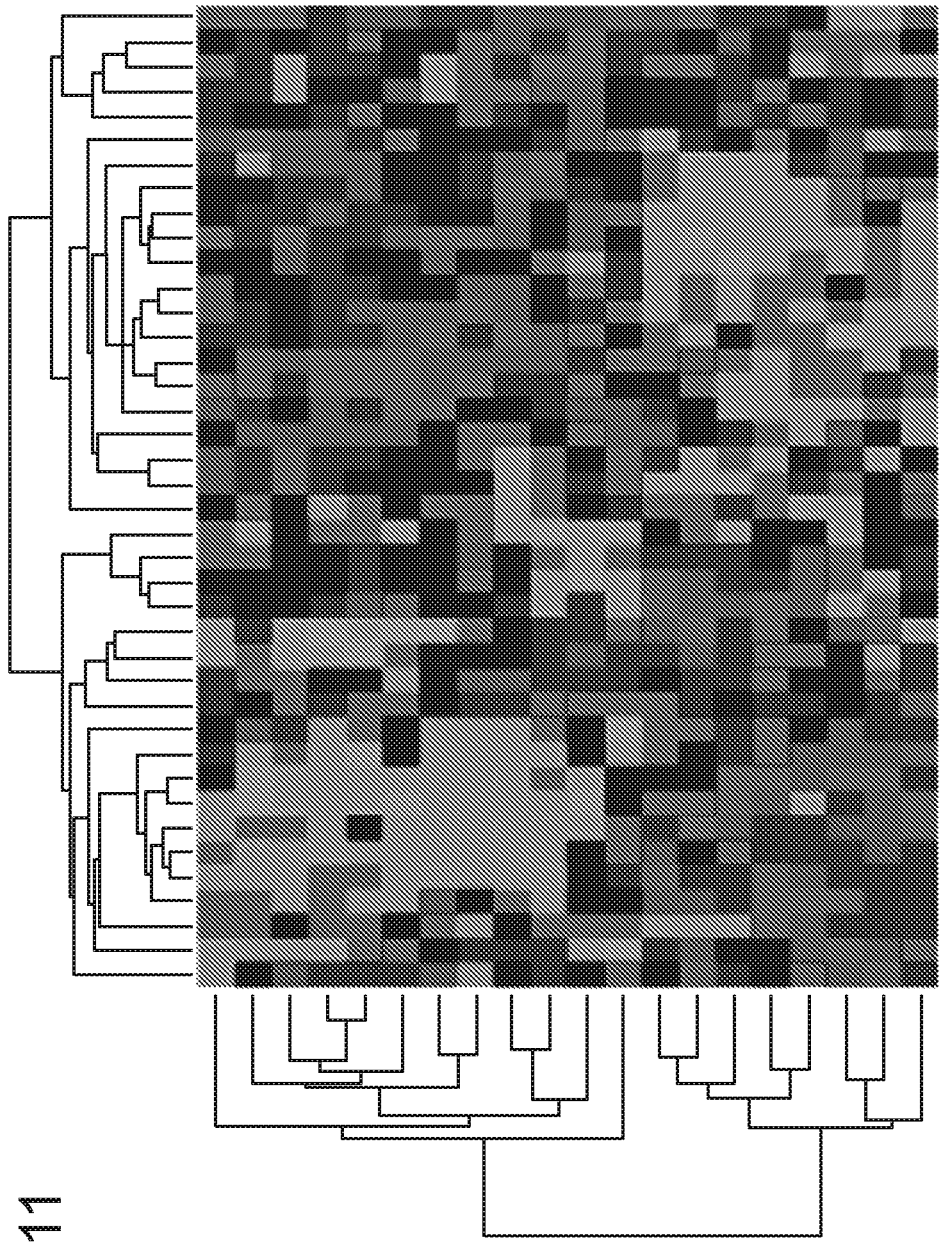
FIG. 11 is a colorgram depicting the hierarchical cluster of a 20-protein NASH without advanced liver fibrosis biomarker panel. 18 of 20 NASH without advanced liver fibrosis samples cluster together and 19 of 20 simple steatosis samples cluster together.

FIGS. 10 and 11 show the hierarchical clustering of the 52-protein and 20-protein NASH without Advanced liver fibrosis Predictors, respectively. For both sets of markers, 18 of 20 NASH without advanced liver fibrosis samples cluster together and 19 of 20 Simple Steatosis samples cluster together.

Simple Steatosis Versus NASH with and without Advanced Liver Fibrosis

Figure 12:
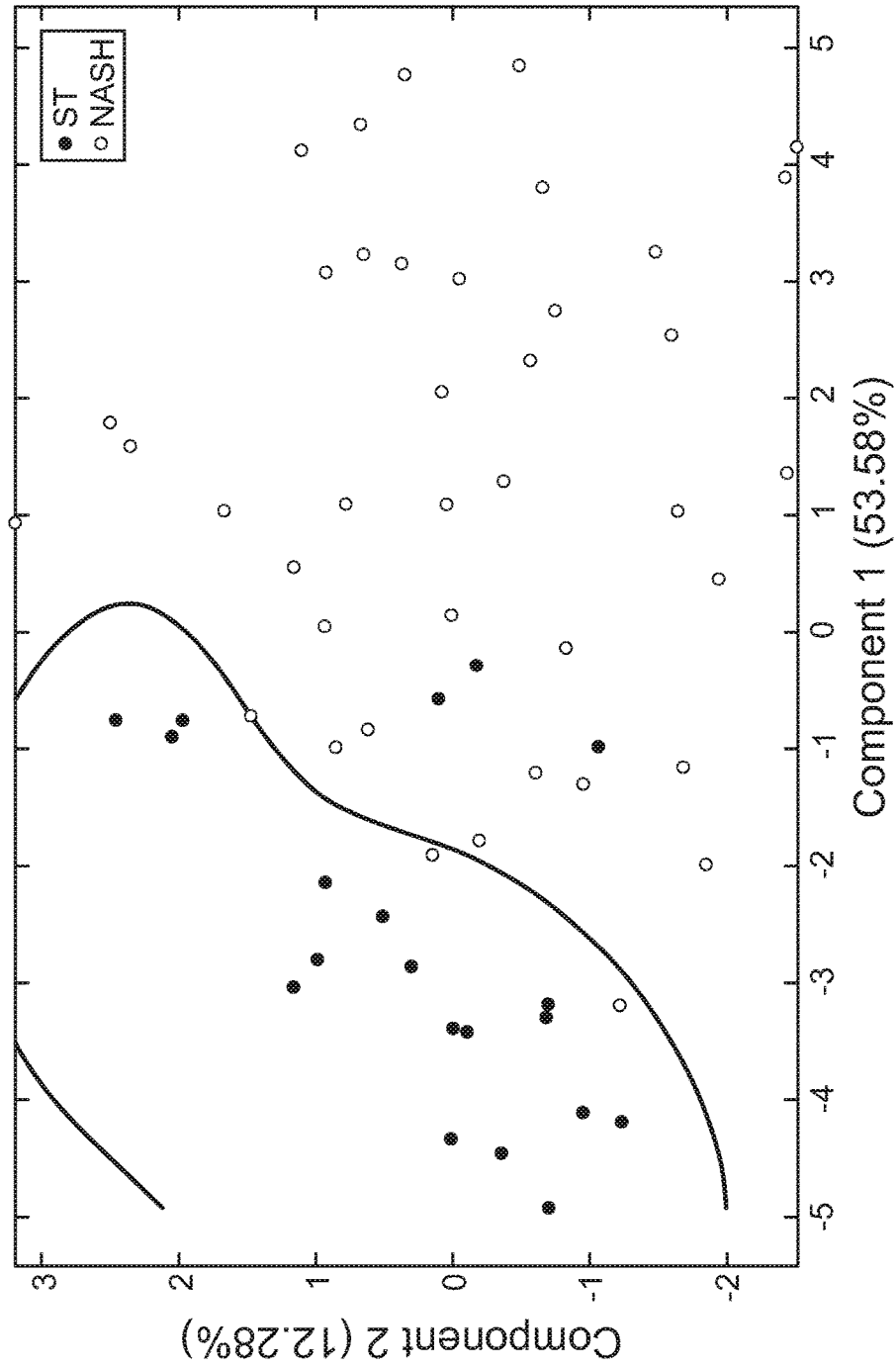
FIG. 12 depicts the performance of a set of 51 protein markers for NASH (NASH with and without advanced liver fibrosis) versus simple steatosis (ST) tested by Leave-One-Out Cross Validation (L1OXV). 2D visualization of support vector machine (SVM) solution. Support vectors are indicated by circles and the line (or plane) that best separates NASH from ST.

A L1OXV prediction accuracy of 88.33% was achieved for predicting Simple Steatosis versus NASH with and without advanced liver fibrosis using a 51-protein NASH Predictor (FIG. 12).

Figure 13:
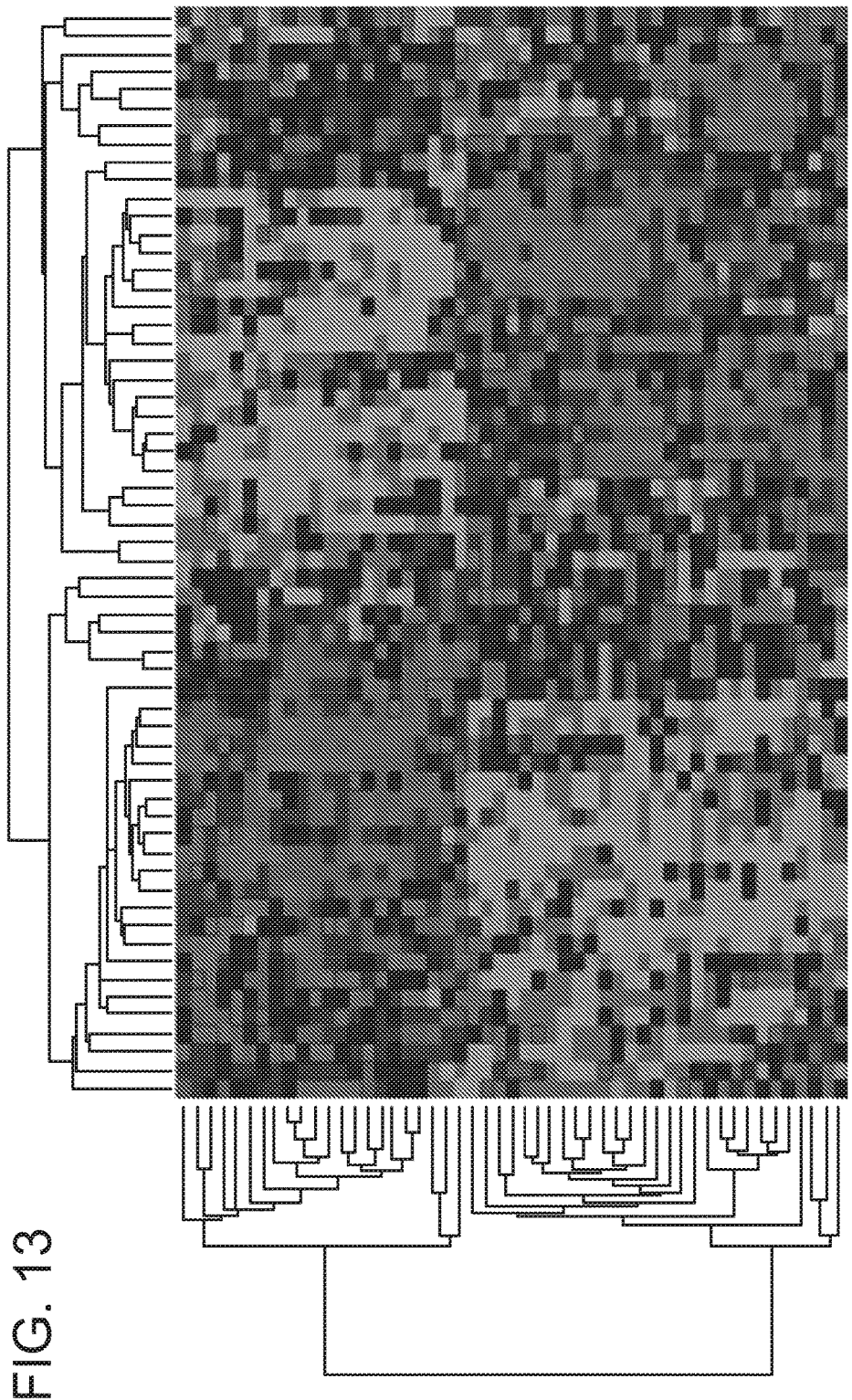
FIG. 13 is a colorgram depicting the hierarchical cluster of a 51-protein NASH biomarker panel. 34 of 40 NASH samples cluster together and 17 of 20 simple steatosis samples cluster together.

FIG. 13 shows the hierarchical clustering of the 51-protein NASH without Advanced Predictor. 34 of 40 NASH samples cluster together and 17 of 20 Simple Steatosis samples cluster together.

NASH with Advanced Liver Fibrosis Versus NASH without Advanced Liver Fibrosis

A L1 OXV prediction accuracy of 85% was achieved for predicting in NASH patients the absence versus the presence of advanced liver fibrosis using a 61-protein Fibrosis Predictor (FIG. 14).

Figure 15:
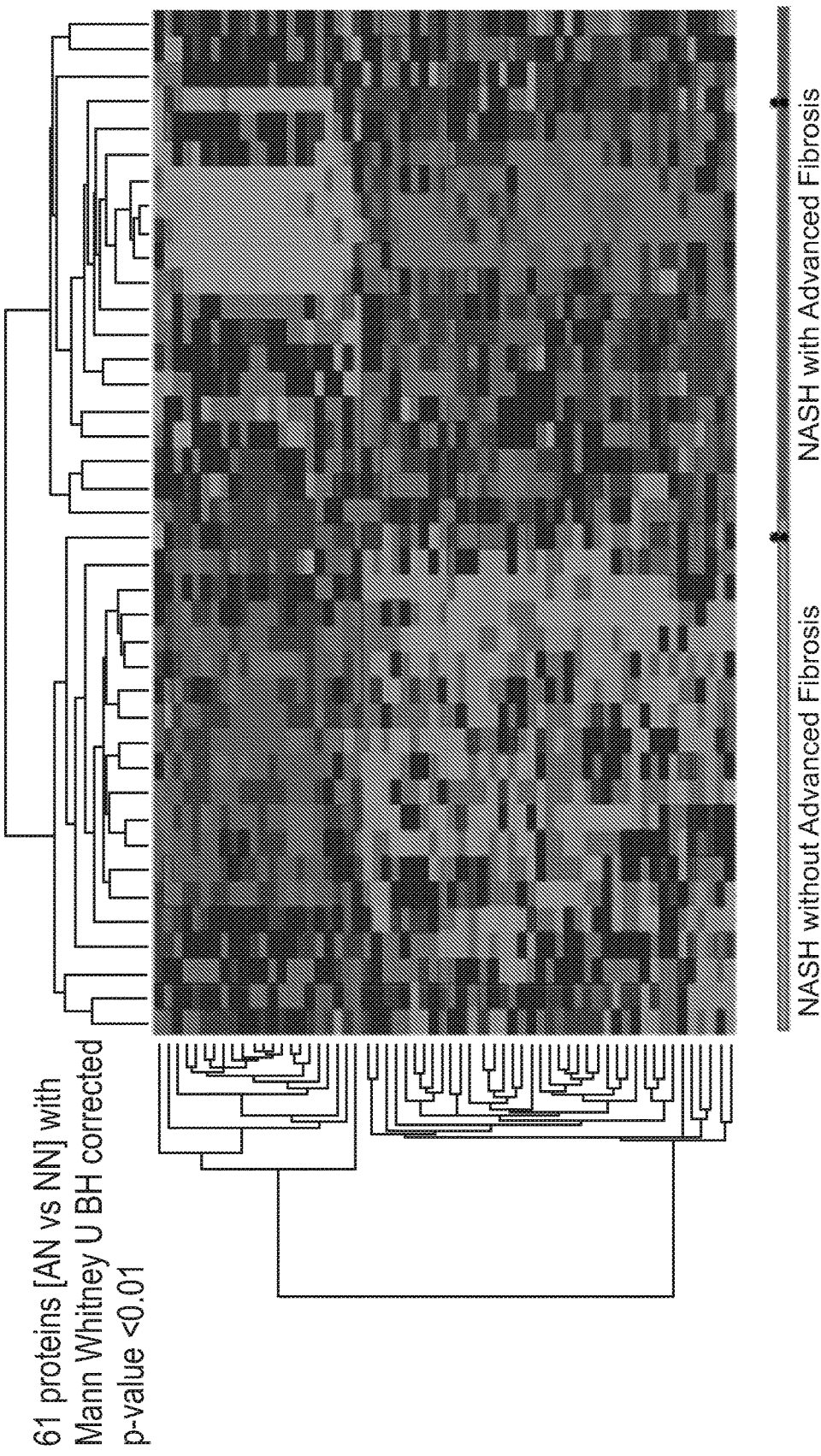
FIG. 15 is a colorgram depicting the hierarchical cluster of a 61-protein fibrosis biomarker panel. 19 of 20 NASH with advanced liver fibrosis samples cluster together and 19 of 20 NASH without advanced liver fibrosis samples cluster together.

FIG. 15 shows the hierarchical clustering of the 61-protein Fibrosis Predictor. 19 of 20 NASH with Advanced liver fibrosis samples cluster together and 19 of 20 NASH without Advanced liver fibrosis samples cluster together.

A rapid, cost-effective, protein-based, and minimally invasive serum diagnostic test that predicts the risk of or diagnoses NASH or advanced liver fibrosis in NASH or differentiates between simple steatosis and NASH will enable sensitive and specific stratification of patients suspected to have NASH or advanced liver fibrosis. Such tests can follow clinical status of patients with NASH and measure or predict treatment response. The present invention also provides effective preventive and pathophysiologically-targeted treatment approaches for NASH and for advanced liver fibrosis in NASH.

Example 2. Development of Markers for Diagnosis of NASH

A listing of markers that discriminate between NASH and simple steatosis, which have a BH p-value of <0.05, is set forth below in Table 1. In Table 1, "FC" represents the "fold change" for each marker, such that a negative value represents a decrease in expression and a positive value represents an increase in expression. For example, an FC of 3.065479 indicates a 3.065479 fold increase in expression of the marker in a sample obtained from a NASH patient versus a sample obtained from a patient with simple steatosis.

TABLE 1

Markers for diagnosis of NASH versus Simple Steatosis

| Target Full Name | Target | UniProt | Entrez Gene ID | Entrez Gene Symbol | FC | p-val | q-val | BH p-val |
|---|---|---|---|---|---|---|---|---|
| Thrombospondin-2 | TSP2 | P35442 | 7058 | THBS2 | 3.065479 | 0 | 0.000001 | 0.000001 |
| Bcl-2-related protein A1 | BFL1 | Q16548 | 597 | BCL2A1 | −1.22869 | 0 | 0.000005 | 0.000009 |
| Insulin-like growth factor-binding protein 7 | IGFBP-7 | Q16270 | 3490 | IGFBP7 | 1.535777 | 0 | 0.000039 | 0.000063 |
| Collectin-11 | Collectin Kidney 1 | Q9BWP8 | 78989 | COLEC11 | 3.110595 | 0 | 0.000051 | 0.000082 |
| Growth/differentiation factor 15 | MIC-1 | Q99988 | 9518 | GDF15 | 1.808874 | 0 | 0.000051 | 0.000082 |
| Tyrosine-protein kinase Yes | YES | P07947 | 7525 | YES1 | 1.231688 | 0 | 0.000051 | 0.000082 |
| Complement component C7 | C7 | P10643 | 730 | C7 | 1.550541 | 0 | 0.000051 | 0.000083 |
| Integrin alpha-I:beta-1 complex | Integrin a1b1 | P56199, P05556 | 3672 3688 | ITGA1 ITGB1 | 2.049952 | 0.000001 | 0.000054 | 0.000088 |
| Transforming growth factor-beta-induced protein ig-h3 | BGH3 | Q15582 | 7045 | TGFBI | 1.44727 | 0.000001 | 0.000112 | 0.000181 |
| HemK methyltransferase family member 2 | HEMK2 | Q9Y5N5 | 29104 | N6AMT1 | −1.274885 | 0.000001 | 0.000112 | 0.000181 |
| Metalloproteinase inhibitor 1 | TIMP-1 | P01033 | 7076 | TIMP1 | 1.328063 | 0.000009 | 0.000648 | 0.00105 |
| NADPH--cytochrome P450 reductase | NADPH-P450 Oxidoreductase | P16435 | 5447 | POR | 2.056624 | 0.000011 | 0.000745 | 0.001206 |
| Plasma protease C1 inhibitor | C1-Esterase Inhibitor | P05155 | 710 | SERPING1 | −1.259024 | 0.000012 | 0.000745 | 0.001206 |
| Aminoacylase-1 | Aminoacylase-1 | Q03154 | 95 | ACY1 | 2.272206 | 0.000016 | 0.000854 | 0.001382 |
| RAC-beta serine/threonine-protein kinase | PKB beta | P31751 | 208 | AKT2 | −1.131722 | 0.000015 | 0.000854 | 0.001382 |
| Galectin-7 | Galectin-7 | P47929 | 3963 | LGALS7 | −1.165193 | 0.000017 | 0.000854 | 0.001382 |
| Tumor necrosis factor ligand superfamily member 8 | CD30 Ligand | P32971 | 944 | TNFSF8 | 1.277617 | 0.000024 | 0.001108 | 0.001793 |
| Apolipoprotein M | ApoM | O95445 | 55937 | APOM | −1.303075 | 0.000023 | 0.001108 | 0.001793 |
| Protein jagged-1 | JAG1 | P78504 | 182 | JAG1 | 1.125109 | 0.000027 | 0.001126 | 0.001823 |
| Discoidin domain-containing receptor 2 | Discoidin domain receptor 2 | Q16832 | 4921 | DDR2 | −1.148549 | 0.000028 | 0.001126 | 0.001823 |

TABLE 1-continued

Markers for diagnosis of NASH versus Simple Steatosis

| Target Full Name | Target | UniProt | Entrez Gene ID | Entrez Gene Symbol | FC | p-val | q-val | BH p-val |
|---|---|---|---|---|---|---|---|---|
| Endothelin-converting enzyme 1 | Endothelin-converting enzyme 1 | P42892 | 1889 | ECE1 | −1.130221 | 0.000038 | 0.001468 | 0.002377 |
| 15-hydroxyprostaglandin dehydrogenase [NAD(+)] | HPG- | P15428 | 3248 | HPGD | −1.167668 | 0.000046 | 0.001636 | 0.002648 |
| Testican-1 | Testican-1 | Q08629 | 6695 | SPOCK1 | −1.320143 | 0.000045 | 0.001636 | 0.002648 |
| Calpain I | Calpain I | P07384 | 823 | CAPN1 | −1.157331 | 0.000052 | 0.001761 | 0.002852 |
|  |  | P04632 | 826 | CAPNS1 |  |  |  |  |
| Leptin receptor | sLeptin R | P48357 | 3953 | LEPR | 1.308705 | 0.000062 | 0.001795 | 0.002906 |
| Afamin | Afamin | P43652 | 173 | AFM | 1.270263 | 0.000059 | 0.001795 | 0.002906 |
| Proteasome activator complex subunit 1 | PSME1 | Q06323 | 5720 | PSME1 | −1.142432 | 0.000059 | 0.001795 | 0.002906 |
| Mammaglobin-B | Mammaglobin 2 | O75556 | 4246 | SCGB2A1 | −1.190161 | 0.000061 | 0.001795 | 0.002906 |
| Interleukin-18 receptor 1 | IL-18 Ra | Q13478 | 8809 | IL18R1 | 1.154353 | 0.000064 | 0.001799 | 0.002912 |
| HERV-H LTR-associating protein 2 | HHLA2 | Q9UM44 | NaN | HHLA2 | −1.168317 | 0.000085 | 0.002304 | 0.00373 |
| Ephrin-B1 | EFNB1 | P98172 | 1947 | EFNB1 | −1.101699 | 0.000093 | 0.002449 | 0.003965 |
| Dipeptidyl peptidase 2 | DPP2 | Q9UHL4 | 29952 | DPP7 | −1.141048 | 0.000097 | 0.002472 | 0.004002 |
| Heat shock protein HSP 90-beta | HSP 90b | P08238 | 3326 | HSP90AB1 | 1.33518 | 0.000125 | 0.003088 | 0.005 |
| Cathepsin Z | CATZ | Q9UBR2 | 1522 | CTSZ | 1.237525 | 0.000162 | 0.003886 | 0.006292 |
| E-selectin | sE-Selectin | P16581 | 6401 | SELE | 1.727444 | 0.00018 | 0.004087 | 0.006618 |
| Ubiquitin carboxyl-terminal hydrolase isozyme L1 | PGP9.5 | P09936 | 7345 | UCHL1 | −1.126877 | 0.00018 | 0.004087 | 0.006618 |
| Glutathione S-transferase P | Glutathione S-transferase Pi | P09211 | 2950 | GSTP1 | −1.113793 | 0.000207 | 0.004576 | 0.00741 |
| Macrophage metalloelastase | MMP-12 | P39900 | 4321 | MMP12 | 1.649152 | 0.000224 | 0.004813 | 0.007793 |
| Semaphorin-5A | SEM5A | Q13591 | 9037 | SEMA5A | 1.256859 | 0.000247 | 0.005044 | 0.008167 |
| Epidermal growth factor receptor | ERBB1 | P00533 | 1956 | EGFR | −1.126575 | 0.000243 | 0.005044 | 0.008167 |
| Caspase-10 | Caspase-10 | Q92851 | 843 | CASP10 | −1.182509 | 0.000254 | 0.005068 | 0.008205 |
| Angiopoietin-2 | Angiopoietin-2 | O15123 | 285 | ANGPT2 | 1.334583 | 0.000276 | 0.00536 | 0.008678 |
| Tyrosine-protein kinase Lyn | LYN | P07948 | 4067 | LYN | −1.432969 | 0.000284 | 0.005388 | 0.008724 |
| Interleukin-19 | IL-19 | Q9UHD0 | 29949 | IL19 | 1.325432 | 0.000325 | 0.006034 | 0.00977 |
| Formimidoyltransferase-cyclodeaminase | FTCD | O95954 | 10841 | FTCD | 2.564912 | 0.00036 | 0.006163 | 0.009978 |
| Ferritin | Ferritin | P02794 | 2495 | FTH1 | 1.843011 | 0.000384 | 0.006163 | 0.009978 |
|  |  | P02792 | 2512 | FTL |  |  |  |  |
| Alcohol dehydrogenase [NADP(+)] | AK1A1 | P14550 | 10327 | AKR1A1 | 1.394939 | 0.000385 | 0.006163 | 0.009978 |
| Latent-transforming growth factor beta-binding protein 4 | LTBP4 | Q8N2S1 | 8425 | LTBP4 | 1.32882 | 0.000385 | 0.006163 | 0.009978 |
| N-acetyl-D-glucosamine kinase | NAGK | Q9UJ70 | 55577 | NAGK | 1.31441 | 0.00036 | 0.006163 | 0.009978 |
| Decorin | Bone proteoglycan II | P07585 | 1634 | DCN | 1.244533 | 0.000385 | 0.006163 | 0.009978 |
| Sphingosine kinase 1 | Sphingosine kinase 1 | Q9NYA1 | 8877 | SPHK1 | −1.296853 | 0.00036 | 0.006163 | 0.009978 |
| Neuropilin-1 | NRP1 | O14786 | 8829 | NRP1 | 1.271087 | 0.000411 | 0.006451 | 0.010445 |
| Interleukin-1 Receptor accessory protein | IL-1 R AcP | Q9NPH3 | 3556 | IL1RAP | −1.313101 | 0.000439 | 0.006756 | 0.010939 |

TABLE 1-continued

Markers for diagnosis of NASH versus Simple Steatosis

| Target Full Name | Target | UniProt | Entrez Gene ID | Entrez Gene Symbol | FC | p-val | q-val | BH p-val |
|---|---|---|---|---|---|---|---|---|
| Kelch-like ECH-associated protein 1 | KEAP1 | Q14145 | 9817 | KEAP1 | −1.087836 | 0.000454 | 0.006869 | 0.011122 |
| Phosphoglycerate kinase 1 | phosphoglycerate kinase 1 | P00558 | 5230 | PGK1 | −1.157608 | 0.000469 | 0.006965 | 0.011278 |
| Interleukin-18-binding protein | IL-18 BPa | O95998 | 10068 | IL18BP | 1.321926 | 0.000485 | 0.007076 | 0.011456 |
| Tyrosine-protein kinase receptor Tie-1, soluble | sTie-1 | P35590 | 7075 | TIE1 | 1.262726 | 0.0005 | 0.007169 | 0.011608 |
| Cell adhesion molecule 1 | Nectin-like protein 2 | Q9BY67 | 23705 | CADM1 | 1.223979 | 0.000518 | 0.007292 | 0.011806 |
| Thrombin | Thrombin | P00734 | 2147 | F2 | −1.327723 | 0.000552 | 0.007635 | 0.012363 |
| Ras-related C3 botulinum toxin substrate 3 | RAC3 | P60763 | 5881 | RAC3 | −1.208255 | 0.000589 | 0.008017 | 0.012981 |
| Semaphorin-6B | SEM6B | Q9H3T3 | 10501 | SEMA6B | 1.36644 | 0.000609 | 0.008146 | 0.013189 |
| Coactosin-like protein | Coactosin-like protein | Q14019 | 23406 | COTL1 | −1.142014 | 0.000668 | 0.008796 | 0.014242 |
| Fatty acid-binding protein, liver | FABPL | P07148 | 2168 | FABP1 | 1.504103 | 0.000692 | 0.008966 | 0.014517 |
| Interferon gamma receptor 2 | INGR2 | P38484 | 3460 | IFNGR2 | 1.251223 | 0.000737 | 0.009401 | 0.015221 |
| Coagulation Factor XI | Coagulation Factor XI | P03951 | 2160 | F11 | −1.18561 | 0.00076 | 0.009408 | 0.015233 |
| Proto-oncogene tyrosine-protein kinase Src | SRCN1 | P12931 | 6714 | SRC | −1.501488 | 0.00076 | 0.009408 | 0.015233 |
| cAMP-regulated phosphoprotein 19 | ARP19 | P56211 | 10776 | ARPP19 | −1.303393 | 0.000834 | 0.010169 | 0.016464 |
| Plexin-C1 | PLXC1 | O60486 | 10154 | PLXNC1 | 1.175642 | 0.000946 | 0.011189 | 0.018116 |
| Ubiquitin-fold modifier-conjugating enzyme 1 | UFC1 | Q9Y3C8 | 51506 | UFC1 | −1.277829 | 0.000944 | 0.011189 | 0.018116 |
| Serine protease HTRA2, mitochondrial | HTRA2 | O43464 | 27429 | HTRA2 | 1.204196 | 0.001067 | 0.01245 | 0.020158 |
| Insulin-like growth factor-binding protein 5 | IGFBP-5 | P24593 | 3488 | IGFBP5 | −1.159805 | 0.001101 | 0.012489 | 0.020221 |
| Cytoplasmic protein NCK1 | NCK1 | P16333 | 4690 | NCK1 | −1.286937 | 0.001101 | 0.012489 | 0.020221 |
| Fibroblast growth factor receptor 4 | FGFR4 | P22455 | 2264 | FGFR4 | −1.141337 | 0.001135 | 0.0127 | 0.020563 |
| Heat shock protein HSP 90-alpha/beta | HSP 90a/b | P07900 P08238 | NaN | HSP90AA1 HSP90AB1 | 1.395128 | 0.001205 | 0.013293 | 0.021524 |
| dCTP pyrophosphatase 1 | XTP3A | Q9H773 | 79077 | DCTPP1 | 1.093548 | 0.001243 | 0.013531 | 0.021909 |
| Angiopoietin-1 receptor, soluble | sTie-2 | Q02763 | 7010 | TEK | 1.159492 | 0.00128 | 0.013755 | 0.022271 |
| Metalloproteinase inhibitor 2 | TIMP-2 | P16035 | 7077 | TIMP2 | 1.136959 | 0.001358 | 0.014395 | 0.023308 |
| Serum amyloid P-component | SAP | P02743 | 325 | APCS | −1.169148 | 0.001429 | 0.014958 | 0.024219 |
| Tumor necrosis factor ligand superfamily member 15 | TNFSF15 | O95150 | 9966 | TNFSF15 | 1.241641 | 0.001531 | 0.015626 | 0.0253 |
| Apolipoprotein B | Apo B | P04114 | 338 | APOB | −1.48263 | 0.001529 | 0.015626 | 0.0253 |
| Platelet-derived growth factor receptor alpha | PDGFRA | P16234 | 5156 | PDGFRA | 1.410604 | 0.001574 | 0.015864 | 0.025686 |
| Macrophage colony-stimulating factor 1 receptor | M-CSF R | P07333 | 1436 | CSF1R | 1.36427 | 0.00162 | 0.015938 | 0.025805 |

TABLE 1-continued

Markers for diagnosis of NASH versus Simple Steatosis

| Target Full Name | Target | UniProt | Entrez Gene ID | Entrez Gene Symbol | FC | p-val | q-val | BH p-val |
|---|---|---|---|---|---|---|---|---|
| Inorganic pyrophosphatase | PPase | Q15181 | 5464 | PPA1 | −1.173844 | 0.001604 | 0.015938 | 0.025805 |
| Tumor necrosis factor receptor superfamily member 1B | TNF sR-II | P20333 | 7133 | TNFRSF1B | 1.151482 | 0.001755 | 0.017061 | 0.027625 |
| Insulin-like growth factor-binding protein 2 | IGFBP-2 | P18065 | 3485 | IGFBP2 | 1.279095 | 0.001975 | 0.01897 | 0.030716 |
| Low affinity immunoglobulin gamma Fc region receptor III-B | FCG3B | O75015 | 2215 | FCGR3B | 1.306755 | 0.002105 | 0.019989 | 0.032365 |
| Ephrin type-B receptor 2 | EPHB2 | P29323 | 2048 | EPHB2 | 1.106023 | 0.002163 | 0.020299 | 0.032866 |
| Cathepsin D | Cathepsin D | P07339 | 1509 | CTSD | 1.613538 | 0.002229 | 0.020451 | 0.033113 |
| Annexin A6 | annexin VI | P08133 | 309 | ANXA6 | −1.187575 | 0.00222 | 0.020451 | 0.033113 |
| Ectonucleotide pyrophosphatase/phosphodiesterase family member 7 | ENPP7 | Q6UWV6 | 339221 | ENPP7 | 1.67697 | 0.002292 | 0.020797 | 0.033673 |
| Matrilysin | MMP-7 | P09237 | 4316 | MMP7 | 1.672905 | 0.002358 | 0.020927 | 0.033883 |
| Proprotein convertase subtilisin/kexin type 7 | PCSK7 | Q16549 | 9159 | PCSK7 | 1.165314 | 0.002356 | 0.020927 | 0.033883 |
| Complement component C6 | C6 | P13671 | 729 | C6 | 1.136743 | 0.00261 | 0.022916 | 0.037104 |
| Tumor necrosis factor receptor superfamily member 6 | Fas, soluble | P25445 | 355 | FAS | 1.487852 | 0.002711 | 0.023301 | 0.037727 |
| Tumor necrosis factor ligand superfamily member 9 | 4-1BB ligand | P41273 | 8744 | TNFSF9 | 1.109113 | 0.002701 | 0.023301 | 0.037727 |
| Fetuin-B | FETUB | Q9UGM5 | 26998 | FETUB | −1.221124 | 0.002786 | 0.023691 | 0.038359 |
| Lumican | Lumican | P51884 | 4060 | LUM | 1.238743 | 0.002866 | 0.024122 | 0.039056 |
| cAMP-specific 3',5'-cyclic phosphodiesterase 4D | PDE4D | Q08499 | 5144 | PDE4D | −1.115908 | 0.002946 | 0.024542 | 0.039738 |
| Lymphocyte antigen 86 | LY86 | O95711 | 9450 | LY86 | −1.100698 | 0.003076 | 0.025366 | 0.04107 |
| Galactoside 3(4)-L-fucosyltransferase | Fucosyltransferase 3 | P21217 | 2525 | FUT3 | 1.668724 | 0.00322 | 0.026294 | 0.042574 |
| Basal Cell Adhesion Molecule | BCAM | P50895 | 4059 | BCAM | 1.139344 | 0.003287 | 0.026314 | 0.042605 |
| Arylsulfatase A | Arylsulfatase A | P15289 | 410 | ARSA | −1.125282 | 0.003287 | 0.026314 | 0.042605 |
| Down syndrome cell adhesion molecule | DSCAM | O60469 | 1826 | DSCAM | 1.117974 | 0.003374 | 0.026747 | 0.043308 |
| beta-nerve growth factor | b-NGF | P01138 | 4803 | NGF | 1.465927 | 0.00347 | 0.027245 | 0.044113 |
| Renin | Renin | P00797 | 5972 | REN | 2.087593 | 0.003665 | 0.027969 | 0.045286 |
| Chorionic somatomammotropin hormone | CSH | P0DML2 P0DML3 | 1442 1443 | CSH1 CSH2 | −1.118059 | 0.003646 | 0.027969 | 0.045286 |
| Tyrosine-protein kinase Lyn, isoform B | LYNB | P07948 | 4067 | LYN | −1.453568 | 0.003664 | 0.027969 | 0.045286 |
| C-type lectin domain family 1 member B | CLC1B | Q9P126 | 51266 | CLEC1B | −1.286613 | 0.003765 | 0.028466 | 0.04609 |
| Tumor necrosis factor ligand superfamily member 12 | TWEAK | O43508 | 8742 | TNFSF12 | 1.022001 | 0.003865 | 0.028686 | 0.046447 |

TABLE 1-continued

Markers for diagnosis of NASH versus Simple Steatosis

| Target Full Name | Target | UniProt | Entrez Gene ID | Entrez Gene Symbol | FC | p-val | q-val | BH p-val |
|---|---|---|---|---|---|---|---|---|
| 40S ribosomal protein SA | 40S ribosomal protein SA | P08865 | 3921 | RPSA | −1.147626 | 0.003861 | 0.028686 | 0.046447 |
| Adhesion G protein-coupled receptor E2 | EMR2 | Q9UHX3 | 30817 | ADGRE2 | 1.380472 | 0.00397 | 0.029201 | 0.04728 |
| Cation-independent mannose-6-phosphate receptor | IGF-II receptor | P11717 | 3482 | IGF2R | 1.118007 | 0.004042 | 0.029465 | 0.047708 |
| Follistatin-related protein 3 | FSTL3 | O95633 | 10272 | FSTL3 | 1.295286 | 0.004296 | 0.030766 | 0.049814 |
| Tropomyosin alpha-4 chain | Tropomyosin 4 | P67936 | 7171 | TPM4 | −1.556559 | 0.004294 | 0.030766 | 0.049814 |

A frequency analysis was performed on the identified markers that discriminate between NASH and simple steatosis. For this analysis, 5-fold cross-validation with 10,000 splits was used. That is, in each split, 32 NASH and 16 simple steatosis (80% or 4/5 of all 60) randomly chosen samples were used. Proteins with BH p<0.01 were identified. This split was repeated 10,000 times. The number of times a protein appears in that list (FREQ) was counted, and those proteins were ranked as set forth below in Table 2.

TABLE 2

Markers for diagnosis of NASH versus Simple Steatosis based on frequency

| Marker Full Name | Marker | UniProt | EntrezGene ID | Entrez Gene Symbol | FREQ | p-value | BH p | FC (AN + NN/ST) |
|---|---|---|---|---|---|---|---|---|
| Thrombospondin-2 | TSP2 | P35442 | 7058 | THBS2 | 9942 | 8.44E−09 | 1.12E−05 | 3.13395341 |
| Bcl-2-related protein A1 | BFL1 | Q16548 | 597 | BCL2A1 | 9723 | 6.21E−08 | 4.11E−05 | −1.2334529 |
| Tyrosine-protein kinase Yes | YES | P07947 | 7525 | YES1 | 9025 | 2.91E−07 | 0.00012838 | 1.23332925 |
| Collectin-11 | Collectin Kidney 1 | Q9BWP8 | 78989 | COLEC11 | 8696 | 5.08E−07 | 0.00016795 | 2.93652727 |
| Insulin-like growth factor-binding protein 7 | IGFBP-7 | Q16270 | 3490 | IGFBP7 | 8220 | 7.38E−07 | 0.00019509 | 1.45811497 |
| HemK methyltransferase family member 2 | HEMK2 | Q9Y5N5 | 29104 | N6AMT1 | 7821 | 9.39E−07 | 0.00020696 | −1.2808124 |
| Growth/differentiation factor 15 | MIC-1 | Q99988 | 9518 | GDF15 | 7588 | 1.62E−06 | 0.00030569 | 1.80209666 |
| Complement component C7 | C7 | P10643 | 730 | C7 | 7302 | 1.93E−06 | 0.00031873 | 1.59067819 |
| Integrin alpha-I:beta-1 complex | Integrin a1b1 | P56199, P05556 | 3672 3688 | ITGA1 ITGB1 | 6791 | 2.52E−06 | 0.00037022 | 2.05213702 |
| RAC-beta serine/threonine-protein kinase | PKB beta | P31751 | 208 | AKT2 | 5939 | 4.01E−06 | 0.00053043 | −1.1365205 |
| Transforming growth factor-beta-induced protein ig-h3 | BGH3 | Q15582 | 7045 | TGFBI | 5495 | 5.47E−06 | 0.00065776 | 1.47761019 |
| NADPH--cytochrome P450 reductase | NADPH-P450 Oxidoreductase | P16435 | 5447 | POR | 4664 | 9.24E−06 | 0.00101751 | 1.96716396 |
| Testican-1 | Testican-1 | Q08629 | 6695 | SPOCK1 | 4504 | 1.02E−05 | 0.00104031 | −1.2885882 |

TABLE 2-continued

Markers for diagnosis of NASH versus Simple Steatosis based on frequency

| Marker Full Name | Marker | UniProt | EntrezGene ID | Entrez Gene Symbol | FREQ | p-value | BH p | FC (AN + NN/ST) |
|---|---|---|---|---|---|---|---|---|
| Aminoacylase-1 | Aminoacylase-1 | Q03154 | 95 | ACY1 | 4173 | 1.30E−05 | 0.00122593 | 2.15610652 |
| Plasma protease C1 inhibitor | C1-Esterase Inhibitor | P05155 | 710 | SERPING1 | 3919 | 1.46E−05 | 0.00128437 | −1.2530913 |
| Discoidin domain-containing receptor 2 | Discoidin domain receptor 2 | Q16832 | 4921 | DDR2 | 3755 | 1.72E−05 | 0.00142178 | −1.1512413 |
| Metalloproteinase inhibitor 1 | TIMP-1 | P01033 | 7076 | TIMP1 | 3525 | 1.93E−05 | 0.00150233 | 1.36753397 |
| Proteasome activator complex subunit 1 | PSME1 | Q06323 | 5720 | PSME1 | 3302 | 2.52E−05 | 0.00185255 | −1.1476763 |
| Mammaglobin-B | Mammaglobin 2 | O75556 | 4246 | SCGB2A1 | 2906 | 3.50E−05 | 0.00220022 | −1.1766924 |
| Leptin receptor | sLeptin R | P48357 | 3953 | LEPR | 2884 | 3.15E−05 | 0.00219118 | 1.30978119 |
| Phosphoglycerate kinase 1 | phosphoglycerate kinase 1 | P00558 | 5230 | PGK1 | 2721 | 3.43E−05 | 0.00220022 | −1.1823505 |
| Interleukin-18 receptor 1 | IL-18 Ra | Q13478 | 8809 | IL18R1 | 2569 | 4.05E−05 | 0.00243458 | 1.15984355 |
| Galectin-7 | Galectin-7 | P47929 | 3963 | LGALS7 | 2210 | 5.97E−05 | 0.00317076 | −1.1683529 |
| Protein jagged-1 | JAG1 | P78504 | 182 | JAG1 | 1999 | 5.38E−05 | 0.00309459 | 1.1258857 |
| Calpain I | Calpain I | P07384 P04632 | 823 826 | CAPN1 CAPNS1 | 1836 | 6.00E−05 | 0.00317076 | −1.1227275 |
| Cathepsin Z | CATZ | Q9UBR2 | 1522 | CTSZ | 1818 | 7.78E−05 | 0.0039577 | 1.27327663 |
| Apolipoprotein M | ApoM | O95445 | 55937 | APOM | 1693 | 0.00012274 | 0.0055954 | −1.3359447 |
| Ephrin-B1 | EFNB1 | P98172 | 1947 | EFNB1 | 1647 | 0.0001541 | 0.00656339 | −1.1137833 |
| HERV-H LTR-associating protein 2 | HHLA2 | Q9UM44 | | HHLA2 | 1598 | 8.97E−05 | 0.00439156 | −1.1331161 |
| Caspase-10 | Caspase-10 | Q92851 | 843 | CASP10 | 1348 | 0.00013883 | 0.00611795 | −1.1817101 |
| Sphingosine kinase 1 | Sphingosine kinase 1 | Q9NYA1 | 8877 | SPHK1 | 1277 | 0.00020479 | 0.00712441 | −1.2861543 |
| Formimidoyltransferase-cyclodeaminase | FTCD | O95954 | 10841 | FTCD | 1260 | 0.0001892 | 0.00694798 | 2.58264673 |
| Decorin | Bone proteoglycan II | P07585 | 1634 | DCN | 1258 | 0.00021496 | 0.00728649 | 1.25434154 |
| Angiopoietin-2 | Angiopoietin-2 | O15123 | 285 | ANGPT2 | 1244 | 0.00017068 | 0.00663656 | 1.42880869 |
| Heat shock protein HSP 90-beta | HSP 90b | P08238 | 3326 | HSP90AB1 | 1235 | 9.49E−05 | 0.00448299 | 1.36659079 |
| Ferritin | Ferritin | P02794 P02792 | 2495 2512 | FTH1 FTL | 1215 | 0.0001852 | 0.00694798 | 1.83314418 |
| 15-hydroxyprostaglandin dehydrogenase [NAD(+)] | HPG- | P15428 | 3248 | HPGD | 1210 | 0.00015887 | 0.00656339 | −1.1146532 |
| Ubiquitin carboxyl-terminal hydrolase isozyme L1 | PGP9.5 | P09936 | 7345 | UCHL1 | 1188 | 0.00016512 | 0.006615 | −1.1258474 |
| Afamin | Afamin | P43652 | 173 | AFM | 1162 | 0.00020188 | 0.00712441 | 1.27829596 |
| Dipeptidyl peptidase 2 | DPP2 | Q9UHL4 | 29952 | DPP7 | 1154 | 0.0002468 | 0.00786794 | −1.1406022 |
| Tyrosine-protein kinase Lyn | LYN | P07948 | 4067 | LYN | 1092 | 0.00025592 | 0.00786794 | −1.4621602 |
| Neuropilin-1 | NRP1 | O14786 | 8829 | NRP1 | 1030 | 0.00025062 | 0.00786794 | 1.30227381 |
| Cell adhesion molecule 1 | Nectin-like protein 2 | Q9BY67 | 23705 | CADM1 | 1001 | 0.00049759 | 0.01306145 | 1.22328157 |
| Proto-oncogene tyrosine-protein kinase Src | SRCN1 | P12931 | 6714 | SRC | 920 | 0.00033564 | 0.00991084 | −1.5325746 |
| Fatty acid-binding protein, liver | FABPL | P07148 | 2168 | FABP1 | 739 | 0.00036117 | 0.01037957 | 1.5529323 |
| Interleukin-19 | IL-19 | Q9UHD0 | 29949 | IL19 | 698 | 0.00033736 | 0.00991084 | 1.35562117 |
| Macrophage metalloelastase | MMP-12 | P39900 | 4321 | MMP12 | 634 | 0.00037939 | 0.01067131 | 1.65727278 |
| E-selectin | sE-Selectin | P16581 | 6401 | SELE | 632 | 0.00022379 | 0.0073961 | 1.75319915 |
| Ras-related C3 botulinum toxin substrate 3 | RAC3 | P60763 | 5881 | RAC3 | 632 | 0.00060367 | 0.01425098 | −1.2176931 |

TABLE 2-continued

Markers for diagnosis of NASH versus Simple Steatosis based on frequency

| Marker Full Name | Marker | UniProt | EntrezGene ID | Entrez Gene Symbol | FREQ | p-value | BH p | FC (AN + NN/ST) |
|---|---|---|---|---|---|---|---|---|
| Coactosin-like protein | Coactosin-like protein | Q14019 | 23406 | COTL1 | 618 | 0.00051418 | 0.01306145 | −1.1498934 |
| Alcohol dehydrogenase [NADP(+)] | AK1A1 | P14550 | 10327 | AKR1A1 | 552 | 0.00040044 | 0.01102892 | 1.4001414 |
| Ubiquitin-fold modifier-conjugating enzyme 1 | UFC1 | Q9Y3C8 | 51506 | UFC1 | 550 | 0.00052364 | 0.01306145 | −1.2354453 |
| Ectonucleotide pyrophosphatase/ phosphodiesterase family member 7 | ENPP7 | Q6UWV6 | 339221 | ENPP7 | 547 | 0.00086708 | 0.01819499 | 1.71543218 |
| N-acetyl-D-glucosamine kinase | NAGK | Q9UJ70 | 55577 | NAGK | 529 | 0.0008983 | 0.01855551 | 1.30602817 |
| Interleukin-18-binding protein | IL-18 BPa | O95998 | 10068 | IL18BP | 526 | 0.000519 | 0.01306145 | 1.35161807 |
| cAMP-specific 3',5'-cyclic phosphodiesterase 4D | PDE4D | Q08499 | 5144 | PDE4D | 512 | 0.00075677 | 0.01667407 | −1.1233526 |
| dCTP pyrophosphatase 1 | XTP3A | Q9H773 | 79077 | DCTPP1 | 494 | 0.0008368 | 0.01784267 | 1.09475924 |
| Glutathione S-transferase P | Glutathione S-transferase Pi | P09211 | 2950 | GSTP1 | 483 | 0.00889601 | 0.08874604 | −1.1140336 |
| Tumor necrosis factor ligand superfamily member 8 | CD30 Ligand | P32971 | 944 | TNFSF8 | 408 | 0.00077695 | 0.01683808 | 1.29538486 |
| Tyrosine-protein kinase receptor Tie-1, soluble | sTie-1 | P35590 | 7075 | TIE1 | 395 | 0.000739 | 0.01655852 | 1.24099344 |
| Heat shock protein HSP 90-alpha/beta | HSP 90a/b | P07900 P08238 | | HSP90AA1 HSP90AB1 | 362 | 0.00047272 | 0.01275368 | 1.3865406 |
| Semaphorin-6B | SEM6B | Q9H3T3 | 10501 | SEMA6B | 290 | 0.00068625 | 0.01564175 | 1.41106265 |
| Low affinity immunoglobulin gamma Fc region receptor III-B | FCG3B | O75015 | 2215 | FCGR3B | 282 | 0.00253901 | 0.04044067 | 1.30523215 |
| Glypican-6 | GPC6 | Q9Y625 | 10082 | GPC6 | 279 | 0.00285406 | 0.04438903 | −1.138374 |
| Endothelin-converting enzyme 1 | Endothelin-converting enzyme 1 | P42892 | 1889 | ECE1 | 266 | 0.0009559 | 0.01944158 | −1.1050534 |
| Latent-transforming growth factor beta-binding protein 4 | LTBP4 | Q8N2S1 | 8425 | LTBP4 | 261 | 0.0006378 | 0.01479249 | 1.32640159 |
| Lumican | Lumican | P51884 | 4060 | LUM | 246 | 0.00124773 | 0.02344187 | 1.24212215 |
| Metalloproteinase inhibitor 2 | TIMP-2 | P16035 | 7077 | TIMP2 | 237 | 0.00101031 | 0.02023674 | 1.14322616 |
| Tumor necrosis factor ligand superfamily member 15 | TNFSF15 | O95150 | 9966 | TNFSF15 | 230 | 0.00055292 | 0.01353639 | 1.23432896 |
| Tyrosine-protein kinase Lyn, isoform B | LYNB | P07948 | 4067 | LYN | 200 | 0.00182506 | 0.03245024 | −1.4634554 |
| Fibroblast growth factor receptor 4 | FGFR4 | P22455 | 2264 | FGFR4 | 191 | 0.00135474 | 0.02453384 | −1.1461719 |
| Interleukin-1 Receptor accessory protein | IL-1 R AcP | Q9NPH3 | 3556 | IL1RAP | 174 | 0.00259668 | 0.04086683 | −1.288934 |
| Apolipoprotein B | Apo B | P04114 | 338 | APOB | 169 | 0.00056389 | 0.01355394 | −1.4401995 |
| Serine protease HTRA2, mitochondrial | HTRA2 | O43464 | 27429 | HTRA2 | 168 | 0.00185474 | 0.03245024 | 1.23161444 |
| Chorionic somatomammotropin hormone | CSH | P0DML2 P0DML3 | 1442 1443 | CSH1 CSH2 | 162 | 0.00125311 | 0.02344187 | −1.1052659 |

TABLE 2-continued

Markers for diagnosis of NASH versus Simple Steatosis based on frequency

| Marker Full Name | Marker | UniProt | EntrezGene ID | Entrez Gene Symbol | FREQ | p-value | BH p | FC (AN + NN/ST) |
|---|---|---|---|---|---|---|---|---|
| Macrophage colony-stimulating factor 1 receptor | M-CSF R | P07333 | 1436 | CSF1R | 159 | 0.00341764 | 0.0507654 | 1.42247319 |
| Lymphocyte antigen 86 | LY86 | O95711 | 9450 | LY86 | 148 | 0.00293992 | 0.04519277 | −1.0952721 |
| Insulin-like growth factor-binding protein 5 | IGFBP-5 | P24593 | 3488 | IGFBP5 | 145 | 0.00112142 | 0.02180182 | −1.1557656 |
| Adhesion G protein-coupled receptor E2 | EMR2 | Q9UHX3 | 30817 | ADGRE2 | 140 | 0.00892831 | 0.08874604 | 1.42839071 |
| Serum amyloid P-component | SAP | P02743 | 325 | APCS | 139 | 0.00109907 | 0.02168616 | −1.1636492 |
| Thrombin | Thrombin | P00734 | 2147 | F2 | 135 | 0.00135341 | 0.02453384 | −1.264436 |
| Complement component C6 | C6 | P13671 | 729 | C6 | 133 | 0.00125898 | 0.02344187 | 1.18188145 |
| Thioredoxin domain-containing protein 12 | TXD12 | O95881 | 51060 | TXNDC12 | 114 | 0.00249751 | 0.0402648 | −1.2122109 |
| EGF-containing fibulin-like extracellular matrix protein 1 | FBLN3 | Q12805 | 2202 | EFEMP1 | 109 | 0.00186552 | 0.03245024 | 1.18696608 |

The top 10 marker proteins for diagnosis of NASH were selected based on the frequency count and BH p-value including the top 3 downregulated and top 7 upregulated proteins. The proteins are:

Thrombospondin-2 (THBS2), Bcl-2-related protein A1 (BCL2A1), Tyrosine-protein kinase (YES1), Collectin-11 (COLEC11), Insulin-like growth factor-binding protein 7 (IGFBP7), HemK methyltransferase family member 2 (N6AMT1), Growth/differentiation factor 15 (GDF15), Complement component C7 (C7), Integrin alpha-I: beta-1 complex (ITGA1 ITGB1), and RAC-beta serine/threonine-protein kinase (AKT2).

Subsequently, every possible combination of these 10 proteins were tested. A 5-fold cross validation with 100 splits for each combination of the top 10 proteins was used, which resulted in 1,023 different predictors with the calculated average accuracy, sensitivity and specificity linked to each marker. The best result was 92.2% average accuracy using the 7-protein signature: THBS2, BCL2A1, COLEC11, IGFBP7, GDF15, C7, and AKT2. However, even with combinations of 3 proteins, more than 91% average accuracy was achieved and the 10-protein combination also achieved 90% average accuracy. A list of the 1,023 marker sets with higher than 75.6% accuracy among the 1,023 marker sets (each average is based on 1,000 predictions) is shown in Table 3, below.

TABLE 3

Markers for NASH versus Simple Steatosis Based on Average Accuracy, Sensitivity and Specificity

|  | AvgAcc | AvgSen | AvgSpe |
|---|---|---|---|
| 1 Protein |  |  |  |
| THBS2 | 83.066667 | 84.5 | 80.2 |
| IGFBP7 | 82.066667 | 93.7 | 58.8 |
| BCL2A1 | 80.6 | 76.9 | 88 |
| C7 | 80.266667 | 87.6 | 65.6 |
| ITGA1 ITGB1 | 79.866667 | 82.3 | 75 |
| COLEC11 | 79.533333 | 84.8 | 69 |
| N6AMT1 | 79.2 | 81.7 | 74.2 |
| GDF15 | 78.133333 | 84.3 | 65.8 |
| AKT2 | 76.6 | 88.6 | 52.6 |
| YES1 | 75.6 | 80.1 | 66.6 |
| 2 Proteins |  |  |  |
| THBS2 N6AMT1 | 90.8 | 92 | 88.4 |
| YES1 COLEC11 | 89.466667 | 89.7 | 89 |
| THBS2 BCL2A1 | 89.066667 | 94.6 | 78 |
| BCL2A1 ITGA1 ITGB1 | 89.066667 | 86.2 | 94.8 |
| YES1 AKT2 | 88.066667 | 91.2 | 81.8 |
| GDF15 C7 | 87.466667 | 91.8 | 78.8 |
| BCL2A1 YES1 | 87 | 88.9 | 83.2 |
| THBS2 COLEC11 | 86.866667 | 88.2 | 84.2 |
| THBS2 YES1 | 86.266667 | 86.3 | 86.2 |
| ITGA1 ITGB1 AKT2 | 86.266667 | 89.5 | 79.8 |

TABLE 3-continued

Markers for NASH versus Simple Steatosis Based on Average Accuracy, Sensitivity and Specificity

|  | AvgAcc | AvgSen | AvgSpe |
|---|---|---|---|
| BCL2A1 COLEC11 | 86 | 89.3 | 79.4 |
| THBS2 IGFBP7 | 85.666667 | 88.7 | 79.6 |
| GDF15 ITGA1 ITGB1 | 85.533333 | 90 | 76.6 |
| THBS2 GDF15 | 85.4 | 86.5 | 83.2 |
| THBS2 AKT2 | 85.333333 | 88.4 | 79.2 |
| THBS2 C7 | 85.133333 | 85.6 | 84.2 |
| BCL2A1 C7 | 84.4 | 85.2 | 82.8 |
| THBS2 ITGA1 ITGB1 | 83.733333 | 84.4 | 82.4 |
| YES1 C7 | 83.533333 | 88.8 | 73 |
| COLEC11 AKT2 | 83.066667 | 89.2 | 70.8 |
| IGFBP7 N6AMT1 | 82.933333 | 88.4 | 72 |
| COLEC11 N6AMT1 | 82.866667 | 82.9 | 82.8 |
| IGFBP7 GDF15 | 82.866667 | 90 | 68.6 |
| N6AMT1 ITGA1 ITGB1 | 82.4 | 80 | 87.2 |
| YES1 N6AMT1 | 82.133333 | 83 | 80.4 |
| C7 ITGA1 ITGB1 | 82.133333 | 89.8 | 66.8 |
| COLEC11 IGFBP7 | 82.066667 | 87.5 | 71.2 |
| BCL2A1 IGFBP7 | 82 | 87.2 | 71.6 |
| IGFBP7 C7 | 82 | 87.9 | 70.2 |
| N6AMT1 GDF15 | 81.8 | 90.7 | 64 |
| BCL2A1 GDF15 | 81.6 | 88 | 68.8 |
| BCL2A1 AKT2 | 81.4 | 86.1 | 72 |
| YES1 IGFBP7 | 81.2 | 84.2 | 75.2 |
| COLEC11 C7 | 81.2 | 87.7 | 68.2 |
| C7 AKT2 | 81.2 | 85.3 | 73 |
| YES1 ITGA1 ITGB1 | 80.466667 | 85.6 | 70.2 |
| COLEC11 GDF15 | 79.933333 | 83.2 | 73.4 |
| IGFBP7 ITGA1 ITGB1 | 79.666667 | 81.6 | 75.8 |
| IGFBP7 AKT2 | 79.533333 | 88.7 | 61.2 |
| COLEC11 ITGA1 ITGB1 | 79.266667 | 84.2 | 69.4 |
| YES1 GDF15 | 79 | 81.6 | 73.8 |
| N6AMT1 AKT2 | 78.933333 | 87.8 | 61.2 |
| BCL2A1 N6AMT1 | 78.666667 | 78.5 | 79 |
| N6AMT1 C7 | 78.533333 | 86.2 | 63.2 |
| GDF15 AKT2 | 76.6 | 80.5 | 68.8 |
| 3 Proteins |  |  |  |
| BCL2A1 ITGA1 ITGB1 AKT2 | 91.933333 | 93.2 | 89.4 |
| BCL2A1 YES1 ITGA1 ITGB1 | 91.866667 | 90.5 | 94.6 |
| THBS2 COLEC11 GDF15 | 90.8 | 93.6 | 85.2 |
| BCL2A1 YES1 AKT2 | 89.933333 | 90 | 89.8 |
| BCL2A1 YES1 COLEC11 | 89.8 | 91.3 | 86.8 |
| THBS2 GDF15 ITGA1 ITGB1 | 89.466667 | 90.8 | 86.8 |
| YES1 COLEC11 AKT2 | 89.466667 | 89.8 | 88.8 |
| THBS2 YES1 N6AMT1 | 89.266667 | 90.9 | 86 |
| THBS2 N6AMT1 AKT2 | 89.266667 | 91.1 | 85.6 |
| THBS2 BCL2A1 N6AMT1 | 88.8 | 90.7 | 85 |
| THBS2 COLEC11 C7 | 88.533333 | 89.7 | 86.2 |
| THBS2 GDF15 C7 | 88.4 | 89.7 | 85.8 |
| THBS2 YES1 AKT2 | 88.2 | 89.3 | 86 |
| THBS2 BCL2A1 GDF15 | 88.133333 | 89.9 | 84.6 |
| BCL2A1 C7 ITGA1 ITGB1 | 88.133333 | 90.3 | 83.8 |
| THBS2 IGFBP7 GDF15 | 88.066667 | 91.2 | 81.8 |
| YES1 GDF15 C7 | 88.066667 | 91.2 | 81.8 |
| THBS2 N6AMT1 C7 | 87.933333 | 89.1 | 85.6 |
| GDF15 C7 ITGA1 ITGB1 | 87.8 | 91.4 | 80.6 |
| THBS2 N6AMT1 GDF15 | 87.6 | 89.6 | 83.6 |
| IGFBP7 GDF15 ITGA1 ITGB1 | 87.6 | 90.1 | 82.6 |
| THBS2 COLEC11 N6AMT1 | 87.533333 | 88.6 | 85.4 |
| BCL2A1 GDF15 ITGA1 ITGB1 | 87.466667 | 93.5 | 75.4 |
| THBS2 YES1 COLEC11 | 87.266667 | 87.7 | 86.4 |
| THBS2 COLEC11 AKT2 | 87.266667 | 89.4 | 83 |
| THBS2 BCL2A1 YES1 | 87.2 | 91.5 | 78.6 |
| THBS2 BCL2A1 AKT2 | 87.2 | 94.7 | 72.2 |
| THBS2 IGFBP7 N6AMT1 | 87.2 | 93.4 | 74.8 |
| BCL2A1 N6AMT1 ITGA1 ITGB1 | 87.066667 | 87.1 | 87 |
| N6AMT1 C7 ITGA1 ITGB1 | 87.066667 | 89.1 | 83 |
| THBS2 BCL2A1 C7 | 87 | 89 | 83 |
| GDF15 C7 AKT2 | 87 | 91.1 | 78.8 |
| YES1 COLEC11 N6AMT1 | 86.933333 | 87.8 | 85.2 |
| N6AMT1 GDF15 ITGA1 ITGB1 | 86.933333 | 92.2 | 76.4 |
| IGFBP7 GDF15 C7 | 86.866667 | 90.3 | 80 |
| THBS2 GDF15 AKT2 | 86.8 | 87.9 | 84.6 |
| GDF15 ITGA1 ITGB1 AKT2 | 86.8 | 93.8 | 72.8 |
| THBS2 YES1 C7 | 86.733333 | 87.7 | 84.8 |
| BCL2A1 YES1 C7 | 86.666667 | 92.1 | 75.8 |

TABLE 3-continued

Markers for NASH versus Simple Steatosis Based on Average Accuracy, Sensitivity and Specificity

| | AvgAcc | AvgSen | AvgSpe |
|---|---|---|---|
| THBS2 YES1 GDF15 | 86.6 | 87.3 | 85.2 |
| THBS2 BCL2A1 COLEC11 | 86.4 | 89.3 | 80.6 |
| BCL2A1 YES1 IGFBP7 | 86.4 | 91.2 | 76.8 |
| COLEC11 IGFBP7 N6AMT1 | 86.4 | 89.2 | 80.8 |
| IGFBP7 N6AMT1 GDF15 | 86.4 | 92.8 | 73.6 |
| BCL2A1 GDF15 C7 | 86.333333 | 89.4 | 80.2 |
| N6AMT1 GDF15 C7 | 86.333333 | 89.9 | 79.2 |
| THBS2 C7 ITGA1 ITGB1 | 86.133333 | 87.3 | 83.8 |
| THBS2 BCL2A1 IGFBP7 | 86.066667 | 92 | 74.2 |
| THBS2 IGFBP7 C7 | 86 | 88.6 | 80.8 |
| THBS2 IGFBP7 AKT2 | 86 | 90.2 | 77.6 |
| BCL2A1 COLEC11 AKT2 | 85.866667 | 91.4 | 74.8 |
| THBS2 C7 AKT2 | 85.8 | 88 | 81.4 |
| BCL2A1 COLEC11 N6AMT1 | 85.466667 | 87 | 82.4 |
| YES1 GDF15 AKT2 | 85.466667 | 86.5 | 83.4 |
| BCL2A1 IGFBP7 GDF15 | 85.266667 | 93.1 | 69.6 |
| THBS2 COLEC11 IGFBP7 | 85.2 | 87 | 81.6 |
| YES1 N6AMT1 GDF15 | 85.2 | 90.4 | 74.8 |
| YES1 GDF15 ITGA1 ITGB1 | 85.133333 | 91 | 73.4 |
| YES1 ITGA1 ITGB1 AKT2 | 85.133333 | 88.9 | 77.6 |
| COLEC11 N6AMT1 AKT2 | 85 | 85.8 | 83.4 |
| BCL2A1 COLEC11 IGFBP7 | 84.8 | 91.7 | 71 |
| C7 ITGA1 ITGB1 AKT2 | 84.733333 | 89.8 | 74.6 |
| YES1 IGFBP7 GDF15 | 84.6 | 89.8 | 74.2 |
| IGFBP7 GDF15 AKT2 | 84.6 | 91.3 | 71.2 |
| THBS2 COLEC11 ITGA1 ITGB1 | 84.466667 | 85.5 | 82.4 |
| BCL2A1 YES1 GDF15 | 84.4 | 89.1 | 75 |
| IGFBP7 N6AMT1 ITGA1 ITGB1 | 84.4 | 87.9 | 77.4 |
| THBS2 YES1 IGFBP7 | 84.2 | 86.7 | 79.2 |
| IGFBP7 C7 ITGA1 ITGB1 | 84.2 | 88.3 | 76 |
| THBS2 N6AMT1 ITGA1 ITGB1 | 84.133333 | 84.8 | 82.8 |
| YES1 N6AMT1 ITGA1 ITGB1 | 84.133333 | 82.7 | 87 |
| THBS2 BCL2A1 ITGA1 ITGB1 | 84.066667 | 83.2 | 85.8 |
| THBS2 YES1 ITGA1 ITGB1 | 84.066667 | 85.6 | 81 |
| N6AMT1 ITGA1 ITGB1 AKT2 | 84.066667 | 83.9 | 84.4 |
| BCL2A1 COLEC11 C7 | 84 | 88.8 | 74.4 |
| YES1 N6AMT1 AKT2 | 84 | 84.6 | 82.8 |
| THBS2 ITGA1 ITGB1 AKT2 | 83.6 | 84.9 | 81 |
| BCL2A1 C7 AKT2 | 83.533333 | 86.6 | 77.4 |
| COLEC11 C7 AKT2 | 83.4 | 89 | 72.2 |
| N6AMT1 GDF15 AKT2 | 83.333333 | 91.4 | 67.2 |
| YES1 COLEC11 IGFBP7 | 83.266667 | 88.7 | 72.4 |
| COLEC11 IGFBP7 AKT2 | 83.2 | 89 | 71.6 |
| YES1 IGFBP7 N6AMT1 | 83 | 88.4 | 72.2 |
| BCL2A1 IGFBP7 AKT2 | 82.866667 | 90.2 | 68.2 |
| IGFBP7 N6AMT1 C7 | 82.866667 | 87.2 | 74.2 |
| COLEC11 C7 ITGA1 ITGB1 | 82.8 | 87.9 | 72.6 |
| IGFBP7 N6AMT1 AKT2 | 82.8 | 89.2 | 70 |
| YES1 IGFBP7 AKT2 | 82.666667 | 85.2 | 77.6 |
| COLEC11 N6AMT1 GDF15 | 82.666667 | 85.8 | 76.4 |
| YES1 C7 ITGA1 ITGB1 | 82.533333 | 88.3 | 71 |
| COLEC11 IGFBP7 C7 | 82.4 | 86.6 | 74 |
| YES1 IGFBP7 ITGA1 ITGB1 | 82.266667 | 85 | 76.8 |
| THBS2 IGFBP7 ITGA1 ITGB1 | 82.2 | 81.6 | 83.4 |
| BCL2A1 GDF15 AKT2 | 82.2 | 89.5 | 67.6 |
| COLEC11 N6AMT1 ITGA1 ITGB1 | 82.066667 | 84.7 | 76.8 |
| COLEC11 GDF15 C7 | 81.866667 | 84.5 | 76.6 |
| COLEC11 N6AMT1 C7 | 81.733333 | 81.3 | 82.6 |
| IGFBP7 C7 AKT2 | 81.733333 | 87.6 | 70 |
| BCL2A1 N6AMT1 GDF15 | 81.666667 | 88 | 69 |
| YES1 C7 AKT2 | 81.6 | 87.4 | 70 |
| BCL2A1 IGFBP7 N6AMT1 | 81.533333 | 87 | 70.6 |
| BCL2A1 YES1 N6AMT1 | 81.266667 | 81.8 | 80.2 |
| YES1 IGFBP7 C7 | 81.266667 | 85.5 | 72.8 |
| BCL2A1 IGFBP7 ITGA1 ITGB1 | 81.2 | 86.5 | 70.6 |
| YES1 COLEC11 C7 | 81.2 | 86.9 | 69.8 |
| COLEC11 IGFBP7 ITGA1 ITGB1 | 81.2 | 85.5 | 72.6 |
| N6AMT1 C7 AKT2 | 81.2 | 86.2 | 71.2 |
| COLEC11 GDF15 AKT2 | 81.066667 | 82.6 | 78 |
| BCL2A1 IGFBP7 C7 | 80.933333 | 87.8 | 67.2 |
| BCL2A1 N6AMT1 AKT2 | 80.866667 | 84.7 | 73.2 |
| BCL2A1 COLEC11 ITGA1 ITGB1 | 80.6 | 85.3 | 71.2 |
| BCL2A1 N6AMT1 C7 | 80.6 | 84.3 | 73.2 |
| YES1 COLEC11 ITGA1 ITGB1 | 80.6 | 83.1 | 75.6 |
| COLEC11 IGFBP7 GDF15 | 80.4 | 82.1 | 77 |
| YES1 COLEC11 GDF15 | 80.333333 | 80.8 | 79.4 |

TABLE 3-continued

Markers for NASH versus Simple Steatosis Based on Average Accuracy, Sensitivity and Specificity

| | AvgAcc | AvgSen | AvgSpe |
|---|---|---|---|
| COLEC11 GDF15 ITGA1 ITGB1 | 80.266667 | 85.6 | 69.6 |
| COLEC11 ITGA1 ITGB1 AKT2 | 80.266667 | 83.4 | 74 |
| YES1 N6AMT1 C7 | 80.066667 | 85 | 70.2 |
| IGFBP7 ITGA1 ITGB1 AKT2 | 79.866667 | 83 | 73.6 |
| BCL2A1 COLEC11 GDF15 | 79.6 | 82 | 74.8 |
| 4 Proteins | | | |
| BCL2A1 YES1 GDF15 AKT2 | 90.866667 | 93.3 | 86 |
| THBS2 COLEC11 N6AMT1 GDF15 | 90.666667 | 93.7 | 84.6 |
| BCL2A1 YES1 ITGA1 ITGB1 AKT2 | 90.6 | 90.3 | 91.2 |
| THBS2 GDF15 C7 ITGA1 ITGB1 | 90.6 | 93.4 | 85 |
| THBS2 YES1 COLEC11 GDF15 | 90.333333 | 92.3 | 86.4 |
| THBS2 COLEC11 GDF15 C7 | 90.266667 | 92.2 | 86.4 |
| BCL2A1 YES1 COLEC11 AKT2 | 90.133333 | 93.6 | 83.2 |
| THBS2 YES1 N6AMT1 AKT2 | 90.066667 | 91.9 | 86.4 |
| THBS2 COLEC11 C7 AKT2 | 90 | 91.8 | 86.4 |
| THBS2 BCL2A1 COLEC11 GDF15 | 90 | 93.8 | 82.4 |
| THBS2 IGFBP7 N6AMT1 C7 | 89.933333 | 93.2 | 83.4 |
| THBS2 N6AMT1 GDF15 ITGA1 ITGB1 | 89.8 | 92.1 | 85.2 |
| THBS2 YES1 GDF15 ITGA1 ITGB1 | 89.8 | 91.5 | 86.4 |
| THBS2 BCL2A1 COLEC11 C7 | 89.6 | 91.6 | 85.6 |
| THBS2 GDF15 ITGA1 ITGB1 AKT2 | 89.533333 | 91.6 | 85.4 |
| N6AMT1 GDF15 C7 ITGA1 ITGB1 | 89.466667 | 93.4 | 81.6 |
| THBS2 COLEC11 GDF15 ITGA1 ITGB1 | 89.266667 | 92.1 | 83.6 |
| THBS2 BCL2A1 GDF15 ITGA1 ITGB1 | 89.266667 | 91.3 | 85.2 |
| THBS2 BCL2A1 YES1 N6AMT1 | 89.266667 | 92.9 | 82 |
| THBS2 YES1 COLEC11 C7 | 89.2 | 92.1 | 83.4 |
| THBS2 BCL2A1 GDF15 AKT2 | 89.2 | 91.2 | 85.2 |
| THBS2 GDF15 C7 AKT2 | 89.133333 | 91.1 | 85.2 |
| THBS2 YES1 N6AMT1 C7 | 89.133333 | 90.8 | 85.8 |
| THBS2 YES1 COLEC11 AKT2 | 89.133333 | 90.9 | 85.6 |
| BCL2A1 N6AMT1 C7 ITGA1 ITGB1 | 89.066667 | 90.1 | 87 |
| THBS2 COLEC11 N6AMT1 C7 | 89.066667 | 91.2 | 84.8 |
| THBS2 COLEC11 IGFBP7 GDF15 | 88.933333 | 92.3 | 82.2 |
| THBS2 IGFBP7 GDF15 ITGA1 ITGB1 | 88.866667 | 91.3 | 84 |
| THBS2 BCL2A1YES1 C7 | 88.866667 | 91.1 | 84.4 |
| THBS2 N6AMT1 C7 ITGA1 ITGB1 | 88.733333 | 91.4 | 83.4 |
| THBS2 BCL2A1 N6AMT1 C7 | 88.666667 | 90.2 | 85.6 |
| THBS2 COLEC11 GDF15 AKT2 | 88.6 | 91.5 | 82.8 |
| THBS2 COLEC11 N6AMT1 AKT2 | 88.6 | 91.2 | 83.4 |
| THBS2 BCL2A1 COLEC11 N6AMT1 | 88.6 | 90 | 85.8 |
| BCL2A1 GDF15 C7 ITGA1 ITGB1 | 88.533333 | 91.8 | 82 |
| THBS2 N6AMT1 C7 AKT2 | 88.533333 | 91.2 | 83.2 |
| THBS2 BCL2A1 N6AMT1 GDF15 | 88.466667 | 89.8 | 85.8 |
| YES1 COLEC11 N6AMT1 AKT2 | 88.4 | 90.2 | 84.8 |
| YES1 N6AMT1 C7 ITGA1 ITGB1 | 88.333333 | 89.8 | 85.4 |
| BCL2A1 YES1 C7 AKT2 | 88.333333 | 93.2 | 78.6 |
| YES1 GDF15 C7 ITGA1 ITGB1 | 88.266667 | 92.6 | 79.6 |
| THBS2 YES1 COLEC11 IGFBP7 | 88.266667 | 90.8 | 83.2 |
| THBS2 COLEC11 IGFBP7 C7 | 88.2 | 89.6 | 85.4 |
| GDF15 C7 ITGA1 ITGB1 AKT2 | 88.133333 | 91.6 | 81.2 |
| THBS2 YES1 COLEC11 N6AMT1 | 88.066667 | 90.4 | 83.4 |
| THBS2 BCL2A1 N6AMT1 AKT2 | 88 | 90.9 | 82.2 |
| THBS2 BCL2A1 YES1 GDF15 | 87.933333 | 89.3 | 85.2 |
| THBS2 BCL2A1 IGFBP7 N6AMT1 | 87.8 | 93.4 | 76.6 |
| IGFBP7 N6AMT1 GDF15 ITGA1 ITGB1 | 87.733333 | 91.4 | 80.4 |
| THBS2 IGFBP7 GDF15 AKT2 | 87.733333 | 91.7 | 79.8 |
| THBS2 IGFBP7 GDF15 C7 | 87.733333 | 89.2 | 84.8 |
| THBS2 BCL2A1 GDF15 C7 | 87.666667 | 90.2 | 82.6 |
| THBS2 BCL2A1 COLEC11 AKT2 | 87.666667 | 90 | 83 |
| THBS2 BCL2A1 YES1 AKT2 | 87.666667 | 93.3 | 76.4 |
| THBS2 N6AMT1 GDF15 AKT2 | 87.6 | 89.2 | 84.4 |
| THBS2 YES1 GDF15 C7 | 87.6 | 88.8 | 85.2 |
| THBS2 BCL2A1 YES1 COLEC11 | 87.6 | 90.1 | 82.6 |
| THBS2 N6AMT1 GDF15 C7 | 87.533333 | 88.7 | 85.2 |
| THBS2 BCL2A1 C7 AKT2 | 87.533333 | 88.3 | 86 |
| THBS2 BCL2A1 IGFBP7 C7 | 87.533333 | 91.2 | 80.2 |
| BCL2A1 C7 ITGA1 ITGB1 AKT2 | 87.466667 | 89.7 | 83 |
| BCL2A1 IGFBP7 N6AMT1 ITGA1 ITGB1 | 87.333333 | 92.5 | 77 |
| THBS2 IGFBP7 N6AMT1 GDF15 | 87.333333 | 91 | 80 |
| THBS2 COLEC11 N6AMT1 ITGA1 ITGB1 | 87.333333 | 88.9 | 84.2 |
| THBS2 YES1 C7 ITGA1 ITGB1 | 87.333333 | 88.2 | 85.6 |
| THBS2 YES1 GDF15 AKT2 | 87.333333 | 88.7 | 84.6 |
| BCL2A1 N6AMT1 ITGA1 ITGB1 AKT2 | 87.2 | 86.7 | 88.2 |
| BCL2A1 IGFBP7 C7 ITGA1 ITGB1 | 87.2 | 89.1 | 83.4 |
| THBS2 COLEC11 IGFBP7 N6AMT1 | 87.2 | 89.9 | 81.8 |

TABLE 3-continued

Markers for NASH versus Simple Steatosis Based on Average Accuracy, Sensitivity and Specificity

| | AvgAcc | AvgSen | AvgSpe |
|---|---|---|---|
| N6AMT1 GDF15 C7 AKT2 | 87.133333 | 90.1 | 81.2 |
| THBS2 BCL2A1 C7 ITGA1 ITGB1 | 87.133333 | 87.3 | 86.8 |
| N6AMT1 C7 ITGA1 ITGB1 AKT2 | 87.066667 | 88.1 | 85 |
| BCL2A1GDF15 C7 AKT2 | 87.066667 | 91.1 | 79 |
| BCL2A1 N6AMT1 GDF15 ITGA1 ITGB1 | 87.066667 | 93.7 | 73.8 |
| THBS2 BCL2A1 IGFBP7 GDF15 | 87.066667 | 91.6 | 78 |
| THBS2 YES1 IGFBP7 N6AMT1 | 87 | 92.2 | 76.6 |
| IGFBP7 GDF15 ITGA1 ITGB1 AKT2 | 86.933333 | 91.7 | 77.4 |
| YES1 N6AMT1 GDF15 C7 | 86.933333 | 91.8 | 77.2 |
| BCL2A1 N6AMT1 GDF15 C7 | 86.933333 | 92.2 | 76.4 |
| IGFBP7 N6AMT1 C7 ITGA1 ITGB1 | 86.866667 | 88.5 | 83.6 |
| YES1 IGFBP7 GDF15 ITGA1 ITGB1 | 86.866667 | 91.3 | 78 |
| THBS2 BCL2A1 N6AMT1 ITGA1 ITGB1 | 86.866667 | 88.4 | 83.8 |
| BCL2A1 YES1 C7 ITGA1 ITGB1 | 86.8 | 91 | 78.4 |
| THBS2 IGFBP7 N6AMT1 AKT2 | 86.733333 | 92.5 | 75.2 |
| BCL2A1 YES1 IGFBP7 AKT2 | 86.666667 | 91.1 | 77.8 |
| THBS2 IGFBP7 C7 ITGA1 ITGB1 | 86.666667 | 87.4 | 85.2 |
| THBS2 COLEC11 IGFBP7 AKT2 | 86.6 | 86.8 | 86.2 |
| THBS2 YES1 IGFBP7 C7 | 86.6 | 88.2 | 83.4 |
| N6AMT1 GDF15 ITGA1 ITGB1 AKT2 | 86.533333 | 92.3 | 75 |
| BCL2A1 YES1 COLEC11 N6AMT1 | 86.533333 | 89.2 | 81.2 |
| BCL2A1 IGFBP7 GDF15 ITGA1 ITGB1 | 86.466667 | 91.1 | 77.2 |
| THBS2 COLEC11 C7 ITGA1 ITGB1 | 86.466667 | 86.6 | 86.2 |
| THBS2 YES1 IGFBP7 AKT2 | 86.466667 | 89.4 | 80.6 |
| IGFBP7 GDF15 C7 ITGA1 ITGB1 | 86.4 | 89.3 | 80.6 |
| THBS2 YES1 N6AMT1 GDF15 | 86.333333 | 87.6 | 83.8 |
| YES1 IGFBP7 C7 ITGA1 ITGB1 | 86.266667 | 90.1 | 78.6 |
| BCL2A1 GDF15 ITGA1 ITGB1 AKT2 | 86.266667 | 92.4 | 74 |
| COLEC11 N6AMT1 C7 AKT2 | 86.2 | 87.6 | 83.4 |
| YES1 GDF15 ITGA1 ITGB1 AKT2 | 86.133333 | 90.7 | 77 |
| THBS2 BCL2A1 COLEC11 IGFBP7 | 86.066667 | 87.3 | 83.6 |
| YES1 N6AMT1 ITGA1 ITGB1 AKT2 | 86 | 84.8 | 88.4 |
| YES1 N6AMT1 GDF15 AKT2 | 85.933333 | 90.8 | 76.2 |
| IGFBP7 GDF15 C7 AKT2 | 85.866667 | 89.4 | 78.8 |
| COLEC11 GDF15 C7 ITGA1 ITGB1 | 85.866667 | 88.7 | 80.2 |
| YES1 IGFBP7 GDF15 AKT2 | 85.866667 | 89.4 | 78.8 |
| BCL2A1 YES1 N6AMT1 AKT2 | 85.866667 | 85.9 | 85.8 |
| THBS2 C7 ITGA1 ITGB1 AKT2 | 85.866667 | 85.7 | 86.2 |
| THBS2 BCL2A1 YES1 IGFBP7 | 85.866667 | 90.1 | 77.4 |
| YES1 IGFBP7 N6AMT1 ITGA1 ITGB1 | 85.733333 | 89.5 | 78.2 |
| BCL2A1 YES1 N6AMT1 ITGA1 ITGB1 | 85.733333 | 85.8 | 85.6 |
| BCL2A1 YES1 GDF15 C7 | 85.666667 | 87.8 | 81.4 |
| THBS2 YES1 IGFBP7 GDF15 | 85.666667 | 88.9 | 79.2 |
| YES1 GDF15 C7 AKT2 | 85.6 | 89.4 | 78 |
| BCL2A1 COLEC11 IGFBP7 N6AMT1 | 85.6 | 88.9 | 79 |
| BCL2A1 YES1 GDF15 ITGA1 ITGB1 | 85.6 | 90.9 | 75 |
| THBS2 COLEC11 IGFBP7 ITGA1 ITGB1 | 85.6 | 86.6 | 83.6 |
| BCL2A1 YES1 COLEC11 IGFBP7 | 85.533333 | 90.2 | 76.2 |
| IGFBP7 N6AMT1 GDF15 C7 | 85.466667 | 90.3 | 75.8 |
| THBS2 IGFBP7 C7 AKT2 | 85.466667 | 89.8 | 76.8 |
| THBS2 YES1 C7 AKT2 | 85.466667 | 85.9 | 84.6 |
| YES1 COLEC11 N6AMT1 C7 | 85.4 | 86 | 84.2 |
| THBS2 YES1 COLEC11 ITGA1 ITGB1 | 85.333333 | 85.9 | 84.2 |
| IGFBP7 C7 ITGA1 ITGB1 AKT2 | 85.266667 | 88.9 | 78 |
| YES1 COLEC11 IGFBP7 N6AMT1 | 85.266667 | 88.5 | 78.8 |
| BCL2A1 IGFBP7 N6AMT1 GDF15 | 85.2 | 93.5 | 68.6 |
| YES1 N6AMT1 GDF15 ITGA1 ITGB1 | 85.133333 | 92.7 | 70 |
| YES1 IGFBP7 GDF15 C7 | 85.133333 | 89.4 | 76.6 |
| BCL2A1 COLEC11 C7 ITGA1 ITGB1 | 85.066667 | 89 | 77.2 |
| BCL2A1 YES1 COLEC11 C7 | 85.066667 | 86.7 | 81.8 |
| THBS2 COLEC11 ITGA1 ITGB1 AKT2 | 84.933333 | 83.8 | 87.2 |
| THBS2 BCL2A1 IGFBP7 AKT2 | 84.866667 | 91.1 | 72.4 |
| THBS2 BCL2A1 COLEC11 ITGA1 ITGB1 | 84.8 | 84.8 | 84.8 |
| THBS2 BCL2A1 IGFBP7 ITGA1 ITGB1 | 84.733333 | 86 | 82.2 |
| BCL2A1 COLEC11 N6AMT1 AKT2 | 84.666667 | 85.7 | 82.6 |
| BCL2A1 IGFBP7 N6AMT1 C7 | 84.6 | 87.9 | 78 |
| IGFBP7 N6AMT1 ITGA1 ITGB1 AKT2 | 84.533333 | 90.9 | 71.8 |
| COLEC11 IGFBP7 N6AMT1 AKT2 | 84.533333 | 89.3 | 75 |
| COLEC11 IGFBP7 C7 ITGA1 ITGB1 | 84.466667 | 87.5 | 78.4 |
| YES1 C7 ITGA1 ITGB1 AKT2 | 84.466667 | 89.2 | 75 |
| COLEC11 IGFBP7 N6AMT1 C7 | 84.4 | 86.4 | 80.4 |
| THBS2 IGFBP7 N6AMT1 ITGA1 ITGB1 | 84.4 | 85.5 | 82.2 |
| IGFBP7 N6AMT1 GDF15 AKT2 | 84.333333 | 91.1 | 70.8 |
| BCL2A1 COLEC11 N6AMT1 C7 | 84.333333 | 88.7 | 75.6 |
| THBS2 YES1 N6AMT1 ITGA1 ITGB1 | 84.333333 | 85.1 | 82.8 |
| THBS2 BCL2A1 YES1 ITGA1 ITGB1 | 84.266667 | 86.2 | 80.4 |

TABLE 3-continued

Markers for NASH versus Simple Steatosis Based on Average Accuracy, Sensitivity and Specificity

|  | AvgAcc | AvgSen | AvgSpe |
|---|---|---|---|
| THBS2 BCL2A1 ITGA1 ITGB1 AKT2 | 84.066667 | 85.2 | 81.8 |
| BCL2A1 YES1 N6AMT1 GDF15 | 84 | 90.7 | 70.6 |
| BCL2A1 COLEC11 IGFBP7 C7 | 83.933333 | 86.5 | 78.8 |
| YES1 IGFBP7 N6AMT1 GDF15 | 83.733333 | 86.9 | 77.4 |
| BCL2A1 COLEC11 N6AMT1 GDF15 | 83.733333 | 86.5 | 78.2 |
| BCL2A1 YES1 IGFBP7 ITGA1 ITGB1 | 83.733333 | 89.5 | 72.2 |
| YES1 COLEC11 C7 AKT2 | 83.666667 | 86.5 | 78 |
| THBS2 YES1 ITGA1 ITGB1 AKT2 | 83.666667 | 84 | 83 |
| BCL2A1 YES1 IGFBP7 N6AMT1 | 83.6 | 90.4 | 70 |
| COLEC11 C7 ITGA1 ITGB1 AKT2 | 83.533333 | 87.9 | 74.8 |
| COLEC11 N6AMT1 GDF15 C7 | 83.533333 | 86 | 78.6 |
| BCL2A1 IGFBP7 GDF15 AKT2 | 83.533333 | 91 | 68.6 |
| YES1 IGFBP7 N6AMT1 C7 | 83.466667 | 89.5 | 71.4 |
| THBS2 N6AMT1 ITGA1 ITGB1 AKT2 | 83.466667 | 84 | 82.4 |
| BCL2A1 IGFBP7 GDF15 C7 | 83.4 | 87.2 | 75.8 |
| BCL2A1 YES1 IGFBP7 GDF15 | 83.266667 | 90.4 | 69 |
| BCL2A1 COLEC11 IGFBP7 AKT2 | 83.2 | 90.2 | 69.2 |
| COLEC11 IGFBP7 ITGA1 ITGB1 AKT2 | 83.133333 | 86.9 | 75.6 |
| COLEC11 N6AMT1 C7 ITGA1 ITGB1 | 83.066667 | 87.5 | 74.2 |
| COLEC11 IGFBP7 GDF15 ITGA1 ITGB1 | 83.066667 | 85.5 | 78.2 |
| YES1 COLEC11 IGFBP7 AKT2 | 83.066667 | 88.1 | 73 |
| BCL2A1 N6AMT1 C7 AKT2 | 82.933333 | 84.9 | 79 |
| THBS2 YES1 IGFBP7 ITGA1 ITGB1 | 82.866667 | 84.3 | 80 |
| YES1 COLEC11 C7 ITGA1 ITGB1 | 82.733333 | 87.9 | 72.4 |
| IGFBP7 N6AMT1 C7 AKT2 | 82.6 | 87.9 | 72 |
| BCL2A1 COLEC11 C7 AKT2 | 82.6 | 87.2 | 73.4 |
| THBS2 IGFBP7 ITGA1 ITGB1 AKT2 | 82.6 | 82.6 | 82.6 |
| COLEC11 IGFBP7 GDF15 C7 | 82.466667 | 84.2 | 79 |
| YES1 COLEC11 IGFBP7 C7 | 82.266667 | 86.2 | 74.4 |
| BCL2A1 N6AMT1 GDF15 AKT2 | 82.266667 | 89.6 | 67.6 |
| COLEC11 IGFBP7 C7 AKT2 | 82.2 | 84.7 | 77.2 |
| YES1 COLEC11 N6AMT1 GDF15 | 82.2 | 84.7 | 77.2 |
| COLEC11 IGFBP7 N6AMT1 ITGA1 ITGB1 | 82.133333 | 84.9 | 76.6 |
| BCL2A1 IGFBP7 N6AMT1 AKT2 | 82.133333 | 87.6 | 71.2 |
| BCL2A1 YES1 N6AMT1 C7 | 81.866667 | 84.2 | 77.2 |
| YES1 COLEC11 IGFBP7 GDF15 | 81.733333 | 83.5 | 78.2 |
| BCL2A1 COLEC11 N6AMT1 ITGA1 ITGB1 | 81.6 | 84.4 | 76 |
| COLEC11 N6AMT1 GDF15 ITGA1 ITGB1 | 81.533333 | 86.6 | 71.4 |
| YES1 COLEC11 N6AMT1 ITGA1 ITGB1 | 81.533333 | 85.3 | 74 |
| BCL2A1 COLEC11 GDF15 C7 | 81.533333 | 85 | 74.6 |
| BCL2A1 YES1 COLEC11 GDF15 | 81.533333 | 84.1 | 76.4 |
| YES1 IGFBP7 C7 AKT2 | 81.466667 | 86.6 | 71.2 |
| BCL2A1 COLEC11 IGFBP7 GDF15 | 81.466667 | 83.5 | 77.4 |
| BCL2A1 IGFBP7 ITGA1 ITGB1 AKT2 | 81.333333 | 86.6 | 70.8 |
| COLEC11 N6AMT1 ITGA1 ITGB1 AKT2 | 81.266667 | 85.8 | 72.2 |
| COLEC11 GDF15 ITGA1 ITGB1 AKT2 | 81.2 | 85.2 | 73.2 |
| YES1 IGFBP7 N6AMT1 AKT2 | 81.2 | 86.9 | 69.8 |
| BCL2A1 YES1 COLEC11 ITGA1 ITGB1 | 81.2 | 85.8 | 72 |
| COLEC11 IGFBP7 GDF15 AKT2 | 81.066667 | 82.4 | 78.4 |
| BCL2A1 COLEC11 IGFBP7 ITGA1 ITGB1 | 81.066667 | 86.7 | 69.8 |
| YES1 IGFBP7 ITGA1 ITGB1 AKT2 | 81 | 85 | 73 |
| YES1 COLEC11 ITGA1 ITGB1 AKT2 | 80.866667 | 83.9 | 74.8 |
| YES1 COLEC11 GDF15 C7 | 80.8 | 82.5 | 77.4 |
| BCL2A1 IGFBP7 C7 AKT2 | 80.8 | 87.4 | 67.6 |
| COLEC11 IGFBP7 N6AMT1 GDF15 | 80.733333 | 82.6 | 77 |
| YES1 N6AMT1 C7 AKT2 | 80.733333 | 86.5 | 69.2 |
| BCL2A1 YES1 IGFBP7 C7 | 80.733333 | 86.3 | 69.6 |
| BCL2A1 COLEC11 ITGA1 ITGB1 AKT2 | 80.666667 | 84.9 | 72.2 |
| BCL2A1 COLEC11 GDF15 ITGA1 ITGB1 | 80.6 | 85.7 | 70.4 |
| BCL2A1 COLEC11 GDF15 AKT2 | 80.333333 | 81.9 | 77.2 |
| COLEC11 GDF15 C7 AKT2 | 80.2 | 82.3 | 76 |
| YES1 COLEC11 GDF15 AKT2 | 80.133333 | 81.4 | 77.6 |
| YES1 COLEC11 IGFBP7 ITGA1 ITGB1 | 80.133333 | 83.1 | 74.2 |
| COLEC11 N6AMT1 GDF15 AKT2 | 79.866667 | 82.8 | 74 |
| YES1 COLEC11 GDF15 ITGA1 ITGB1 | 79.6 | 83.5 | 71.8 |
| 5 Proteins | | | |
| BCL2A1 N6AMT1 GDF15 C7 ITGA1 ITGB1 | 91.866667 | 95 | 85.6 |
| THBS2 YES1 COLEC11 GDF15 C7 | 91.666667 | 94.5 | 86 |
| THBS2 BCL2A1 COLEC11 GDF15 C7 | 91.666667 | 94.7 | 85.6 |
| THBS2 BCL2A1 COLEC11 N6AMT1 GDF15 | 91.6 | 93.9 | 87 |
| THBS2 COLEC11 N6AMT1 GDF15 AKT2 | 91.266667 | 94.6 | 84.6 |
| THBS2 N6AMT1 GDF15 ITGA1 ITGB1 AKT2 | 90.733333 | 92.9 | 86.4 |
| YES1 N6AMT1 GDF15 C7 ITGA1 ITGB1 | 90.6 | 93.8 | 84.2 |
| THBS2 BCL2A1 COLEC11 GDF15 AKT2 | 90.6 | 93.6 | 84.6 |
| THBS2 BCL2A1 YES1 COLEC11 GDF15 | 90.6 | 94.5 | 82.8 |

TABLE 3-continued

Markers for NASH versus Simple Steatosis Based on Average Accuracy, Sensitivity and Specificity

| | AvgAcc | AvgSen | AvgSpe |
|---|---|---|---|
| THBS2 COLEC11 IGFBP7 GDF15 C7 | 90.533333 | 92.7 | 86.2 |
| THBS2 COLEC11 IGFBP7 N6AMT1 GDF15 | 90.533333 | 93.1 | 85.4 |
| THBS2 IGFBP7 GDF15 C7 ITGA1 ITGB1 | 90.466667 | 92.7 | 86 |
| THBS2 YES1 N6AMT1 C7 ITGA1 ITGB1 | 90.4 | 91.5 | 88.2 |
| THBS2 YES1 COLEC11 N6AMT1 GDF15 | 90.4 | 92.5 | 86.2 |
| THBS2 COLEC11 GDF15 C7 AKT2 | 90.333333 | 93.1 | 84.8 |
| THBS2 YES1 COLEC11 GDF15 ITGA1 ITGB1 | 90.333333 | 92.9 | 85.2 |
| THBS2 YES1 N6AMT1 GDF15 ITGA1 ITGB1 | 90.266667 | 93 | 84.8 |
| THBS2 YES1 COLEC11 IGFBP7 GDF15 | 90.2 | 93.9 | 82.8 |
| THBS2 BCL2A1 N6AMT1 GDF15 ITGA1 ITGB1 | 90.2 | 92.2 | 86.2 |
| THBS2 N6AMT1 GDF15 C7 ITGA1 ITGB1 | 90 | 93 | 84 |
| THBS2 COLEC11 IGFBP7 N6AMT1 C7 | 90 | 91.6 | 86.8 |
| THBS2 YES1 COLEC11 N6AMT1 C7 | 90 | 91.9 | 86.2 |
| THBS2 YES1 GDF15 C7 ITGA1 ITGB1 | 89.733333 | 92.1 | 85 |
| THBS2 BCL2A1 COLEC11 C7 AKT2 | 89.733333 | 90.9 | 87.4 |
| THBS2 BCL2A1 COLEC11 IGFBP7 N6AMT1 | 89.666667 | 91.8 | 85.4 |
| THBS2 YES1 N6AMT1 GDF15 C7 | 89.6 | 90 | 88.8 |
| THBS2 BCL2A1 GDF15 ITGA1 ITGB1 AKT2 | 89.6 | 91.4 | 86 |
| THBS2 YES1 GDF15 ITGA1 ITGB1 AKT2 | 89.533333 | 92.4 | 83.8 |
| THBS2 COLEC11 N6AMT1 GDF15 C7 | 89.4 | 91 | 86.2 |
| THBS2 BCL2A1 YES1 N6AMT1 AKT2 | 89.4 | 91.5 | 85.2 |
| THBS2 IGFBP7 N6AMT1 C7 AKT2 | 89.333333 | 91.7 | 84.6 |
| THBS2 YES1 IGFBP7 N6AMT1 C7 | 89.333333 | 91.8 | 84.4 |
| THBS2 COLEC11 GDF15 ITGA1 ITGB1 AKT2 | 89.266667 | 92.5 | 82.8 |
| N6AMT1 GDF15 C7 ITGA1 ITGB1 AKT2 | 89.2 | 93 | 81.6 |
| THBS2 COLEC11 IGFBP7 GDF15 ITGA1 ITGB1 | 89.2 | 91.8 | 84 |
| THBS2 BCL2A1 GDF15 C7 ITGA1 ITGB1 | 89.133333 | 91 | 85.4 |
| THBS2 BCL2A1 YES1 COLEC11 N6AMT1 | 89.133333 | 90.9 | 85.6 |
| THBS2 BCL2A1 C7 ITGA1 ITGB1 AKT2 | 89.066667 | 91.2 | 84.8 |
| THBS2 BCL2A1 N6AMT1 C7 ITGA1 ITGB1 | 89.066667 | 93 | 81.2 |
| THBS2 BCL2A1 IGFBP7 GDF15 ITGA1 ITGB1 | 89.066667 | 91.9 | 83.4 |
| THBS2 COLEC11 IGFBP7 GDF15 AKT2 | 89 | 91.1 | 84.8 |
| THBS2 BCL2A1 COLEC11 IGFBP7 GDF15 | 89 | 92.2 | 82.6 |
| THBS2 YES1 COLEC11 IGFBP7 N6AMT1 | 88.933333 | 91.4 | 84 |
| THBS2 BCL2A1 COLEC11 GDF15 ITGA1 ITGB1 | 88.933333 | 91.5 | 83.8 |
| THBS2 YES1 COLEC11 GDF15 AKT2 | 88.866667 | 91.1 | 84.4 |
| THBS2 IGFBP7 N6AMT1 GDF15 ITGA1 ITGB1 | 88.8 | 90.7 | 85 |
| THBS2 BCL2A1 N6AMT1 C7 AKT2 | 88.8 | 92.2 | 82 |
| THBS2 BCL2A1 COLEC11 N6AMT1 AKT2 | 88.733333 | 91.3 | 83.6 |
| THBS2 BCL2A1 YES1 N6AMT1 C7 | 88.733333 | 91.4 | 83.4 |
| THBS2 BCL2A1 YES1 IGFBP7 N6AMT1 | 88.733333 | 93.5 | 79.2 |
| THBS2 IGFBP7 N6AMT1 GDF15 AKT2 | 88.666667 | 91.5 | 83 |
| THBS2 N6AMT1 GDF15 C7 AKT2 | 88.6 | 90.5 | 84.8 |
| BCL2A1 IGFBP7 N6AMT1 GDF15 ITGA1 ITGB1 | 88.533333 | 91.4 | 82.8 |
| BCL2A1 YES1 IGFBP7 N6AMT1 ITGA1 ITGB1 | 88.533333 | 94 | 77.6 |
| THBS2 IGFBP7 N6AMT1 GDF15 C7 | 88.533333 | 91.3 | 83 |
| IGFBP7 N6AMT1 GDF15 C7 ITGA1 ITGB1 | 88.466667 | 92.1 | 81.2 |
| BCL2A1 GDF15 C7 ITGA1 ITGB1 AKT2 | 88.466667 | 91.3 | 82.8 |
| THBS2 IGFBP7 GDF15 C7 AKT2 | 88.4 | 91.1 | 83 |
| THBS2 COLEC11 N6AMT1 GDF15 ITGA1 ITGB1 | 88.4 | 90.8 | 83.6 |
| THBS2 YES1 IGFBP7 N6AMT1 GDF15 | 88.4 | 90.8 | 83.6 |
| THBS2 BCL2A1 YES1 GDF15 ITGA1 ITGB1 | 88.4 | 90.1 | 85 |
| THBS2 YES1 GDF15 C7 AKT2 | 88.333333 | 90.2 | 84.6 |
| THBS2 BCL2A1 IGFBP7 C7 AKT2 | 88.333333 | 92.4 | 80.2 |
| THBS2 BCL2A1 IGFBP7 N6AMT1 C7 | 88.333333 | 92.4 | 80.2 |
| IGFBP7 N6AMT1 C7 ITGA1 ITGB1 AKT2 | 88.266667 | 90.2 | 84.4 |
| BCL2A1 YES1 N6AMT1 ITGA1 ITGB1 AKT2 | 88.266667 | 88 | 88.8 |
| THBS2 YES1 IGFBP7 GDF15 C7 | 88.266667 | 89.4 | 86 |
| THBS2 BCL2A1 N6AMT1 GDF15 C7 | 88.266667 | 91.2 | 82.4 |
| THBS2 BCL2A1 COLEC11 C7 ITGA1 ITGB1 | 88.266667 | 90.1 | 84.6 |
| THBS2 GDF15 C7 ITGA1 ITGB1 AKT2 | 88.2 | 91.3 | 82 |
| THBS2 IGFBP7 GDF15 ITGA1 ITGB1 AKT2 | 88.2 | 89.7 | 85.2 |
| THBS2 BCL2A1 COLEC11 IGFBP7 C7 | 88.2 | 92.1 | 80.4 |
| THBS2 COLEC11 IGFBP7 N6AMT1 ITGA1 ITGB1 | 88.133333 | 90 | 84.4 |
| THBS2 BCL2A1 YES1 COLEC11 C7 | 88.133333 | 90.3 | 83.8 |
| THBS2 BCL2A1 YES1 COLEC11 IGFBP7 | 88.133333 | 90.5 | 83.4 |
| BCL2A1 N6AMT1 C7 ITGA1 ITGB1 AKT2 | 88.066667 | 91.4 | 81.4 |
| BCL2A1 YES1 GDF15 C7 ITGA1 ITGB1 | 88.066667 | 92.3 | 79.6 |
| THBS2 COLEC11 N6AMT1 C7 AKT2 | 88.066667 | 89.9 | 84.4 |
| THBS2 COLEC11 N6AMT1 C7 ITGA1 ITGB1 | 88.066667 | 90.1 | 84 |
| THBS2 YES1 IGFBP7 GDF15 ITGA1 ITGB1 | 88.066667 | 89 | 86.2 |
| THBS2 BCL2A1 IGFBP7 GDF15 C7 | 88.066667 | 89.8 | 84.6 |
| THBS2 BCL2A1 YES1 GDF15 AKT2 | 88.066667 | 89.6 | 85 |
| THBS2 N6AMT1 C7 ITGA1 ITGB1 AKT2 | 88 | 89.7 | 84.6 |
| THBS2 YES1 COLEC11 IGFBP7 C7 | 88 | 90.5 | 83 |
| THBS2 BCL2A1 COLEC11 N6AMT1 ITGA1 ITGB1 | 88 | 88.9 | 86.2 |

TABLE 3-continued

Markers for NASH versus Simple Steatosis Based on Average Accuracy, Sensitivity and Specificity

| | AvgAcc | AvgSen | AvgSpe |
|---|---|---|---|
| YES1 GDF15 C7 ITGA1 ITGB1 AKT2 | 87.933333 | 92.1 | 79.6 |
| THBS2 COLEC11 IGFBP7 C7 AKT2 | 87.933333 | 90.1 | 83.6 |
| THBS2 BCL2A1 GDF15 C7 AKT2 | 87.933333 | 89.4 | 85 |
| THBS2 BCL2A1 COLEC11 IGFBP7 ITGA1 ITGB1 | 87.933333 | 88.6 | 86.6 |
| BCL2A1 N6AMT1 GDF15 ITGA1 ITGB1 AKT2 | 87.866667 | 93.3 | 77 |
| THBS2 BCL2A1 COLEC11 N6AMT1 C7 | 87.866667 | 91.2 | 81.2 |
| THBS2 BCL2A1 YES1 C7 ITGA1ITGB1 | 87.866667 | 89.5 | 84.6 |
| BCL2A1 YES1 COLEC11 IGFBP7 N6AMT1 | 87.8 | 89.7 | 84 |
| THBS2 BCL2A1 IGFBP7 N6AMT1 GDF15 | 87.8 | 90.6 | 82.2 |
| BCL2A1 YES1 GDF15 C7 AKT2 | 87.733333 | 91.8 | 79.6 |
| THBS2 YES1 COLEC11 C7 AKT2 | 87.733333 | 90.4 | 82.4 |
| THBS2 YES1 COLEC11 IGFBP7 AKT2 | 87.733333 | 89.9 | 83.4 |
| BCL2A1 YES1 N6AMT1 C7 ITGA1 ITGB1 | 87.666667 | 88.6 | 85.8 |
| THBS2 IGFBP7 N6AMT1 C7 ITGA1 ITGB1 | 87.666667 | 88.7 | 85.6 |
| IGFBP7 N6AMT1 GDF15 ITGA1 ITGB1 AKT2 | 87.6 | 91.7 | 79.4 |
| BCL2A1 YES1 C7 ITGA1 ITGB1 AKT2 | 87.6 | 89.8 | 83.2 |
| THBS2 YES1 N6AMT1 C7 AKT2 | 87.6 | 89.7 | 83.4 |
| BCL2A1 IGFBP7 GDF15 C7 ITGA1 ITGB1 | 87.533333 | 89.6 | 83.4 |
| THBS2 YES1 COLEC11 N6AMT1 AKT2 | 87.533333 | 90.7 | 81.2 |
| THBS2 BCL2A1 IGFBP7 C7 ITGA1 ITGB1 | 87.466667 | 89.4 | 83.6 |
| YES1 IGFBP7 N6AMT1 C7 ITGA1 ITGB1 | 87.4 | 89.5 | 83.2 |
| THBS2 BCL2A1 YES1 IGFBP7 C7 | 87.333333 | 90.5 | 81 |
| BCL2A1 IGFBP7 C7 ITGA1 ITGB1 AKT2 | 87.266667 | 89.3 | 83.2 |
| THBS2 YES1 IGFBP7 C7 ITGA1 ITGB1 | 87.266667 | 89.2 | 83.4 |
| THBS2 YES1 IGFBP7 GDF15 AKT2 | 87.266667 | 90.5 | 80.8 |
| YES1 IGFBP7 C7 ITGA1 ITGB1 AKT2 | 87.2 | 91 | 79.6 |
| THBS2 BCL2A1 YES1 COLEC11 AKT2 | 87.2 | 90.4 | 80.8 |
| BCL2A1 IGFBP7 N6AMT1 ITGA1 ITGB1 AKT2 | 87.133333 | 92.9 | 75.6 |
| BCL2A1 YES1 N6AMT1 GDF15 C7 | 87.133333 | 90.9 | 79.6 |
| THBS2 COLEC11 GDF15 C7 ITGA1 ITGB1 | 87.133333 | 89.8 | 81.8 |
| THBS2 BCL2A1 YES1 IGFBP7 GDF15 | 87.133333 | 90.3 | 80.8 |
| THBS2 COLEC11 C7 ITGA1 ITGB1 AKT2 | 87.066667 | 88.9 | 83.4 |
| THBS2 YES1 C7 ITGA1 ITGB1 AKT2 | 87.066667 | 88.2 | 84.8 |
| THBS2 BCL2A1 IGFBP7 GDF15 AKT2 | 87.066667 | 90.2 | 80.8 |
| THBS2 BCL2A1 COLEC11 IGFBP7 AKT2 | 87.066667 | 88.7 | 83.8 |
| THBS2 BCL2A1 YES1 C7 AKT2 | 87.066667 | 88.2 | 84.8 |
| YES1 IGFBP7 GDF15 ITGA1 ITGB1 AKT2 | 86.933333 | 90.7 | 79.4 |
| YES1 IGFBP7 N6AMT1 GDF15 ITGA1 ITGB1 | 86.866667 | 91 | 78.6 |
| BCL2A1 IGFBP7 N6AMT1 C7 ITGA1 ITGB1 | 86.866667 | 90.9 | 78.8 |
| BCL2A1 YES1 COLEC11 N6AMT1 AKT2 | 86.866667 | 89.6 | 81.4 |
| THBS2 IGFBP7 C7 ITGA1 ITGB1 AKT2 | 86.866667 | 88.2 | 84.2 |
| THBS2 BCL2A1 N6AMT1 GDF15 AKT2 | 86.866667 | 88.1 | 84.4 |
| THBS2 BCL2A1 YES1 N6AMT1 GDF15 | 86.866667 | 88.4 | 83.8 |
| THBS2 COLEC11 IGFBP7 N6AMT1 AKT2 | 86.8 | 88.5 | 83.4 |
| THBS2 BCL2A1 YES1 N6AMT1 ITGA1 ITGB1 | 86.8 | 88.4 | 83.6 |
| IGFBP7 GDF15 C7 ITGA1 ITGB1 AKT2 | 86.733333 | 89.3 | 81.6 |
| BCL2A1 YES1 IGFBP7 GDF15 ITGA1 ITGB1 | 86.666667 | 90.5 | 79 |
| THBS2 YES1 N6AMT1 GDF15 AKT2 | 86.666667 | 89 | 82 |
| THBS2 YES1 IGFBP7 N6AMT1 AKT2 | 86.666667 | 92.5 | 75 |
| THBS2 YES1 COLEC11 C7 ITGA1ITGB1 | 86.666667 | 87.3 | 85.4 |
| YES1 N6AMT1 GDF15 ITGA1 ITGB1 AKT2 | 86.6 | 93.2 | 73.4 |
| YES1 IGFBP7 GDF15 C7 ITGA1 ITGB1 | 86.6 | 89.8 | 80.2 |
| BCL2A1 IGFBP7 GDF15 ITGA1 ITGB1 AKT2 | 86.533333 | 89.9 | 79.8 |
| BCL2A1 YES1 N6AMT1 GDF15 ITGA1 ITGB1 | 86.533333 | 94.3 | 71 |
| BCL2A1 YES1 IGFBP7 C7 ITGA1 ITGB1 | 86.533333 | 89.1 | 81.4 |
| YES1 N6AMT1 C7 ITGA1 ITGB1 AKT2 | 86.466667 | 89.1 | 81.2 |
| THBS2 BCL2A1IGFBP7 N6AMT1 AKT2 | 86.466667 | 92.7 | 74 |
| YES1 COLEC11 IGFBP7 N6AMT1 AKT2 | 86.4 | 89.3 | 80.6 |
| THBS2 YES1 COLEC11 IGFBP7 ITGA1 ITGB1 | 86.4 | 86 | 87.2 |
| THBS2 BCL2A1 YES1 COLEC11 ITGA1 ITGB1 | 86.4 | 88.5 | 82.2 |
| YES1 N6AMT1 GDF15 C7 AKT2 | 86.266667 | 88.9 | 81 |
| THBS2 BCL2A1 YES1 GDF15 C7 | 86.266667 | 88.1 | 82.6 |
| BCL2A1 COLEC11 GDF15 C7 ITGA1 ITGB1 | 86.2 | 89.4 | 79.8 |
| THBS2 COLEC11 IGFBP7 C7 ITGA1 ITGB1 | 86.2 | 86.6 | 85.4 |
| YES1 COLEC11 N6AMT1 C7 AKT2 | 86.133333 | 86.5 | 85.4 |
| BCL2A1 N6AMT1 GDF15 C7 AKT2 | 86.133333 | 90.3 | 77.8 |
| BCL2A1 COLEC11 IGFBP7 C7 AKT2 | 86.066667 | 87.5 | 83.2 |
| THBS2 YES1 IGFBP7 C7 AKT2 | 86 | 87.8 | 82.4 |
| BCL2A1 COLEC11 IGFBP7 N6AMT1 C7 | 85.933333 | 88.4 | 81 |
| BCL2A1 YES1 IGFBP7 N6AMT1 C7 | 85.933333 | 89.7 | 78.4 |
| BCL2A1 YES1 GDF15 ITGA1 ITGB1 AKT2 | 85.866667 | 92.7 | 72.2 |
| COLEC11 IGFBP7 N6AMT1 C7 ITGA1 ITGB1 | 85.733333 | 90.2 | 76.8 |
| YES1 IGFBP7 N6AMT1 ITGA1 ITGB1 AKT2 | 85.733333 | 90.6 | 76 |
| THBS2 YES1 COLEC11 N6AMT1 ITGA1 ITGB1 | 85.733333 | 87 | 83.2 |
| COLEC11 GDF15 C7 ITGA1 ITGB1 AKT2 | 85.6 | 89.8 | 77.2 |
| BCL2A1 IGFBP7 N6AMT1 GDF15 C7 | 85.6 | 89.5 | 77.8 |

TABLE 3-continued

Markers for NASH versus Simple Steatosis Based on Average Accuracy, Sensitivity and Specificity

| | AvgAcc | AvgSen | AvgSpe |
|---|---|---|---|
| BCL2A1 COLEC11 IGFBP7 N6AMT1 AKT2 | 85.533333 | 91 | 74.6 |
| BCL2A1 YES1 IGFBP7 N6AMT1 GDF15 | 85.466667 | 91.6 | 73.2 |
| COLEC11 N6AMT1 GDF15 C7 ITGA1 ITGB1 | 85.4 | 89.2 | 77.8 |
| YES1 IGFBP7 N6AMT1 GDF15 C7 | 85.4 | 87.3 | 81.6 |
| THBS2 BCL2A1 IGFBP7 ITGA1 ITGB1 AKT2 | 85.4 | 87.5 | 81.2 |
| THBS2 COLEC11 N6AMT1 ITGA1 ITGB1 AKT2 | 85.266667 | 85.8 | 84.2 |
| BCL2A1 COLEC11 IGFBP7 GDF15 C7 | 85.2 | 86.3 | 83 |
| BCL2A1 YES1 COLEC11 C7 AKT2 | 85.2 | 87.6 | 80.4 |
| THBS2 IGFBP7 N6AMT1 ITGA1 ITGB1 AKT2 | 85.2 | 86.1 | 83.4 |
| THBS2 YES1 N6AMT1 ITGA1 ITGB1 AKT2 | 85.2 | 84.3 | 87 |
| THBS2 BCL2A1 YES1 ITGA1 ITGB1 AKT2 | 85.133333 | 85.1 | 85.2 |
| YES1 IGFBP7 N6AMT1 GDF15 AKT2 | 85.066667 | 90.3 | 74.6 |
| BCL2A1 YES1 COLEC11 C7 ITGA1 ITGB1 | 85 | 88.6 | 77.8 |
| YES1 COLEC11 N6AMT1 C7 ITGA1ITGB1 | 84.933333 | 89.1 | 76.6 |
| BCL2A1 COLEC11 N6AMT1 C7 AKT2 | 84.933333 | 87.2 | 80.4 |
| THBS2 YES1 IGFBP7 N6AMT1ITGA1 ITGB1 | 84.933333 | 86.3 | 82.2 |
| THBS2 BCL2A1 COLEC11 ITGA1 ITGB1 AKT2 | 84.933333 | 85.7 | 83.4 |
| COLEC11 IGFBP7 C7 ITGA1 ITGB1 AKT2 | 84.866667 | 89.6 | 75.4 |
| COLEC11 IGFBP7 N6AMT1 GDF15 ITGA1 ITGB1 | 84.866667 | 88.1 | 78.4 |
| THBS2 BCL2A1 IGFBP7 N6AMT1 ITGA1 ITGB1 | 84.866667 | 86 | 82.6 |
| THBS2 BCL2A1 YES1 IGFBP7 AKT2 | 84.866667 | 91.3 | 72 |
| YES1 COLEC11 IGFBP7 N6AMT1 C7 | 84.8 | 86.8 | 80.8 |
| BCL2A1 IGFBP7 GDF15 C7 AKT2 | 84.733333 | 87.6 | 79 |
| THBS2 COLEC11 IGFBP7 ITGA1 ITGB1 AKT2 | 84.733333 | 84.3 | 85.6 |
| COLEC11 IGFBP7 N6AMT1 C7 AKT2 | 84.666667 | 86.6 | 80.8 |
| BCL2A1 COLEC11 N6AMT1 GDF15 AKT2 | 84.666667 | 88 | 78 |
| IGFBP7 N6AMT1 GDF15 C7 AKT2 | 84.6 | 88.1 | 77.6 |
| BCL2A1 YES1 IGFBP7 GDF15 C7 | 84.6 | 88.5 | 76.8 |
| THBS2 BCL2A1 N6AMT1 ITGA1 ITGB1 AKT2 | 84.6 | 86.5 | 80.8 |
| BCL2A1 YES1 COLEC11 N6AMT1 C7 | 84.533333 | 85.8 | 82 |
| COLEC11 IGFBP7 N6AMT1 GDF15 C7 | 84.4 | 88.8 | 75.6 |
| THBS2 YES1 COLEC11 ITGA1 ITGB1 AKT2 | 84.4 | 85.8 | 81.6 |
| YES1 IGFBP7 GDF15 C7 AKT2 | 84.333333 | 86.4 | 80.2 |
| BCL2A1 YES1 N6AMT1 GDF15 AKT2 | 84.333333 | 91.5 | 70 |
| BCL2A1 COLEC11 N6AMT1 C7 ITGA1 ITGB1 | 84.266667 | 90.2 | 72.4 |
| BCL2A1 COLEC11 N6AMT1 GDF15 C7 | 84.266667 | 87.3 | 78.2 |
| BCL2A1 COLEC11 IGFBP7 C7 ITGA1 ITGB1 | 84.266667 | 87.2 | 78.4 |
| BCL2A1 IGFBP7 N6AMT1 C7 AKT2 | 84.2 | 87.9 | 76.8 |
| BCL2A1 YES1 IGFBP7 C7 AKT2 | 84.133333 | 89.4 | 73.6 |
| YES1 IGFBP7 N6AMT1 C7 AKT2 | 84.066667 | 88.8 | 74.6 |
| BCL2A1 COLEC11 IGFBP7 GDF15 ITGA1 ITGB1 | 84.066667 | 87.4 | 77.4 |
| BCL2A1 YES1 IGFBP7 ITGA1 ITGB1 AKT2 | 84.066667 | 90.6 | 71 |
| THBS2 YES1 IGFBP7 ITGA1 ITGB1 AKT2 | 84 | 84.7 | 82.6 |
| BCL2A1 IGFBP7 N6AMT1 GDF15 AKT2 | 83.933333 | 92.1 | 67.6 |
| YES1 COLEC11 GDF15 C7 ITGA1 ITGB1 | 83.866667 | 87 | 77.6 |
| COLEC11 N6AMT1 C7 ITGA1 ITGB1 AKT2 | 83.8 | 88.3 | 74.8 |
| BCL2A1 COLEC11 IGFBP7 N6AMT1 GDF15 | 83.8 | 86.8 | 77.8 |
| BCL2A1 YES1 IGFBP7 GDF15 AKT2 | 83.8 | 90.4 | 70.6 |
| COLEC11 IGFBP7 GDF15 C7 ITGA1 ITGB1 | 83.733333 | 86.8 | 77.6 |
| YES1 COLEC11 N6AMT1 GDF15 ITGA1 ITGB1 | 83.6 | 87.6 | 75.6 |
| BCL2A1 YES1 COLEC11 IGFBP7 C7 | 83.6 | 85.1 | 80.6 |
| YES1 COLEC11 IGFBP7 C7 AKT2 | 83.533333 | 86.2 | 78.2 |
| YES1 COLEC11 IGFBP7 C7 ITGA1 ITGB1 | 83.533333 | 87.7 | 75.2 |
| COLEC11 N6AMT1 GDF15 C7 AKT2 | 83.466667 | 86.2 | 78 |
| BCL2A1 COLEC11 IGFBP7 N6AMT1 ITGA1 ITGB1 | 83.333333 | 85.4 | 79.2 |
| YES1 COLEC11 IGFBP7 ITGA1 ITGB1 AKT2 | 83.266667 | 87.3 | 75.2 |
| BCL2A1 YES1 COLEC11 GDF15 ITGA1 ITGB1 | 83.2 | 88 | 73.6 |
| COLEC11 IGFBP7 N6AMT1 ITGA1 ITGB1 AKT2 | 83.066667 | 86.9 | 75.4 |
| COLEC11 IGFBP7 GDF15 ITGA1 ITGB1 AKT2 | 83 | 85.6 | 77.8 |
| COLEC11 IGFBP7 GDF15 C7 AKT2 | 82.933333 | 85.4 | 78 |
| BCL2A1 YES1 COLEC11 IGFBP7 AKT2 | 82.933333 | 87.5 | 73.8 |
| COLEC11 N6AMT1 GDF15 ITGA1 ITGB1 AKT2 | 82.866667 | 87.3 | 74 |
| BCL2A1 YES1 COLEC11 GDF15 C7 | 82.8 | 86.2 | 76 |
| YES1 COLEC11 C7 ITGA1 ITGB1 AKT2 | 82.666667 | 86.6 | 74.8 |
| YES1 COLEC11 IGFBP7 GDF15 C7 | 82.666667 | 85.1 | 77.8 |
| BCL2A1 YES1 COLEC11 N6AMT1 GDF15 | 82.666667 | 85.9 | 76.2 |
| YES1 COLEC11 N6AMT1 ITGA1 ITGB1 AKT2 | 82.533333 | 87.1 | 73.4 |
| BCL2A1 COLEC11 IGFBP7 ITGA1 ITGB1 AKT2 | 82.533333 | 85.8 | 76 |
| COLEC11 IGFBP7 N6AMT1 GDF15 AKT2 | 82.466667 | 84 | 79.4 |
| BCL2A1 COLEC11 C7 ITGA1 ITGB1 AKT2 | 82.466667 | 86.3 | 74.8 |
| BCL2A1 COLEC11 N6AMT1 GDF15 ITGA1 ITGB1 | 82.4 | 87.3 | 72.6 |
| BCL2A1 YES1 COLEC11 IGFBP7 GDF15 | 82.4 | 82.6 | 82 |
| YES1 COLEC11 GDF15 ITGA1 ITGB1 AKT2 | 82.333333 | 86.5 | 74 |
| YES1 COLEC11 N6AMT1 GDF15 C7 | 82.333333 | 84.6 | 77.8 |
| THBS2 BCL2A1 YES1 IGFBP7 ITGA1 ITGB1 | 82.266667 | 85.4 | 76 |
| BCL2A1 COLEC11 N6AMT1 ITGA1 ITGB1 AKT2 | 82.133333 | 84.9 | 76.6 |

TABLE 3-continued

Markers for NASH versus Simple Steatosis Based on Average Accuracy, Sensitivity and Specificity

|  | AvgAcc | AvgSen | AvgSpe |
|---|---|---|---|
| BCL2A1 YES1 COLEC11 GDF15 AKT2 | 82.133333 | 84.2 | 78 |
| YES1 COLEC11 IGFBP7 N6AMT1 ITGA1 ITGB1 | 82 | 84.6 | 76.8 |
| YES1 COLEC11 IGFBP7 GDF15 ITGA1 ITGB1 | 81.933333 | 86.9 | 72 |
| BCL2A1 YES1 IGFBP7 N6AMT1 AKT2 | 81.866667 | 88.6 | 68.4 |
| YES1 COLEC11 IGFBP7 N6AMT1 GDF15 | 81.666667 | 84 | 77 |
| BCL2A1 YES1 N6AMT1 C7 AKT2 | 81.533333 | 87.6 | 69.4 |
| BCL2A1 COLEC11 GDF15 C7 AKT2 | 81.466667 | 85.5 | 73.4 |
| BCL2A1 YES1 COLEC11 IGFBP7 ITGA1 ITGB1 | 81.2 | 85.3 | 73 |
| YES1 COLEC11 IGFBP7 GDF15 AKT2 | 81.133333 | 82.2 | 79 |
| BCL2A1 YES1 COLEC11 N6AMT1 ITGA1 ITGB1 | 81.133333 | 85.5 | 72.4 |
| BCL2A1 COLEC11 IGFBP7 GDF15 AKT2 | 81.066667 | 84.1 | 75 |
| YES1 COLEC11 GDF15 C7 AKT2 | 80.933333 | 83.3 | 76.2 |
| BCL2A1 COLEC11 GDF15 ITGA1 ITGB1 AKT2 | 80.666667 | 84.9 | 72.2 |
| BCL2A1 YES1 COLEC11 ITGA1 ITGB1 AKT2 | 80.133333 | 84.6 | 71.2 |
| YES1 COLEC11 N6AMT1 GDF15 AKT2 | 78.866667 | 80.8 | 75 |
| 6 Proteins |  |  |  |
| THBS2 IGFBP7 N6AMT1 GDF15 C7 ITGA1 ITGB1 | 91.933333 | 93.7 | 88.4 |
| THBS2 BCL2A1 COLEC11 N6AMT1 GDF15 AKT2 | 91.8 | 94.2 | 87 |
| BCL2A1 YES1 N6AMT1 GDF15 C7 ITGA1 ITGB1 | 91.533333 | 94.1 | 86.4 |
| THBS2 COLEC11 IGFBP7 GDF15 C7 AKT2 | 91.333333 | 94.2 | 85.6 |
| THBS2 YES1 COLEC11 IGFBP7 GDF15 C7 | 91.133333 | 93.6 | 86.2 |
| THBS2 BCL2A1 YES1 GDF15 C7 ITGA1 ITGB1 | 91.133333 | 93 | 87.4 |
| THBS2 BCL2A1 YES1 COLEC11 GDF15 AKT2 | 91.133333 | 94.1 | 85.2 |
| THBS2 YES1 COLEC11 GDF15 C7 AKT2 | 91.066667 | 93.4 | 86.4 |
| THBS2 BCL2A1 IGFBP7 N6AMT1 GDF15 C7 | 91.066667 | 93.5 | 86.2 |
| THBS2 BCL2A1 COLEC11 IGFBP7 GDF15 C7 | 91 | 94.1 | 84.8 |
| THBS2 N6AMT1 GDF15 C7 ITGA1 ITGB1 AKT2 | 90.866667 | 93.1 | 86.4 |
| THBS2 BCL2A1 YES1 COLEC11 IGFBP7 GDF15 | 90.8 | 93.6 | 85.2 |
| THBS2 BCL2A1 COLEC11 IGFBP7 N6AMT1 GDF15 | 90.733333 | 93.4 | 85.4 |
| THBS2 YES1 N6AMT1 GDF15 C7 ITGA1 ITGB1 | 90.666667 | 93.7 | 84.6 |
| THBS2 COLEC11 IGFBP7 GDF15 ITGA1 ITGB1 AKT2 | 90.6 | 92.1 | 87.6 |
| THBS2 COLEC11 IGFBP7 N6AMT1 GDF15 C7 | 90.533333 | 93.7 | 84.2 |
| THBS2 YES1 COLEC11 N6AMT1 GDF15 C7 | 90.533333 | 93.9 | 83.8 |
| THBS2 BCL2A1 COLEC11 N6AMT1 GDF15 ITGA1 ITGB1 | 90.466667 | 93.9 | 83.6 |
| THBS2 BCL2A1 YES1 COLEC11 GDF15 C7 | 90.466667 | 93.1 | 85.2 |
| THBS2 BCL2A1 N6AMT1 GDF15 ITGA1 ITGB1 AKT2 | 90.4 | 92.8 | 85.6 |
| THBS2 BCL2A1 COLEC11 N6AMT1 GDF15 C7 | 90.4 | 92.4 | 86.4 |
| THBS2 BCL2A1 YES1 C7 ITGA1 ITGB1 AKT2 | 90.266667 | 92.4 | 86 |
| THBS2 BCL2A1 YES1 COLEC11 GDF15 ITGA1 ITGB1 | 90.266667 | 92.6 | 85.6 |
| THBS2 YES1 COLEC11 GDF15 ITGA1 ITGB1 AKT2 | 90.2 | 92.9 | 84.8 |
| THBS2 YES1 COLEC11 IGFBP7 N6AMT1 GDF15 | 90.2 | 93.2 | 84.2 |
| THBS2 BCL2A1 YES1 COLEC11 N6AMT1 C7 | 90.2 | 92.4 | 85.8 |
| THBS2 COLEC11 N6AMT1 GDF15 C7 AKT2 | 90.133333 | 91.4 | 87.6 |
| THBS2 BCL2A1 COLEC11 IGFBP7 GDF15 ITGA1 ITGB1 | 90.133333 | 92.6 | 85.2 |
| THBS2 BCL2A1 YES1 N6AMT1 C7 ITGA1 ITGB1 | 90.133333 | 93.2 | 84 |
| YES1 IGFBP7 N6AMT1 GDF15 C7 ITGA1 ITGB1 | 90.066667 | 93.8 | 82.6 |
| THBS2 BCL2A1 N6AMT1 GDF15 C7 ITGA1 ITGB1 | 90.066667 | 93.9 | 82.4 |
| THBS2 BCL2A1 COLEC11 GDF15 C7 AKT2 | 90.066667 | 92.1 | 86 |
| THBS2 BCL2A1 COLEC11 N6AMT1 C7 AKT2 | 90 | 92.3 | 85.4 |
| BCL2A1 N6AMT1 GDF15 C7 ITGA1 ITGB1 AKT2 | 89.933333 | 93.8 | 82.2 |
| THBS2 COLEC11 N6AMT1 GDF15 C7 ITGA1 ITGB1 | 89.933333 | 92.3 | 85.2 |
| THBS2 YES1 COLEC11 N6AMT1 GDF15 ITGA1 ITGB1 | 89.933333 | 92.9 | 84 |
| THBS2 BCL2A1 IGFBP7 N6AMT1 C7 ITGA1 ITGB1 | 89.933333 | 91.7 | 86.4 |
| THBS2 IGFBP7 N6AMT1 C7 ITGA1 ITGB1 AKT2 | 89.866667 | 91.4 | 86.8 |
| THBS2 COLEC11 IGFBP7 N6AMT1 GDF15 AKT2 | 89.866667 | 93.9 | 81.8 |
| THBS2 YES1 COLEC11 IGFBP7 C7 AKT2 | 89.866667 | 92.1 | 85.4 |
| THBS2 BCL2A1 YES1 IGFBP7 N6AMT1 C7 | 89.866667 | 94.5 | 80.6 |
| THBS2 COLEC11 IGFBP7 N6AMT1 GDF15 ITGA1 ITGB1 | 89.8 | 92 | 85.4 |
| THBS2 YES1 IGFBP7 N6AMT1 C7 AKT2 | 89.8 | 93.1 | 83.2 |
| THBS2 YES1 COLEC11 N6AMT1 GDF15 AKT2 | 89.8 | 92.4 | 84.6 |
| THBS2 BCL2A1 GDF15 C7 ITGA1 ITGB1 AKT2 | 89.8 | 91.1 | 87.2 |
| YES1 N6AMT1 GDF15 C7 ITGA1 ITGB1 AKT2 | 89.733333 | 93.8 | 81.6 |
| THBS2 IGFBP7 GDF15 C7 ITGA1 ITGB1 AKT2 | 89.733333 | 91.5 | 86.2 |
| THBS2 BCL2A1 COLEC11 IGFBP7 GDF15 AKT2 | 89.666667 | 92.5 | 84 |
| THBS2 COLEC11 IGFBP7 N6AMT1 C7 AKT2 | 89.6 | 91.8 | 85.2 |
| THBS2 BCL2A1 IGFBP7 GDF15 C7 ITGA1 ITGB1 | 89.6 | 92 | 84.8 |
| THBS2 BCL2A1 IGFBP7 N6AMT1 C7 AKT2 | 89.6 | 93.1 | 82.6 |
| THBS2 IGFBP7 GDF15 C7 ITGA1 ITGB1 AKT2 | 89.533333 | 92.2 | 84.2 |
| THBS2 YES1 IGFBP7 GDF15 C7 ITGA1 ITGB1 | 89.533333 | 91.9 | 84.8 |
| THBS2 BCL2A1 YES1 GDF15 ITGA1 ITGB1 AKT2 | 89.533333 | 91.9 | 84.8 |
| THBS2 COLEC11 GDF15 C7 ITGA1 ITGB1 AKT2 | 89.466667 | 90.1 | 88.2 |
| THBS2 YES1 COLEC11 IGFBP7 GDF15 AKT2 | 89.466667 | 91.3 | 85.8 |
| THBS2 BCL2A1 N6AMT1 C7 ITGA1 ITGB1 AKT2 | 89.466667 | 92.6 | 83.2 |
| THBS2 BCL2A1 COLEC11 IGFBP7 N6AMT1 C7 | 89.466667 | 92.4 | 83.6 |
| THBS2 BCL2A1 COLEC11 IGFBP7 N6AMT1 AKT2 | 89.4 | 91.6 | 85 |

TABLE 3-continued

Markers for NASH versus Simple Steatosis Based on Average Accuracy, Sensitivity and Specificity

| | AvgAcc | AvgSen | AvgSpe |
|---|---|---|---|
| BCL2A1 IGFBP7 N6AMT1 GDF15 C7 ITGA1 ITGB1 | 89.333333 | 93.5 | 81 |
| THBS2 YES1 COLEC11 N6AMT1 C7 AKT2 | 89.333333 | 90.8 | 86.4 |
| THBS2 BCL2A1 YES1 COLEC11 N6AMT1 GDF15 | 89.333333 | 93.2 | 81.6 |
| IGFBP7 N6AMT1 GDF15 C7 ITGA1 ITGB1 AKT2 | 89.266667 | 92.6 | 82.6 |
| THBS2 YES1 N6AMT1 C7 ITGA1 ITGB1 AKT2 | 89.266667 | 91.2 | 85.4 |
| THBS2 YES1 N6AMT1 GDF15 ITGA1 ITGB1 AKT2 | 89.266667 | 91.6 | 84.6 |
| THBS2 YES1 N6AMT1 GDF15 C7 AKT2 | 89.2 | 91.5 | 84.6 |
| THBS2 YES1 IGFBP7 GDF15 C7 AKT2 | 89.2 | 91.3 | 85 |
| THBS2 BCL2A1 COLEC11 IGFBP7 C7 ITGA1 ITGB1 | 89.133333 | 90.6 | 86.2 |
| THBS2 BCL2A1 YES1 COLEC11 N6AMT1 ITGA1 ITGB1 | 89.133333 | 90.5 | 86.4 |
| THBS2 BCL2A1IGFBP7 C7 ITGA1 ITGB1 AKT2 | 89 | 91.1 | 84.8 |
| THBS2 BCL2A1 YES1 IGFBP7 C7 AKT2 | 89 | 92 | 83 |
| THBS2 YES1 COLEC11 IGFBP7 GDF15 ITGA1 ITGB1 | 88.933333 | 91.3 | 84.2 |
| THBS2 BCL2A1 YES1 IGFBP7 GDF15 ITGA1 ITGB1 | 88.933333 | 90.9 | 85 |
| THBS2 YES1 IGFBP7 GDF15 ITGA1 ITGB1 AKT2 | 88.866667 | 90.2 | 86.2 |
| THBS2 YES1 IGFBP7 N6AMT1 GDF15 ITGA1 ITGB1 | 88.866667 | 91.2 | 84.2 |
| THBS2 YES1 COLEC11 GDF15 C7 ITGA1 ITGB1 | 88.866667 | 90.5 | 85.6 |
| THBS2 BCL2A1 COLEC11 GDF15 C7 ITGA1 ITGB1 | 88.866667 | 91.3 | 84 |
| THBS2 BCL2A1 YES1 N6AMT1 GDF15 ITGA1 ITGB1 | 88.866667 | 91.8 | 83 |
| THBS2 YES1 GDF15 C7 ITGA1 ITGB1 AKT2 | 88.8 | 91.7 | 83 |
| THBS2 YES1 IGFBP7 N6AMT1 C7 ITGA1 ITGB1 | 88.8 | 90.3 | 85.8 |
| THBS2 YES1 IGFBP7 N6AMT1 GDF15 C7 | 88.8 | 91.2 | 84 |
| THBS2 YES1 COLEC11 C7 ITGA1 ITGB1 AKT2 | 88.8 | 90.5 | 85.4 |
| THBS2 BCL2A1 YES1 GDF15 C7 AKT2 | 88.8 | 91.3 | 83.8 |
| THBS2 BCL2A1 YES1 IGFBP7 N6AMT1 GDF15 | 88.8 | 90.8 | 84.8 |
| THBS2 COLEC11 N6AMT1 GDF15 ITGA1 ITGB1 AKT2 | 88.733333 | 89.8 | 86.6 |
| BCL2A1 YES1 N6AMT1 C7 ITGA1 ITGB1 AKT2 | 88.666667 | 90.5 | 85 |
| BCL2A1 YES1 IGFBP7 GDF15 C7 ITGA1 ITGB1 | 88.666667 | 92.6 | 80.8 |
| BCL2A1 YES1 IGFBP7 N6AMT1 C7 ITGA1 ITGB1 | 88.666667 | 90.1 | 85.8 |
| THBS2 YES1 COLEC11 IGFBP7 N6AMT1 C7 | 88.666667 | 90 | 86 |
| THBS2 BCL2A1 COLEC11 GDF15 ITGA1 ITGB1 AKT2 | 88.6 | 90.7 | 84.4 |
| THBS2 BCL2A1 YES1 IGFBP7 GDF15 C7 | 88.6 | 90.7 | 84.4 |
| THBS2 BCL2A1 COLEC11 N6AMT1 C7 ITGA1 ITGB1 | 88.533333 | 90.9 | 83.8 |
| BCL2A1 IGFBP7 N6AMT1 C7 ITGA1 ITGB1 AKT2 | 88.466667 | 91.2 | 83 |
| THBS2 BCL2A1 IGFBP7 GDF15 C7 AKT2 | 88.466667 | 90 | 85.4 |
| THBS2 BCL2A1 YES1 COLEC11 IGFBP7 C7 | 88.466667 | 91.4 | 82.6 |
| THBS2 BCL2A1 YES1 COLEC11 IGFBP7 N6AMT1 | 88.466667 | 92 | 81.4 |
| THBS2 COLEC11 N6AMT1 C7 ITGA1 ITGB1 AKT2 | 88.4 | 89.9 | 85.4 |
| THBS2 YES1 COLEC11 N6AMT1 C7 ITGA1 ITGB1 | 88.4 | 91.1 | 83 |
| THBS2 BCL2A1 YES1 IGFBP7 C7 ITGA1 ITGB1 | 88.4 | 90.5 | 84.2 |
| THBS2 BCL2A1 YES1 COLEC11 C7 ITGA1 ITGB1 | 88.4 | 90.2 | 84.8 |
| THBS2 COLEC11 IGFBP7 C7 ITGA1 ITGB1 AKT2 | 88.333333 | 90.6 | 83.8 |
| THBS2 YES1 COLEC11 N6AMT1 ITGA1 ITGB1 AKT2 | 88.266667 | 90.4 | 84 |
| THBS2 COLEC11 IGFBP7 GDF15 C7 ITGA1 ITGB1 | 88.2 | 90.8 | 83 |
| THBS2 BCL2A1 N6AMT1 GDF15 C7 AKT2 | 88.2 | 89.9 | 84.8 |
| THBS2 BCL2A1 N6AMT1 C7 AKT2 | 88.2 | 90.7 | 83.2 |
| YES1 IGFBP7 GDF15 C7 ITGA1 ITGB1 AKT2 | 88.133333 | 91.3 | 81.8 |
| BCL2A1 YES1 GDF15 C7 ITGA1 ITGB1 AKT2 | 88.133333 | 92 | 80.4 |
| BCL2A1 IGFBP7 N6AMT1 GDF15 ITGA1 ITGB1 AKT2 | 88.066667 | 92 | 80.2 |
| BCL2A1 YES1 IGFBP7 N6AMT1 ITGA1 ITGB1 AKT2 | 88.066667 | 93.1 | 78 |
| THBS2 BCL2A1 COLEC11 IGFBP7 C7 AKT2 | 88.066667 | 89.6 | 85 |
| THBS2 YES1 COLEC11 IGFBP7 N6AMT1 AKT2 | 88 | 91.1 | 81.8 |
| THBS2 BCL2A1 YES1 COLEC11 C7 AKT2 | 88 | 90.1 | 83.8 |
| THBS2 BCL2A1 YES1 COLEC11 N6AMT1 AKT2 | 88 | 90 | 84 |
| BCL2A1 IGFBP7 GDF15 C7 ITGA1 ITGB1 AKT2 | 87.933333 | 91.5 | 80.8 |
| BCL2A1 YES1 IGFBP7 GDF15 ITGA1 ITGB1 AKT2 | 87.933333 | 91.5 | 80.8 |
| THBS2 YES1 COLEC11 IGFBP7 C7 ITGA1 ITGB1 | 87.933333 | 90.2 | 83.4 |
| THBS2 BCL2A1 COLEC11 N6AMT1 ITGA1 ITGB1 AKT2 | 87.933333 | 88.3 | 87.2 |
| YES1 IGFBP7 N6AMT1 C7 ITGA1 ITGB1 AKT2 | 87.866667 | 89.8 | 84 |
| BCL2A1 YES1 IGFBP7 C7 ITGA1 ITGB1 AKT2 | 87.866667 | 89.6 | 84.4 |
| THBS2 IGFBP7 N6AMT1 GDF15 ITGA1 ITGB1 AKT2 | 87.866667 | 90.4 | 82.8 |
| THBS2 BCL2A1 YES1 N6AMT1 GDF15 C7 | 87.8 | 89.9 | 83.6 |
| BCL2A1 YES1 IGFBP7 GDF15 ITGA1 ITGB1 | 87.733333 | 92.2 | 78.8 |
| THBS2 YES1 IGFBP7 N6AMT1 GDF15 AKT2 | 87.733333 | 90.7 | 81.8 |
| THBS2 BCL2A1 COLEC11 IGFBP7 N6AMT1 ITGA1 ITGB1 | 87.733333 | 90.8 | 81.6 |
| THBS2 BCL2A1 IGFBP7 N6AMT1 GDF15 ITGA1 ITGB1 | 87.666667 | 89.2 | 84.6 |
| THBS2 BCL2A1 IGFBP7 N6AMT1 GDF15 AKT2 | 87.6 | 90.3 | 82.2 |
| THBS2 BCL2A1 IGFBP7 GDF15 ITGA1 ITGB1 AKT2 | 87.466667 | 91.3 | 79.8 |
| BCL2A1 YES1 N6AMT1 GDF15 C7 AKT2 | 87.4 | 91.7 | 78.8 |
| BCL2A1 YES1 IGFBP7 N6AMT1 GDF15 C7 | 87.333333 | 90.5 | 81 |
| THBS2 BCL2A1 YES1 IGFBP7 GDF15 AKT2 | 87.2 | 89.7 | 82.2 |
| THBS2 BCL2A1 YES1 IGFBP7 N6AMT1 AKT2 | 87.066667 | 93.6 | 74 |
| THBS2 BCL2A1 YES1 COLEC11 IGFBP7 AKT2 | 87.066667 | 88.5 | 84.2 |
| THBS2 BCL2A1 COLEC11 C7 ITGA1ITGB1 AKT2 | 87 | 89.1 | 82.8 |
| COLEC11 IGFBP7 N6AMT1 GDF15 C7 AKT2 | 86.933333 | 88.6 | 83.6 |

TABLE 3-continued

Markers for NASH versus Simple Steatosis Based on Average Accuracy, Sensitivity and Specificity

| | AvgAcc | AvgSen | AvgSpe |
|---|---|---|---|
| BCL2A1 YES1 N6AMT1 GDF15 ITGA1ITGB1 AKT2 | 86.8 | 93.7 | 73 |
| THBS2 BCL2A1 YES1 N6AMT1 GDF15 AKT2 | 86.733333 | 88.4 | 83.4 |
| YES1 COLEC11 IGFBP7 GDF15 C7 ITGA1 ITGB1 | 86.666667 | 90.4 | 79.2 |
| THBS2 COLEC11 IGFBP7 N6AMT1 ITGA1 ITGB1 AKT2 | 86.666667 | 87.5 | 85 |
| BCL2A1 YES1 COLEC11 N6AMT1 C7 AKT2 | 86.6 | 87.7 | 84.4 |
| THBS2 BCL2A1 YES1 COLEC11 ITGA1 ITGB1 AKT2 | 86.6 | 87.5 | 84.8 |
| THBS2 YES1 COLEC11 IGFBP7 N6AMT1 ITGA1 ITGB1 | 86.533333 | 87.5 | 84.6 |
| BCL2A1 COLEC11 N6AMT1 GDF15 C7 ITGA1 ITGB1 | 86.466667 | 88.3 | 82.8 |
| THBS2 YES1 IGFBP7 C7 ITGA1 ITGB1 AKT2 | 86.466667 | 87.2 | 85 |
| BCL2A1 YES1 COLEC11 IGFBP7 N6AMT1 C7 | 86.266667 | 88.1 | 82.6 |
| THBS2 BCL2A1 YES1 COLEC11 IGFBP7 ITGA1 ITGB1 | 86.266667 | 88.1 | 82.6 |
| YES1 IGFBP7 N6AMT1 GDF15 ITGA1 ITGB1 AKT2 | 86.2 | 90.4 | 77.8 |
| YES1 COLEC11 N6AMT1 GDF15 C7 ITGA1 ITGB1 | 86 | 90.2 | 77.6 |
| YES1 COLEC11 IGFBP7 N6AMT1 GDF15 C7 | 86 | 87.6 | 82.8 |
| BCL2A1 COLEC11 N6AMT1 C7 ITGA1 ITGB1 AKT2 | 86 | 90.2 | 77.6 |
| BCL2A1 COLEC11 IGFBP7 GDF15 C7 ITGA1 ITGB1 | 86 | 90.1 | 77.8 |
| THBS2 BCL2A1 COLEC11 IGFBP7 ITGA1 ITGB1 AKT2 | 86 | 86.4 | 85.2 |
| COLEC11 IGFBP7 N6AMT1 GDF15 C7 ITGA1 ITGB1 | 85.933333 | 89.7 | 78.4 |
| THBS2 COLEC11 IGFBP7 N6AMT1 C7 ITGA1 ITGB1 | 85.933333 | 86.6 | 84.6 |
| YES1 COLEC11 IGFBP7 N6AMT1 C7 ITGA1 ITGB1 | 85.866667 | 90 | 77.6 |
| BCL2A1 COLEC11 IGFBP7 N6AMT1 C7 AKT2 | 85.866667 | 88.1 | 81.4 |
| THBS2 YES1 COLEC11 IGFBP7 ITGA1 ITGB1 AKT2 | 85.8 | 85.6 | 86.2 |
| THBS2 BCL2A 1IGFBP7 N6AMT1 ITGA1 ITGB1 AKT2 | 85.8 | 87.5 | 82.4 |
| YES1 COLEC11 IGFBP7 C7 ITGA1 ITGB1 AKT2 | 85.733333 | 89 | 79.2 |
| BCL2A1 YES1 IGFBP7 GDF15 C7 AKT2 | 85.666667 | 89.1 | 78.8 |
| YES1 IGFBP7 N6AMT1 GDF15 C7 AKT2 | 85.6 | 88 | 80.8 |
| THBS2 BCL2A1 YES1 IGFBP7 N6AMT1 ITGA1 ITGB1 | 85.466667 | 87.6 | 81.2 |
| BCL2A1 COLEC11 IGFBP7 N6AMT1 GDF15 AKT2 | 85.4 | 88.9 | 78.4 |
| BCL2A1 YES1 COLEC11 GDF15 C7 ITGA1 ITGB1 | 85.4 | 89.7 | 76.8 |
| BCL2A1 YES1 COLEC11 IGFBP7 N6AMT1 AKT2 | 85.4 | 89 | 78.2 |
| THBS2 BCL2A1 YES1 N6AMT1 ITGA1 ITGB1 AKT2 | 85.4 | 87.9 | 80.4 |
| YES1 COLEC11 GDF15 C7 ITGA1 ITGB1 AKT2 | 85.266667 | 87.9 | 80 |
| BCL2A1 IGFBP7 N6AMT1 GDF15 C7 AKT2 | 85.266667 | 88 | 79.8 |
| BCL2A1 COLEC11 IGFBP7 N6AMT1 C7 ITGA1 ITGB1 | 85.2 | 89.8 | 76 |
| YES1 COLEC11 IGFBP7 GDF15 ITGA1 ITGB1 AKT2 | 85.133333 | 86.4 | 82.6 |
| BCL2A1 YES1 IGFBP7 N6AMT1 GDF15 AKT2 | 85 | 90.2 | 74.6 |
| COLEC11 IGFBP7 N6AMT1 GDF15 ITGA1 ITGB1 AKT2 | 84.933333 | 88.6 | 77.6 |
| BCL2A1 YES1 COLEC11 N6AMT1 GDF15 ITGA1 ITGB1 | 84.933333 | 90.5 | 73.8 |
| COLEC11 N6AMT1 GDF15 C7 ITGA1 ITGB1 AKT2 | 84.866667 | 89.1 | 76.4 |
| YES1 COLEC11 IGFBP7 N6AMT1 C7 AKT2 | 84.866667 | 85.4 | 83.8 |
| BCL2A1 YES1 COLEC11 C7 ITGA1ITGB1 AKT2 | 84.733333 | 90 | 74.2 |
| BCL2A1 YES1 COLEC11 IGFBP7 N6AMT1 GDF15 | 84.733333 | 87.3 | 79.6 |
| THBS2 YES1 IGFBP7 N6AMT1 ITGA1 ITGB1 AKT2 | 84.733333 | 85.6 | 83 |
| BCL2A1 COLEC11 IGFBP7 C7 ITGA1 ITGB1 AKT2 | 84.666667 | 87.8 | 78.4 |
| BCL2A1 YES1 COLEC11 IGFBP7 C7 ITGA1 ITGB1 | 84.666667 | 88.8 | 76.4 |
| BCL2A1 COLEC11 IGFBP7 N6AMT1 GDF15 ITGA1 ITGB1 | 84.533333 | 87.6 | 78.4 |
| YES1 COLEC11 N6AMT1 GDF15 ITGA1 ITGB1 AKT2 | 84.466667 | 88.9 | 75.6 |
| BCL2A1 COLEC11 IGFBP7 N6AMT1 GDF15 C7 | 84.466667 | 85.8 | 81.8 |
| COLEC11 IGFBP7 GDF15 C7 ITGA1 ITGB1 AKT2 | 84.4 | 85.6 | 82 |
| BCL2A1 YES1 COLEC11 IGFBP7 GDF15 ITGA1 ITGB1 | 84.4 | 87.3 | 78.6 |
| COLEC11 IGFBP7 N6AMT1 C7 ITGA1 ITGB1 AKT2 | 84.2 | 88.3 | 76 |
| YES1 COLEC11 N6AMT1 C7 ITGA1 ITGB1 AKT2 | 84.133333 | 87.6 | 77.2 |
| BCL2A1 YES1 COLEC11 N6AMT1 C7 ITGA1 ITGB1 | 84.133333 | 87.6 | 77.2 |
| YES1 COLEC11 N6AMT1 GDF15 C7 AKT2 | 84.066667 | 86.5 | 79.2 |
| YES1 COLEC11 IGFBP7 N6AMT1 GDF15 ITGA1 ITGB1 | 84.066667 | 87.4 | 77.4 |
| BCL2A1 YES1 COLEC11 N6AMT1 GDF15 C7 | 84 | 86.6 | 78.8 |
| YES1 COLEC11 IGFBP7 N6AMT1 GDF15 AKT2 | 83.933333 | 85.6 | 80.6 |
| BCL2A1 COLEC11 N6AMT1 GDF15 ITGA1 ITGB1 AKT2 | 83.933333 | 89.9 | 72 |
| BCL2A1 YES1 COLEC11 IGFBP7 N6AMT1 ITGA1 ITGB1 | 83.933333 | 86.3 | 79.2 |
| BCL2A1 COLEC11 N6AMT1 GDF15 C7 AKT2 | 83.733333 | 86.6 | 78 |
| BCL2A1 COLEC11 GDF15 C7 ITGA1 ITGB1 AKT2 | 83.666667 | 87.6 | 75.8 |
| BCL2A1 YES1 COLEC11 GDF15 ITGA1 ITGB1 AKT2 | 83.666667 | 87.5 | 76 |
| THBS2 BCL2A1 YES1 IGFBP7 ITGA1 ITGB1 AKT2 | 83.666667 | 85 | 81 |
| BCL2A1 YES1 COLEC11 IGFBP7 C7 AKT2 | 83.533333 | 86 | 78.6 |
| YES1 COLEC11 IGFBP7 GDF15 C7 AKT2 | 83.466667 | 85.2 | 80 |
| BCL2A1 YES1 COLEC11 IGFBP7 GDF15 AKT2 | 83.466667 | 84.2 | 82 |

TABLE 3-continued

Markers for NASH versus Simple Steatosis Based on Average Accuracy, Sensitivity and Specificity

|  | AvgAcc | AvgSen | AvgSpe |
|---|---|---|---|
| BCL2A1 YES1 COLEC11 N6AMT1 GDF15 AKT2 | 83.4 | 85.8 | 78.6 |
| YES1 COLEC11 IGFBP7 N6AMT1 ITGA1 ITGB1 AKT2 | 83.333333 | 86.6 | 76.8 |
| BCL2A1 YES1 IGFBP7 N6AMT1 C7 AKT2 | 83.266667 | 87.9 | 74 |
| BCL2A1 YES1 COLEC11 N6AMT1 ITGA1 ITGB1 AKT2 | 83.133333 | 87.6 | 74.2 |
| BCL2A1 COLEC11 IGFBP7 GDF15 ITGA1 ITGB1 AKT2 | 83.066667 | 87.3 | 74.6 |
| BCL2A1 YES1 COLEC11 IGFBP7 ITGA1 ITGB1 AKT2 | 82.733333 | 86.9 | 74.4 |
| BCL2A1 YES1 COLEC11 GDF15 C7 AKT2 | 82.6 | 84.6 | 78.6 |
| BCL2A1 COLEC11 IGFBP7 GDF15 C7 AKT2 | 82.4 | 85.3 | 76.6 |
| BCL2A1 COLEC11 IGFBP7 N6AMT1 ITGA1 ITGB1 AKT2 | 82.4 | 86.5 | 74.2 |
| BCL2A1 YES1 COLEC11 IGFBP7 GDF15 C7 | 82.4 | 83.7 | 79.8 |
| 7 Proteins | | | |
| THBS2 BCL2A1 COLEC11 IGFBP7 GDF15 C7 AKT2 | 92.2 | 95.8 | 85 |
| THBS2 BCL2A1 N6AMT1 GDF15 C7 ITGA1 ITGB1 AKT2 | 91.733333 | 94.8 | 85.6 |
| THBS2 BCL2A1 YES1 COLEC11 IGFBP7 GDF15 C7 | 91.466667 | 95 | 84.4 |
| THBS2 YES1 N6AMT1 GDF15 C7 ITGA1 ITGB1 AKT2 | 91.333333 | 93.8 | 86.4 |
| THBS2 BCL2A1 YES1 GDF15 C7 AKT2 | 91.266667 | 94.7 | 84.4 |
| THBS2 BCL2A1 COLEC11 IGFBP7 N6AMT1 GDF15 C7 | 91.2 | 94.6 | 84.4 |
| THBS2 YES1 IGFBP7 N6AMT1 GDF15 C7 ITGA1 ITGB1 | 91.133333 | 94.4 | 84.6 |
| THBS2 BCL2A1 YES1 N6AMT1 C7 ITGA1 ITGB1 AKT2 | 91.133333 | 94.1 | 85.2 |
| THBS2 BCL2A1IGFBP7 N6AMT1 GDF15 C7 ITGA1 ITGB1 | 91 | 94.2 | 84.6 |
| BCL2A1 YES1 N6AMT1 GDF15 C7 ITGA1I TGB1 AKT2 | 90.933333 | 95 | 82.8 |
| THBS2 YES1 COLEC11 IGFBP7 N6AMT1 GDF15 C7 | 90.866667 | 94.4 | 83.8 |
| THBS2 BCL2A1 IGFBP7 GDF15 C7 AKT2 | 90.866667 | 93.4 | 85.8 |
| THBS2 BCL2A1 IGFBP7 N6AMT1 C7 ITGA1 ITGB1 AKT2 | 90.8 | 93.3 | 85.8 |
| THBS2 BCL2A1 YES1 N6AMT1 GDF15 ITGA1 ITGB1 AKT2 | 90.733333 | 93.1 | 86 |
| THBS2 BCL2A1 YES1 COLEC11 IGFBP7 GDF15 AKT2 | 90.733333 | 94.3 | 83.6 |
| YES1 IGFBP7 N6AMT1 GDF15 C7 ITGA1 ITGB1 AKT2 | 90.666667 | 94.1 | 83.8 |
| THBS2 YES1 COLEC11 IGFBP7 GDF15 C7 ITGA1 ITGB1 | 90.666667 | 93.5 | 85 |
| THBS2 BCL2A1 COLEC11 N6AMT1 GDF15 C7 ITGA1 ITGB1 | 90.6 | 93.4 | 85 |
| THBS2 COLEC11 IGFBP7 N6AMT1 GDF15 C7 AKT2 | 90.533333 | 93.4 | 84.8 |
| THBS2 BCL2A1 YES1 N6AMT1 GDF15 C7 ITGA1 ITGB1 | 90.533333 | 93.5 | 84.6 |
| THBS2 IGFBP7 N6AMT1 GDF15 C7 ITGA1 ITGB1 AKT2 | 90.466667 | 93.4 | 84.6 |
| THBS2 BCL2A1 COLEC11 GDF15 C7 ITGA1 ITGB1 AKT2 | 90.466667 | 92.9 | 85.6 |
| THBS2 COLEC11 IGFBP7 GDF15 C7 ITGA1 ITGB1 AKT2 | 90.4 | 93.6 | 84 |
| THBS2 BCL2A1 YES1 IGFBP7 N6AMT1 C7 ITGA1 ITGB1 | 90.4 | 93.2 | 84.8 |
| THBS2 BCL2A1 YES1 COLEC11 N6AMT1 GDF15 | 90.4 | 93.3 | 84.6 |
| THBS2 BCL2A1 COLEC11 IGFBP7 N6AMT1 GDF15 AKT2 | 90.333333 | 93.4 | 84.2 |
| THBS2 BCL2A1 COLEC11 IGFBP7 N6AMT1 GDF15 ITGA1 ITGB1 | 90.333333 | 93.2 | 84.6 |
| BCL2A1 YES1 IGFBP7 N6AMT1 GDF15 C7 ITGA1 ITGB1 | 90.266667 | 94 | 82.8 |
| THBS2 YES1 COLEC11 GDF15 C7 ITGA1 ITGB1 AKT2 | 90.266667 | 92 | 86.8 |
| THBS2 BCL2A1 IGFBP7 GDF15 C7 ITGA1 ITGB1 AKT2 | 90.266667 | 92.9 | 85 |
| THBS2 BCL2A1 COLEC11 IGFBP7 GDF15 C7 ITGA1 ITGB1 | 90.266667 | 92.7 | 85.4 |
| THBS2 BCL2A1 YES1 GDF15 C7 ITGA1 ITGB1 AKT2 | 90.266667 | 93 | 84.8 |
| THBS2 BCL2A1 YES1 N6AMT1 GDF15 C7 AKT2 | 90.266667 | 92.7 | 85.4 |
| THBS2 YES1 COLEC11 IGFBP7 GDF15 C7 AKT2 | 90.2 | 93.6 | 83.4 |
| THBS2 BCL2A1 YES1 COLEC11 N6AMT1 GDF15 C7 | 90.2 | 93 | 84.6 |
| THBS2 YES1 COLEC11 IGFBP7 N6AMT1 C7 ITGA1 ITGB1 | 90.133333 | 91.7 | 87 |
| THBS2 YES1 IGFBP7 GDF15 C7 ITGA1 ITGB1 AKT2 | 90 | 92.4 | 85.2 |
| THBS2 BCL2A1 COLEC11 IGFBP7 N6AMT1 C7 AKT2 | 90 | 92.1 | 85.8 |
| THBS2 BCL2A1 YES1 IGFBP7 C7 ITGA1 ITGB1 AKT2 | 90 | 92.5 | 85 |
| THBS2 COLEC11 IGFBP7 N6AMT1 GDF15 ITGA1 ITGB1 AKT2 | 89.933333 | 91.8 | 86.2 |
| THBS2 COLEC11 N6AMT1 GDF15 C7 ITGB1 AKT2 | 89.866667 | 91.6 | 86.4 |
| THBS2 BCL2A1 COLEC11 N6AMT1 GDF15 ITGA1 ITGB1 AKT2 | 89.866667 | 91.8 | 86 |
| THBS2 BCL2A1 YES1 IGFBP7 GDF15 ITGA1 ITGB1 AKT2 | 89.866667 | 91.5 | 86.6 |
| THBS2 YES1 COLEC11 N6AMT1 GDF15 C7 AKT2 | 89.8 | 93 | 83.4 |
| THBS2 BCL2A1 YES1 COLEC11 IGFBP7 GDF15 ITGA1 ITGB1 | 89.733333 | 92.6 | 84 |
| THBS2 YES1 COLEC11 IGFBP7 N6AMT1 GDF15 AKT2 | 89.666667 | 92.8 | 83.4 |
| THBS2 BCL2A1 YES1 IGFBP7 N6AMT1 GDF15 ITGA1 ITGB1 | 89.666667 | 92.1 | 84.8 |
| THBS2 YES1 IGFBP7 N6AMT1 C7 ITGA1 ITGB1 AKT2 | 89.6 | 92.2 | 84.4 |
| THBS2 YES1 COLEC11IGFBP7 GDF15 ITGA1 ITGB1 AKT2 | 89.533333 | 92.3 | 84 |
| THBS2 YES1 IGFBP7 N6AMT1 GDF15 ITGA1 ITGB1 AKT2 | 89.466667 | 90.8 | 86.8 |

TABLE 3-continued

Markers for NASH versus Simple Steatosis Based on Average Accuracy, Sensitivity and Specificity

| | AvgAcc | AvgSen | AvgSpe |
|---|---|---|---|
| THBS2 BCL2A1 YES1 IGFBP7 N6AMT1 C7 AKT2 | 89.466667 | 91.7 | 85 |
| THBS2 BCL2A1 YES1 COLEC11 N6AMT1 C7 AKT2 | 89.466667 | 91.3 | 85.8 |
| THBS2 YES1 COLEC11 N6AMT1 GDF15 C7 ITGA1 ITGB1 | 89.4 | 91.9 | 84.4 |
| THBS2 BCL2A1 YES1 COLEC11 N6AMT1 ITGA1 ITGB1 AKT2 | 89.4 | 90.8 | 86.6 |
| THBS2 BCL2A1 YES1 COLEC11 N6AMT1 GDF15 ITGA1 ITGB1 | 89.4 | 92.2 | 83.8 |
| THBS2 COLEC11 IGFBP7 N6AMT1 GDF15 C7 ITGA1 ITGB1 | 89.266667 | 91.4 | 85 |
| THBS2 BCL2A1 YES1 COLEC11 GDF15 C7 ITGA1 ITGB1 | 89.266667 | 91.1 | 85.6 |
| THBS2 YES1 COLEC11 IGFBP7 N6AMT1 GDF15 ITGA1 ITGB1 | 89.2 | 91.4 | 84.8 |
| THBS2 BCL2A1 COLEC11 IGFBP7 N6AMT1 C7 ITGA1 ITGB1 | 89.2 | 90.8 | 86 |
| THBS2 BCL2A1 YES1 IGFBP7 GDF15 C7 ITGA1 ITGB1 | 89.2 | 92 | 83.6 |
| THBS2 YES1 COLEC11 N6AMT1 GDF15 ITGA1 ITGB1 AKT2 | 89.133333 | 91.2 | 85 |
| THBS2 BCL2A1IGFBP7 N6AMT1 GDF15 ITGA1 ITGB1 AKT2 | 89.133333 | 91.8 | 83.8 |
| THBS2 BCL2A1 YES1 COLEC11 IGFBP7 N6AMT1 C7 | 89.133333 | 91.1 | 85.2 |
| THBS2 BCL2A1 YES1 COLEC11 N6AMT1 GDF15 AKT2 | 89.066667 | 92.1 | 83 |
| THBS2 BCL2A1 COLEC11 N6AMT1 GDF15 C7 AKT2 | 89 | 91.4 | 84.2 |
| THBS2 BCL2A1 YES1 COLEC11 C7 ITGA1 ITGB1 AKT2 | 89 | 90.1 | 86.8 |
| THBS2 BCL2A1 YES1 COLEC11 GDF15 ITGA1 ITGB1 AKT2 | 89 | 90.8 | 85.4 |
| BCL2A1 YES1 IGFBP7 GDF15 C7 ITGA1 ITGB1 AKT2 | 88.933333 | 92.4 | 82 |
| BCL2A1 IGFBP7 N6AMT1 GDF15 C7 ITGA1 ITGB1 AKT2 | 88.8 | 93.3 | 79.8 |
| THBS2 YES1 IGFBP7 GDF15 C7 AKT2 | 88.666667 | 90.3 | 85.4 |
| THBS2 BCL2A1 COLEC11 IGFBP7 GDF15 ITGA1 ITGB1 AKT2 | 88.666667 | 91.5 | 83 |
| THBS2 BCL2A1 YES1 COLEC11 IGFBP7 N6AMT1 AKT2 | 88.666667 | 91.5 | 83 |
| THBS2 BCL2A1 COLEC11 IGFBP7 N6AMT1 ITGA1 ITGB1 AKT2 | 88.6 | 89.5 | 86.8 |
| THBS2 YES1 COLEC11 IGFBP7 N6AMT1 C7 AKT2 | 88.533333 | 89.8 | 86 |
| THBS2 BCL2A1 YES1 IGFBP7 N6AMT1 GDF15 C7 | 88.533333 | 91.5 | 82.6 |
| THBS2 BCL2A1 YES1 COLEC11 N6AMT1 C7 ITGA1 ITGB1 | 88.4 | 89.3 | 86.6 |
| BCL2A1 YES1 IGFBP7 N6AMT1 C7 ITGA1 ITGB1 AKT2 | 88.333333 | 91 | 83 |
| THBS2 YES1 COLEC11 N6AMT1 C7 ITGA1 ITGB1 AKT2 | 88.333333 | 90.1 | 84.8 |
| THBS2 BCL2A1 YES1 IGFBP7 GDF15 C7 AKT2 | 88.2 | 89.6 | 85.4 |
| THBS2 BCL2A1 COLEC11 N6AMT1 C7 ITGA1 ITGB1 AKT2 | 88.066667 | 90.2 | 83.8 |
| THBS2 BCL2A1 YES1 COLEC11 IGFBP7 C7 AKT2 | 88.066667 | 89.6 | 85 |
| THBS2 BCL2A1 YES1 COLEC11 IGFBP7 N6AMT1 ITGA1 ITGB1 | 88.066667 | 89.4 | 85.4 |
| THBS2 COLEC11 IGFBP7 N6AMT1 C7 ITGA1 ITGB1 AKT2 | 88 | 89.8 | 84.4 |
| THBS2 YES1 COLEC11 IGFBP7 C7 ITGA1 ITGB1 AKT2 | 88 | 89.1 | 85.8 |
| THBS2 BCL2A1 YES1 IGFBP7 N6AMT1 GDF15 AKT2 | 87.933333 | 91.5 | 80.8 |
| THBS2 BCL2A1 COLEC11 IGFBP7 C7 ITGA1 ITGB1 AKT2 | 87.866667 | 89.1 | 85.4 |
| BCL2A1 YES1 IGFBP7 N6AMT1 GDF15 ITGA1 ITGB1 AKT2 | 87.533333 | 91.9 | 78.8 |
| THBS2 BCL2A1 YES1 COLEC11 IGFBP7 C7 ITGA1 ITGB1 | 87.533333 | 88.9 | 84.8 |
| YES1 COLEC11 IGFBP7 N6AMT1 GDF15 C7 ITGA1 ITGB1 | 87.266667 | 91.4 | 79 |
| THBS2 YES1 COLEC11 IGFBP7 N6AMT1 ITGA1 ITGB1 AKT2 | 87.066667 | 89.1 | 83 |
| YES1 COLEC11 IGFBP7 N6AMT1 C7 ITGA1 ITGB1 AKT2 | 86.733333 | 90.1 | 80 |
| THBS2 BCL2A1 YES1 IGFBP7 N6AMT1 ITGA1 ITGB1 AKT2 | 86.733333 | 88.8 | 82.6 |
| BCL2A1 YES1 COLEC11 N6AMT1 GDF15 C7 ITGA1 ITGB1 | 86.666667 | 89.6 | 80.8 |
| BCL2A1 YES1 COLEC11 IGFBP7 N6AMT1 C7 ITGA1 ITGB1 | 86.666667 | 89.4 | 81.2 |
| THBS2 BCL2A1 YES1 COLEC11 IGFBP7 ITGA1 ITGB1 AKT2 | 86.6 | 87.4 | 85 |
| BCL2A1 YES1 COLEC11 IGFBP7 N6AMT1 GDF15 C7 | 86.533333 | 87.4 | 84.8 |
| YES1 COLEC11 N6AMT1 GDF15 C7 ITGA1 ITGB1 AKT2 | 86.4 | 90.3 | 78.6 |
| BCL2A1 YES1 COLEC11 IGFBP7 GDF15 C7 ITGA1 ITGB1 | 86.333333 | 88.5 | 82 |
| COLEC11 IGFBP7 N6AMT1 GDF15 C7 ITGA1 ITGB1 AKT2 | 86.266667 | 90.2 | 78.4 |
| YES1 COLEC11 IGFBP7 N6AMT1 GDF15 ITGA1 ITGB1 AKT2 | 86 | 88.8 | 80.4 |

TABLE 3-continued

Markers for NASH versus Simple Steatosis Based on Average Accuracy, Sensitivity and Specificity

|  | AvgAcc | AvgSen | AvgSpe |
|---|---|---|---|
| BCL2A1 YES1 COLEC11 IGFBP7 N6AMT1 C7 AKT2 | 86 | 88 | 82 |
| BCL2A1 COLEC11 IGFBP7 N6AMT1 C7 ITGA1 ITGB1 AKT2 | 85.8 | 89.4 | 78.6 |
| BCL2A1 YES1 IGFBP7 N6AMT1 GDF15 C7 AKT2 | 85.8 | 87.7 | 82 |
| BCL2A1 YES1 COLEC11 N6AMT1 GDF15 C7 AKT2 | 85.8 | 87.9 | 81.6 |
| YES1 COLEC11 IGFBP7 N6AMT1 GDF15 C7 AKT2 | 85.466667 | 86.6 | 83.2 |
| BCL2A1 YES1 COLEC11 IGFBP7 N6AMT1 GDF15 ITGA1 ITGB1 | 85.466667 | 89.1 | 78.2 |
| BCL2A1 COLEC11 IGFBP7 N6AMT1 GDF15 C7 ITGA1 ITGB1 | 85.4 | 88.7 | 78.8 |
| BCL2A1 COLEC11 IGFBP7 N6AMT1 GDF15 ITGA1 ITGB1 AKT2 | 85.333333 | 88.2 | 79.6 |
| BCL2A1 YES1 COLEC11 N6AMT1 C7 ITGA1 ITGB1 AKT2 | 85.333333 | 89.9 | 76.2 |
| BCL2A1 COLEC11 N6AMT1 GDF15 C7 ITGA1 ITGB1 AKT2 | 85.266667 | 89.7 | 76.4 |
| BCL2A1 YES1 COLEC11 IGFBP7 N6AMT1 ITGA1 ITGB1 AKT2 | 85.066667 | 88.3 | 78.6 |
| BCL2A1 YES1 COLEC11 IGFBP7 C7 ITGA1 ITGB1 AKT2 | 84.666667 | 89 | 76 |
| BCL2A1 YES1 COLEC11 IGFBP7 N6AMT1 GDF15 AKT2 | 84.6 | 88.6 | 76.6 |
| BCL2A1 YES1 COLEC11 N6AMT1 GDF15 ITGA1 ITGB1 AKT2 | 84.533333 | 89.4 | 74.8 |
| YES1 COLEC11 IGFBP7 GDF15 C7 ITGA1 ITGB1 AKT2 | 84.333333 | 87.1 | 78.8 |
| BCL2A1 COLEC11 IGFBP7 GDF15 C7 ITGA1 ITGB1 AKT2 | 84.266667 | 89 | 74.8 |
| BCL2A1 YES1 COLEC11 IGFBP7 GDF15 C7 AKT2 | 84.133333 | 85.4 | 81.6 |
| BCL2A1 COLEC11 IGFBP7 N6AMT1 GDF15 C7 AKT2 | 84.066667 | 85.3 | 81.6 |
| BCL2A1 YES1 COLEC11 GDF15 C7 ITGA1 ITGB1 AKT2 | 83.933333 | 86.9 | 78 |
| BCL2A1 YES1 COLEC11 IGFBP7 GDF15 ITGA1 ITGB1 AKT2 | 83 | 87.4 | 74.2 |
| 8 Proteins |  |  |  |
| THBS2 BCL2A1 YES1 IGFBP7 N6AMT1 GDF15 C7 ITGA1 ITGB1 | 91.866667 | 94.3 | 87 |
| THBS2 BCL2A1 COLEC11 IGFBP7 N6AMT1 GDF15 C7 ITGA1 ITGB1 | 91.466667 | 93.8 | 86.8 |
| THBS2 BCL2A1 YES1 IGFBP7 GDF15 C7 ITGA1 ITGB1 AKT2 | 91.266667 | 94.1 | 85.6 |
| THBS2 BCL2A1 YES1 COLEC11 N6AMT1 GDF15 C7 ITGA1 ITGB1 | 91.266667 | 93 | 87.8 |
| THBS2 BCL2A1 YES1 COLEC11 IGFBP7 GDF15 C7 AKT2 | 91.2 | 93.9 | 85.8 |
| THBS2 BCL2A1 IGFBP7 N6AMT1 GDF15 C7 ITGA1 ITGB1 AKT2 | 91.133333 | 94.7 | 84 |
| THBS2 BCL2A1 YES1 COLEC11 N6AMT1 GDF15 C7 AKT2 | 90.933333 | 93.8 | 85.2 |
| THBS2 BCL2A1 YES1 IGFBP7 N6AMT1 C7 ITGA1 ITGB1 AKT2 | 90.866667 | 93.7 | 85.2 |
| THBS2 BCL2A1 YES1 COLEC11 IGFBP7 N6AMT1 GDF15 C7 | 90.866667 | 94.1 | 84.4 |
| THBS2 YES1 COLEC11 IGFBP7 N6AMT1 GDF15 C7 AKT2 | 90.733333 | 93.7 | 84.8 |
| THBS2 BCL2A1 YES1 COLEC11 IGFBP7 GDF15 C7 ITGA1 ITGB1 | 90.6 | 93.3 | 85.2 |
| THBS2 YES1 IGFBP7 N6AMT1 GDF15 C7 ITGA1 ITGB1 AKT2 | 90.533333 | 93.3 | 85 |
| THBS2 BCL2A1 COLEC11IGFBP7 N6AMT1 GDF15 C7 AKT2 | 90.533333 | 94.1 | 83.4 |
| THBS2 BCL2A1 YES1 N6AMT1 GDF15 C7 ITGA1 ITGB1 AKT2 | 90.466667 | 93.6 | 84.2 |
| THBS2 YES1 COLEC11 IGFBP7 N6AMT1 GDF15 C7 ITGA1 ITGB1 | 90.333333 | 91.7 | 87.6 |
| THBS2 BCL2A1 COLEC11 N6AMT1 GDF15 C7 ITGA1 ITGB1 AKT2 | 90.333333 | 92.4 | 86.2 |
| THBS2 COLEC11 IGFBP7 N6AMT1 GDF15 C7 ITGA1 ITGB1 AKT2 | 90.133333 | 93.4 | 83.6 |
| THBS2 BCL2A1 COLEC11 IGFBP7 N6AMT1 C7 ITGA1 ITGB1 AKT2 | 89.933333 | 91.1 | 87.6 |
| THBS2 BCL2A1 YES1 COLEC11 IGFBP7 GDF15 ITGA1 ITGB1 AKT2 | 89.933333 | 92.7 | 84.4 |
| THBS2 BCL2A1 YES1 COLEC11 IGFBP7 N6AMT1 GDF15 ITGA1 ITGB1 | 89.933333 | 92.9 | 84 |
| BCL2A1 YES1 IGFBP7 N6AMT1 GDF15 C7 ITGA1 ITGB1 AKT2 | 89.866667 | 92.4 | 84.8 |
| THBS2 BCL2A1 YES1 COLEC11 IGFBP7 N6AMT1 C7 AKT2 | 89.866667 | 92.3 | 85 |
| THBS2 YES1 COLEC11 IGFBP7 GDF15 C7 ITGA1 ITGB1 AKT2 | 89.8 | 93 | 83.4 |

TABLE 3-continued

Markers for NASH versus Simple Steatosis Based on Average Accuracy, Sensitivity and Specificity

| | AvgAcc | AvgSen | AvgSpe |
|---|---|---|---|
| THBS2 BCL2A1 COLEC11 IGFBP7 GDF15 C7 ITGA1 ITGB1 AKT2 | 89.666667 | 91.8 | 85.4 |
| THBS2 BCL2A1 YES1 COLEC11 IGFBP7 N6AMT1 GDF15 AKT2 | 89.666667 | 92.8 | 83.4 |
| THBS2 BCL2A1 COLEC11 IGFBP7 N6AMT1 GDF15 ITGA1 ITGB1 AKT2 | 89.6 | 91.9 | 85 |
| THBS2 YES1 COLEC11 IGFBP7 N6AMT1 C7 ITGA1 ITGB1 AKT2 | 89.333333 | 91.2 | 85.6 |
| THBS2 BCL2A1 YES1 IGFBP7 N6AMT1 GDF15 C7 AKT2 | 89.266667 | 92.2 | 83.4 |
| THBS2 BCL2A1 YES1 COLEC11 GDF15 C7 ITGA1 ITGB1 AKT2 | 89.266667 | 91.9 | 84 |
| THBS2 BCL2A1 YES1 COLEC11 N6AMT1 GDF15 ITGA1 ITGB1 AKT2 | 89.066667 | 90.6 | 86 |
| THBS2 BCL2A1 YES1 IGFBP7 N6AMT1 GDF15 ITGA1 ITGB1 AKT2 | 89 | 91.5 | 84 |
| THBS2 BCL2A1 YES1 COLEC11 N6AMT1 C7 ITGA1 ITGB1 AKT2 | 88.8 | 91.2 | 84 |
| THBS2 BCL2A1 YES1 COLEC11 IGFBP7 N6AMT1 C7 ITGA1 ITGB1 | 88.8 | 90.3 | 85.8 |
| THBS2 YES1 COLEC11 IGFBP7 N6AMT1 GDF15 ITGA1 ITGB1 AKT2 | 88.733333 | 91.4 | 83.4 |
| THBS2 BCL2A1 YES1 COLEC11 IGFBP7 C7 ITGA1 ITGB1 AKT2 | 88.533333 | 89.7 | 86.2 |
| THBS2 YES1 COLEC11 N6AMT1 GDF15 C7 ITGA1 ITGB1 AKT2 | 88.466667 | 91.4 | 82.6 |
| THBS2 BCL2A1 YES1 COLEC11 IGFBP7 N6AMT1 ITGA1 ITGB1 AKT2 | 88.2 | 89.1 | 86.4 |
| BCL2A1 COLEC11 IGFBP7 N6AMT1 GDF15 C7 ITGA1 ITGB1 AKT2 | 87.533333 | 91.7 | 79.2 |
| BCL2A1 YES1 COLEC11 IGFBP7 GDF15 C7 ITGA1 ITGB1 AKT2 | 87.466667 | 90.4 | 81.6 |
| BCL2A1 YES1 COLEC11 N6AMT1 GDF15 C7 ITGA1 ITGB1 AKT2 | 87.066667 | 90.8 | 79.6 |
| YES1 COLEC11 IGFBP7 N6AMT1 GDF15 C7 ITGA1 ITGB1 AKT2 | 87 | 90.4 | 80.2 |
| BCL2A1 YES1 COLEC11 IGFBP7 N6AMT1 GDF15 C7 ITGA1 ITGB1 | 86.733333 | 91.6 | 77 |
| BCL2A1 YES1 COLEC11 IGFBP7 N6AMT1 GDF15 C7 AKT2 | 86.2 | 88.8 | 81 |
| BCL2A1 YES1 COLEC11 IGFBP7 N6AMT1 C7 ITGA1 ITGB1 AKT2 | 86.066667 | 89.1 | 80 |
| BCL2A1 YES1 COLEC11 IGFBP7 N6AMT1 GDF15 ITGA1 ITGB1 AKT2 | 85.466667 | 90.1 | 76.2 |

9 Proteins

| | AvgAcc | AvgSen | AvgSpe |
|---|---|---|---|
| THBS2 BCL2A1 YES1 COLEC11 IGFBP7 N6AMT1 GDF15 ITGA1 ITGB1 AKT2 | 92.066667 | 94.4 | 87.4 |
| THBS2 BCL2A1 YES1 IGFBP7 N6AMT1 GDF15 C7 ITGA1 ITGB1 AKT2 | 91.466667 | 95.2 | 84 |
| THBS2 BCL2A1 COLEC11 IGFBP7 N6AMT1 GDF15 C7 ITGA1 ITGB1 AKT2 | 91.2 | 93.7 | 86.2 |
| THBS2 BCL2A1 YES1 COLEC11 IGFBP7 N6AMT1 GDF15 C7 AKT2 | 90.866667 | 94.3 | 84 |
| THBS2 YES1 COLEC11 IGFBP7 N6AMT1 GDF15 C7 ITGA1 ITGB1 AKT2 | 90.666667 | 92.8 | 86.4 |
| THBS2 BCL2A1 YES1 COLEC11 IGFBP7 N6AMT1 GDF15 C7 ITGA1 ITGB1 | 90.4 | 92.8 | 85.6 |
| THBS2 BCL2A1 YES1 COLEC11 IGFBP7 N6AMT1 C7 ITGA1 ITGB1 AKT2 | 90.133333 | 92.9 | 84.6 |
| THBS2 BCL2A1 YES1 COLEC11 IGFBP7 GDF15 C7 ITGA1 ITGB1 AKT2 | 89.933333 | 92.3 | 85.2 |
| THBS2 BCL2A1 YES1 COLEC11 N6AMT1 GDF15 C7 ITGA1 ITGB1 AKT2 | 89.8 | 92.4 | 84.6 |
| BCL2A1 YES1 COLEC11 IGFBP7 N6AMT1 GDF15 C7 ITGA1 ITGB1 AKT2 | 86.4 | 90.5 | 78.2 |

10 Proteins

| | AvgAcc | AvgSen | AvgSpe |
|---|---|---|---|
| THBS2 BCL2A1 YES1 COLEC11 IGFBP7 N6AMT1 GDF15 C7 ITGA1 ITGB1 AKT2 | 90.333333 | 94.3 | 82.4 |

Example 3. Development of Multiplex Predictors for Discriminating Between NASH with Advanced Liver Fibrosis and NASH without Advanced Liver Fibrosis A listing of markers that discriminate between NASH with advanced liver fibrosis or without advanced liver fibrosis, which have a BH p-value of <0.05, is set forth below in Table 4. In Table 4, "FC" represents the "fold change" for each marker, such that a negative value represents a decrease in expression and a positive value represents an increase in expression. For example, an FC of 2.198697 indicates a 2.198697 fold increase in expression of the marker in a sample obtained from a NASH patient with advanced liver fibrosis versus a sample obtained from a patient without advanced liver fibrosis.

TABLE 4

Markers for diagnosis of NASH with advanced liver fibrosis versus NASH without advanced liver fibrosis

| Target Full Name | Target | UniProt | Entrez Gene ID | Entrez Gene Symbol | FC | p-val | q-val | BH p-val |
|---|---|---|---|---|---|---|---|---|
| E-selectin | E-Selectin | P16581 | 6401 | SELE | 2.198697 | 0 | 0 | 0 |
| Insulin-like growth factor-binding protein 7 | IGFBP-7 | Q16270 | 3490 | IGFBP7 | 1.52405 | 0 | 0.000003 | 0.000008 |
| Thrombospondin-2 | TSP2 | P35442 | 7058 | THBS2 | 2.580788 | 0 | 0.000006 | 0.000013 |
| Complement component C7 | C7 | P10643 | 730 | C7 | 1.551308 | 0 | 0.000023 | 0.000056 |
| Collectin-11 | Collectin Kidney 1 | Q9BWP8 | 78989 | COLEC11 | 2.721347 | 0 | 0.000042 | 0.000102 |
| Decorin | Bone proteoglycan II | P07585 | 1634 | DCN | 1.310681 | 0 | 0.000043 | 0.000104 |
| Latent-transforming growth factor beta-binding protein 4 | LTBP4 | Q8N2S1 | 8425 | LTBP4 | 1.487923 | 0.000002 | 0.000135 | 0.000327 |
| N-acetyl-D-glucosamine kinase | NAGK | Q9UJ70 | 55577 | NAGK | 1.481484 | 0.000002 | 0.000161 | 0.000387 |
| C-C motif chemokine 21 | 6Ckine | O00585 | 6366 | CCL21 | 1.604114 | 0.000004 | 0.000219 | 0.000528 |
| Interleukin-1 receptor type 2 | IL-1 sRII | P27930 | 7850 | IL1R2 | 1.3602 | 0.000008 | 0.000386 | 0.000931 |
| Prolactin | PRL | P01236 | 5617 | PRL | −1.166382 | 0.000008 | 0.000386 | 0.000931 |
| Insulin-like growth factor-binding protein 5 | IGFBP-5 | P24593 | 3488 | IGFBP5 | −1.264953 | 0.000008 | 0.000386 | 0.000931 |
| Metalloproteinase inhibitor 1 | TIMP-1 | P01033 | 7076 | TIMP1 | 1.361688 | 0.000009 | 0.000389 | 0.00094 |
| Matrilysin | MMP-7 | P09237 | 4316 | MMP7 | 2.010545 | 0.000016 | 0.000633 | 0.001528 |
| Carboxypeptidase B2 | TAFI | Q96IY4 | 1361 | CPB2 | −1.249178 | 0.000017 | 0.000633 | 0.001528 |
| Scavenger receptor cysteine-rich type 1 protein M130 | sCD163 | Q86VB7 | 9332 | CD163 | 1.597583 | 0.000022 | 0.000641 | 0.001547 |
| Interferon gamma | IFN-g | P01579 | 3458 | IFNG | 1.251538 | 0.000019 | 0.000641 | 0.001547 |
| Ephrin type-B receptor 4 | EphB4 | P54760 | 2050 | EPHB4 | −1.204008 | 0.000022 | 0.000641 | 0.001547 |
| Cadherin-15 | CAD15 | P55291 | 1013 | CDH15 | −1.235201 | 0.000022 | 0.000641 | 0.001547 |
| Spondin-1 | Spondin-1 | Q9HCB6 | 10418 | SPON1 | 1.626456 | 0.000026 | 0.000708 | 0.001708 |
| Interleukin-6 receptor subunit beta | gp130, soluble | P40189 | 3572 | IL6ST | 1.298101 | 0.000027 | 0.000717 | 0.001731 |
| Tyrosine-protein kinase receptor Tie-1, soluble | sTie-1 | P35590 | 7075 | TIE1 | 1.314915 | 0.000035 | 0.000862 | 0.002081 |
| Brain-specific serine protease 4 | BSSP4 | Q9GZN4 | 64063 | PRSS22 | 1.678923 | 0.000052 | 0.001175 | 0.002836 |
| ADP-ribosyl cyclase/cyclic ADP-ribose hydrolase 2 | BST1 | Q10588 | 683 | BST1 | 1.61308 | 0.000054 | 0.001175 | 0.002836 |
| Calpain I | Calpain I | P07384 P04632 | 823 826 | CAPN1 CAPNS1 | −1.142567 | 0.000053 | 0.001175 | 0.002836 |
| Laminin | Laminin | P25391, P07942, P11047 | 284217 3912 3915 | LAMA1 LAMB1 LAMC1 | 1.465222 | 0.000059 | 0.00124 | 0.002993 |
| Roundabout homolog 2 | ROBO2 | Q9HCK4 | 6092 | ROBO2 | 1.352892 | 0.000062 | 0.001252 | 0.003023 |
| Plexin-B2 | PLXB2 | O15031 | 23654 | PLXNB2 | 1.430223 | 0.000082 | 0.001448 | 0.003495 |
| C-type mannose receptor 2 | MRC2 | Q9UBG0 | 9902 | MRC2 | 1.341373 | 0.000079 | 0.001448 | 0.003495 |
| Chordin-like protein 1 | CRDL1 | Q9BU40 | 91851 | CHRDL1 | 1.281279 | 0.000077 | 0.001448 | 0.003495 |
| Death-associated protein kinase 2 | DAPK2 | Q9UIK4 | 23604 | DAPK2 | −1.186162 | 0.000082 | 0.001448 | 0.003495 |
| CD48 antigen | CD48 | P09326 | 962 | CD48 | 1.232569 | 0.000094 | 0.001472 | 0.003553 |
| Acid sphingomyelinase-like phosphodiesterase 3a | ASM3A | Q92484 | 10924 | SMPDL3A | −1.192554 | 0.000091 | 0.001472 | 0.003553 |

TABLE 4-continued

Markers for diagnosis of NASH with advanced liver fibrosis versus NASH without advanced liver fibrosis

| Target Full Name | Target | UniProt | Entrez Gene ID | Entrez Gene Symbol | FC | p-val | q-val | BH p-val |
|---|---|---|---|---|---|---|---|---|
| Tumor necrosis factor receptor superfamily member 3 | Lymphotoxin b R | P36941 | 4055 | LTBR | −1.200656 | 0.000087 | 0.001472 | 0.003553 |
| Vitamin K-dependent protein C | Protein C | P04070 | 5624 | PROC | −1.236297 | 0.000094 | 0.001472 | 0.003553 |
| Dickkopf-like protein 1 | Soggy-1 | Q9UK85 | 27120 | DKKL1 | −1.167534 | 0.000097 | 0.001479 | 0.003571 |
| Follistatin-related protein 3 | FSTL3 | O95633 | 10272 | FSTL3 | 1.4443 | 0.000123 | 0.001814 | 0.004378 |
| Semaphorin-6B | SEM6B | Q9H3T3 | 10501 | SEMA6B | 1.452502 | 0.00014 | 0.001969 | 0.004753 |
| SLAM family member 5 | SLAF5 | Q9UIB8 | 8832 | CD84 | −1.172939 | 0.00014 | 0.001969 | 0.004753 |
| UMP-CMP kinase | Cytidylate kinase | P30085 | 51727 | CMPK1 | −1.185196 | 0.000145 | 0.001988 | 0.004799 |
| Alpha-2-macroglobulin | a2-Macroglobulin | P01023 | 2 | A2M | 1.46191 | 0.000159 | 0.002126 | 0.005132 |
| Interleukin-1 receptor-like 1 | IL-1 R4 | Q01638 | 9173 | IL1RL1 | 1.857614 | 0.000171 | 0.00213 | 0.005141 |
| Interleukin-6 receptor subunit alpha | IL-6 sRa | P08887 | 3570 | IL6R | 1.381579 | 0.000171 | 0.00213 | 0.005141 |
| Serine/threonine-protein kinase 17B | DRAK2 | O94768 | 9262 | STK17B | −1.171313 | 0.000168 | 0.00213 | 0.005141 |
| C-C motif chemokine 19 | MIP-3b | Q99731 | 6363 | CCL19 | 1.532404 | 0.000179 | 0.002162 | 0.005218 |
| Dual specificity tyrosine-phosphorylation-regulated kinase 3 | DYRK3 | O43781 | 8444 | DYRK3 | −1.199538 | 0.000182 | 0.002162 | 0.005218 |
| Glypican-3 | Glypican 3 | P51654 | 2719 | GPC3 | 1.501386 | 0.000195 | 0.002267 | 0.005472 |
| Macrophage colony-stimulating factor 1 receptor | M-CSF R | P07333 | 1436 | CSF1R | 1.562468 | 0.00025 | 0.002849 | 0.006877 |
| Galectin-3-binding protein | LG3BP | Q08380 | 3959 | LGALS3BP | 1.719962 | 0.000266 | 0.002912 | 0.00703 |
| Metalloproteinase inhibitor 2 | TIMP-2 | P16035 | 7077 | TIMP2 | 1.149363 | 0.000264 | 0.002912 | 0.00703 |
| Plexin-C1 | PLXC1 | O60486 | 10154 | PLXNC1 | 1.226673 | 0.000283 | 0.003035 | 0.007326 |
| Cell adhesion molecule 3 | Nectin-like protein 1 | Q8N126 | 57863 | CADM3 | −1.159425 | 0.000291 | 0.003047 | 0.007354 |
| Growth/differentiation factor 8 | Myostatin | O14793 | 2660 | MSTN | −1.189557 | 0.000299 | 0.003047 | 0.007354 |
| Ribosome maturation protein SBDS | SBDS | Q9Y3A5 | 51119 | SBDS | −1.228944 | 0.0003 | 0.003047 | 0.007354 |
| Leukemia inhibitory factor receptor | LIF sR | P42702 | 3977 | LIFR | 1.303084 | 0.000318 | 0.003169 | 0.007649 |
| Angiopoietin-1 receptor, soluble | sTie-2 | Q02763 | 7010 | TEK | 1.206799 | 0.000339 | 0.00332 | 0.008014 |
| Non-receptor tyrosine-protein kinase TYK2 | TYK2 | P29597 | 7297 | TYK2 | −1.178701 | 0.000381 | 0.00366 | 0.008834 |
| Serine protease 27 | Marapsin | Q9BQR3 | 83886 | PRSS27 | −1.135599 | 0.000397 | 0.003745 | 0.009039 |
| Alpha-(1,3)-fucosyltransferase 5 | FUT5 | Q11128 | 2527 | FUT5 | 1.506621 | 0.000407 | 0.003781 | 0.009125 |
| Inosine-5'-monophosphate dehydrogenase 2 | IMDH2 | P12268 | 3615 | IMPDH2 | −1.176933 | 0.000428 | 0.003907 | 0.00943 |
| Mitogen-activated protein kinase kinase kinase 7:TGF-beta-activated kinase 1 and MAP3K7-binding protein 1 fusion | TAK1-TAB1 | O43318 Q15750 | 6885 10454 | MAP3K7 TAB1 | −1.153498 | 0.000461 | 0.004138 | 0.009989 |
| Kallikrein-14 | kallikrein 14 | Q9P0G3 | 43847 | KLK14 | −1.166541 | 0.000476 | 0.004208 | 0.010156 |
| Opioid-binding protein/cell adhesion molecule | OBCAM | Q14982 | 4978 | OPCML | −1.149857 | 0.000535 | 0.004532 | 0.010938 |
| Mannan-binding lectin serine protease 1 | MASP3 | P48740 | 5648 | MASP1 | −1.205303 | 0.000543 | 0.004532 | 0.010938 |
| Protein disulfide-isomerase A3 | Protein disulfide isomerase A3 | P30101 | 2923 | PDIA3 | −1.218791 | 0.000542 | 0.004532 | 0.010938 |
| Methionine aminopeptidase 1 | METAP1 | P53582 | 23173 | METAP1 | −1.428601 | 0.000546 | 0.004532 | 0.010938 |

TABLE 4-continued

Markers for diagnosis of NASH with advanced liver fibrosis versus NASH without advanced liver fibrosis

| Target Full Name | Target | UniProt | Entrez Gene ID | Entrez Gene Symbol | FC | p-val | q-val | BH p-val |
|---|---|---|---|---|---|---|---|---|
| Troponin T, cardiac muscle | Troponin T | P45379 | 7139 | TNNT2 | −1.179093 | 0.000574 | 0.004656 | 0.011239 |
| Mothers against decapentaplegic homolog 2 | SMAD2 | Q15796 | 4087 | SMAD2 | −1.492167 | 0.000578 | 0.004656 | 0.011239 |
| Interleukin-19 | IL-19 | Q9UHD0 | 29949 | IL19 | 1.331094 | 0.000611 | 0.004784 | 0.011547 |
| Receptor-type tyrosine-protein kinase FLT3 | Flt-3 | P36888 | 2322 | FLT3 | −1.174392 | 0.000609 | 0.004784 | 0.011547 |
| Contactin-4 | Contactin-4 | Q8IWV2 | 152330 | CNTN4 | 1.2382 | 0.000649 | 0.005004 | 0.012079 |
| Matrilin-2 | MATN2 | O00339 | 4147 | MATN2 | 1.19346 | 0.000684 | 0.005205 | 0.012562 |
| Neural cell adhesion molecule L1 | NCAM-L1 | P32004 | 3897 | L1CAM | 1.393174 | 0.000723 | 0.0053 | 0.012793 |
| Calcium/calmodulin-dependent protein kinase type 1 | CAMK1 | Q14012 | 8536 | CAMK1 | −1.133514 | 0.000723 | 0.0053 | 0.012793 |
| Insulin-like growth factor-binding protein 3 | IGFBP-3 | P17936 | 3486 | IGFBP3 | −1.324207 | 0.000726 | 0.0053 | 0.012793 |
| Cadherin-6 | Cadherin-6 | P55285 | 1004 | CDH6 | −1.160317 | 0.000767 | 0.005525 | 0.013335 |
| Biglycan | BGN | P21810 | 633 | BGN | 1.245891 | 0.000804 | 0.005718 | 0.013802 |
| A disintegrin and metalloproteinase with thrombospondin motifs 13 | ATS13 | Q76LX8 | 11093 | ADAMTS13 | 1.430683 | 0.000859 | 0.005883 | 0.014199 |
| Complement component 1 Q subcomponent-binding protein, mitochondrial | C1QBP | Q07021 | 708 | C1QBP | −1.158099 | 0.000853 | 0.005883 | 0.014199 |
| Abelson tyrosine-protein kinase 2 | ABL2 | P42684 | 27 | ABL2 | −1.189391 | 0.000857 | 0.005883 | 0.014199 |
| Angiopoietin-2 | Angiopoietin-2 | O15123 | 285 | ANGPT2 | 1.29304 | 0.000928 | 0.006277 | 0.015151 |
| Dickkopf-related protein 3 | DKK3 | Q9UBP4 | 27122 | DKK3 | −1.130963 | 0.000952 | 0.006321 | 0.015257 |
| Junctional adhesion molecule B | JAM-B | P57087 | 58494 | JAM2 | −1.194111 | 0.000958 | 0.006321 | 0.015257 |
| Neurogenic locus notch homolog protein 3 | Notch-3 | Q9UM47 | 4854 | NOTCH3 | 1.342559 | 0.001012 | 0.006446 | 0.015559 |
| Legumain | LGMN | Q99538 | 5641 | LGMN | −1.134811 | 0.001004 | 0.006446 | 0.015559 |
| Interferon regulatory factor 1 | IRF1 | P10914 | 3659 | IRF1 | −1.159258 | 0.001012 | 0.006446 | 0.015559 |
| Insulin receptor | IR | P06213 | 3643 | INSR | 1.508313 | 0.001128 | 0.006943 | 0.016757 |
| Granzyme A | granzyme A | P12544 | 3001 | GZMA | 1.247711 | 0.001128 | 0.006943 | 0.016757 |
| cGMP-dependent 3',5'-cyclic phosphodiesterase | cGMP-stimulated PDE | O00408 | 5138 | PDE2A | −1.152451 | 0.00111 | 0.006943 | 0.016757 |
| Calcineurin subunit B type 1 | Calcineurin B a | P63098 | 5534 | PPP3R1 | −1.143408 | 0.001147 | 0.00698 | 0.016847 |
| Oncostatin-M | OSM | P13725 | 5008 | OSM | −1.153112 | 0.001256 | 0.007557 | 0.01824 |
| SLAM family member 7 | SLAF7 | Q9NQ25 | 57823 | SLAMF7 | 1.799454 | 0.001391 | 0.007809 | 0.018848 |
| Lumican | Lumican | P51884 | 4060 | LUM | 1.254092 | 0.001323 | 0.007809 | 0.018848 |
| Appetite-regulating hormone | ghrelin | Q9UBU3 | 51738 | GHRL | −1.119504 | 0.001392 | 0.007809 | 0.018848 |
| Tumor necrosis factor receptor superfamily member 11A | RANK | Q9Y6Q6 | 8792 | TNFRSF11A | −1.139362 | 0.001396 | 0.007809 | 0.018848 |
| OCIA domain-containing protein 1 | OCAD1 | Q9NX40 | 54940 | OCIAD1 | −1.168552 | 0.001397 | 0.007809 | 0.018848 |
| ATP-dependent RNA helicase DDX19B | DEAD-box protein 19B | Q9UMR2 | 11269 | DDX19B | −1.192287 | 0.001326 | 0.007809 | 0.018848 |
| Transgelin-2 | Transgelin-2 | P37802 | 8407 | TAGLN2 | −1.324529 | 0.001396 | 0.007809 | 0.018848 |
| Stanniocalcin-1 | Stanniocalcin-1 | P52823 | 6781 | STC1 | 1.475875 | 0.001435 | 0.007939 | 0.019162 |
| Vascular endothelial growth factor receptor 2 | VEGF sR2 | P35968 | 3791 | KDR | −1.156875 | 0.001456 | 0.007975 | 0.019249 |
| cGMP-inhibited 3',5'-cyclic phosphodiesterase A | PDE3A | Q14432 | 5139 | PDE3A | −1.139876 | 0.001546 | 0.008384 | 0.020238 |

TABLE 4-continued

Markers for diagnosis of NASH with advanced liver fibrosis versus NASH without advanced liver fibrosis

| Target Full Name | Target | UniProt | Entrez Gene ID | Entrez Gene Symbol | FC | p-val | q-val | BH p-val |
|---|---|---|---|---|---|---|---|---|
| Apolipoprotein M | ApoM | O95445 | 55937 | APOM | −1.320646 | 0.001633 | 0.008767 | 0.021161 |
| Kallistatin | Kallistatin | P29622 | 5267 | SERPINA4 | −1.137587 | 0.001792 | 0.009531 | 0.023006 |
| 3-phosphoinositide-dependent protein kinase 1 | PDPK1 | O15530 | 5170 | PDPK1 | −1.576541 | 0.001814 | 0.009552 | 0.023055 |
| WNT1-inducible-signaling pathway protein 1 | WISP-1 | O95388 | 8840 | WISP1 | −1.156086 | 0.001833 | 0.009563 | 0.023083 |
| Testican-2 | Testican-2 | Q92563 | 9806 | SPOCK2 | 1.265259 | 0.001917 | 0.009905 | 0.023908 |
| Semaphorin-3E | Semaphorin 3E | O15041 | 9723 | SEMA3E | 1.37833 | 0.002114 | 0.009981 | 0.024091 |
| EGF-containing fibulin-like extracellular matrix protein 1 | FBLN3 | Q12805 | 2202 | EFEMP1 | 1.208492 | 0.002005 | 0.009981 | 0.024091 |
| cAMP-specific 3',5'-cyclic phosphodiesterase 4D | PDE4D | Q08499 | 5144 | PDE4D | −1.096492 | 0.002107 | 0.009981 | 0.024091 |
| Ephrin type-A receptor 1 | EphA1 | P21709 | 2041 | EPHA1 | −1.131355 | 0.002002 | 0.009981 | 0.024091 |
| Apolipoprotein D | Apo D | P05090 | 347 | APOD | −1.152256 | 0.002084 | 0.009981 | 0.024091 |
| Ubiquitin-conjugating enzyme E2 G2 | UB2G2 | P60604 | 7327 | UBE2G2 | −1.156046 | 0.001998 | 0.009981 | 0.024091 |
| SLIT and NTRK-like protein 1 | SLIK1 | Q96PX8 | 114798 | SLITRK1 | −1.190187 | 0.002106 | 0.009981 | 0.024091 |
| Serum amyloid P-component | SAP | P02743 | 325 | APCS | −1.211199 | 0.002103 | 0.009981 | 0.024091 |
| Protein SET | SET | Q01105 | 6418 | SET | −1.242922 | 0.002104 | 0.009981 | 0.024091 |
| Ubiquitin-fold modifier-conjugating enzyme 1 | UFC1 | Q9Y3C8 | 51506 | UFC1 | −1.291946 | 0.002104 | 0.009981 | 0.024091 |
| Protein jagged-1 | JAG1 | P78504 | 182 | JAG1 | 1.104509 | 0.002216 | 0.010284 | 0.024822 |
| Scavenger receptor class F member 1 | SREC-I | Q14162 | 8578 | SCARF1 | −1.279569 | 0.002206 | 0.010284 | 0.024822 |
| Low affinity immunoglobulin epsilon Fc receptor | CD23 | P06734 | 2208 | FCER2 | 1.388161 | 0.002333 | 0.010648 | 0.0257 |
| Calreticulin | calreticulin | P27797 | 811 | CALR | −1.123443 | 0.002317 | 0.010648 | 0.0257 |
| GRB2-related adapter protein 2 | GRB2-related adapter protein 2 | O75791 | 9402 | GRAP2 | −1.152447 | 0.002574 | 0.01165 | 0.028119 |
| Small ubiquitin-related modifier 3 | SUMO3 | P55854 | 6613 | SUMO3 | −1.332723 | 0.002643 | 0.011767 | 0.028403 |
| Eukaryotic translation initiation factor 4H | eIF-4H | Q15056 | 7458 | EIF4H | −1.562494 | 0.002643 | 0.011767 | 0.028403 |
| Immunoglobulin A | IgA | P01876 P01877 | 3493 3494 | IGHA1 IGHA2 | 1.496353 | 0.002851 | 0.012493 | 0.030155 |
| Tyrosine-protein kinase Fer | FER | P16591 | 2241 | FER | −1.873493 | 0.002841 | 0.012493 | 0.030155 |
| SHC-transforming protein 1 | SHC1 | P29353 | 6464 | SHC1 | −1.190681 | 0.002909 | 0.012569 | 0.030338 |
| Carbonic anhydrase 13 | Carbonic anhydrase XIII | Q8N1Q1 | 377677 | CA13 | −2.028238 | 0.002915 | 0.012569 | 0.030338 |
| Retinol-binding protein 4 | RBP | P02753 | 5950 | RBP4 | −1.240567 | 0.002969 | 0.012703 | 0.030662 |
| RAC-alpha/beta/gamma serine/threonine-protein kinase | PKB a/b/g | P31749 P31751 Q9Y243 | 207 208 10000 | AKT1 AKT2 AKT3 | −1.156897 | 0.00313 | 0.01319 | 0.031836 |
| Tyrosine-protein kinase BTK | BTK | Q06187 | 695 | BTK | −1.59002 | 0.003131 | 0.01319 | 0.031836 |
| Arylsulfatase B | ARSB | P15848 | 411 | ARSB | −1.161396 | 0.003279 | 0.013632 | 0.032903 |
| Tyrosine-protein phosphatase non-receptor type 1 | PTP-1B | P18031 | 5770 | PTPN1 | −1.163378 | 0.003285 | 0.013632 | 0.032903 |
| Dipeptidyl peptidase 2 | DPP2 | Q9UHL4 | 29952 | DPP7 | −1.13783 | 0.003442 | 0.013964 | 0.033704 |
| Cellular tumor antigen p53 | p53 | P04637 | 7157 | TP53 | −1.181769 | 0.003433 | 0.013964 | 0.033704 |
| Dual specificity protein phosphatase 3 | DUS3 | P51452 | 1845 | DUSP3 | −1.740885 | 0.003441 | 0.013964 | 0.033704 |
| Integrin alpha-I:beta-1 complex | Integrin a1b1 | P56199, P05556 | 3672 3688 | ITGA1 ITGB1 | 1.600396 | 0.003534 | 0.014231 | 0.03435 |

TABLE 4-continued

Markers for diagnosis of NASH with advanced liver fibrosis versus NASH without advanced liver fibrosis

| Target Full Name | Target | UniProt | Entrez Gene ID | Entrez Gene Symbol | FC | p-val | q-val | BH p-val |
|---|---|---|---|---|---|---|---|---|
| Carbohydrate sulfotransferase 15 | ST4S6 | Q7LFX5 | 51363 | CHST15 | 1.269116 | 0.003605 | 0.014411 | 0.034783 |
| Growth/differentiation factor 15 | MIC-1 | Q99988 | 9518 | GDF15 | 1.501098 | 0.003805 | 0.014994 | 0.03619 |
| Dual 3',5'-cyclic-AMP and -GMP phosphodiesterase 11A | PDE11 | Q9HCR9 | 50940 | PDE11A | −1.082979 | 0.003779 | 0.014994 | 0.03619 |
| Plasma kallikrein | Prekallikrein | P03952 | 3818 | KLKB1 | −1.161389 | 0.003949 | 0.015311 | 0.036956 |
| S-phase kinase-associated protein 1 | SKP1 | P63208 | 6500 | SKP1 | −1.179141 | 0.003968 | 0.015311 | 0.036956 |
| Hexokinase-1 | HXK1 | P19367 | 3098 | HK1 | −1.208277 | 0.00397 | 0.015311 | 0.036956 |
| Ficolin-2 | FCN2 | Q15485 | 2220 | FCN2 | −1.11858 | 0.004164 | 0.015651 | 0.037776 |
| alpha-2-macroglobulin receptor-associated protein | RAP | P30533 | 4043 | LRPAP1 | −1.16721 | 0.004172 | 0.015651 | 0.037776 |
| Sphingosine kinase 1 | Sphingosine kinase 1 | Q9NYA1 | 8877 | SPHK1 | −1.214232 | 0.004165 | 0.015651 | 0.037776 |
| Translationally-controlled tumor protein | TCTP | P13693 | 7178 | TPT1 | −1.529571 | 0.004164 | 0.015651 | 0.037776 |
| CD166 antigen | ALCAM | Q13740 | 214 | ALCAM | 1.224059 | 0.004537 | 0.016805 | 0.040562 |
| Contactin-2 | CNTN2 | Q02246 | 6900 | CNTN2 | 1.177942 | 0.004572 | 0.016805 | 0.040562 |
| Kelch-like ECH-associated protein 1 | KEAP1 | Q14145 | 9817 | KEAP1 | −1.247987 | 0.004569 | 0.016805 | 0.040562 |
| 14-3-3 protein sigma | STRATIFIN | P31947 | 2810 | SFN | −1.106047 | 0.004777 | 0.017029 | 0.041103 |
| cGMP-specific 3',5'-cyclic phosphodiesterase | PDE5A | O76074 | 8654 | PDE5A | −1.112397 | 0.004777 | 0.017029 | 0.041103 |
| Breast cancer anti-estrogen resistance protein 3 | BCAR3 | O75815 | 8412 | BCAR3 | −1.11608 | 0.004788 | 0.017029 | 0.041103 |
| Kallikrein-12 | kallikrein 12 | Q9UKR0 | 43849 | KLK12 | −1.14702 | 0.004773 | 0.017029 | 0.041103 |
| Estradiol 17-beta-dehydrogenase 1 | 17-beta-HSD 1 | P14061 | 3292 | HSD17B1 | −1.160112 | 0.004778 | 0.017029 | 0.041103 |
| Alpha-L-iduronidase | IDUA | P35475 | 3425 | IDUA | 1.184298 | 0.005247 | 0.01831 | 0.044194 |
| 15-hydroxyprostaglandin dehydrogenase [NAD(+)] | HPG- | P15428 | 3248 | HPGD | −1.135027 | 0.005228 | 0.01831 | 0.044194 |
| Tropomyosin alpha-4 chain | Tropomyosin 4 | P67936 | 7171 | TPM4 | −1.795125 | 0.005248 | 0.01831 | 0.044194 |
| Insulin-like growth factor 1 receptor | IGF-I sR | P08069 | 3480 | IGF1R | 1.207011 | 0.005486 | 0.019017 | 0.045902 |
| Prolyl endopeptidase FAP | SEPR | Q12884 | 2191 | FAP | 1.187241 | 0.005732 | 0.019288 | 0.046556 |
| Netrin-1 | NET1 | O95631 | 9423 | NTN1 | 1.161156 | 0.005737 | 0.019288 | 0.046556 |
| C-X-C motif chemokine 5 | ENA-78 | P42830 | 6374 | CXCL5 | −1.136935 | 0.00574 | 0.019288 | 0.046556 |
| Tumor necrosis factor receptor superfamily member 10A | TRAIL R1 | O00220 | 8797 | TNFRSF10A | −1.174672 | 0.00574 | 0.019288 | 0.046556 |
| Platelet glycoprotein VI | GPVI | Q9HCN6 | 51206 | GP6 | −1.428465 | 0.00574 | 0.019288 | 0.046556 |
| Aminoacylase-1 | Aminoacylase-1 | Q03154 | 95 | ACY1 | 1.533248 | 0.006277 | 0.019672 | 0.047481 |
| Neuronal cell adhesion molecule | Nr-CAM | Q92823 | 4897 | NRCAM | 1.372224 | 0.005977 | 0.019672 | 0.047481 |
| Desmoglein-2 | Desmoglein-2 | Q14126 | 1829 | DSG2 | 1.23219 | 0.006235 | 0.019672 | 0.047481 |
| L-lactate dehydrogenase B chain | LDH-H 1 | P07195 | 3945 | LDHB | 1.152213 | 0.006276 | 0.019672 | 0.047481 |
| Tumor necrosis factor receptor superfamily member 13B | TACI | O14836 | 23495 | TNFRSF13B | −1.103317 | 0.005998 | 0.019672 | 0.047481 |
| Lymphocyte antigen 86 | LY86 | O95711 | 9450 | LY86 | −1.110173 | 0.006254 | 0.019672 | 0.047481 |
| Trypsin-3 | TRY3 | P35030 | 5646 | PRSS3 | −1.119263 | 0.006272 | 0.019672 | 0.047481 |
| Prolactin receptor | Prolactin Receptor | P16471 | 5618 | PRLR | −1.173599 | 0.006258 | 0.019672 | 0.047481 |
| TGF-beta receptor type-2 | TGF-b R II | P37173 | 7048 | TGFBR2 | −1.251683 | 0.006005 | 0.019672 | 0.047481 |
| Adenylate kinase isoenzyme 1 | Myokinase, human | P00568 | 203 | AK1 | −1.358926 | 0.006285 | 0.019672 | 0.047481 |
| Tyrosine-protein kinase CSK | CSK | P41240 | 1445 | CSK | −1.451042 | 0.006145 | 0.019672 | 0.047481 |
| Ubiquitin-fold modifier 1 | UFM1 | P61960 | 51569 | UFM1 | −1.451768 | 0.006145 | 0.019672 | 0.047481 |

TABLE 4-continued

Markers for diagnosis of NASH with advanced liver fibrosis versus NASH without advanced liver fibrosis

| Target Full Name | Target | UniProt | Entrez Gene ID | Entrez Gene Symbol | FC | p-val | q-val | BH p-val |
|---|---|---|---|---|---|---|---|---|
| G2/mitotic-specific cyclin-B1 | Cyclin B1 | P14635 | 891 | CCNB1 | −1.154507 | 0.006552 | 0.020285 | 0.048962 |
| Casein kinase II subunit alpha | CSK21 | P68400 | 1457 | CSNK2A1 | −1.158565 | 0.006555 | 0.020285 | 0.048962 |
| C-X-C motif chemokine 6 | GCP-2 | P80162 | 6372 | CXCL6 | 1.388726 | 0.006715 | 0.020547 | 0.049594 |
| Beta-Ala-His dipeptidase | CNDP1 | Q96KN2 | 84735 | CNDP1 | −1.35111 | 0.006705 | 0.020547 | 0.049594 |
| Complement C1s subcomponent | C1s | P09871 | 716 | C1S | −1.203351 | 0.006799 | 0.020688 | 0.049933 |

A frequency analysis was performed on the identified markers that discriminate between NASH with advanced liver fibrosis versus NASH without advanced liver fibrosis. For this analysis, 5-fold cross-validation with 10,000 splits was used. That is, in each split, 16 NASH with advanced liver fibrosis and 16 NASH without advanced liver fibrosis (80% or 4/5 of all 40) randomly chosen samples were used. Proteins with BH p<0.01 were identified. This split was repeated 10,000 times. The number of times a protein appears in that list (FREQ) was counted, and those proteins were ranked as set forth below in Table 5.

TABLE 5

Predictors of Fibrosis - NASH with advanced liver fibrosis versus NASH without advanced liver fibrosis

| Target Full Name | Target | UniProt | Entrez Gene ID | Entrez Gene Symbol | FREQ | p-value | BH p | FC (AN/NN) |
|---|---|---|---|---|---|---|---|---|
| E-selectin | E-Selectin | P16581 | 6401 | SELE | 10000 | 1.55E−11 | 2.05E−08 | 2.30713326 |
| Thrombospondin-2 | TSP2 | P35442 | 7058 | THBS2 | 10000 | 3.16E−09 | 2.09E−06 | 2.63725126 |
| Insulin-like growth factor-binding protein 7 | IGFBP-7 | Q16270 | 3490 | IGFBP7 | 10000 | 1.85E−08 | 8.15E−06 | 1.48384792 |
| Collectin-11 | Collectin Kidney 1 | Q9BWP8 | 78989 | COLEC11 | 9833 | 7.99E−08 | 2.64E−05 | 2.57298459 |
| N-acetyl-D-glucosamine kinase | NAGK | Q9UJ70 | 55577 | NAGK | 8821 | 5.10E−07 | 0.00013475 | 1.4783134 |
| Complement component C7 | C7 | P10643 | 730 | C7 | 8533 | 9.56E−07 | 0.00021072 | 1.59627501 |
| Insulin-like growth factor-binding protein 5 | IGFBP-5 | P24593 | 3488 | IGFBP5 | 7426 | 1.94E−06 | 0.00028463 | −1.268398 |
| Decorin | Bone proteoglycan II | P07585 | 1634 | DCN | 7414 | 1.15E−06 | 0.00021759 | 1.32547312 |
| Interleukin-1 receptor type 2 | IL-1 sRII | P27930 | 7850 | IL1R2 | 7263 | 1.92E−06 | 0.00028463 | 1.33127247 |
| C-C motif chemokine 21 | 6Ckine | O00585 | 6366 | CCL21 | 6378 | 3.43E−06 | 0.00045363 | 1.60972473 |
| Latent-transforming growth factor beta-binding protein 4 | LTBP4 | Q8N2S1 | 8425 | LTBP4 | 5813 | 4.12E−06 | 0.00049547 | 1.47718575 |
| Metalloproteinase inhibitor 1 | TIMP-1 | P01033 | 7076 | TIMP1 | 4765 | 8.09E−06 | 0.00089151 | 1.40536301 |
| Scavenger receptor cysteine-rich type 1 protein M130 | SCD163 | Q86VB7 | 9332 | CD163 | 3482 | 2.10E−05 | 0.00203016 | 1.61452628 |
| Brain-specific serine protease 4 | BSSP4 | Q9GZN4 | 64063 | PRSS22 | 3413 | 2.15E−05 | 0.00203016 | 1.66344407 |
| Alpha-2-macroglobulin | a2-Macroglobulin | P01023 | 2 | A2M | 3150 | 2.67E−05 | 0.00215929 | 1.572759 |
| Matrilysin | MMP-7 | P09237 | 4316 | MMP7 | 3129 | 2.78E−05 | 0.00215929 | 2.07191792 |
| Chordin-like protein 1 | CRDL1 | Q9BU40 | 91851 | CHRDL1 | 3075 | 2.77E−05 | 0.00215929 | 1.30893719 |
| Roundabout homolog 2 | ROBO2 | Q9HCK4 | 6092 | ROBO2 | 2742 | 4.19E−05 | 0.00291545 | 1.38385912 |

TABLE 5-continued

Predictors of Fibrosis - NASH with advanced liver fibrosis versus NASH without advanced liver fibrosis

| Target Full Name | Target | UniProt | Entrez Gene ID | Entrez Gene Symbol | FREQ | p-value | BH p | FC (AN/NN) |
|---|---|---|---|---|---|---|---|---|
| Tyrosine-protein kinase receptor Tie-1, soluble | sTie-1 | P35590 | 7075 | TIE1 | 2509 | 3.35E−05 | 0.00246022 | 1.30189313 |
| Prolactin | PRL | P01236 | 5617 | PRL | 2444 | 5.72E−05 | 0.00308218 | −1.166593 |
| Laminin | Laminin | P25391, P07942, P11047 | 284217 3912 3915 | LAMA1 LAMB1 LAMC1 | 2417 | 5.17E−05 | 0.00308218 | 1.45040966 |
| Interleukin-1 receptor-like 1 | IL-1 R4 | Q01638 | 9173 | IL1RL1 | 2385 | 5.83E−05 | 0.00308218 | 1.9626542 |
| Interferon gamma | IFN-g | P01579 | 3458 | IFNG | 2312 | 5.27E−05 | 0.00308218 | 1.26272952 |
| CD48 antigen | CD48 | P09326 | 962 | CD48 | 2289 | 7.62E−05 | 0.00323507 | 1.22379192 |
| C-type mannose receptor 2 | MRC2 | Q9UBG0 | 9902 | MRC2 | 2231 | 9.09E−05 | 0.00343222 | 1.36455692 |
| SLAM family member 5 | SLAF5 | Q9UIB8 | 8832 | CD84 | 2129 | 5.57E−05 | 0.00308218 | −1.1972678 |
| Semaphorin-6B | SEM6B | Q9H3T3 | 10501 | SEMA6B | 2091 | 6.48E−05 | 0.00317152 | 1.51371363 |
| Interleukin-6 receptor subunit alpha | IL-6 sRa | P08887 | 3570 | IL6R | 2083 | 6.40E−05 | 0.00317152 | 1.35297275 |
| Vitamin K-dependent protein C | Protein C | P04070 | 5624 | PROC | 2002 | 8.26E−05 | 0.00323507 | −1.257634 |
| Follistatin-related protein 3 | FSTL3 | O95633 | 10272 | FSTL3 | 1968 | 7.42E−05 | 0.00323507 | 1.49203357 |
| Interleukin-6 receptor subunit beta | gp130, soluble | P40189 | 3572 | IL6ST | 1959 | 7.82E−05 | 0.00323507 | 1.30912905 |
| ADP-ribosyl cyclase/cyclic ADP-ribose hydrolase 2 | BST1 | Q10588 | 683 | BST1 | 1918 | 5.25E−05 | 0.00308218 | 1.57553853 |
| Metalloproteinase inhibitor 2 | TIMP-2 | P16035 | 7077 | TIMP2 | 1855 | 8.28E−05 | 0.00323507 | 1.17546039 |
| Plexin-B2 | PLXB2 | O15031 | 23654 | PLXNB2 | 1839 | 7.64E−05 | 0.00323507 | 1.49049742 |
| Alpha-(1,3)-fucosyltransferase 5 | FUT5 | Q11128 | 2527 | FUT5 | 1686 | 0.00012511 | 0.0043526 | 1.54972281 |
| Angiopoietin-2 | Angiopoietin-2 | O15123 | 285 | ANGPT2 | 1536 | 0.00021395 | 0.00662421 | 1.41159473 |
| Macrophage colony-stimulating factor 1 receptor | M-CSF R | P07333 | 1436 | CSF1R | 1483 | 8.32E−05 | 0.00323507 | 1.63513674 |
| Spondin-1 | Spondin-1 | Q9HCB6 | 10418 | SPON1 | 1474 | 0.00010244 | 0.00376198 | 1.6524851 |
| Troponin T, cardiac muscle | Troponin T | P45379 | 7139 | TNNT2 | 1447 | 0.00015494 | 0.00512081 | −1.1975044 |
| Glypican-3 | Glypican 3 | P51654 | 2719 | GPC3 | 1421 | 0.00011158 | 0.0039869 | 1.50217941 |
| Interleukin-19 | IL-19 | Q9UHD0 | 29949 | IL19 | 1108 | 0.00021546 | 0.00662421 | 1.36208261 |
| Matrilin-2 | MATN2 | O00339 | 4147 | MATN2 | 982 | 0.00037514 | 0.01078121 | 1.19856929 |
| Biglycan | BGN | P21810 | 633 | BGN | 973 | 0.00015061 | 0.00510542 | 1.24537085 |
| Contactin-4 | Contactin-4 | Q8IWV2 | 152330 | CNTN4 | 872 | 1.70E−04 | 0.00548852 | 1.28198938 |
| Galectin-3-binding protein | LG3BP | Q08380 | 3959 | LGALS3BP | 868 | 0.00057022 | 0.0138173 | 1.70493865 |
| Neurogenic locus notch homolog protein 3 | Notch-3 | Q9UM47 | 4854 | NOTCH3 | 844 | 0.00034897 | 0.01048499 | 1.35341053 |
| Methionine aminopeptidase 1 | METAP1 | P53582 | 23173 | METAP1 | 748 | 0.0003971 | 0.01114856 | −1.4325311 |
| Death-associated protein kinase 2 | DAPK2 | Q9UIK4 | 23604 | DAPK2 | 719 | 0.00040479 | 0.01114856 | −1.1905103 |
| Neuronal cell adhesion molecule | Nr-CAM | Q92823 | 4897 | NRCAM | 649 | 5.14E−04 | 0.0135914 | 1.41807642 |
| Transgelin-2 | Transgelin-2 | P37802 | 8407 | TAGLN2 | 639 | 0.00036706 | 0.01078121 | −1.3420277 |
| cGMP-inhibited 3′,5′-cyclic phosphodiesterase A | PDE3A | Q14432 | 5139 | PDE3A | 638 | 0.0004302 | 0.01160674 | −1.1652086 |
| Transforming growth factor-beta-induced protein ig-h3 | BGH3 | Q15582 | 7045 | TGFBI | 538 | 0.0007221 | 0.01564934 | 1.34051628 |
| Insulin-like growth factor-binding protein 3 | IGFBP-3 | P17936 | 3486 | IGFBP3 | 526 | 0.00086749 | 0.0174876 | −1.3295389 |
| Dual specificity tyrosine-phosphorylation-regulated kinase 3 | DYRK3 | O43781 | 8444 | DYRK3 | 523 | 0.0005537 | 0.0138173 | −1.2085409 |
| Non-receptor tyrosine-protein kinase TYK2 | TYK2 | P29597 | 7297 | TYK2 | 497 | 0.00083529 | 0.01725402 | −1.1673508 |
| Neural cell adhesion molecule L1 | NCAM-L1 | P32004 | 3897 | L1CAM | 450 | 0.00147577 | 0.02379235 | 1.43452591 |

TABLE 5-continued

Predictors of Fibrosis - NASH with advanced liver fibrosis versus NASH without advanced liver fibrosis

| Target Full Name | Target | UniProt | Entrez Gene ID | Entrez Gene Symbol | FREQ | p-value | BH p | FC (AN/NN) |
|---|---|---|---|---|---|---|---|---|
| Mothers against decapentaplegic homolog 2 | SMAD2 | Q15796 | 4087 | SMAD2 | 447 | 6.87E−04 | 0.01563644 | −1.5106892 |
| Plexin-C1 | PLXC1 | O60486 | 10154 | PLXNC1 | 439 | 0.00276405 | 0.03060633 | 1.22513301 |
| Leukemia inhibitory factor receptor | LIF sR | P42702 | 3977 | LIFR | 438 | 0.00057485 | 0.0138173 | 1.33348824 |
| Angiopoietin-1 receptor, soluble | sTie-2 | Q02763 | 7010 | TEK | 418 | 0.00063759 | 0.01505172 | 1.21454674 |
| Interferon regulatory factor 1 | IRF1 | P10914 | 3659 | IRF1 | 394 | 3.47E−03 | 0.03447254 | −1.1507322 |
| Mitogen-activated protein kinase kinase kinase 7:TGF-beta-activated kinase 1 and MAP3K7-binding protein 1 fusion | TAK1-TAB1 | O43318 Q15750 | 6885 10454 | MAP3K7 TAB1 | 388 | 0.00069387 | 0.01563644 | −1.1627976 |
| Ribosome maturation protein SBDS | SBDS | Q9Y3A5 | 51119 | SBDS | 363 | 0.00057225 | 0.0138173 | −1.2374064 |
| Cadherin-6 | Cadherin-6 | P55285 | 1004 | CDH6 | 351 | 0.33310803 | 0.55532007 | −1.1756748 |
| C-C motif chemokine 19 | MIP-3b | Q99731 | 6363 | CCL19 | 331 | 0.00076812 | 0.01637837 | 1.52266709 |
| EGF-containing fibulin-like extracellular matrix protein 1 | FBLN3 | Q12805 | 2202 | EFEMP1 | 326 | 0.00182086 | 0.02607714 | 1.21117549 |
| Netrin-1 | NET1 | O95631 | 9423 | NTN1 | 321 | 0.0019226 | 0.02647574 | 1.1812846 |
| Insulin receptor | IR | P06213 | 3643 | INSR | 318 | 0.00106512 | 0.01983232 | 1.44730968 |
| Tyrosine-protein kinase Fer | FER | P16591 | 2241 | FER | 313 | 0.00056278 | 0.0138173 | −1.9347712 |
| Junctional adhesion molecule B | JAM-B | P57087 | 58494 | JAM2 | 301 | 0.00137131 | 0.02345459 | −1.2061748 |
| Ephrin type-A receptor 1 | EphA1 | P21709 | 2041 | EPHA1 | 290 | 0.00122626 | 0.02171091 | −1.1398957 |
| A disintegrin and metalloproteinase with thrombospondin motifs 13 | ATS13 | Q76LX8 | 11093 | ADAMTS13 | 288 | 0.00070171 | 0.01563644 | 1.46563583 |
| Carboxypeptidase B2 | TAFI | Q96IY4 | 1361 | CPB2 | 281 | 0.00121272 | 0.02171091 | −1.1536384 |
| Testican-2 | Testican-2 | Q92563 | 9806 | SPOCK2 | 280 | 0.00172877 | 0.02539374 | 1.26490528 |
| CD166 antigen | ALCAM | Q13740 | 214 | ALCAM | 277 | 0.00070967 | 0.01563644 | 1.22306961 |
| Protein jagged-1 | JAG1 | P78504 | 182 | JAG1 | 275 | 0.00170274 | 0.02539374 | 1.10586606 |
| Lumican | Lumican | P51884 | 4060 | LUM | 268 | 0.00214523 | 0.02726916 | 1.2485412 |
| Protein SET | SET | Q01105 | 6418 | SET | 265 | 0.00254715 | 0.02902872 | −1.1711389 |
| Growth/differentiation factor 8 | Myostatin | O14793 | 2660 | MSTN | 261 | 0.00081949 | 0.01719623 | −1.1811786 |
| Granzyme A | granzyme A | P12544 | 3001 | GZMA | 255 | 0.00113551 | 0.02084929 | 1.25769195 |
| Abelson tyrosine-protein kinase 2 | ABL2 | P42684 | 27 | ABL2 | 245 | 0.00106248 | 0.01983232 | −1.1947117 |
| Inosine-5′-monophosphate dehydrogenase 2 | IMDH2 | P12268 | 3615 | IMPDH2 | 243 | 0.00087306 | 0.0174876 | −1.1263739 |
| Ubiquitin-fold modifier 1 | UFM1 | P61960 | 51569 | UFM1 | 237 | 0.00100709 | 0.01983232 | −1.4992519 |
| ATP-dependent RNA helicase DDX19B | DEAD-box protein 19B | Q9UMR2 | 11269 | DDX19B | 234 | 0.0018641 | 0.02621638 | −1.1999529 |
| Calpain I | Calpain I | P07384 P04632 | 823 826 | CAPN1 CAPNS1 | 230 | 0.00123171 | 0.02171091 | −1.0982339 |
| Desmoglein-2 | Desmoglein-2 | Q14126 | 1829 | DSG2 | 209 | 0.00183447 | 0.02607714 | 1.32559866 |
| Tumor necrosis factor receptor superfamily member 3 | Lymphotoxin b R | P36941 | 4055 | LTBR | 207 | 0.00106018 | 0.01983232 | −1.1243404 |
| Carbohydrate sulfotransferase 15 | ST4S6 | Q7LFX5 | 51363 | CHST15 | 206 | 0.00197485 | 0.02664032 | 1.29687756 |
| Kallikrein-12 | kallikrein 12 | Q9UKR0 | 43849 | KLK12 | 204 | 0.0026014 | 0.02914447 | −1.1612454 |
| Calcium/calmodulin-dependent protein kinase type 1 | CAMK1 | Q14012 | 8536 | CAMK1 | 204 | 0.00600638 | 0.04764928 | −1.1477111 |
| Tyrosine-protein kinase BTK | BTK | Q06187 | 695 | BTK | 190 | 0.00102245 | 0.01983232 | −1.6071013 |
| Stanniocalcin-1 | Stanniocalcin-1 | P52823 | 6781 | STC1 | 184 | 0.00415748 | 0.03831546 | 1.49830922 |

TABLE 5-continued

Predictors of Fibrosis - NASH with advanced liver fibrosis versus NASH without advanced liver fibrosis

| Target Full Name | Target | UniProt | Entrez Gene ID | Entrez Gene Symbol | FREQ | p-value | BH p | FC (AN/NN) |
|---|---|---|---|---|---|---|---|---|
| Tumor necrosis factor receptor superfamily member 11A | RANK | Q9Y6Q6 | 8792 | TNFRSF11A | 183 | 0.00212137 | 0.02722774 | −1.1412683 |
| Serine/threonine-protein kinase MRCK beta | MRCKB | Q9Y5S2 | 9578 | CDC42BPB | 178 | 0.00205168 | 0.02698895 | −1.1894352 |
| Small ubiquitin-related modifier 3 | SUMO3 | P55854 | 6613 | SUMO3 | 177 | 0.00143647 | 0.02373764 | −1.3243449 |
| OCIA domain-containing protein 1 | OCAD1 | Q9NX40 | 54940 | OCIAD1 | 177 | 0.00163264 | 0.02505797 | −1.1802382 |
| cAMP-specific 3',5'-cyclic phosphodiesterase 4D | PDE4D | Q08499 | 5144 | PDE4D | 176 | 0.00371623 | 0.03534431 | −1.0943653 |
| Receptor-type tyrosine-protein kinase FLT3 | Flt-3 | P36888 | 2322 | FLT3 | 163 | 0.0015383 | 0.02420991 | −1.170116 |
| Oncostatin-M | OSM | P13725 | 5008 | OSM | 163 | 0.00196283 | 0.02664032 | −1.1500906 |
| Ubiquitin-fold modifier-conjugating enzyme 1 | UFC1 | Q9Y3C8 | 51506 | UFC1 | 162 | 0.00243215 | 0.02896655 | −1.2264801 |
| Ficolin-2 | FCN2 | Q15485 | 2220 | FCN2 | 160 | 0.0023929 | 0.02896655 | −1.1260655 |
| Semaphorin-3E | Semaphorin 3E | O15041 | 9723 | SEMA3E | 160 | 0.00294221 | 0.03155875 | 1.39268349 |
| Insulin-like growth factor 1 receptor | IGF-I sR | P08069 | 3480 | IGF1R | 157 | 0.00533507 | 0.04463897 | 1.24112096 |
| 3-phosphoinositide-dependent protein kinase 1 | PDPK1 | O15530 | 5170 | PDPK1 | 156 | 0.00164905 | 0.02505797 | −1.5803285 |
| Arylsulfatase B | ARSB | P15848 | 411 | ARSB | 156 | 0.0025914 | 0.02914447 | −1.1695902 |
| Low affinity immunoglobulin epsilon Fc receptor | CD23 | P06734 | 2208 | FCER2 | 152 | 2.52E-03 | 2.90E-02 | 1.42807052 |
| Immunoglobulin A | IgA | P01876 P01877 | 3493 3494 | IGHA1 IGHA2 | 152 | 3.71E-03 | 0.03534431 | 1.54169693 |
| Carbonic anhydrase 13 | Carbonic anhydrase XIII | Q8N1Q1 | 377677 | CA13 | 143 | 0.00223184 | 0.0278749 | −2.016682 |
| Hexokinase-1 | HXK1 | P19367 | 3098 | HK1 | 140 | 0.002476 | 0.02896655 | −1.2253769 |
| Dual specificity protein phosphatase 3 | DUS3 | P51452 | 1845 | DUSP3 | 139 | 0.00170976 | 0.02539374 | −1.7551108 |
| Tyrosine-protein phosphatase non-receptor type 1 | PTP-1B | P18031 | 5770 | PTPN1 | 139 | 0.00296027 | 0.03155875 | −1.1728468 |
| Translationally-controlled tumor protein | TCTP | P13693 | 7178 | TPT1 | 132 | 0.00138877 | 0.02345459 | −1.5719152 |
| Cell adhesion molecule 3 | Nectin-like protein 1 | Q8N126 | 57863 | CADM3 | 132 | 0.00145936 | 0.02379235 | −1.1578146 |
| Ubiquitin-conjugating enzyme E2 G2 | UB2G2 | P60604 | 7327 | UBE2G2 | 132 | 0.00301115 | 0.03159317 | −1.1394347 |
| Tropomyosin alpha-4 chain | Tropomyosin 4 | P67936 | 7171 | TPM4 | 126 | 0.002984 | 0.03155875 | −1.6682352 |
| Acid sphingomyelinase-like phosphodiesterase 3a | ASM3A | Q92484 | 10924 | SMPDL3A | 123 | 0.00162981 | 0.02505797 | −1.1523182 |
| CD109 antigen | CD109 | Q6YHK3 | 135228 | CD109 | 120 | 0.00736151 | 0.0523904 | 1.20886755 |
| Appetite-regulating hormone | ghrelin | Q9UBU3 | 51738 | GHRL | 112 | 0.00250245 | 0.02896655 | −1.1180089 |
| Integrin alpha-I:beta-1 complex | Integrin a1b1 | P56199, P05556 | 3672 3688 | ITGA1 ITGB1 | 109 | 0.00180241 | 0.02607714 | 1.62845681 |
| Growth/differentiation factor 15 | MIC-1 | Q99988 | 9518 | GDF15 | 108 | 0.00200765 | 0.02680917 | 1.50554981 |
| Eukaryotic translation initiation factor 5A-1 | eIF-5A-1 | P63241 | 1984 | EIF5A | 107 | 0.00417354 | 0.03831546 | −1.1483579 |
| Dermatopontin | DERM | Q07507 | 1805 | DPT | 106 | 0.00714843 | 0.05221122 | 1.26301525 |
| Cadherin-15 | CAD15 | P55291 | 1013 | CDH15 | 104 | 0.0014016 | 0.02345459 | −1.1479781 |
| Eukaryotic translation initiation factor 4H | eIF-4H | Q15056 | 7458 | EIF4H | 103 | 0.00211822 | 0.02722774 | −1.5676585 |
| C-X-C motif chemokine 6 | GCP-2 | P80162 | 6372 | CXCL6 | 103 | 0.00225614 | 0.0278749 | 1.44692399 |

TABLE 5-continued

Predictors of Fibrosis - NASH with advanced liver fibrosis versus NASH without advanced liver fibrosis

| Target Full Name | Target | UniProt | Entrez Gene ID | Entrez Gene Symbol | FREQ | p-value | BH p | FC (AN/NN) |
|---|---|---|---|---|---|---|---|---|
| SLAM family member 7 | SLAF7 | Q9NQ25 | 57823 | SLAMF7 | 102 | 0.00129384 | 0.02250595 | 1.93390324 |
| SLIT and NTRK-like protein 1 | SLIK1 | Q96PX8 | 114798 | SLITRK1 | 101 | 0.00206194 | 0.02698895 | −1.1962088 |

The top 10 marker proteins for diagnosis of NASH with Advanced liver fibrosis were selected based on the frequency count and BH p-value including the top 1 down-regulated and top 9 upregulated proteins. The proteins are: E-selectin (SELE), Insulin-like growth factor-binding protein 7 (IGFBP7), Insulin-like growth factor-binding protein 5 (IGFBP-5), Thrombospondin-2 (TSP2), Complement component C7 (C7), Collectin-11 (COLEC11), Decorin (DCN), N-acetyl-D-glucosamine kinase (NAGK), C—C motif chemokine 21 (CCL21), and interleukin-1 receptor type 2 (IL1R2).

Subsequently, every possible combination of these 10 proteins was tested. A 5-fold cross validation was used with 100 splits for each combination of the Top 10 proteins, which resulted in 1,023 different markers with the calculated average accuracy, sensitivity and specificity linked to each marker. The best result was 99.5% average accuracy using three 5- or 6-protein signatures: (1). SELE, IGFBP7, NAGK, C7, and DCN; (2). SELE, IGFBP7, C7, IGFBP5, DCN, and IL1R2; (3). SELE, IGFBP7, NAGK, C7, IGFBP5, and DCN. However, even with combinations of 2 proteins more than 97% average accuracy was achieved and the 10-protein combination also achieved 95.2% average accuracy. A list of the top markers with higher than 77.3% average accuracy among the 1,023 protein sets (each average is based on 1,000 predictions) is shown in Table 6, below.

TABLE 6

Markers For NASH With Advanced liver fibrosis Versus NASH Without Advanced liver fibrosis Based On Average Accuracy, Sensitivity and Specificity

| | AvgAcc | AvgSen | AvgSpe |
|---|---|---|---|
| 1 Protein | | | |
| COLEC11 | 92.7 | 95.8 | 89.6 |
| SELE | 90.7 | 99.2 | 82.2 |
| IGFBP7 | 88.2 | 90 | 86.4 |
| THBS2 | 84.5 | 87.8 | 81.2 |
| C7 | 84 | 77 | 91 |
| IGFBP5 | 84 | 86.2 | 81.8 |
| DCN | 82.6 | 91 | 74.2 |
| NAGK | 80.1 | 87 | 73.2 |
| IL1R2 | 78.3 | 76.6 | 80 |
| CCL21 | 77.3 | 70 | 84.6 |
| 2 Proteins | | | |
| SELE IGFBP7 | 97.9 | 98.4 | 97.4 |
| SELE IGFBP5 | 96.9 | 95 | 98.8 |
| IGFBP7 IL1R2 | 96.2 | 94 | 98.4 |
| SELE C7 | 95.9 | 96.8 | 95 |
| SELE NAGK | 95.6 | 95.6 | 95.6 |
| IGFBP5 CCL21 | 95.3 | 92.6 | 98 |
| COLEC11 NAGK | 94.2 | 95.6 | 92.8 |
| THBS2 COLEC11 | 94.1 | 93.6 | 94.6 |
| IGFBP7 NAGK | 94.1 | 88.2 | 100 |
| SELE DCN | 94 | 100 | 88 |
| COLEC11 IGFBP5 | 94 | 93 | 95 |
| IGFBP7 IGFBP5 | 92.6 | 87.8 | 97.4 |
| IGFBP7 COLEC11 | 91.5 | 92.2 | 90.8 |
| IGFBP7 DCN | 91.3 | 91.8 | 90.8 |
| THBS2 NAGK | 90.7 | 88.6 | 92.8 |
| COLEC11 CCL21 | 90.6 | 94.4 | 86.8 |
| DCN IL1R2 | 90.5 | 90 | 91 |
| SELE THBS2 | 90.4 | 95.6 | 85.2 |
| SELE IL1R2 | 90.3 | 94.6 | 86 |
| COLEC11 DCN | 90.3 | 95.8 | 84.8 |
| NAGK CCL21 | 90.1 | 90 | 90.2 |
| IGFBP7 C7 | 90 | 89.6 | 90.4 |
| SELE COLEC11 | 89.9 | 96.4 | 83.4 |
| SELE CCL21 | 89.9 | 97.4 | 82.4 |
| COLEC11 C7 | 89.9 | 94 | 85.8 |
| THBS2 C7 | 89.8 | 90.2 | 89.4 |
| IGFBP5 DCN | 89.7 | 81.2 | 98.2 |

TABLE 6-continued

Markers For NASH With Advanced liver fibrosis
Versus NASH Without Advanced liver fibrosis
Based On Average Accuracy, Sensitivity and Specificity

|  | AvgAcc | AvgSen | AvgSpe |
|---|---|---|---|
| THBS2 IL1R2 | 89.3 | 89 | 89.6 |
| NAGK DCN | 89.1 | 88.6 | 89.6 |
| DCN CCL21 | 89.1 | 89.8 | 88.4 |
| THBS2 CCL21 | 88.8 | 93.2 | 84.4 |
| IGFBP7 CCL21 | 88.8 | 95 | 82.6 |
| C7 IGFBP5 | 88.5 | 92.2 | 84.8 |
| THBS2 IGFBP5 | 88.4 | 86.2 | 90.6 |
| THBS2 DCN | 87.6 | 95 | 80.2 |
| NAGK IL1R2 | 87.3 | 87.2 | 87.4 |
| NAGK C7 | 86.3 | 87.2 | 85.4 |
| C7 CCL21 | 86.1 | 84.4 | 87.8 |
| THBS2 IGFBP7 | 85.3 | 82.8 | 87.8 |
| COLEC11 IL1R2 | 85.2 | 87.6 | 82.8 |
| C7 DCN | 84.8 | 87 | 82.6 |
| IL1R2 CCL21 | 83.6 | 76.8 | 90.4 |
| IGFBP5 IL1R2 | 83.1 | 87.8 | 78.4 |
| C7 IL1R2 | 82 | 76 | 88 |
| NAGK IGFBP5 | 79.1 | 78.8 | 79.4 |
| 3 Proteins |  |  |  |
| SELE IGFBP7 C7 | 98 | 98.8 | 97.2 |
| SELE IGFBP7 IGFBP5 | 97.9 | 98.6 | 97.2 |
| SELE NAGK C7 | 97.8 | 95.6 | 100 |
| SELE IGFBP7 IL1R2 | 97.7 | 96.2 | 99.2 |
| SELE NAGK IL1R2 | 97.4 | 95.6 | 99.2 |
| SELE NAGK IGFBP5 | 97.1 | 95.2 | 99 |
| SELE C7 IGFBP5 | 96.9 | 95.8 | 98 |
| IGFBP7 IGFBP5 IL1R2 | 96.7 | 93.6 | 99.8 |
| SELE IGFBP7 NAGK | 96.6 | 93.8 | 99.4 |
| SELE C7 DCN | 96.5 | 100 | 93 |
| SELE IGFBP5 IL1R2 | 96.1 | 95 | 97.2 |
| THBS2 NAGK C7 | 96.1 | 95.2 | 97 |
| SELE COLEC11 NAGK | 96 | 95.6 | 96.4 |
| SELE NAGK DCN | 96 | 95 | 97 |
| IGFBP7 DCN IL1R2 | 96 | 94.4 | 97.6 |
| IGFBP5 DCN CCL21 | 95.8 | 96.6 | 95 |
| SELE IGFBP7 DCN | 95.6 | 96.2 | 95 |
| IGFBP5 IL1R2 CCL21 | 95.4 | 95 | 95.8 |
| THBS2 COLEC11 CCL21 | 95.3 | 96.2 | 94.4 |
| IGFBP7 NAGK C7 | 95.3 | 91.8 | 98.8 |
| IGFBP7 COLEC11 NAGK | 95 | 94.8 | 95.2 |
| COLEC11 NAGK C7 | 95 | 94.2 | 95.8 |
| COLEC11 NAGK IL1R2 | 95 | 95 | 95 |
| SELE NAGK CCL21 | 94.9 | 95.4 | 94.4 |
| SELE C7 IL1R2 | 94.9 | 95 | 94.8 |
| THBS2 COLEC11 NAGK | 94.9 | 94.4 | 95.4 |
| IGFBP7 IGFBP5 DCN | 94.7 | 92.4 | 97 |
| THBS2 COLEC11 DCN | 94.6 | 95 | 94.2 |
| IGFBP7 NAGK DCN | 94.5 | 90.4 | 98.6 |
| IGFBP7 NAGK CCL21 | 94.3 | 94 | 94.6 |
| IGFBP7 C7 IL1R2 | 94.2 | 91.4 | 97 |
| SELE COLEC11 C7 | 93.9 | 95.6 | 92.2 |
| THBS2 COLEC11 IL1R2 | 93.7 | 93.4 | 94 |
| COLEC11 NAGK IGFBP5 | 93.7 | 95.2 | 92.2 |
| IGFBP5 DCN IL1R2 | 93.7 | 91 | 96.4 |
| SELE THBS2 NAGK | 93.6 | 95.2 | 92 |
| SELE THBS2 IL1R2 | 93.6 | 95.6 | 91.6 |
| IGFBP7 IL1R2 CCL21 | 93.6 | 89.8 | 97.4 |
| SELE COLEC11 IGFBP5 | 93.5 | 97.2 | 89.8 |
| SELE THBS2 COLEC11 | 93.4 | 91.4 | 95.4 |
| SELE IGFBP5 CCL21 | 93.4 | 98.2 | 88.6 |
| SELE DCN IL1R2 | 93.4 | 99.4 | 87.4 |
| THBS2 COLEC11 IGFBP5 | 93.4 | 93.2 | 93.6 |
| COLEC11 NAGK DCN | 93.4 | 94.8 | 92 |
| SELE IGFBP5 DCN | 93.3 | 97.8 | 88.8 |
| SELE IGFBP7 CCL21 | 93.2 | 97.8 | 88.6 |
| IGFBP7 NAGK IGFBP5 | 93.2 | 86.6 | 99.8 |
| IGFBP7 COLEC11 IL1R2 | 93.1 | 91.2 | 95 |
| COLEC11 IGFBP5 DCN | 93.1 | 94.2 | 92 |
| SELE C7 CCL21 | 93 | 93.4 | 92.6 |
| SELE DCN CCL21 | 92.9 | 99.4 | 86.4 |
| THBS2 COLEC11 C7 | 92.9 | 91.8 | 94 |
| IGFBP7 C7 DCN | 92.9 | 90 | 95.8 |
| C7 DCN CCL21 | 92.9 | 94.6 | 91.2 |

TABLE 6-continued

Markers For NASH With Advanced liver fibrosis
Versus NASH Without Advanced liver fibrosis
Based On Average Accuracy, Sensitivity and Specificity

|  | AvgAcc | AvgSen | AvgSpe |
|---|---|---|---|
| SELE THBS2 CCL21 | 92.8 | 94.6 | 91 |
| NAGK DCN CCL21 | 92.8 | 95.4 | 90.2 |
| IGFBP7 COLEC11 IGFBP5 | 92.7 | 92.6 | 92.8 |
| COLEC11 DCN CCL21 | 92.7 | 94.4 | 91 |
| NAGK IGFBP5 IL1R2 | 92.7 | 93.4 | 92 |
| THBS2 NAGK CCL21 | 92.6 | 94.2 | 91 |
| SELE THBS2 C7 | 92.4 | 93.6 | 91.2 |
| IGFBP7 NAGK IL1R2 | 92.4 | 85.8 | 99 |
| COLEC11 C7 CCL21 | 92.4 | 94.4 | 90.4 |
| THBS2 C7 IL1R2 | 92.3 | 94 | 90.6 |
| COLEC11 NAGK CCL21 | 92.3 | 91.4 | 93.2 |
| NAGK IL1R2 CCL21 | 92.3 | 91.2 | 93.4 |
| THBS2 IL1R2 CCL21 | 92.2 | 94.4 | 90 |
| IGFBP7 COLEC11 DCN | 92.2 | 93.8 | 90.6 |
| IGFBP7 IGFBP5 CCL21 | 92.2 | 90.2 | 94.2 |
| THBS2 IGFBP7 COLEC11 | 92.1 | 91 | 93.2 |
| THBS2 NAGK IGFBP5 | 92.1 | 90.2 | 94 |
| THBS2 NAGK DCN | 92.1 | 92.4 | 91.8 |
| NAGK IGFBP5 CCL21 | 92.1 | 94.2 | 90 |
| C7 IGFBP5 DCN | 92 | 88.4 | 95.6 |
| SELE THBS2 DCN | 91.9 | 95.2 | 88.6 |
| SELE IGFBP7 COLEC11 | 91.9 | 97.4 | 86.4 |
| SELE IL1R2 CCL21 | 91.9 | 96.8 | 87 |
| IGFBP7 DCN CCL21 | 91.9 | 94.4 | 89.4 |
| SELE THBS2 IGFBP5 | 91.8 | 94.6 | 89 |
| THBS2 IGFBP5 IL1R2 | 91.8 | 91.8 | 91.8 |
| IGFBP7 COLEC11 CCL21 | 91.6 | 93 | 90.2 |
| COLEC11 IGFBP5 IL1R2 | 91.6 | 93 | 90.2 |
| SELE COLEC11 DCN | 91.5 | 98 | 85 |
| SELE COLEC11 CCL21 | 91.5 | 94.6 | 88.4 |
| NAGK C7 CCL21 | 91.4 | 89.8 | 93 |
| THBS2 DCN CCL21 | 91.2 | 93.6 | 88.8 |
| THBS2 C7 IGFBP5 | 91.1 | 91.8 | 90.4 |
| THBS2 IGFBP7 C7 | 91 | 91.6 | 90.4 |
| THBS2 IGFBP7 IL1R2 | 91 | 86.2 | 95.8 |
| THBS2 IGFBP7 CCL21 | 90.8 | 94.8 | 86.8 |
| NAGK IGFBP5 DCN | 90.8 | 89.6 | 92 |
| SELE THBS2 IGFBP7 | 90.7 | 92.2 | 89.2 |
| NAGK DCN IL1R2 | 90.6 | 95.4 | 85.8 |
| THBS2 IGFBP7 NAGK | 90.5 | 88.2 | 92.8 |
| C7 DCN IL1R2 | 90.5 | 91.6 | 89.4 |
| THBS2 NAGK IL1R2 | 90.4 | 89.2 | 91.6 |
| THBS2 IGFBP5 CCL21 | 90.4 | 93.8 | 87 |
| IGFBP7 C7 IGFBP5 | 90.4 | 88.4 | 92.4 |
| SELE COLEC11 IL1R2 | 90.3 | 95.4 | 85.2 |
| THBS2 C7 CCL21 | 90.2 | 93.8 | 86.6 |
| THBS2 C7 DCN | 90.1 | 92 | 88.2 |
| NAGK C7 DCN | 90.1 | 94.4 | 85.8 |
| C7 IGFBP5 IL1R2 | 90 | 92 | 88 |
| DCN IL1R2 CCL21 | 90 | 90.2 | 89.8 |
| COLEC11 C7 DCN | 89.8 | 93.2 | 86.4 |
| COLEC11 IGFBP5 CCL21 | 89.8 | 91.6 | 88 |
| COLEC11 IL1R2 CCL21 | 89.7 | 91 | 88.4 |
| COLEC11 C7 IGFBP5 | 89.6 | 94 | 85.2 |
| COLEC11 DCN IL1R2 | 89.4 | 91.6 | 87.2 |
| IGFBP7 COLEC11 C7 | 89.3 | 92.2 | 86.4 |
| COLEC11 C7 IL1R2 | 89 | 93.6 | 84.4 |
| NAGK C7 IL1R2 | 89 | 91.4 | 86.6 |
| NAGK C7 IGFBP5 | 88.5 | 92.4 | 84.6 |
| THBS2 IGFBP7 DCN | 88 | 89.2 | 86.8 |
| THBS2 IGFBP5 DCN | 87.9 | 91.2 | 84.6 |
| C7 IL1R2 CCL21 | 87.6 | 86 | 89.2 |
| THBS2 DCN IL1R2 | 86.6 | 88.4 | 84.8 |
| C7 IGFBP5 CCL21 | 86.5 | 85.4 | 87.6 |
| IGFBP7 C7 CCL21 | 86.4 | 81.6 | 91.2 |
| THBS2 IGFBP7 IGFBP5 | 85.8 | 86.4 | 85.2 |
| 4 Proteins |  |  |  |
| SELE C7 IGFBP5 DCN | 98.9 | 98.8 | 99 |
| SELE NAGK C7 DCN | 98.9 | 98.4 | 99.4 |
| SELE IGFBP7 C7 IL1R2 | 98.3 | 97.6 | 99 |
| SELE IGFBP7 IGFBP5 IL1R2 | 98.1 | 97.4 | 98.8 |
| SELE IGFBP7 C7 IGFBP5 | 98 | 96.4 | 99.6 |
| SELE NAGK IGFBP5 IL1R2 | 97.9 | 96 | 99.8 |

TABLE 6-continued

Markers For NASH With Advanced liver fibrosis
Versus NASH Without Advanced liver fibrosis
Based On Average Accuracy, Sensitivity and Specificity

|  | AvgAcc | AvgSen | AvgSpe |
|---|---|---|---|
| SELE NAGK C7 IL1R2 | 97.8 | 95.8 | 99.8 |
| SELE C7 DCN IL1R2 | 97.7 | 99.6 | 95.8 |
| SELE IGFBP7 NAGK C7 | 97.4 | 94.8 | 100 |
| SELE IGFBP7 IGFBP5 DCN | 97.3 | 98.8 | 95.8 |
| SELE IGFBP7 NAGK IL1R2 | 97.2 | 94.8 | 99.6 |
| SELE IGFBP7 NAGK IGFBP5 | 97.2 | 94.4 | 100 |
| SELE C7 IGFBP5 IL1R2 | 97.1 | 97 | 97.2 |
| SELE IGFBP5 DCN CCL21 | 96.9 | 98.8 | 95 |
| SELE NAGK C7 IGFBP5 | 96.9 | 93.8 | 100 |
| SELE IGFBP7 C7 DCN | 96.9 | 99.8 | 94 |
| IGFBP7 C7 DCN IL1R2 | 96.7 | 94 | 99.4 |
| SELE IGFBP7 COLEC11 IGFBP5 | 96.6 | 97.2 | 96 |
| NAGK DCN IL1R2 CCL21 | 96.4 | 96.8 | 96 |
| SELE IGFBP7 NAGK DCN | 96.4 | 94.2 | 98.6 |
| IGFBP7 NAGK IL1R2 CCL21 | 96.2 | 95.8 | 96.6 |
| IGFBP7 COLEC11 NAGK IL1R2 | 96.2 | 95.8 | 96.6 |
| THBS2 NAGK C7 IGFBP5 | 96.2 | 93.8 | 98.6 |
| SELE NAGK IL1R2 CCL21 | 96.1 | 95.6 | 96.6 |
| SELE NAGK IGFBP5 DCN | 96 | 92.8 | 99.2 |
| IGFBP7 IGFBP5 DCN IL1R2 | 95.9 | 91.8 | 100 |
| THBS2 NAGK C7 IL1R2 | 95.9 | 95.8 | 96 |
| THBS2 COLEC11 IGFBP5 CCL21 | 95.9 | 96 | 95.8 |
| THBS2 IGFBP7 COLEC11 NAGK | 95.9 | 95.6 | 96.2 |
| IGFBP7 DCN IL1R2 CCL21 | 95.8 | 96.4 | 95.2 |
| IGFBP7 NAGK DCN CCL21 | 95.8 | 97.2 | 94.4 |
| SELE IGFBP7 IGFBP5 CCL21 | 95.8 | 95.6 | 96 |
| SELE THBS2 NAGK IGFBP5 | 95.8 | 95.2 | 96.4 |
| SELE THBS2 COLEC11 CCL21 | 95.8 | 95.6 | 96 |
| IGFBP7 NAGK C7 DCN | 95.6 | 91.8 | 99.4 |
| SELE COLEC11 NAGK IGFBP5 | 95.6 | 95.4 | 95.8 |
| IGFBP7 NAGK IGFBP5 CCL21 | 95.4 | 96 | 94.8 |
| IGFBP7 NAGK IGFBP5 DCN | 95.4 | 91.6 | 99.2 |
| IGFBP7 NAGK C7 CCL21 | 95.3 | 94 | 96.6 |
| IGFBP7 NAGK C7 IGFBP5 | 95.3 | 95.6 | 95 |
| THBS2 COLEC11 NAGK C7 | 95.3 | 94.2 | 96.4 |
| SELE C7 DCN CCL21 | 95.3 | 97.4 | 93.2 |
| SELE THBS2 NAGK IL1R2 | 95.3 | 95.8 | 94.8 |
| IGFBP5 DCN IL1R2 CCL21 | 95.2 | 95.4 | 95 |
| THBS2 COLEC11 NAGK IGFBP5 | 95.2 | 95.8 | 94.6 |
| SELE IGFBP5 DCN IL1R2 | 95.2 | 97.4 | 93 |
| SELE NAGK IGFBP5 CCL21 | 95.2 | 94 | 96.4 |
| SELE IGFBP7 COLEC11 C7 | 95.2 | 95 | 95.4 |
| NAGK C7 DCN CCL21 | 95.1 | 95.8 | 94.4 |
| THBS2 COLEC11 C7 CCL21 | 95.1 | 95 | 95.2 |
| THBS2 COLEC11 NAGK IL1R2 | 95.1 | 96.4 | 93.8 |
| SELE C7 IGFBP5 CCL21 | 95.1 | 95.8 | 94.4 |
| IGFBP7 COLEC11 NAGK DCN | 95 | 94.8 | 95.2 |
| THBS2 IGFBP7 COLEC11 CCL21 | 95 | 95.6 | 94.4 |
| SELE THBS2 NAGK C7 | 95 | 94.2 | 95.8 |
| NAGK IGFBP5 IL1R2 CCL21 | 94.9 | 94.8 | 95 |
| THBS2 COLEC11 NAGK CCL21 | 94.9 | 94.2 | 95.6 |
| SELE IGFBP7 DCN CCL21 | 94.9 | 99.6 | 90.2 |
| SELE THBS2 COLEC11 IL1R2 | 94.9 | 95.8 | 94 |
| SELE IGFBP7 NAGK CCL21 | 94.8 | 94.6 | 95 |
| SELE THBS2 COLEC11 DCN | 94.8 | 94.4 | 95.2 |
| NAGK C7 IGFBP5 CCL21 | 94.7 | 94.6 | 94.8 |
| SELE NAGK DCN IL1R2 | 94.7 | 94.6 | 94.8 |
| SELE THBS2 COLEC11 NAGK | 94.7 | 94.2 | 95.2 |
| COLEC11 NAGK C7 IGFBP5 | 94.6 | 95.8 | 93.4 |
| THBS2 NAGK C7 DCN | 94.6 | 94.4 | 94.8 |
| SELE COLEC11 NAGK IL1R2 | 94.6 | 95.2 | 94 |
| SELE IGFBP7 C7 CCL21 | 94.6 | 95.8 | 93.4 |
| THBS2 COLEC11 IGFBP5 DCN | 94.5 | 96.2 | 92.8 |
| THBS2 COLEC11 C7 IL1R2 | 94.5 | 95 | 94 |
| SELE C7 IL1R2 CCL21 | 94.5 | 94.8 | 94.2 |
| SELE IGFBP7 COLEC11 DCN | 94.5 | 98.4 | 90.6 |
| SELE IGFBP7 COLEC11 NAGK | 94.5 | 95.2 | 93.8 |
| COLEC11 NAGK IGFBP5 IL1R2 | 94.4 | 94.4 | 94.4 |
| COLEC11 NAGK C7 IL1R2 | 94.4 | 93.6 | 95.2 |
| THBS2 COLEC11 IGFBP5 IL1R2 | 94.4 | 95.2 | 93.6 |
| SELE NAGK C7 CCL21 | 94.4 | 94.4 | 94.4 |
| SELE COLEC11 C7 IGFBP5 | 94.4 | 94.8 | 94 |
| SELE IGFBP7 DCN IL1R2 | 94.4 | 95.4 | 93.4 |
| IGFBP7 IGFBP5 IL1R2 CCL21 | 94.3 | 89.8 | 98.8 |

TABLE 6-continued

Markers For NASH With Advanced liver fibrosis
Versus NASH Without Advanced liver fibrosis
Based On Average Accuracy, Sensitivity and Specificity

| | AvgAcc | AvgSen | AvgSpe |
|---|---|---|---|
| IGFBP7 C7 IGFBP5 DCN | 94.3 | 91 | 97.6 |
| SELE COLEC11 NAGK C7 | 94.3 | 94.6 | 94 |
| SELE THBS2 COLEC11 C7 | 94.3 | 93.6 | 95 |
| NAGK C7 IL1R2 CCL21 | 94.2 | 94 | 94.4 |
| COLEC11 NAGK C7 DCN | 94.2 | 94 | 94.4 |
| IGFBP7 NAGK DCN IL1R2 | 94.2 | 90.2 | 98.2 |
| IGFBP7 COLEC11 NAGK C7 | 94.2 | 93.6 | 94.8 |
| THBS2 COLEC11 NAGK DCN | 94.2 | 95 | 93.4 |
| THBS2 IGFBP7 NAGK C7 | 94.2 | 92.6 | 95.8 |
| SELE COLEC11 IGFBP5 IL1R2 | 94.2 | 97 | 91.4 |
| SELE THBS2 COLEC11 IGFBP5 | 94.2 | 94.6 | 93.8 |
| COLEC11 NAGK DCN IL1R2 | 94.1 | 95.2 | 93 |
| SELE IGFBP7 IL1R2 CCL21 | 94.1 | 95.8 | 92.4 |
| SELE THBS2 IGFBP7 IGFBP5 | 94.1 | 94.6 | 93.6 |
| THBS2 COLEC11 IL1R2 CCL21 | 94 | 93.4 | 94.6 |
| THBS2 NAGK IL1R2 CCL21 | 93.9 | 94.4 | 93.4 |
| THBS2 NAGK IGFBP5 CCL21 | 93.9 | 95.4 | 92.4 |
| SELE COLEC11 C7 IL1R2 | 93.9 | 96.4 | 91.4 |
| SELE IGFBP7 COLEC11 CCL21 | 93.9 | 95 | 92.8 |
| IGFBP7 C7 IGFBP5 IL1R2 | 93.8 | 92.4 | 95.2 |
| IGFBP7 NAGK C7 IL1R2 | 93.8 | 92.6 | 95 |
| IGFBP7 COLEC11 NAGK IGFBP5 | 93.8 | 93.2 | 94.4 |
| SELE NAGK DCN CCL21 | 93.8 | 94.4 | 93.2 |
| SELE THBS2 NAGK DCN | 93.8 | 95.6 | 92 |
| SELE THBS2 IGFBP7 IL1R2 | 93.8 | 94.4 | 93.2 |
| SELE THBS2 C7 IL1R2 | 93.7 | 93.8 | 93.6 |
| SELE THBS2 C7 IGFBP5 | 93.7 | 94.2 | 93.2 |
| NAGK IGFBP5 DCN CCL21 | 93.6 | 97.2 | 90 |
| IGFBP7 COLEC11 DCN IL1R2 | 93.6 | 95 | 92.2 |
| THBS2 NAGK C7 CCL21 | 93.6 | 95 | 92.2 |
| THBS2 COLEC11 DCN CCL21 | 93.6 | 93.6 | 93.6 |
| THBS2 COLEC11 DCN IL1R2 | 93.6 | 94.2 | 93 |
| SELE THBS2 IGFBP5 IL1R2 | 93.6 | 94.4 | 92.8 |
| IGFBP7 COLEC11 NAGK CCL21 | 93.5 | 95.6 | 91.4 |
| THBS2 IGFBP7 COLEC11 DCN | 93.5 | 94.2 | 92.8 |
| THBS2 IGFBP7 COLEC11 IGFBP5 | 93.5 | 92.2 | 94.8 |
| SELE COLEC11 IL1R2 CCL21 | 93.5 | 95.6 | 91.4 |
| SELE COLEC11 IGFBP5 CCL21 | 93.5 | 95 | 92 |
| SELE THBS2 IGFBP5 DCN | 93.5 | 95.6 | 91.4 |
| SELE THBS2 IGFBP7 C7 | 93.5 | 92.6 | 94.4 |
| SELE THBS2 IGFBP7 NAGK | 93.5 | 95.6 | 91.4 |
| C7 IGFBP5 DCN CCL21 | 93.4 | 93.2 | 93.6 |
| COLEC11 NAGK C7 CCL21 | 93.4 | 94.4 | 92.4 |
| IGFBP7 COLEC11 IGFBP5 CCL21 | 93.4 | 94.6 | 92.2 |
| THBS2 IGFBP5 DCN CCL21 | 93.4 | 95 | 91.8 |
| THBS2 NAGK IGFBP5 DCN | 93.4 | 91.6 | 95.2 |
| SELE COLEC11 C7 CCL21 | 93.4 | 94.2 | 92.6 |
| COLEC11 NAGK IGFBP5 CCL21 | 93.3 | 94.2 | 92.4 |
| COLEC11 NAGK IGFBP5 DCN | 93.3 | 96.2 | 90.4 |
| THBS2 C7 IL1R2 CCL21 | 93.3 | 95.2 | 91.4 |
| THBS2 IGFBP7 COLEC11 IL1R2 | 93.3 | 92.6 | 94 |
| SELE DCN IL1R2 CCL21 | 93.3 | 99.4 | 87.2 |
| SELE THBS2 IGFBP7 COLEC11 | 93.3 | 92.4 | 94.2 |
| SELE COLEC11 IGFBP5 DCN | 93.2 | 95.6 | 90.8 |
| SELE THBS2 IGFBP7 DCN | 93.2 | 97 | 89.4 |
| THBS2 DCN IL1R2 CCL21 | 93.1 | 94.6 | 91.6 |
| THBS2 NAGK DCN CCL21 | 93.1 | 95.2 | 91 |
| SELE IGFBP5 IL1R2 CCL21 | 93.1 | 94 | 92.2 |
| IGFBP7 IGFBP5 DCN CCL21 | 93 | 90.8 | 95.2 |
| THBS2 IGFBP7 NAGK CCL21 | 93 | 95.2 | 90.8 |
| SELE COLEC11 C7 DCN | 93 | 94.8 | 91.2 |
| SELE COLEC11 NAGK CCL21 | 93 | 95.6 | 90.4 |
| SELE THBS2 C7 CCL21 | 93 | 95.8 | 90.2 |
| C7 IGFBP5 DCN IL1R2 | 92.9 | 92.4 | 93.4 |
| THBS2 C7 DCN CCL21 | 92.9 | 97.2 | 88.6 |
| THBS2 COLEC11 C7 IGFBP5 | 92.9 | 91.8 | 94 |
| THBS2 IGFBP7 COLEC11 C7 | 92.9 | 92.4 | 93.4 |
| SELE THBS2 DCN IL1R2 | 92.9 | 95 | 90.8 |
| IGFBP7 COLEC11 DCN CCL21 | 92.8 | 95.6 | 90 |
| THBS2 IGFBP7 IL1R2 CCL21 | 92.8 | 96.2 | 89.4 |
| SELE THBS2 IL1R2C CL21 | 92.8 | 95 | 90.6 |
| COLEC11 NAGK IL1R2 CCL21 | 92.7 | 93 | 92.4 |
| THBS2 IGFBP7 NAGK IGFBP5 | 92.7 | 90.6 | 94.8 |
| THBS2 IGFBP5 IL1R2 CCL21 | 92.6 | 95.4 | 89.8 |

TABLE 6-continued

Markers For NASH With Advanced liver fibrosis
Versus NASH Without Advanced liver fibrosis
Based On Average Accuracy, Sensitivity and Specificity

|  | AvgAcc | AvgSen | AvgSpe |
|---|---|---|---|
| SELE THBS2 NAGK CCL21 | 92.6 | 94.2 | 91 |
| THBS2 C7 IGFBP5 IL1R2 | 92.5 | 92.2 | 92.8 |
| THBS2 COLEC11 C7 DCN | 92.5 | 93.6 | 91.4 |
| THBS2 IGFBP7 NAGK DCN | 92.5 | 92.2 | 92.8 |
| NAGK IGFBP5 DCN IL1R2 | 92.4 | 95.2 | 89.6 |
| IGFBP7 COLEC11 IL1R2 CCL21 | 92.4 | 94.6 | 90.2 |
| COLEC11 IGFBP5 DCN CCL21 | 92.3 | 94.4 | 90.2 |
| THBS2 NAGK DCN IL1R2 | 92.3 | 91.6 | 93 |
| SELE IGFBP7 COLEC11 IL1R2 | 92.3 | 97.6 | 87 |
| THBS2 NAGK IGFBP5 IL1R2 | 92.2 | 90.6 | 93.8 |
| THBS2 C7 IGFBP5 CCL21 | 92.1 | 95.8 | 88.4 |
| SELE COLEC11 DCN CCL21 | 92.1 | 93.6 | 90.6 |
| SELE COLEC11 NAGK DCN | 92.1 | 93.2 | 91 |
| SELE THBS2 C7 DCN | 92.1 | 94.4 | 89.8 |
| NAGK C7 IGFBP5 DCN | 92 | 94.4 | 89.6 |
| IGFBP7 COLEC11 IGFBP5 IL1R2 | 92 | 88.2 | 95.8 |
| COLEC11 C7 DCN CCL21 | 91.9 | 94.4 | 89.4 |
| IGFBP7 C7 DCN CCL21 | 91.9 | 91.6 | 92.2 |
| SELE THBS2 IGFBP5 CCL21 | 91.9 | 95.4 | 88.4 |
| NAGK C7 IGFBP5 IL1R2 | 91.7 | 95.8 | 87.6 |
| COLEC11 IGFBP5 DCN IL1R2 | 91.7 | 94 | 89.4 |
| IGFBP7 COLEC11 C7 CCL21 | 91.7 | 94.4 | 89 |
| IGFBP7 NAGK IGFBP5 IL1R2 | 91.5 | 83.2 | 99.8 |
| THBS2 C7 IGFBP5 DCN | 91.5 | 92.8 | 90.2 |
| SELE THBS2 DCN CCL21 | 91.5 | 93.6 | 89.4 |
| COLEC11 DCN IL1R2 CCL21 | 91.4 | 94.8 | 88 |
| COLEC11 C7 IGFBP5 CCL21 | 91.4 | 92.4 | 90.4 |
| THBS2 IGFBP7 C7 IL1R2 | 91.4 | 90.4 | 92.4 |
| THBS2 IGFBP7 IGFBP5 IL1R2 | 91.3 | 88.2 | 94.4 |
| THBS2 IGFBP7 C7 IGFBP5 | 91.2 | 91.6 | 90.8 |
| SELE THBS2 IGFBP7 CCL21 | 91.1 | 94.8 | 87.4 |
| C7 DCN IL1R2 CCL21 | 91 | 91.8 | 90.2 |
| IGFBP7 COLEC11 C7 DCN | 91 | 93 | 89 |
| SELE COLEC11 DCN IL1R2 | 91 | 97 | 85 |
| IGFBP7 COLEC11 IGFBP5 DCN | 90.9 | 92.2 | 89.6 |
| THBS2 IGFBP7 DCN CCL21 | 90.8 | 94.6 | 87 |
| COLEC11 IGFBP5 IL1R2 CCL21 | 90.7 | 92.6 | 88.8 |
| COLEC11 NAGK DCN CCL21 | 90.5 | 92.8 | 88.2 |
| NAGKC7 DCN IL1R2 | 90.4 | 94.4 | 86.4 |
| IGFBP7 C7 IGFBP5 CCL21 | 90.4 | 87 | 93.8 |
| IGFBP7 COLEC11 C7 IL1R2 | 90.3 | 91.6 | 89 |
| C7 IGFBP5 IL1R2 CCL21 | 90.2 | 91.4 | 89 |
| THBS2 IGFBP7 NAGK IL1R2 | 90.2 | 89 | 91.4 |
| THBS2 IGFBP5 DCN IL1R2 | 90.1 | 87.6 | 92.6 |
| THBS2 IGFBP7 DCN IL1R2 | 90.1 | 90.2 | 90 |
| THBS2 IGFBP7 C7 DCN | 90 | 91 | 89 |
| IGFBP7 C7 IL1R2 CCL21 | 89.9 | 86 | 93.8 |
| COLEC11 C7 DCN IL1R2 | 89.8 | 94.2 | 85.4 |
| IGFBP7 COLEC11 C7 IGFBP5 | 89.8 | 92.6 | 87 |
| THBS2 IGFBP7 C7 CCL21 | 89.8 | 94.2 | 85.4 |
| COLEC11 C7 IGFBP5 IL1R2 | 89.6 | 94.4 | 84.8 |
| THBS2 IGFBP7 IGFBP5 CCL21 | 89.6 | 93.8 | 85.4 |
| COLEC11 C7 IGFBP5 DCN | 89.5 | 94 | 85 |
| THBS2 C7 DCN IL1R2 | 89.3 | 93.4 | 85.2 |
| COLEC11 C7 IL1R2 CCL21 | 89.1 | 92.6 | 85.6 |
| THBS2 IGFBP7 IGFBP5 DCN | 88.2 | 89.8 | 86.6 |
| 5 Proteins | | | |
| SELE IGFBP7 NAGK C7 DCN | 99.5 | 99.2 | 99.8 |
| SELE C7 IGFBP5 DCN IL1R2 | 99.3 | 99.6 | 99 |
| SELE IGFBP7 C7 IGFBP5 DCN | 99.2 | 99.6 | 98.8 |
| SELE IGFBP7 C7 DCN IL1R2 | 98.5 | 99.2 | 97.8 |
| SELE IGFBP7 NAGK IGFBP5 IL1R2 | 98 | 96 | 100 |
| SELE NAGK C7 DCN IL1R2 | 97.9 | 96.6 | 99.2 |
| SELE NAGK C7 IGFBP5 IL1R2 | 97.9 | 95.8 | 100 |
| SELE NAGK C7 IGFBP5 DCN | 97.9 | 95.8 | 100 |
| IGFBP7 NAGK C7 IGFBP5 DCN | 97.7 | 95.8 | 99.6 |
| SELE IGFBP7 NAGK C7 IGFBP5 | 97.7 | 95.4 | 100 |
| SELE IGFBP7 IGFBP5 DCN CCL21 | 97.5 | 99 | 96 |
| SELE IGFBP7 IGFBP5 DCN IL1R2 | 97.4 | 96.6 | 98.2 |
| SELE IGFBP7 NAGK IGFBP5 DCN | 97.4 | 95 | 99.8 |
| SELE IGFBP7 C7 IGFBP5 IL1R2 | 97.3 | 94.8 | 99.8 |
| IGFBP7 NAGK IGFBP5 DCN CCL21 | 97.2 | 97.4 | 97 |
| IGFBP7 NAGK C7 IGFBP5 CCL21 | 97 | 95 | 99 |

TABLE 6-continued

Markers For NASH With Advanced liver fibrosis
Versus NASH Without Advanced liver fibrosis
Based On Average Accuracy, Sensitivity and Specificity

|  | AvgAcc | AvgSen | AvgSpe |
|---|---|---|---|
| SELE NAGK IGFBP5 DCN IL1R2 | 96.9 | 94.6 | 99.2 |
| SELE IGFBP7 NAGK C7 IL1R2 | 96.9 | 93.8 | 100 |
| SELE NAGK C7 IGFBP5 CCL21 | 96.8 | 96 | 97.6 |
| SELE THBS2 NAGK C7 IGFBP5 | 96.8 | 96.4 | 97.2 |
| IGFBP7 NAGK C7 DCN IL1R2 | 96.7 | 94.8 | 98.6 |
| SELE IGFBP7 C7 DCN CCL21 | 96.7 | 99.8 | 93.6 |
| SELE THBS2 COLEC11 NAGK DCN | 96.6 | 97.2 | 96 |
| SELEC7 IGFBP5 DCN CCL21 | 96.5 | 98.6 | 94.4 |
| IGFBP7 NAGK IGFBP5 DCN IL1R2 | 96.4 | 92.8 | 100 |
| SELE IGFBP7 NAGK DCN IL1R2 | 96.4 | 94.8 | 98 |
| SELE THBS2 IGFBP7 NAGK IGFBP5 | 96.4 | 94 | 98.8 |
| SELE IGFBP7 DCN IL1R2 CCL21 | 96.3 | 98.8 | 93.8 |
| SELE IGFBP7 IGFBP5 IL1R2 CCL21 | 96.3 | 95 | 97.6 |
| SELE IGFBP7 NAGK IL1R2 CCL21 | 96.2 | 94 | 98.4 |
| SELE THBS2 COLEC11 IGFBP5 IL1R2 | 96.2 | 97.6 | 94.8 |
| THBS2 COLEC11 C7 IL1R2 CCL21 | 96.1 | 96 | 96.2 |
| SELE C7 DCN IL1R2 CCL21 | 96.1 | 98.6 | 93.6 |
| NAGK C7 IGFBP5 DCN CCL21 | 96 | 98 | 94 |
| SELE NAGK IGFBP5 IL1R2 CCL21 | 96 | 94.4 | 97.6 |
| THBS2 COLEC11 IGFBP5 IL1R2 CCL21 | 95.9 | 96.4 | 95.4 |
| SELE THBS2 NAGK IGFBP5 IL1R2 | 95.9 | 95 | 96.8 |
| SELE THBS2 IGFBP7 IGFBP5 IL1R2 | 95.9 | 95 | 96.8 |
| NAGK C7 DCN IL1R2 CCL21 | 95.8 | 97 | 94.6 |
| SELE IGFBP7 COLEC11 IGFBP5 IL1R2 | 95.8 | 97.6 | 94 |
| SELE THBS2 IGFBP7 C7 IL1R2 | 95.8 | 93.6 | 98 |
| IGFBP7 NAGK C7 IGFBP5 IL1R2 | 95.7 | 95 | 96.4 |
| THBS2 COLEC11 NAGK C7 IL1R2 | 95.7 | 96.6 | 94.8 |
| THBS2 COLEC11 NAGK C7 IGFBP5 | 95.6 | 95.6 | 95.6 |
| THBS2 IGFBP7 NAGK C7 DCN | 95.6 | 94.4 | 96.8 |
| SELE C7 IGFBP5 IL1R2 CCL21 | 95.6 | 95.8 | 95.4 |
| SELE COLEC11 NAGK IGFBP5 IL1R2 | 95.6 | 95.2 | 96 |
| SELE THBS2 NAGK C7 DCN | 95.6 | 95.6 | 95.6 |
| SELE THBS2 IGFBP7 NAGK IL1R2 | 95.6 | 95.2 | 96 |
| IGFBP7 C7 IGFBP5 DCN IL1R2 | 95.5 | 92.2 | 98.8 |
| IGFBP7 COLEC11 NAGK DCN IL1R2 | 95.5 | 94.4 | 96.6 |
| IGFBP7 COLEC11 NAGK IGFBP5 IL1R2 | 95.5 | 96.6 | 94.4 |
| THBS2 NAGK IGFBP5 DCN IL1R2 | 95.5 | 94 | 97 |
| THBS2 COLEC11 NAGK IL1R2 CCL21 | 95.5 | 95.4 | 95.6 |
| SELE IGFBP5 DCN IL1R2 CCL21 | 95.5 | 97.6 | 93.4 |
| SELE NAGK C7 IL1R2 CCL21 | 95.5 | 94.8 | 96.2 |
| SELE THBS2 NAGK C7 IL1R2 | 95.5 | 94.2 | 96.8 |
| THBS2 IGFBP7 COLEC11 IGFBP5 CCL21 | 95.4 | 95.2 | 95.6 |
| SELE IGFBP7 NAGK IGFBP5 CCL21 | 95.4 | 92.4 | 98.4 |
| SELE THBS2 C7 IGFBP5 IL1R2 | 95.4 | 94.4 | 96.4 |
| THBS2 NAGK C7 DCN IL1R2 | 95.3 | 94.4 | 96.2 |
| THBS2 NAGK C7 IGFBP5 IL1R2 | 95.3 | 93.6 | 97 |
| THBS2 COLEC11 NAGK IGFBP5 IL1R2 | 95.3 | 95.8 | 94.8 |
| THBS2 COLEC11 NAGK C7 CCL21 | 95.3 | 95.4 | 95.2 |
| SELE IGFBP7 C7 IL1R2 CCL21 | 95.3 | 95.8 | 94.8 |
| SELE IGFBP7 NAGK C7 CCL21 | 95.3 | 95.6 | 95 |
| SELE THBS2 COLEC11 IL1R2 CCL21 | 95.3 | 93.8 | 96.8 |
| SELE THBS2 COLEC11 IGFBP5 CCL21 | 95.3 | 94 | 96.6 |
| SELE THBS2 COLEC11 NAGK C7 | 95.3 | 95.4 | 95.2 |
| IGFBP7 NAGK C7 IL1R2 CCL21 | 95.2 | 94 | 96.4 |
| THBS2 COLEC11 C7 DCN CCL21 | 95.2 | 96.6 | 93.8 |
| THBS2 COLEC11 NAGK C7 DCN | 95.2 | 96.6 | 93.8 |
| THBS2 IGFBP7 NAGK C7 IGFBP5 | 95.2 | 93.4 | 97 |
| SELE THBS2 COLEC11 NAGK CCL21 | 95.2 | 94.4 | 96 |
| SELE THBS2 IGFBP7 COLEC11 IL1R2 | 95.2 | 94.8 | 95.6 |
| NAGK IGFBP5 DCN IL1R2 CCL21 | 95.1 | 97.6 | 92.6 |
| IGFBP7 NAGK DCN IL1R2 CCL21 | 95.1 | 95.4 | 94.8 |
| IGFBP7 NAGK IGFBP5 IL1R2 CCL21 | 95.1 | 95.2 | 95 |
| IGFBP7 COLEC11 NAGK C7 IL1R2 | 95.1 | 95.2 | 95 |
| THBS2 COLEC11 IGFBP5 DCN CCL21 | 95.1 | 94.6 | 95.6 |
| SELE NAGK C7 DCN CCL21 | 95.1 | 97 | 93.2 |
| SELE IGFBP7 C7 IGFBP5 CCL21 | 95.1 | 94 | 96.2 |
| SELE THBS2 COLEC11 DCN CCL21 | 95.1 | 96 | 94.2 |
| IGFBP7 IGFBP5 DCN IL1R2 CCL21 | 95 | 93.4 | 96.6 |
| THBS2 IGFBP7 COLEC11 IL1R2 CCL21 | 95 | 94.2 | 95.8 |
| THBS2 IGFBP7 COLEC11 NAGK IL1R2 | 95 | 95.8 | 94.2 |
| THBS2 IGFBP7 COLEC11 NAGK C7 | 95 | 95.2 | 94.8 |
| SELE NAGK IGFBP5 DCN CCL21 | 95 | 92.4 | 97.6 |
| SELE IGFBP7 COLEC11 C7 CCL21 | 95 | 96.2 | 93.8 |
| SELE IGFBP7 COLEC11 NAGK C7 | 95 | 94.4 | 95.6 |

TABLE 6-continued

Markers For NASH With Advanced liver fibrosis
Versus NASH Without Advanced liver fibrosis
Based On Average Accuracy, Sensitivity and Specificity

|  | AvgAcc | AvgSen | AvgSpe |
|---|---|---|---|
| SELE THBS2 C7 IGFBP5 DCN | 95 | 95.4 | 94.6 |
| SELE THBS2 COLEC11 IGFBP5 DCN | 95 | 94.4 | 95.6 |
| THBS2 COLEC11 C7 IGFBP5 IL1R2 | 94.9 | 94.8 | 95 |
| THBS2 COLEC11 NAGK DCN IL1R2 | 94.9 | 94.6 | 95.2 |
| SELE NAGK DCN IL1R2 CCL21 | 94.9 | 95 | 94.8 |
| SELE COLEC11 NAGK C7 IGFBP5 | 94.9 | 94.8 | 95 |
| SELE IGFBP7 COLEC11 NAGK IL1R2 | 94.9 | 96.2 | 93.6 |
| SELE THBS2 IGFBP7 COLEC11 CCL21 | 94.9 | 93.2 | 96.6 |
| C7 IGFBP5 DCN IL1R2 CCL21 | 94.8 | 95.8 | 93.8 |
| IGFBP7 NAGK C7 DCN CCL21 | 94.8 | 93 | 96.6 |
| IGFBP7 COLEC11 NAGK C7 CCL21 | 94.8 | 96 | 93.6 |
| THBS2 NAGK C7 IL1R2 CCL21 | 94.8 | 95.6 | 94 |
| THBS2 IGFBP7 COLEC11 NAGK CCL21 | 94.8 | 95.8 | 93.8 |
| SELE COLEC11 NAGK C7 IL1R2 | 94.8 | 96.4 | 93.2 |
| SELE THBS2 C7 DCN IL1R2 | 94.8 | 94.2 | 95.4 |
| SELE THBS2 IGFBP7 DCN IL1R2 | 94.8 | 95.4 | 94.2 |
| SELE THBS2 IGFBP7 IGFBP5 DCN | 94.8 | 97.2 | 92.4 |
| SELE THBS2 IGFBP7 NAGK C7 | 94.8 | 94.8 | 94.8 |
| SELE THBS2 IGFBP7 COLEC11 NAGK | 94.8 | 95.4 | 94.2 |
| IGFBP7 COLEC11 NAGK IGFBP5 DCN | 94.7 | 94.4 | 95 |
| THBS2 COLEC11 NAGK DCN CCL21 | 94.7 | 94.4 | 95 |
| THBS2 IGFBP7 NAGK C7 IL1R2 | 94.7 | 93.6 | 95.8 |
| THBS2 COLEC11 C7 IL1R2 | 94.7 | 94.8 | 94.6 |
| THBS2 IGFBP7 COLEC11 C7 DCN | 94.7 | 95.2 | 94.2 |
| SELE COLEC11 C7 IGFBP5 IL1R2 | 94.7 | 94.6 | 94.8 |
| SELE IGFBP7 COLEC11 IGFBP5 DCN | 94.7 | 95.6 | 93.8 |
| SELE IGFBP7 COLEC11 C7 IL1R2 | 94.7 | 95 | 94.4 |
| COLEC11 NAGK C7 DCN IL1R2 | 94.6 | 94 | 95.2 |
| IGFBP7 COLEC11 NAGK C7 IGFBP5 | 94.6 | 95.6 | 93.6 |
| THBS2 COLEC11 DCN IL1R2 CCL21 | 94.6 | 95.4 | 93.8 |
| THBS2 COLEC11 C7 DCN IL1R2 | 94.6 | 94.4 | 94.8 |
| THBS2 IGFBP7 C7 IL1R2 CCL21 | 94.6 | 95 | 94.2 |
| THBS2 IGFBP7 COLEC11 DCN CCL21 | 94.6 | 94.4 | 94.8 |
| THBS2 IGFBP7 COLEC11 NAGK DCN | 94.6 | 94.8 | 94.4 |
| SELE THBS2 COLEC11 C7 CCL21 | 94.6 | 94.6 | 94.6 |
| SELE THBS2 COLEC11 C7 IGFBP5 | 94.6 | 94.6 | 94.6 |
| SELE THBS2 COLEC11 NAGK IGFBP5 | 94.6 | 94.8 | 94.4 |
| SELE THBS2 IGFBP7 C7 IGFBP5 | 94.6 | 91.4 | 97.8 |
| THBS2 COLEC11 IGFBP5 DCN IL1R2 | 94.5 | 95.6 | 93.4 |
| SELE THBS2 COLEC11 DCN IL1R2 | 94.5 | 94.4 | 94.6 |
| COLEC11 NAGK C7 IGFBP5 DCN | 94.4 | 92.6 | 96.2 |
| IGFBP7 C7 IGFBP5 DCN CCL21 | 94.4 | 91.8 | 97 |
| THBS2 NAGK IGFBP5 IL1R2 CCL21 | 94.4 | 94 | 94.8 |
| THBS2 IGFBP7 NAGK C7 CCL21 | 94.4 | 94.4 | 94.4 |
| THBS2 IGFBP7 COLEC11 IGFBP5 IL1R2 | 94.4 | 92.4 | 96.4 |
| IGFBP7 COLEC11 IGFBP5 DCN CCL21 | 94.3 | 96 | 92.6 |
| IGFBP7 COLEC11 IGFBP5 DCN IL1R2 | 94.3 | 94.6 | 94 |
| THBS2 NAGK C7 IGFBP5 CCL21 | 94.3 | 93.6 | 95 |
| SELE IGFBP7 NAGK DCN CCL21 | 94.3 | 94.8 | 93.8 |
| SELE THBS2 COLEC11 C7 IL1R2 | 94.3 | 94.2 | 94.4 |
| SELE THBS2 IGFBP7 COLEC11 C7 | 94.3 | 92.6 | 96 |
| THBS2 IGFBP7 NAGK DCN CCL21 | 94.2 | 95.2 | 93.2 |
| THBS2 IGFBP7 COLEC11 DCN IL1R2 | 94.2 | 94.6 | 93.8 |
| SELE COLEC11 NAGK IGFBP5 CCL21 | 94.2 | 94.8 | 93.6 |
| SELE COLEC11 NAGK IGFBP5 DCN | 94.2 | 95 | 93.4 |
| SELE THBS2 COLEC11 NAGK IL1R2 | 94.2 | 95.4 | 93 |
| COLEC11 NAGK IGFBP5 DCN IL1R2 | 94.1 | 94.6 | 93.6 |
| THBS2 COLEC11 NAGK IGFBP5 DCN | 94.1 | 94.8 | 93.4 |
| THBS2 IGFBP7 COLEC11 IGFBP5 DCN | 94.1 | 93.4 | 94.8 |
| SELE COLEC11 NAGK C7 DCN | 94.1 | 94.2 | 94 |
| SELE IGFBP7 COLEC11 C7 DCN | 94.1 | 94.8 | 93.4 |
| SELE THBS2 NAGK IGFBP5 DCN | 94.1 | 94.2 | 94 |
| SELE COLEC11 C7 IGFBP5 CCL21 | 94 | 95.6 | 92.4 |
| SELE COLEC11 NAGK DCN IL1R2 | 94 | 94.8 | 93.2 |
| SELE IGFBP7 COLEC11 DCN IL1R2 | 94 | 98.6 | 89.4 |
| SELE THBS2 NAGK DCN IL1R2 | 94 | 96.2 | 91.8 |
| SELE THBS2 IGFBP7 IL1R2 CCL21 | 94 | 95.6 | 92.4 |
| COLEC11 NAGK IGFBP5 DCN CCL21 | 93.9 | 94.4 | 93.4 |
| THBS2 NAGK C7 IGFBP5 DCN | 93.9 | 91 | 96.8 |
| THBS2 COLEC11 C7 IGFBP5 CCL21 | 93.9 | 93.6 | 94.2 |
| THBS2 COLEC11 C7 IGFBP5 DCN | 93.9 | 95.2 | 92.6 |
| THBS2 IGFBP7 NAGK IL1R2 CCL21 | 93.9 | 94 | 93.8 |
| THBS2 IGFBP7 COLEC11 C7 CCL21 | 93.9 | 94.6 | 93.2 |
| SELE COLEC11 NAGK C7 CCL21 | 93.9 | 95.6 | 92.2 |

TABLE 6-continued

Markers For NASH With Advanced liver fibrosis
Versus NASH Without Advanced liver fibrosis
Based On Average Accuracy, Sensitivity and Specificity

|  | AvgAcc | AvgSen | AvgSpe |
|---|---|---|---|
| SELE THBS2 NAGK C7 CCL21 | 93.9 | 95.2 | 92.6 |
| SELE THBS2 IGFBP7 COLEC11 DCN | 93.9 | 93.2 | 94.6 |
| COLEC11 NAGK C7 IGFBP5 CCL21 | 93.8 | 94 | 93.6 |
| IGFBP7 COLEC11 NAGK C7 DCN | 93.8 | 94.8 | 92.8 |
| THBS2 C7 IGFBP5 DCN CCL21 | 93.8 | 96.2 | 91.4 |
| THBS2 COLEC11 NAGK IGFBP5 CCL21 | 93.8 | 94.2 | 93.4 |
| THBS2 IGFBP7 NAGK IGFBP5 CCL21 | 93.8 | 94.4 | 93.2 |
| THBS2 IGFBP7 COLEC11 C7 IGFBP5 | 93.8 | 93.6 | 94 |
| THBS2 IGFBP7 COLEC11 NAGK IGFBP5 | 93.8 | 94.2 | 93.4 |
| SELE COLEC11 IGFBP5 DCN IL1R2 | 93.8 | 96 | 91.6 |
| SELE THBS2 COLEC11 C7 DCN | 93.8 | 93.6 | 94 |
| SELE THBS2 IGFBP7 C7 DCN | 93.8 | 93.6 | 94 |
| NAGK C7 IGFBP5 IL1R2 CCL21 | 93.7 | 94.4 | 93 |
| IGFBP7 COLEC11 NAGK DCN CCL21 | 93.7 | 96 | 91.4 |
| SELE IGFBP7 COLEC11 NAGK IGFBP5 | 93.7 | 93.6 | 93.8 |
| SELE THBS2 IGFBP5 DCN IL1R2 | 93.7 | 96.2 | 91.2 |
| SELE IGFBP7 COLEC11 IGFBP5 CCL21 | 93.6 | 93.8 | 93.4 |
| SELE IGFBP7 COLEC11 C7 IGFBP5 | 93.6 | 94 | 93.2 |
| IGFBP7 COLEC11 NAGK IGFBP5 CCL21 | 93.5 | 95 | 92 |
| THBS2 IGFBP7 C7 DCN CCL21 | 93.5 | 94.6 | 92.4 |
| SELE COLEC11 IGFBP5 IL1R2 CCL21 | 93.5 | 95.4 | 91.6 |
| SELE THBS2 IGFBP7 IGFBP5 CCL21 | 93.5 | 96.4 | 90.6 |
| SELE IGFBP7 COLEC11 NAGK DCN | 93.4 | 94.8 | 92 |
| IGFBP7 C7 IGFBP5 IL1R2 CCL21 | 93.3 | 90.2 | 96.4 |
| THBS2 NAGK C7 DCN CCL21 | 93.3 | 94 | 92.6 |
| SELE COLEC11 IGFBP5 DCN CCL21 | 93.3 | 95.4 | 91.2 |
| SELE IGFBP7 COLEC11 NAGK CCL21 | 93.3 | 96.6 | 90 |
| SELE COLEC11 C7 DCN IL1R2 | 93.2 | 94.4 | 92 |
| SELE COLEC11 NAGK DCN CCL21 | 93.2 | 95 | 91.4 |
| SELE IGFBP7 COLEC11 DCN CCL21 | 93.2 | 95.2 | 91.2 |
| COLEC11 NAGK DCN IL1R2 CCL21 | 93.1 | 93.8 | 92.4 |
| IGFBP7 C7 DCN IL1R2 CCL21 | 93.1 | 90 | 96.2 |
| SELE THBS2 DCN IL1R2 CCL21 | 93.1 | 95.4 | 90.8 |
| COLEC11 NAGK C7 IGFBP5 IL1R2 | 93 | 94 | 92 |
| THBS2 IGFBP7 NAGK IGFBP5 DCN | 93 | 92.2 | 93.8 |
| SELE COLEC11 C7 IL1R2 CCL21 | 93 | 94.4 | 91.6 |
| SELE COLEC11 C7 IGFBP5 DCN | 93 | 93.6 | 92.4 |
| SELE COLEC11 NAGK IL1R2 CCL21 | 93 | 94.2 | 91.8 |
| THBS2 C7 IGFBP5 IL1R2 CCL21 | 92.9 | 94.2 | 91.6 |
| SELE COLEC11 C7 DCN CCL21 | 92.9 | 95.2 | 90.6 |
| SELE THBS2 NAGK DCN CCL21 | 92.9 | 95.6 | 90.2 |
| SELE THBS2 NAGK IL1R2 CCL21 | 92.8 | 94.6 | 91 |
| SELE THBS2 IGFBP7 DCN CCL21 | 92.8 | 93.6 | 92 |
| SELE THBS2 IGFBP7 C7 CCL21 | 92.8 | 95.4 | 90.2 |
| THBS2 NAGK DCN IL1R2 CCL21 | 92.7 | 93.8 | 91.6 |
| COLEC11 C7 IGFBP5 DCN CCL21 | 92.6 | 95.6 | 89.6 |
| SELE THBS2 IGFBP7 COLEC11 IGFBP5 | 92.6 | 90.8 | 94.4 |
| IGFBP7 COLEC11 NAGK IL1R2 CCL21 | 92.5 | 95.2 | 89.8 |
| COLEC11 NAGK C7 DCN CCL21 | 92.4 | 94.4 | 90.4 |
| IGFBP7 COLEC11 C7 DCN CCL21 | 92.4 | 94.4 | 90.4 |
| THBS2 C7 DCN IL1R2 CCL21 | 92.4 | 94.2 | 90.6 |
| THBS2 C7 IGFBP5 DCN IL1R2 | 92.4 | 95.6 | 89.2 |
| SELE THBS2 IGFBP7 NAGK DCN | 92.4 | 93.6 | 91.2 |
| NAGK C7 IGFBP5 DCN IL1R2 | 92.3 | 97.6 | 87 |
| IGFBP7 COLEC11 C7 IL1R2 CCL21 | 92.3 | 93.4 | 91.2 |
| THBS2 IGFBP5 DCN IL1R2 CCL21 | 92.3 | 95.4 | 89.2 |
| THBS2 IGFBP7 NAGK DCN IL1R2 | 92.3 | 91 | 93.6 |
| SELE COLEC11 DCN IL1R2 CCL21 | 92.3 | 95 | 89.6 |
| SELE THBS2C7 IL1R2 CCL21 | 92.3 | 94.4 | 90.2 |
| SELE THBS2 NAGK IGFBP5 CCL21 | 92.2 | 94.2 | 90.2 |
| IGFBP7 COLEC11 C7 DCN IL1R2 | 92.1 | 94.8 | 89.4 |
| IGFBP7 COLEC11 C7 IGFBP5 CCL21 | 92.1 | 94.4 | 89.8 |
| SELE IGFBP5 DCN CCL21 | 92.1 | 95.2 | 89 |
| THBS2 NAGK IGFBP5 DCN CCL21 | 92 | 94.6 | 89.4 |
| COLEC11 IGFBP5 DCN IL1R2 CCL21 | 91.9 | 95.2 | 88.6 |
| COLEC11 NAGK C7 IL1R2 CCL21 | 91.9 | 92.6 | 91.2 |
| THBS2 IGFBP7 DCN IL1R2 CCL21 | 91.9 | 94.2 | 89.6 |
| THBS2 IGFBP7 NAGK IGFBP5 IL1R2 | 91.9 | 90 | 93.8 |
| SELE IGFBP7 COLEC11 IL1R2 CCL21 | 91.9 | 94.4 | 89.4 |
| COLEC11 NAGK IGFBP5 IL1R2 CCL21 | 91.8 | 93.4 | 90.2 |
| THBS2 IGFBP7 C7 DCN IL1R2 | 91.8 | 90.8 | 92.8 |
| SELE THBS2 IGFBP7 NAGK CCL21 | 91.8 | 92.4 | 91.2 |
| COLEC11 C7 DCN IL1R2 CCL21 | 91.7 | 94.2 | 89.2 |
| SELE THBS2 IGFBP5 IL1R2 CCL21 | 91.7 | 94 | 89.4 |

TABLE 6-continued

Markers For NASH With Advanced liver fibrosis
Versus NASH Without Advanced liver fibrosis
Based On Average Accuracy, Sensitivity and Specificity

|  | AvgAcc | AvgSen | AvgSpe |
|---|---|---|---|
| THBS2 IGFBP7 IGFBP5 IL1R2 CCL21 | 91.6 | 93.4 | 89.8 |
| THBS2 IGFBP7 C7 IGFBP5 IL1R2 | 91.6 | 92 | 91.2 |
| SELE THBS2 C7 DCN CCL21 | 91.5 | 94.2 | 88.8 |
| SELE THBS2 C7 IGFBP5 CCL21 | 91.5 | 94 | 89 |
| IGFBP7 COLEC11 C7 IGFBP5 DCN | 91.4 | 94.8 | 88 |
| THBS2 IGFBP7 IGFBP5 DCN CCL21 | 91.3 | 95.4 | 87.2 |
| IGFBP7 COLEC11 IGFBP5 IL1R2 CCL21 | 91.2 | 93.6 | 88.8 |
| IGFBP7 COLEC11 DCN IL1R2 CCL21 | 91.1 | 93.4 | 88.8 |
| COLEC11 C7 IGFBP5 IL1R2 CCL21 | 90.9 | 94 | 87.8 |
| IGFBP7 COLEC11 C7 IGFBP5 IL1R2 | 90.9 | 92.4 | 89.4 |
| THBS2 IGFBP7 C7 IGFBP5 CCL21 | 90.8 | 94.4 | 87.2 |
| COLEC11 C7 IGFBP5 DCN IL1R2 | 90.7 | 94.8 | 86.6 |
| THBS2 IGFBP7 C7 IGFBP5 DCN | 90.6 | 91.4 | 89.8 |
| THBS2 IGFBP7 IGFBP5 DCN IL1R2 | 90.5 | 91.8 | 89.2 |
| 6 Proteins |  |  |  |
| SELE IGFBP7 C7 IGFBP5 DCN IL1R2 | 99.5 | 99.4 | 99.6 |
| SELE IGFBP7 NAGK C7 IGFBP5 DCN | 99.5 | 99 | 100 |
| SELE NAGK C7 DCN IL1R2 | 99 | 98 | 100 |
| SELE IGFBP7 NAGK IGFBP5 DCN IL1R2 | 98.1 | 96.2 | 100 |
| IGFBP7 NAGK C7 IGFBP5 DCN CCL21 | 97.9 | 97.2 | 98.6 |
| SELE IGFBP7 C7 IGFBP5 DCN CCL21 | 97.9 | 99.8 | 96 |
| SELE IGFBP7 C7 DCN IL1R2 CCL21 | 97.7 | 99.2 | 96.2 |
| SELE THBS2 IGFBP7 NAGK IGFBP5 IL1R2 | 97.7 | 96.6 | 98.8 |
| SELE IGFBP7 NAGK C7 IGFBP5 IL1R2 | 97.6 | 95.2 | 100 |
| SELE THBS2 IGFBP7 IGFBP5 DCN IL1R2 | 97.5 | 96.8 | 98.2 |
| SELE NAGK IGFBP5 DCN IL1R2 CCL21 | 97 | 96 | 98 |
| SELE NAGK C7 IGFBP5 DCN IL1R2 | 97 | 94.2 | 99.8 |
| SELE IGFBP7 IGFBP5 DCN IL1R2 CCL21 | 97 | 97.8 | 96.2 |
| SELE IGFBP7 NAGK IGFBP5 IL1R2 CCL21 | 96.9 | 94.4 | 99.4 |
| SELE THBS2 IGFBP7 NAGK C7 IL1R2 | 96.9 | 96.2 | 97.6 |
| THBS2 IGFBP7 NAGK C7 IGFBP5 IL1R2 | 96.8 | 96.4 | 97.2 |
| SELE THBS2 NAGK C7 IGFBP5 IL1R2 | 96.8 | 95.8 | 97.8 |
| IGFBP7 C7 IGFBP5 DCN IL1R2 CCL21 | 96.7 | 95.2 | 98.2 |
| IGFBP7 NAGK C7 IGFBP5 DCN IL1R2 | 96.7 | 94.4 | 99 |
| SELE IGFBP7 NAGK IGFBP5 DCN CCL21 | 96.5 | 95.8 | 97.2 |
| SELE C7 IGFBP5 DCN IL1R2 CCL21 | 96.4 | 97.2 | 95.6 |
| SELE NAGK C7 DCN IL1R2 CCL21 | 96.4 | 95.4 | 97.4 |
| SELE THBS2 C7 IGFBP5 DCN IL1R2 | 96.4 | 95.4 | 97.4 |
| SELE THBS2 NAGK C7 IGFBP5 DCN | 96.4 | 94.6 | 98.2 |
| SELE THBS2 IGFBP7 C7 IGFBP5 DCN | 96.4 | 97.2 | 95.6 |
| IGFBP7 NAGK IGFBP5 DCN IL1R2 CCL21 | 96.3 | 96 | 96.6 |
| SELE IGFBP7 COLEC11 IGFBP5 DCN IL1R2 | 96.2 | 98.6 | 93.8 |
| SELE IGFBP7 NAGK C7 DCN CCL21 | 96.1 | 98.2 | 94 |
| SELE THBS2 NAGK C7 DCN IL1R2 | 96.1 | 95 | 97.2 |
| SELE THBS2 IGFBP7 C7 IGFBP5 IL1R2 | 96.1 | 94.8 | 97.4 |
| SELE THBS2 IGFBP7 NAGK C7 DCN | 96.1 | 95.6 | 96.6 |
| SELE IGFBP7 NAGK DCN IL1R2 CCL21 | 96 | 94.8 | 97.2 |
| SELE THBS2 IGFBP7 NAGK C7 IGFBP5 | 96 | 93.8 | 98.2 |
| THBS2 NAGK C7 IGFBP5 IL1R2 CCL21 | 95.9 | 95 | 96.8 |
| THBS2 COLEC11 NAGK DCN IL1R2 CCL21 | 95.9 | 95 | 96.8 |
| THBS2 IGFBP7 NAGK C7 IL1R2 CCL21 | 95.9 | 96.6 | 95.2 |
| THBS2 IGFBP7 COLEC11 NAGK IL1R2 CCL21 | 95.9 | 95.6 | 96.2 |
| SELE NAGK C7 IGFBP5 DCN CCL21 | 95.9 | 95.6 | 96.2 |
| THBS2 IGFBP7 COLEC11 C7 IGFBP5 CCL21 | 95.8 | 95 | 96.6 |
| SELE THBS2 COLEC11 NAGK DCN IL1R2 | 95.8 | 96 | 95.6 |
| SELE THBS2 IGFBP7 NAGK IGFBP5 DCN | 95.8 | 95.6 | 96 |
| SELE THBS2 IGFBP7 COLEC11 NAGK IGFBP5 | 95.8 | 95.6 | 96 |
| IGFBP7 NAGK C7 IGFBP5 IL1R2 CCL21 | 95.7 | 92.8 | 98.6 |
| THBS2 COLEC11 IGFBP5 DCN IL1R2 CCL21 | 95.7 | 96 | 95.4 |
| SELE NAGK C7 IGFBP5 IL1R2 CCL21 | 95.7 | 95.6 | 95.8 |
| SELE IGFBP7 C7 IGFBP5 IL1R2 CCL21 | 95.7 | 95.6 | 95.8 |
| SELE IGFBP7 COLEC11 NAGK C7 IGFBP5 | 95.7 | 96 | 95.4 |
| IGFBP7 COLEC11 NAGK C7 IGFBP5 CCL21 | 95.6 | 95.2 | 96 |
| THBS2 IGFBP7 COLEC11 IGFBP5 DCN IL1R2 | 95.6 | 97 | 94.2 |
| SELE COLEC11 NAGK IGFBP5 DCN IL1R2 | 95.6 | 95.2 | 96 |
| SELE COLEC11 NAGK C7 IGFBP5 DCN | 95.6 | 96 | 95.2 |
| SELE THBS2 COLEC11 NAGK DCN CCL21 | 95.6 | 96.2 | 95 |
| SELE THBS2 IGFBP7 C7 DCN IL1R2 | 95.6 | 96 | 95.2 |
| SELE THBS2 COLEC11 NAGK C7 CCL21 | 95.5 | 94.4 | 96.6 |
| IGFBP7 COLEC11 NAGK IGFBP5 IL1R2 CCL21 | 95.4 | 96.4 | 94.4 |
| IGFBP7 COLEC11 NAGK C7 IL1R2 CCL21 | 95.4 | 97.2 | 93.6 |
| THBS2 COLEC11 C7 IGFBP5 DCN CCL21 | 95.4 | 95 | 95.8 |
| THBS2 IGFBP7 COLEC11 NAGK C7 IL1R2 | 95.4 | 95.4 | 95.4 |

TABLE 6-continued

Markers For NASH With Advanced liver fibrosis
Versus NASH Without Advanced liver fibrosis
Based On Average Accuracy, Sensitivity and Specificity

|  | AvgAcc | AvgSen | AvgSpe |
|---|---|---|---|
| SELE IGFBP7 NAGK C7 IGFBP5 CCL21 | 95.4 | 94.6 | 96.2 |
| SELE THBS2 COLEC11 NAGK IGFBP5 CCL21 | 95.4 | 96.8 | 94 |
| SELE THBS2 IGFBP7 COLEC11 C7 IGFBP5 | 95.4 | 95.2 | 95.6 |
| SELE THBS2 IGFBP7 COLEC11 NAGK DCN | 95.4 | 94.8 | 96 |
| THBS2 NAGK C7 IGFBP5 DCN IL1R2 | 95.3 | 94 | 96.6 |
| THBS2 IGFBP7 NAGK C7 IGFBP5 CCL21 | 95.3 | 94.6 | 96 |
| THBS2 IGFBP7 COLEC11 IGFBP5 IL1R2 CCL21 | 95.3 | 96.2 | 94.4 |
| THBS2 IGFBP7 COLEC11 NAGK DCN IL1R2 | 95.3 | 95.2 | 95.4 |
| SELE THBS2 NAGK IGFBP5 DCN IL1R2 | 95.3 | 94.8 | 95.8 |
| SELE THBS2 COLEC11 IGFBP5 IL1R2 CCL21 | 95.3 | 95 | 95.6 |
| SELE THBS2 COLEC11 IGFBP5 DCN CCL21 | 95.3 | 94.4 | 96.2 |
| SELE THBS2 COLEC11 C7 IGFBP5 CCL21 | 95.3 | 94.6 | 96 |
| SELE THBS2 COLEC11 C7 IGFBP5 IL1R2 | 95.3 | 95 | 95.6 |
| SELE THBS2 COLEC11 NAGK IL1R2 CCL21 | 95.3 | 95 | 95.6 |
| SELE THBS2 COLEC11 NAGK C7 DCN | 95.3 | 96.2 | 94.4 |
| SELE THBS2 COLEC11 NAGK C7 IGFBP5 | 95.3 | 95 | 95.6 |
| SELE THBS2 IGFBP7 COLEC11 C7 IL1R2 | 95.3 | 95.2 | 95.4 |
| THBS2 COLEC11 C7 IGFBP5 DCN IL1R2 | 95.2 | 94 | 96.4 |
| THBS2 IGFBP7 COLEC11 NAGK C7 CCL21 | 95.2 | 94.8 | 95.6 |
| SELE IGFBP7 COLEC11 NAGK IGFBP5 DCN | 95.2 | 95.2 | 95.2 |
| SELE IGFBP7 COLEC11 NAGK C7 DCN | 95.2 | 94.6 | 95.8 |
| SELE THBS2 IGFBP7 COLEC11 IL1R2 CCL21 | 95.2 | 95.2 | 95.2 |
| SELE THBS2 IGFBP7 COLEC11 DCN IL1R2 | 95.2 | 94.8 | 95.6 |
| SELE THBS2 IGFBP7 COLEC11 NAGK C7 | 95.2 | 95.8 | 94.6 |
| COLEC11 NAGK C7 IGFBP5 DCN IL1R2 | 95.1 | 94.6 | 95.6 |
| IGFBP7 COLEC11 NAGK C7 DCN IL1R2 | 95.1 | 95.4 | 94.8 |
| THBS2 IGFBP7 COLEC11 NAGK DCN CCL21 | 95.1 | 96 | 94.2 |
| THBS2 IGFBP7 COLEC11 NAGK C7 IGFBP5 | 95.1 | 94.8 | 95.4 |
| SELE IGFBP7 COLEC11 C7 IL1R2 CCL21 | 95.1 | 95.2 | 95 |
| SELE THBS2 COLEC11 DCN IL1R2 CCL21 | 95.1 | 95.4 | 94.8 |
| SELE THBS2 COLEC11 C7 DCN IL1R2 | 95.1 | 95 | 95.2 |
| SELE THBS2 COLEC11 NAGK IGFBP5 IL1R2 | 95.1 | 94.4 | 95.8 |
| SELE THBS2 COLEC11 NAGK IGFBP5 DCN | 95.1 | 94.4 | 95.8 |
| SELE THBS2 IGFBP7 NAGK DCN IL1R2 | 95.1 | 95.8 | 94.4 |
| NAGK C7 IGFBP5 DCN IL1R2 CCL21 | 95 | 96.6 | 93.4 |
| THBS2 COLEC11 NAGK C7 IGFBP5 DCN | 95 | 96.2 | 93.8 |
| THBS2 IGFBP7 COLEC11 C7 IGFBP5 DCN | 95 | 93.2 | 96.8 |
| SELE IGFBP7 COLEC11 IGFBP5 DCN CCL21 | 95 | 97 | 93 |
| IGFBP7 COLEC11 NAGK IGFBP5 DCN IL1R2 | 94.9 | 96 | 93.8 |
| THBS2 IGFBP7 NAGK C7 DCN IL1R2 | 94.9 | 93.4 | 96.4 |
| SELE THBS2 COLEC11 IGFBP5 DCN IL1R2 | 94.9 | 95.6 | 94.2 |
| SELE THBS2 IGFBP7 C7 IL1R2 CCL21 | 94.9 | 95.6 | 94.2 |
| SELE THBS2 IGFBP7 COLEC11 NAGK CCL21 | 94.9 | 94.6 | 95.2 |
| THBS2 COLEC11 C7 DCN IL1R2 CCL21 | 94.8 | 94.4 | 95.2 |
| THBS2 IGFBP7 COLEC11 DCN IL1R2 CCL21 | 94.8 | 94.6 | 95 |
| THBS2 IGFBP7 COLEC11 IGFBP5 DCN CCL21 | 94.8 | 94.6 | 95 |
| THBS2 IGFBP7 COLEC11 C7 IGFBP5 IL1R2 | 94.8 | 94.6 | 95 |
| THBS2 COLEC11 NAGK IGFBP5 DCN IL1R2 | 94.7 | 94.8 | 94.6 |
| THBS2 COLEC11 NAGK C7 IL1R2 CCL21 | 94.7 | 93.6 | 95.8 |
| THBS2 COLEC11 NAGK C7 IGFBP5 IL1R2 | 94.7 | 95.2 | 94.2 |
| THBS2 IGFBP7 COLEC11 NAGK IGFBP5 DCN | 94.7 | 95.4 | 94 |
| SELE COLEC11 C7 IGFBP5 DCN IL1R2 | 94.7 | 96.2 | 93.2 |
| SELE THBS2 NAGK C7 IL1R2 CCL21 | 94.7 | 96 | 93.4 |
| SELE THBS2 IGFBP7 COLEC11 DCN CCL21 | 94.7 | 94 | 95.4 |
| IGFBP7 NAGK C7 DCN IL1R2 CCL21 | 94.6 | 95 | 94.2 |
| THBS2 IGFBP7 COLEC11 C7 DCN CCL21 | 94.6 | 94.6 | 94.6 |
| SELE COLEC11 NAGK C7 DCN CCL21 | 94.6 | 96.4 | 92.8 |
| SELE THBS2 COLEC11 NAGK C7 IL1R2 | 94.6 | 94.2 | 95 |
| SELE THBS2 IGFBP7 COLEC11 IGFBP5 DCN | 94.6 | 94 | 95.2 |
| SELE THBS2 IGFBP7 COLEC11 NAGK IL1R2 | 94.6 | 93.8 | 95.4 |
| IGFBP7 COLEC11 NAGK C7 DCN CCL21 | 94.5 | 94.6 | 94.4 |
| IGFBP7 COLEC11 NAGK C7 IGFBP5 DCN | 94.5 | 94.4 | 94.6 |
| THBS2 IGFBP7 NAGK C7 DCN CCL21 | 94.5 | 94.4 | 94.6 |
| THBS2 IGFBP7 COLEC11 NAGK C7 DCN | 94.5 | 94.8 | 94.2 |
| THBS2 C7 IGFBP5 DCN IL1R2 CCL21 | 94.4 | 95.4 | 93.4 |
| THBS2 COLEC11 NAGK C7 IGFBP5 CCL21 | 94.4 | 94.8 | 94 |
| SELE IGFBP7 COLEC11 C7 IGFBP5 DCN | 94.4 | 93.8 | 95 |
| SELE IGFBP7 COLEC11 NAGK C7 IL1R2 | 94.4 | 93.4 | 95.4 |
| SELE THBS2 COLEC11 C7 IL1R2 CCL21 | 94.4 | 93.6 | 95.2 |
| SELE THBS2 IGFBP7 COLEC11 C7 DCN | 94.4 | 93.8 | 95 |
| IGFBP7 COLEC11 NAGK C7 IGFBP5 IL1R2 | 94.3 | 94.4 | 94.2 |
| THBS2 COLEC11 NAGK IGFBP5 IL1R2 CCL21 | 94.3 | 93.4 | 95.2 |
| THBS2 IGFBP7 C7 IGFBP5 IL1R2 CCL21 | 94.3 | 95.6 | 93 |
| THBS2 IGFBP7 NAGK IGFBP5 DCN IL1R2 | 94.3 | 94.4 | 94.2 |

TABLE 6-continued

Markers For NASH With Advanced liver fibrosis
Versus NASH Without Advanced liver fibrosis
Based On Average Accuracy, Sensitivity and Specificity

| | AvgAcc | AvgSen | AvgSpe |
|---|---|---|---|
| THBS2 IGFBP7 COLEC11 NAGK IGFBP5 CCL21 | 94.3 | 95.2 | 93.4 |
| SELE COLEC11 NAGK C7 IGFBP5 IL1R2 | 94.3 | 95 | 93.6 |
| SELE IGFBP7 NAGK C7 IL1R2 CCL21 | 94.3 | 93 | 95.6 |
| SELE IGFBP7 COLEC11 C7 DCN IL1R2 | 94.3 | 95 | 93.6 |
| SELE IGFBP7 COLEC11 C7 IGFBP5 CCL21 | 94.3 | 95.6 | 93 |
| SELE THBS2 NAGK DCN IL1R2 CCL21 | 94.3 | 96.2 | 92.4 |
| SELE THBS2 COLEC11 C7 DCN CCL21 | 94.3 | 94.2 | 94.4 |
| THBS2 NAGK C7 DCN IL1R2 CCL21 | 94.2 | 95.8 | 92.6 |
| THBS2 IGFBP7 C7 DCN IL1R2 CCL21 | 94.2 | 94.8 | 93.6 |
| THBS2 IGFBP7 COLEC11 NAGK IGFBP5 IL1R2 | 94.2 | 94.8 | 93.6 |
| SELE COLEC11 C7 IGFBP5 DCN CCL21 | 94.2 | 94.8 | 93.6 |
| SELE IGFBP7 COLEC11 NAGK DCN IL1R2 | 94.2 | 94.4 | 94 |
| COLEC11 NAGK C7 IGFBP5 IL1R2 CCL21 | 94.1 | 94.6 | 93.6 |
| THBS2 COLEC11 NAGK IGFBP5 DCN CCL21 | 94.1 | 93.6 | 94.6 |
| SELE COLEC11 NAGK IGFBP5 DCN CCL21 | 94.1 | 94.6 | 93.6 |
| SELE COLEC11 NAGK C7 IL1R2 CCL21 | 94.1 | 95 | 93.2 |
| SELE IGFBP7 COLEC11 NAGK IGFBP5 IL1R2 | 94.1 | 94 | 94.2 |
| SELE THBS2 NAGK IGFBP5 IL1R2 CCL21 | 94.1 | 95.8 | 92.4 |
| SELE THBS2 IGFBP7 IGFBP5 IL1R2 CCL21 | 94.1 | 96 | 92.2 |
| SELE THBS2 IGFBP7 COLEC11 IGFBP5 CCL21 | 94.1 | 93.2 | 95 |
| SELE THBS2 IGFBP7 COLEC11 C7 CCL21 | 94.1 | 93 | 95.2 |
| THBS2 COLEC11 C7 IGFBP5 IL1R2 CCL21 | 94 | 93.8 | 94.2 |
| THBS2 IGFBP7 NAGK IGFBP5 IL1R2 CCL21 | 94 | 94.2 | 93.8 |
| THBS2 IGFBP7 COLEC11 C7 IL1R2 CCL21 | 94 | 95.2 | 92.8 |
| SELE IGFBP7 COLEC11 C7 IGFBP5 IL1R2 | 94 | 94.6 | 93.4 |
| SELE THBS2 IGFBP7 C7 DCN CCL21 | 94 | 95.8 | 92.2 |
| THBS2 IGFBP7 NAGK C7 IGFBP5 DCN | 93.9 | 92.8 | 95 |
| THBS2 IGFBP7 COLEC11 C7 DCN IL1R2 | 93.9 | 93.6 | 94.2 |
| SELE THBS2 NAGK C7 IGFBP5 CCL21 | 93.9 | 95.6 | 92.2 |
| SELE THBS2 COLEC11 C7 IGFBP5 DCN | 93.9 | 93.6 | 94.2 |
| SELE THBS2 IGFBP7 NAGK C7 CCL21 | 93.9 | 95.8 | 92 |
| COLEC11 NAGK IGFBP5 DCN IL1R2 CCL21 | 93.8 | 94 | 93.6 |
| THBS2 NAGK C7 IGFBP5 DCN CCL21 | 93.8 | 95.4 | 92.2 |
| THBS2 COLEC11 NAGK C7 DCN CCL21 | 93.8 | 92.8 | 94.8 |
| SELE IGFBP7 COLEC11 NAGK IGFBP5 CCL21 | 93.7 | 94.4 | 93 |
| SELE COLEC11 IGFBP5 DCN IL1R2 CCL21 | 93.6 | 95 | 92.2 |
| SELE COLEC11 NAGK C7 IGFBP5 CCL21 | 93.6 | 93.8 | 93.4 |
| SELE IGFBP7 COLEC11 C7 DCN CCL21 | 93.6 | 93.8 | 93.4 |
| SELE THBS2 NAGK C7 DCN CCL21 | 93.6 | 95.4 | 91.8 |
| SELE THBS2 IGFBP7 NAGK IL1R2 CCL21 | 93.6 | 94 | 93.2 |
| IGFBP7 COLEC11 C7 DCN IL1R2 CCL21 | 93.5 | 93.8 | 93.2 |
| IGFBP7 COLEC11 C7 IGFBP5 IL1R2 CCL21 | 93.5 | 93.2 | 93.8 |
| SELE COLEC11 C7 IGFBP5 IL1R2 CCL21 | 93.5 | 94.6 | 92.4 |
| SELE COLEC11 NAGK C7 DCN IL1R2 | 93.5 | 94 | 93 |
| COLEC11 NAGK C7 IGFBP5 DCN CCL21 | 93.4 | 94.8 | 92 |
| THBS2 COLEC11 NAGK C7 DCN IL1R2 | 93.4 | 92.8 | 94 |
| SELE COLEC11 NAGK IGFBP5 IL1R2 CCL21 | 93.4 | 94 | 92.8 |
| SELE IGFBP7 COLEC11 IGFBP5 IL1R2 CCL21 | 93.4 | 96 | 90.8 |
| SELE THBS2 C7 DCN IL1R2 CCL21 | 93.4 | 96 | 90.8 |
| SELE THBS2 IGFBP7 COLEC11 IGFBP5 IL1R2 | 93.4 | 92.2 | 94.6 |
| IGFBP7 COLEC11 NAGK IGFBP5 DCN CCL21 | 93.3 | 93.8 | 92.8 |
| SELE COLEC11 NAGK DCN IL1R2 CCL21 | 93.3 | 94.2 | 92.4 |
| SELE IGFBP7 COLEC11 NAGK C7 CCL21 | 93.3 | 93.2 | 93.4 |
| THBS2 IGFBP7 NAGK IGFBP5 DCN CCL21 | 93.2 | 94.8 | 91.6 |
| SELE THBS2 IGFBP7 DCN IL1R2 CCL21 | 93.2 | 95.6 | 90.8 |
| COLEC11 NAGK C7 DCN IL1R2 CCL21 | 93.1 | 94.4 | 91.8 |
| IGFBP7 COLEC11 C7 IGFBP5 DCN CCL21 | 93 | 93.8 | 92.2 |
| THBS2 NAGK IGFBP5 DCN IL1R2 CCL21 | 93 | 94.2 | 91.8 |
| SELE THBS2 C7 IGFBP5 IL1R2 CCL21 | 93 | 94.6 | 91.4 |
| SELE THBS2 IGFBP7 IGFBP5 DCN CCL21 | 93 | 94.4 | 91.6 |
| SELE THBS2 IGFBP7 C7 IGFBP5 CCL21 | 92.8 | 93.6 | 92 |
| SELE THBS2 IGFBP7 NAGK DCN CCL21 | 92.8 | 94.2 | 91.4 |
| SELE IGFBP7 COLEC11 NAGK IL1R2 CCL21 | 92.7 | 95.2 | 90.2 |
| SELE COLEC11 C7 DCN IL1R2 CCL21 | 92.6 | 95 | 90.2 |
| SELE THBS2 IGFBP7 NAGK IGFBP5 CCL21 | 92.6 | 94.6 | 90.6 |
| IGFBP7 COLEC11 IGFBP5 DCN IL1R2 CCL21 | 92.5 | 94.8 | 90.2 |
| IGFBP7 COLEC11 NAGK DCN IL1R2 CCL21 | 92.5 | 95.6 | 89.4 |
| THBS2 IGFBP7 NAGK DCN IL1R2 CCL21 | 92.5 | 95 | 90 |
| SELE THBS2 IGFBP5 DCN IL1R2 CCL21 | 92.5 | 95 | 90 |
| SELE THBS2 C7 IGFBP5 DCN CCL21 | 92.4 | 93.8 | 91 |
| IGFBP7 COLEC11 C7 IGFBP5 DCN IL1R2 | 92 | 93 | 91 |
| SELE IGFBP7 COLEC11 DCN IL1R2 CCL21 | 92 | 95.2 | 88.8 |
| THBS2 IGFBP7 IGFBP5 DCN IL1R2 CCL21 | 91.9 | 95.2 | 88.6 |
| SELE IGFBP7 COLEC11 NAGK DCN CCL21 | 91.9 | 94 | 89.8 |

TABLE 6-continued

Markers For NASH With Advanced liver fibrosis
Versus NASH Without Advanced liver fibrosis
Based On Average Accuracy, Sensitivity and Specificity

|  | AvgAcc | AvgSen | AvgSpe |
|---|---|---|---|
| COLEC11 C7 IGFBP5 DCN IL1R2 CCL21 | 91.8 | 93 | 90.6 |
| THBS2 IGFBP7 C7 IGFBP5 DCN CCL21 | 91.8 | 93.8 | 89.8 |
| SELE THBS2 NAGK IGFBP5 DCN CCL21 | 91.1 | 94.2 | 88 |
| THBS2 IGFBP7 C7 IGFBP5 DCN IL1R2 | 90.1 | 90.2 | 90 |
| 7 Proteins | | | |
| SELE IGFBP7 NAGK C7 IGFBP5 DCN IL1R2 | 98.2 | 96.4 | 100 |
| SELE THBS2 NAGK C7 IGFBP5 DCN IL1R2 | 97.4 | 95.8 | 99 |
| SELE THBS2 IGFBP7 NAGK C7 IGFBP5 DCN | 97.2 | 96.4 | 98 |
| IGFBP7 NAGK C7 IGFBP5 DCN IL1R2 CCL21 | 97.1 | 96 | 98.2 |
| SELE IGFBP7 NAGK C7 DCN IL1R2 CCL21 | 97 | 99 | 95 |
| SELE IGFBP7 C7 IGFBP5 DCN IL1R2 CCL21 | 96.9 | 99.2 | 94.6 |
| SELE THBS2 IGFBP7 NAGK C7 IGFBP5 IL1R2 | 96.8 | 94.8 | 98.8 |
| SELE IGFBP7 NAGK C7 IGFBP5 DCN CCL21 | 96.6 | 97 | 96.2 |
| SELE THBS2 IGFBP7 COLEC11 NAGK IGFBP5 IL1R2 | 96.4 | 97 | 95.8 |
| SELE IGFBP7 NAGK IGFBP5 DCN IL1R2 CCL21 | 96.3 | 94.8 | 97.8 |
| SELE THBS2 IGFBP7 C7 IGFBP5 DCN IL1R2 | 96.3 | 96 | 96.6 |
| THBS2 IGFBP7 COLEC11 NAGK C7 IGFBP5 CCL21 | 96.2 | 94.8 | 97.6 |
| SELE IGFBP7 COLEC11 NAGK IGFBP5 DCN IL1R2 | 96.2 | 96.2 | 96.2 |
| SELE THBS2 IGFBP7 NAGK IGFBP5 DCN IL1R2 | 96.2 | 95.6 | 96.8 |
| THBS2 IGFBP7 COLEC11 C7 IGFBP5 IL1R2 CCL21 | 95.9 | 96.8 | 95 |
| SELE IGFBP7 COLEC11 NAGK C7 DCN IL1R2 | 95.9 | 95.8 | 96 |
| SELE IGFBP7 NAGK C7 IGFBP5 IL1R2 CCL21 | 95.8 | 94.4 | 97.2 |
| SELE THBS2 COLEC11 C7 IGFBP5 DCN CCL21 | 95.8 | 95.8 | 95.8 |
| SELE THBS2 IGFBP7 COLEC11 IGFBP5 IL1R2 CCL21 | 95.8 | 95.6 | 96 |
| SELE THBS2 IGFBP7 COLEC11 NAGK DCN IL1R2 | 95.8 | 95.2 | 96.4 |
| THBS2 IGFBP7 NAGK C7 IGFBP5 IL1R2 CCL21 | 95.7 | 95 | 96.4 |
| IGFBP7 COLEC11 NAGK C7 IGFBP5 IL1R2 CCL21 | 95.6 | 96.2 | 95 |
| SELE IGFBP7 COLEC11 DCN IL1R2 CCL21 | 95.6 | 95.6 | 95.6 |
| SELE THBS2 IGFBP7 COLEC11 NAGK IGFBP5 CCL21 | 95.6 | 95.6 | 95.6 |
| SELE THBS2 COLEC11 NAGK C7 IL1R2 | 95.6 | 95.8 | 95.4 |
| THBS2 COLEC11 NAGK C7 DCN IL1R2 CCL21 | 95.5 | 96 | 95 |
| SELE NAGK C7 IGFBP5 DCN IL1R2 CCL21 | 95.5 | 95.4 | 95.6 |
| SELE IGFBP7 COLEC11 NAGK C7 IGFBP5 DCN | 95.5 | 96 | 95 |
| SELE THBS2 COLEC11 NAGK C7 DCN IL1R2 | 95.5 | 94 | 97 |
| SELE THBS2 COLEC11 NAGK IL1R2 CCL21 | 95.4 | 95.2 | 95.6 |
| SELE THBS2 IGFBP7 COLEC11 NAGK C7 CCL21 | 95.4 | 96.2 | 94.6 |
| THBS2 COLEC11 NAGK IGFBP5 DCN IL1R2 CCL21 | 95.3 | 94.4 | 96.2 |
| SELE THBS2 NAGK C7 IGFBP5 IL1R2 CCL21 | 95.3 | 95.8 | 94.8 |
| SELE THBS2 COLEC11 NAGK DCN IL1R2 CCL21 | 95.3 | 95.4 | 95.2 |
| SELE THBS2 COLEC11 NAGK IGFBP5 DCN IL1R2 | 95.3 | 96.4 | 94.2 |
| SELE THBS2 COLEC11 NAGK C7 DCN CCL21 | 95.3 | 96 | 94.6 |
| SELE THBS2 COLEC11 NAGK C7 IGFBP5 CCL21 | 95.3 | 95.2 | 95.4 |
| SELE THBS2 IGFBP7 C7 IGFBP5 IL1R2 CCL21 | 95.3 | 96.2 | 94.4 |
| SELE THBS2 IGFBP7 NAGK C7 DCN IL1R2 | 95.3 | 94 | 96.6 |
| SELE THBS2 IGFBP7 COLEC11 C7 DCN CCL21 | 95.3 | 94.4 | 96.2 |
| SELE THBS2 IGFBP7 COLEC11 NAGK C7 DCN | 95.3 | 95.6 | 95 |
| IGFBP7 COLEC11 NAGK C7 IGFBP5 DCN IL1R2 | 95.2 | 94.6 | 95.8 |
| THBS2 IGFBP7 COLEC11 NAGK DCN IL1R2 CCL21 | 95.2 | 95.6 | 94.8 |
| SELE IGFBP7 COLEC11 C7 IGFBP5 DCN IL1R2 | 95.2 | 94.8 | 95.6 |
| SELE THBS2 COLEC11 NAGK C7 IGFBP5 DCN | 95.2 | 94.6 | 95.8 |
| SELE THBS2 IGFBP7 COLEC11 C7 IGFBP5 CCL21 | 95.2 | 95 | 95.4 |
| THBS2 IGFBP7 NAGK C7 DCN IL1R2 CCL21 | 95.1 | 95.2 | 95 |
| SELE THBS2 IGFBP7 COLEC11 NAGK C7 IGFBP5 | 95.1 | 96.4 | 93.8 |
| IGFBP7 COLEC11 NAGK C7 IGFBP5 DCN CCL21 | 95 | 95.6 | 94.4 |
| THBS2 IGFBP7 COLEC11 C7 DCN IL1R2 CCL21 | 95 | 95 | 95 |
| THBS2 IGFBP7 COLEC11 NAGK IGFBP5 DCN IL1R2 | 95 | 94.8 | 95.2 |
| THBS2 NAGK C7 IGFBP5 DCN IL1R2 CCL21 | 94.9 | 95.6 | 94.2 |
| SELE IGFBP7 COLEC11 C7 IGFBP5 IL1R2 CCL21 | 94.9 | 95.4 | 94.4 |
| SELE IGFBP7 COLEC11 NAGK IGFBP5 DCN CCL21 | 94.9 | 95 | 94.8 |
| SELE IGFBP7 COLEC11 C7 IGFBP5 IL1R2 | 94.9 | 94.4 | 95.4 |
| SELE THBS2 COLEC11 NAGK C7 IGFBP5 IL1R2 | 94.9 | 95 | 94.8 |
| THBS2 COLEC11 C7 IGFBP5 DCN IL1R2 CCL21 | 94.8 | 94.6 | 95 |
| THBS2 COLEC11 NAGK C7 IGFBP5 DCN CCL21 | 94.8 | 95.2 | 94.4 |
| SELE IGFBP7 COLEC11 NAGK C7 IGFBP5 CCL21 | 94.8 | 95.4 | 94.2 |
| SELE THBS2 COLEC11 IGFBP5 DCN IL1R2 CCL21 | 94.8 | 93.8 | 96.2 |
| SELE THBS2 IGFBP7 COLEC11 NAGK DCN CCL21 | 94.8 | 94.4 | 95.2 |
| SELE THBS2 IGFBP7 COLEC11 IGFBP5 DCN CCL21 | 94.7 | 95 | 94.4 |
| THBS2 IGFBP7 NAGK C7 IGFBP5 DCN CCL21 | 94.6 | 95.2 | 94 |
| THBS2 IGFBP7 COLEC11 NAGK C7 DCN CCL21 | 94.6 | 95.4 | 93.8 |
| THBS2 IGFBP7 COLEC11 NAGK C7 DCN IL1R2 | 94.6 | 93.6 | 95.6 |
| SELE THBS2 COLEC11 NAGK IGFBP5 IL1R2 CCL21 | 94.6 | 95 | 94.2 |
| SELE THBS2 IGFBP7 COLEC11 IGFBP5 DCN IL1R2 | 94.6 | 94.6 | 94.6 |
| SELE COLEC11 NAGK C7 IGFBP5 IL1R2 CCL21 | 94.5 | 96.4 | 92.6 |

TABLE 6-continued

Markers For NASH With Advanced liver fibrosis
Versus NASH Without Advanced liver fibrosis
Based On Average Accuracy, Sensitivity and Specificity

| | AvgAcc | AvgSen | AvgSpe |
|---|---|---|---|
| SELE THBS2 COLEC11 C7 DCN IL1R2 CCL21 | 94.5 | 96.2 | 92.8 |
| SELE THBS2 COLEC11 C7 IGFBP5 IL1R2 CCL21 | 94.5 | 95.2 | 93.8 |
| THBS2 IGFBP7 COLEC11 C7 IGFBP5 DCN CCL21 | 94.4 | 93.8 | 95 |
| THBS2 IGFBP7 COLEC11 NAGK C7 IGFBP5 IL1R2 | 94.4 | 94.6 | 94.2 |
| SELE COLEC11 NAGK C7 IGFBP5 DCN IL1R2 | 94.4 | 94.6 | 94.2 |
| SELE IGFBP7 COLEC11 C7 DCN IL1R2 CCL21 | 94.4 | 95.4 | 93.4 |
| SELE IGFBP7 COLEC11 NAGK C7 DCN CCL21 | 94.4 | 95.8 | 93 |
| IGFBP7 COLEC11 NAGK C7 DCN IL1R2 CCL21 | 94.3 | 95.4 | 93.2 |
| THBS2 COLEC11 NAGK C7 IGFBP5 DCN IL1R2 | 94.3 | 93.8 | 94.8 |
| THBS2 IGFBP7 COLEC11 NAGK C7 IL1R2 CCL21 | 94.3 | 93.4 | 95.2 |
| SELE THBS2 COLEC11 NAGK IGFBP5 DCN CCL21 | 94.3 | 94.6 | 94 |
| COLEC11 NAGK C7 IGFBP5 DCN IL1R2 CCL21 | 94.2 | 95.6 | 92.8 |
| SELE COLEC11 NAGK IGFBP5 DCN IL1R2 CCL21 | 94.2 | 95.4 | 93 |
| SELE THBS2 COLEC11 NAGK C7 IL1R2 CCL21 | 94.2 | 94.4 | 94 |
| THBS2 IGFBP7 COLEC11 IGFBP5 DCN IL1R2 CCL21 | 94.1 | 94.2 | 94 |
| THBS2 IGFBP7 COLEC11 NAGK IGFBP5 DCN CCL21 | 94.1 | 94.2 | 94 |
| THBS2 IGFBP7 COLEC11 NAGK C7 IGFBP5 DCN | 94.1 | 94.8 | 93.4 |
| SELE THBS2 IGFBP7 COLEC11 NAGK IGFBP5 DCN | 94.1 | 93.8 | 94.4 |
| IGFBP7 COLEC11 NAGK IGFBP5 DCN IL1R2 CCL21 | 94 | 94.6 | 93.4 |
| THBS2 IGFBP7 COLEC11 NAGK IGFBP5 IL1R2 CCL21 | 94 | 95 | 93 |
| SELE THBS2 NAGK IGFBP5 DCN IL1R2 CCL21 | 94 | 95.8 | 92.2 |
| SELE THBS2 NAGK C7 IGFBP5 DCN CCL21 | 94 | 95.6 | 92.4 |
| SELE THBS2 IGFBP7 NAGK C7 IGFBP5 CCL21 | 94 | 94.4 | 93.6 |
| SELE IGFBP7 COLEC11 NAGK C7 IL1R2 CCL21 | 93.9 | 95.4 | 92.4 |
| SELE THBS2 IGFBP7 COLEC11 C7 IL1R2 CCL21 | 93.9 | 93.8 | 94 |
| SELE THBS2 IGFBP7 COLEC11 C7 DCN IL1R2 | 93.9 | 93 | 94.8 |
| SELE THBS2 IGFBP7 COLEC11 C7 IGFBP5 DCN | 93.9 | 93.8 | 94 |
| THBS2 COLEC11 NAGK C7 IGFBP5 IL1R2 CCL21 | 93.8 | 92.8 | 94.8 |
| SELE COLEC11 NAGK C7 IGFBP5 DCN CCL21 | 93.8 | 95.2 | 92.4 |
| SELE IGFBP7 COLEC11 NAGK IGFBP5 IL1R2 CCL21 | 93.8 | 94.4 | 93.2 |
| SELE THBS2 COLEC11 C7 IGFBP5 IL1R2 | 93.8 | 91.4 | 96.2 |
| IGFBP7 COLEC11 C7 IGFBP5 DCN IL1R2 CCL21 | 93.7 | 95.2 | 92.2 |
| SELE THBS2 IGFBP7 NAGK DCN IL1R2 CCL21 | 93.7 | 95.4 | 92 |
| SELE IGFBP7 COLEC11 IGFBP5 DCN IL1R2 CCL21 | 93.6 | 95.6 | 91.6 |
| SELE IGFBP7 COLEC11 C7 IGFBP5 DCN CCL21 | 93.6 | 94 | 93.2 |
| SELE THBS2 IGFBP7 NAGK DCN CCL21 | 93.6 | 96 | 91.2 |
| SELE COLEC11 C7 IGFBP5 DCN IL1R2 CCL21 | 93.5 | 95.2 | 91.8 |
| THBS2 IGFBP7 NAGK C7 IGFBP5 DCN IL1R2 | 93.4 | 93 | 93.8 |
| SELE THBS2 COLEC11 C7 IGFBP5 DCN IL1R2 | 93.4 | 93 | 93.8 |
| SELE THBS2 IGFBP7 NAGK C7 IL1R2 CCL21 | 93.4 | 94.4 | 92.4 |
| THBS2 IGFBP7 COLEC11 C7 DCN IL1R2 CCL21 | 93.3 | 93.4 | 93.2 |
| THBS2 IGFBP7 C7 IGFBP5 DCN IL1R2 CCL21 | 93.2 | 95.2 | 91.2 |
| SELE THBS2 NAGK C7 DCN IL1R2 CCL21 | 93.2 | 94.6 | 91.8 |
| SELE THBS2 IGFBP7 NAGK IGFBP5 IL1R2 CCL21 | 92.9 | 95.8 | 90 |
| SELE THBS2 IGFBP7 NAGK IGFBP5 DCN CCL21 | 92.9 | 94.6 | 91.2 |
| SELE THBS2 IGFBP7 C7 DCN IL1R2 CCL21 | 92.8 | 94.8 | 90.8 |
| THBS2 IGFBP7 NAGK IGFBP5 DCN IL1R2 CCL21 | 92.7 | 94.6 | 90.8 |
| SELE THBS2 IGFBP7 IGFBP5 DCN IL1R2 CCL21 | 92.7 | 94.6 | 90.8 |
| SELE COLEC11 NAGK C7 DCN IL1R2 CCL21 | 92.6 | 94 | 91.2 |
| SELE THBS2 IGFBP7 C7 IGFBP5 DCN CCL21 | 92.4 | 94.2 | 90.6 |
| SELE THBS2 C7 IGFBP5 DCN IL1R2 CCL21 | 92.1 | 94.6 | 89.6 |
| SELE IGFBP7 COLEC11 NAGK DCN IL1R2 CCL21 | 91.4 | 94.2 | 88.6 |
| 8 Proteins | | | |
| SELE THBS2 IGFBP7 NAGK C7 IGFBP5 DCN IL1R2 | 96.1 | 95.8 | 96.4 |
| SELE THBS2 IGFBP7 COLEC11 C7 DCN IL1R2 CCL21 | 96.1 | 96.8 | 95.4 |
| SELE IGFBP7 NAGK C7 IGFBP5 DCN IL1R2 CCL21 | 96 | 95.4 | 96.6 |
| SELE THBS2 IGFBP7 COLEC11 NAGK IGFBP5 IL1R2 CCL21 | 95.9 | 95.2 | 96.6 |
| SELE THBS2 COLEC11 NAGK C7 DCN IL1R2 CCL21 | 95.7 | 96.2 | 95.2 |
| THBS2 IGFBP7 COLEC11 C7 IGFBP5 DCN IL1R2 CCL21 | 95.6 | 95.6 | 95.6 |
| SELE THBS2 IGFBP7 COLEC11 NAGK C7 IGFBP5 CCL21 | 95.5 | 95.8 | 95.2 |
| SELE THBS2 IGFBP7 COLEC11 IGFBP5 DCN IL1R2 CCL21 | 95.4 | 96.2 | 94.6 |
| SELE THBS2 IGFBP7 COLEC11 NAGK C7 IGFBP5 DCN | 95.4 | 95.6 | 95.2 |
| SELE THBS2 COLEC11 NAGK IGFBP5 DCN IL1R2 CCL21 | 95.3 | 95.4 | 95.2 |
| SELE THBS2 IGFBP7 COLEC11 NAGK IGFBP5 DCN IL1R2 | 95.3 | 95.2 | 95.4 |
| SELE THBS2 IGFBP7 COLEC11 NAGK C7 DCN IL1R2 | 95.3 | 94.4 | 96.2 |
| SELE THBS2 IGFBP7 COLEC11 NAGK C7 IGFBP5 IL1R2 | 95.3 | 95.8 | 94.8 |
| THBS2 IGFBP7 NAGK C7 IGFBP5 DCN IL1R2 CCL21 | 95.2 | 95 | 95.4 |
| SELE THBS2 IGFBP7 COLEC11 C7 IGFBP5 DCN IL1R2 | 95.2 | 95.6 | 94.8 |
| SELE THBS2 IGFBP7 COLEC11 NAGK IGFBP5 DCN CCL21 | 95.1 | 95.6 | 94.6 |
| THBS2 IGFBP7 COLEC11 NAGK C7 IGFBP5 DCN CCL21 | 95 | 95 | 95 |
| SELE THBS2 IGFBP7 COLEC11 C7 IGFBP5 DCN CCL21 | 95 | 94.6 | 95.4 |
| THBS2 COLEC11 NAGK C7 IGFBP5 DCN IL1R2 CCL21 | 94.9 | 96.6 | 93.2 |

TABLE 6-continued

Markers For NASH With Advanced liver fibrosis
Versus NASH Without Advanced liver fibrosis
Based On Average Accuracy, Sensitivity and Specificity

| | AvgAcc | AvgSen | AvgSpe |
|---|---|---|---|
| SELE IGFBP7 COLEC11 NAGK C7 IGFBP5 DCN IL1R2 | 94.9 | 94.6 | 95.2 |
| SELE THBS2 COLEC11 NAGK C7 IGFBP5 IL1R2 CCL21 | 94.9 | 95.2 | 94.6 |
| SELE THBS2 IGFBP7 C7 IGFBP5 DCN IL1R2 CCL21 | 94.9 | 96.2 | 93.6 |
| SELE THBS2 IGFBP7 NAGK C7 DCN IL1R2 CCL21 | 94.8 | 96 | 93.6 |
| SELE IGFBP7 COLEC11 NAGK IGFBP5 DCN IL1R2 CCL21 | 94.7 | 95.8 | 93.6 |
| SELE THBS2 COLEC11 C7 IGFBP5 DCN IL1R2 CCL21 | 94.7 | 94.4 | 95 |
| THBS2 IGFBP7 COLEC11 NAGK C7 IGFBP5 IL1R2 CCL21 | 94.6 | 94.8 | 94.4 |
| SELE IGFBP7 COLEC11 NAGK C7 IGFBP5 IL1R2 CCL21 | 94.6 | 94.6 | 94.6 |
| THBS2 IGFBP7 COLEC11 NAGK C7 IGFBP5 DCN IL1R2 | 94.5 | 93.8 | 95.2 |
| SELE THBS2 COLEC11 NAGK C7 IGFBP5 DCN CCL21 | 94.5 | 95 | 94 |
| SELE THBS2 IGFBP7 NAGK C7 IGFBP5 IL1R2 CCL21 | 94.5 | 94.6 | 94.4 |
| SELE THBS2 IGFBP7 COLEC11 C7 IGFBP5 IL1R2 CCL21 | 94.5 | 95 | 94 |
| SELE THBS2 IGFBP7 COLEC11 NAGK DCN IL1R2 CCL21 | 94.5 | 94.6 | 94.4 |
| SELE THBS2 IGFBP7 COLEC11 NAGK C7 DCN CCL21 | 94.4 | 95.4 | 93.4 |
| THBS2 IGFBP7 COLEC11 NAGK IGFBP5 DCN IL1R2 CCL21 | 94.3 | 95 | 93.6 |
| SELE IGFBP7 COLEC11 C7 IGFBP5 DCN IL1R2 CCL21 | 94.3 | 95.8 | 92.8 |
| IGFBP7 COLEC11 NAGK C7 IGFBP5 DCN IL1R2 CCL21 | 94.2 | 95.2 | 93.2 |
| SELE IGFBP7 COLEC11 NAGK C7 IGFBP5 DCN CCL21 | 94.2 | 96 | 92.4 |
| THBS2 IGFBP7 COLEC11 NAGK C7 DCN IL1R2 CCL21 | 94.1 | 94.6 | 93.6 |
| SELE IGFBP7 COLEC11 NAGK C7 DCN IL1R2 CCL21 | 94.1 | 96.2 | 92 |
| SELE THBS2 IGFBP7 COLEC11 NAGK C7 IL1R2 CCL21 | 94.1 | 93.6 | 94.6 |
| SELE COLEC11 NAGK C7 IGFBP5 DCN IL1R2 CCL21 | 93.9 | 95.4 | 92.4 |
| SELE THBS2 COLEC11 NAGK C7 IGFBP5 DCN IL1R2 | 93.9 | 94 | 93.8 |
| SELE THBS2 NAGK C7 IGFBP5 DCN IL1R2 CCL21 | 93.7 | 94.8 | 92.6 |
| SELE THBS2 IGFBP7 NAGK IGFBP5 DCN IL1R2 CCL21 | 93.5 | 95.8 | 91.2 |
| SELE THBS2 IGFBP7 NAGK C7 IGFBP5 DCN CCL21 | 93.5 | 94 | 93 |
| 9 Proteins | | | |
| SELE THBS2 IGFBP7 COLEC11 NAGK C7 IGFBP5 IL1R2 CCL21 | 95.8 | 96.2 | 95.4 |
| SELE THBS2 COLEC11 NAGK C7 IGFBP5 DCN IL1R2 CCL21 | 95.1 | 95.6 | 94.6 |
| THBS2 IGFBP7 COLEC11 NAGK C7 IGFBP5 DCN IL1R2 CCL21 | 95 | 94 | 96 |
| SELE THBS2 IGFBP7 COLEC11 NAGK C7 DCN IL1R2 CCL21 | 94.6 | 94.8 | 94.4 |
| SELE THBS2 IGFBP7 COLEC11 NAGK IGFBP5 DCN IL1R2 CCL21 | 94.6 | 93.6 | 95.6 |
| SELE THBS2 IGFBP7 COLEC11 NAGK C7 IGFBP5 DCN IL1R2 | 94.5 | 94.2 | 94.8 |
| SELE THBS2 IGFBP7 COLEC11 C7 IGFBP5 DCN IL1R2 CCL21 | 94.4 | 96 | 92.8 |
| SELE THBS2 IGFBP7 COLEC11 NAGK C7 IGFBP5 DCN CCL21 | 94.2 | 93.8 | 94.6 |
| SELE THBS2 IGFBP7 NAGK C7 IGFBP5 DCN IL1R2 CCL21 | 93.8 | 94.2 | 93.4 |
| SELE IGFBP7 COLEC11 NAGK C7 IGFBP5 DCN IL1R2 CCL21 | 93.7 | 94 | 93.4 |
| 10 Proteins | | | |
| SELE THBS2 IGFBP7 COLEC11 NAGK C7 IGFBP5 DCN IL1R2 CCL21 | 95.2 | 95.6 | 94.8 |

Example 4. ELISA Validation of SOMAscan-Identified Serum Protein Biomarkers for NASH and for Fibrosis ELISA were performed to confirm the differential expression of the serum protein biomarkers identified by SOMAscan as described above.

Four serum proteins were selected and have been confirmed by ELISA as potent biomarkers with the highest accuracy for discriminating between (1) NASH versus Simple Steatosis, (2) NASH without Advanced Fibrosis (F0-2) versus Simple Steatosis, and (3) NASH with Advanced Fibrosis (F3-4) versus NASH without Advanced Fibrosis (F0-2).

Figure 16:
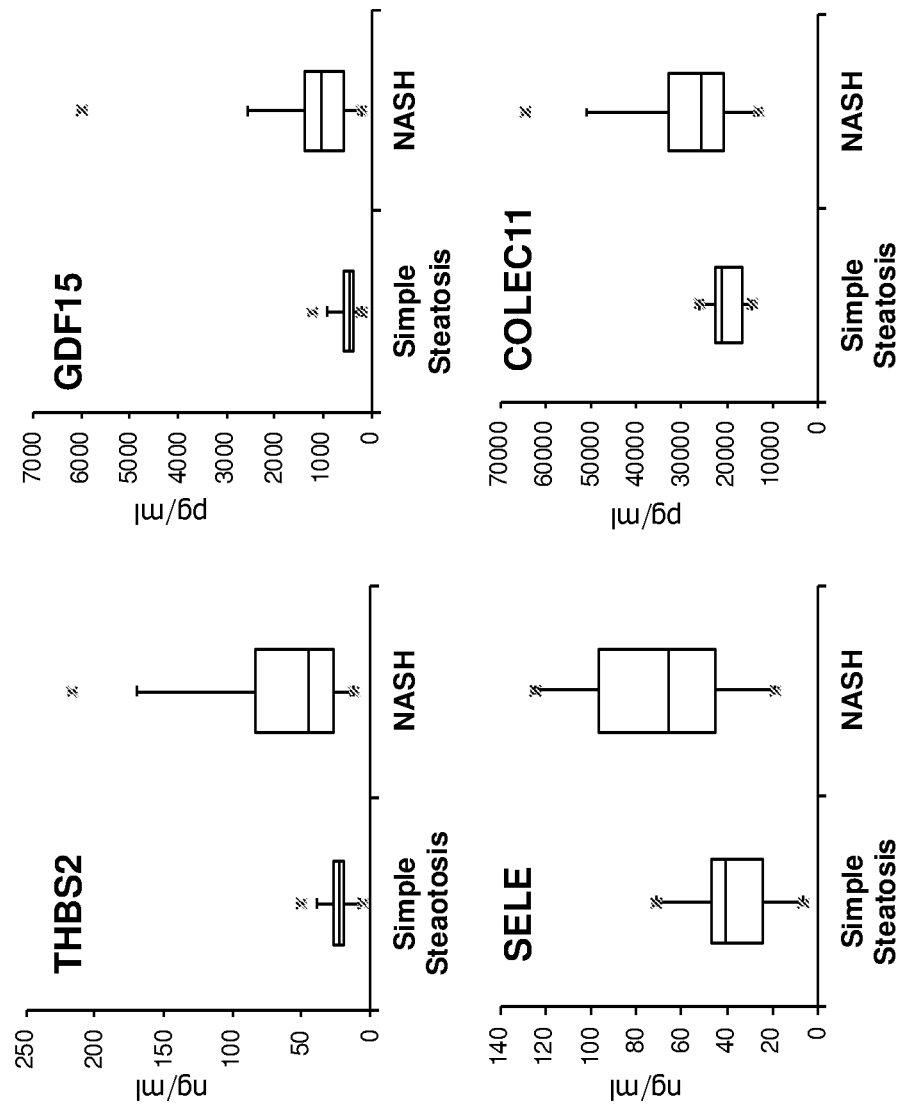
FIG. 16 is a combination of Box and Whisker plots depicting the median protein levels of four protein markers for NASH versus simple steatosis as determined by ELISA.

For this validation, expression levels of THBS2, GDF15, SELE, and COLEC11 from the same 60 samples that had been analyzed by SOMAscan, as described above, were determined by ELISA. As seen in FIG. 16, visualized by Box and Whisker Plots of median protein levels, each of these four proteins was significantly increased in NASH as compared to Simple Steatosis, confirming the SOMAscan data. This analysis confirms that each of these proteins is a NASH biomarker.

Figure 17:
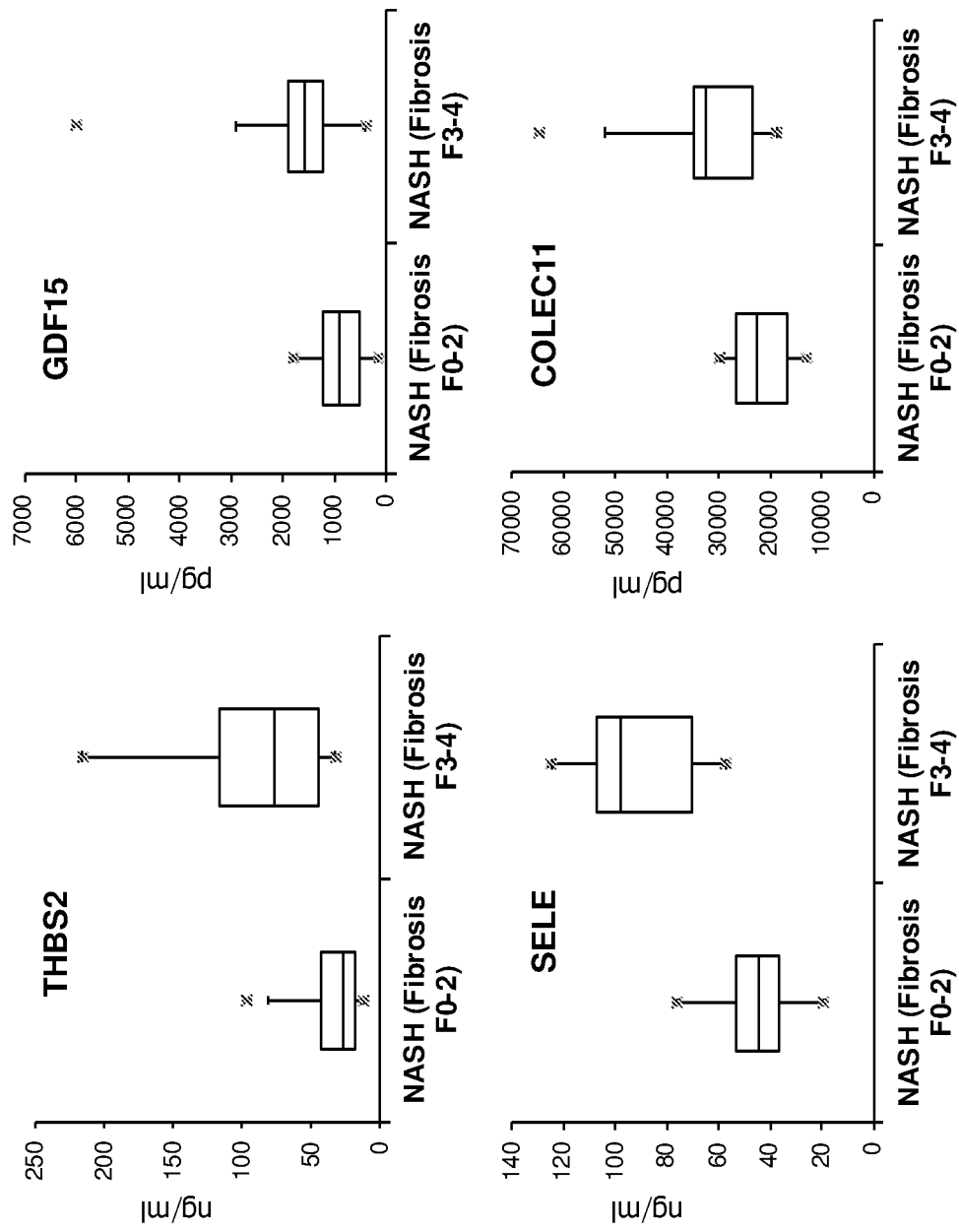
FIG. 17 is a combination of Box and Whisker plots depicting the median protein levels of four protein markers for NASH with advanced fibrosis (F3-4) versus NASH without advanced fibrosis (F0-2).

Similarly, comparison of NASH with Advanced Fibrosis (F3-4) to NASH without Advanced Fibrosis (F0-2) demonstrates that each of these four proteins was also increased significantly in NASH with Advanced Fibrosis (F3-4) versus NASH without Advanced Fibrosis (F0-2), as shown in FIG. 17. Thus, these four proteins are biomarkers for both NASH as well as for fibrosis stage.

Figure 18:
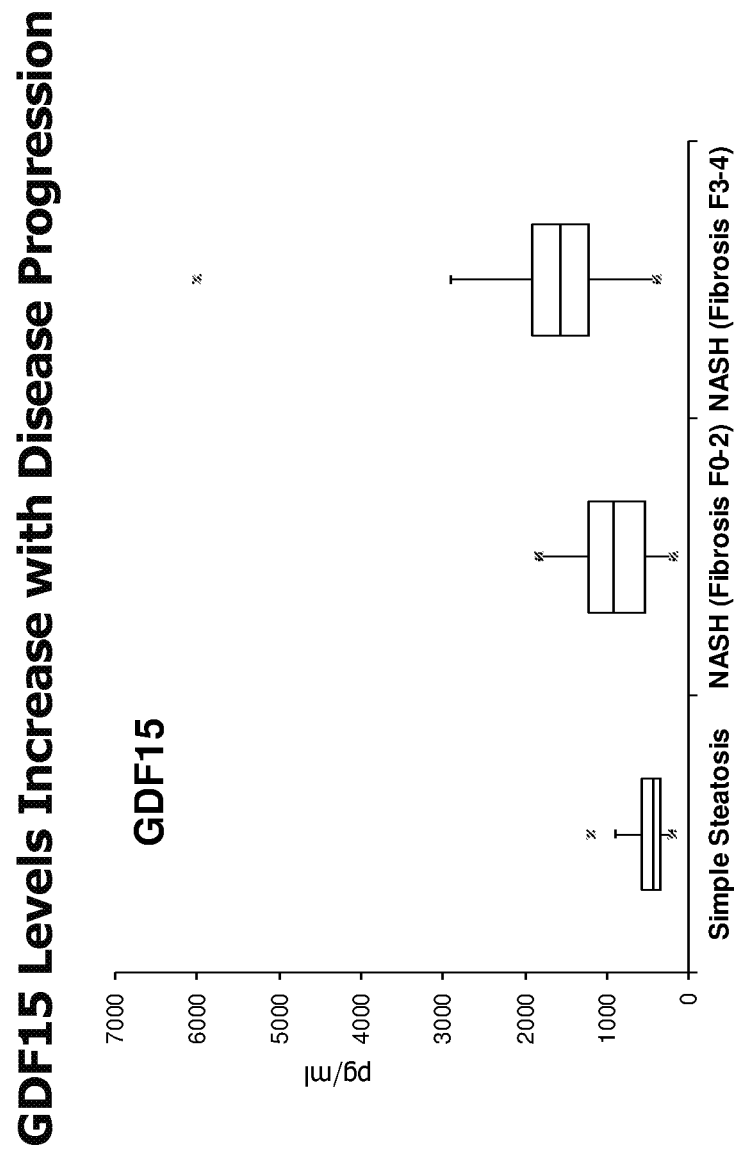
FIG. 18 is a Box and Whisker plot depicting an increasing level of GDF15 as determined by ELISA in samples of simple steatosis to NASH without advanced fibrosis and simple steatosis to NASH with advanced fibrosis.

To further highlight the rising levels of these biomarkers with disease progression, FIG. 18 demonstrates an increasing level of GDF15 from simple steatosis to NASH without advanced fibrosis and further to NASH with advanced fibrosis.

Figure 19:
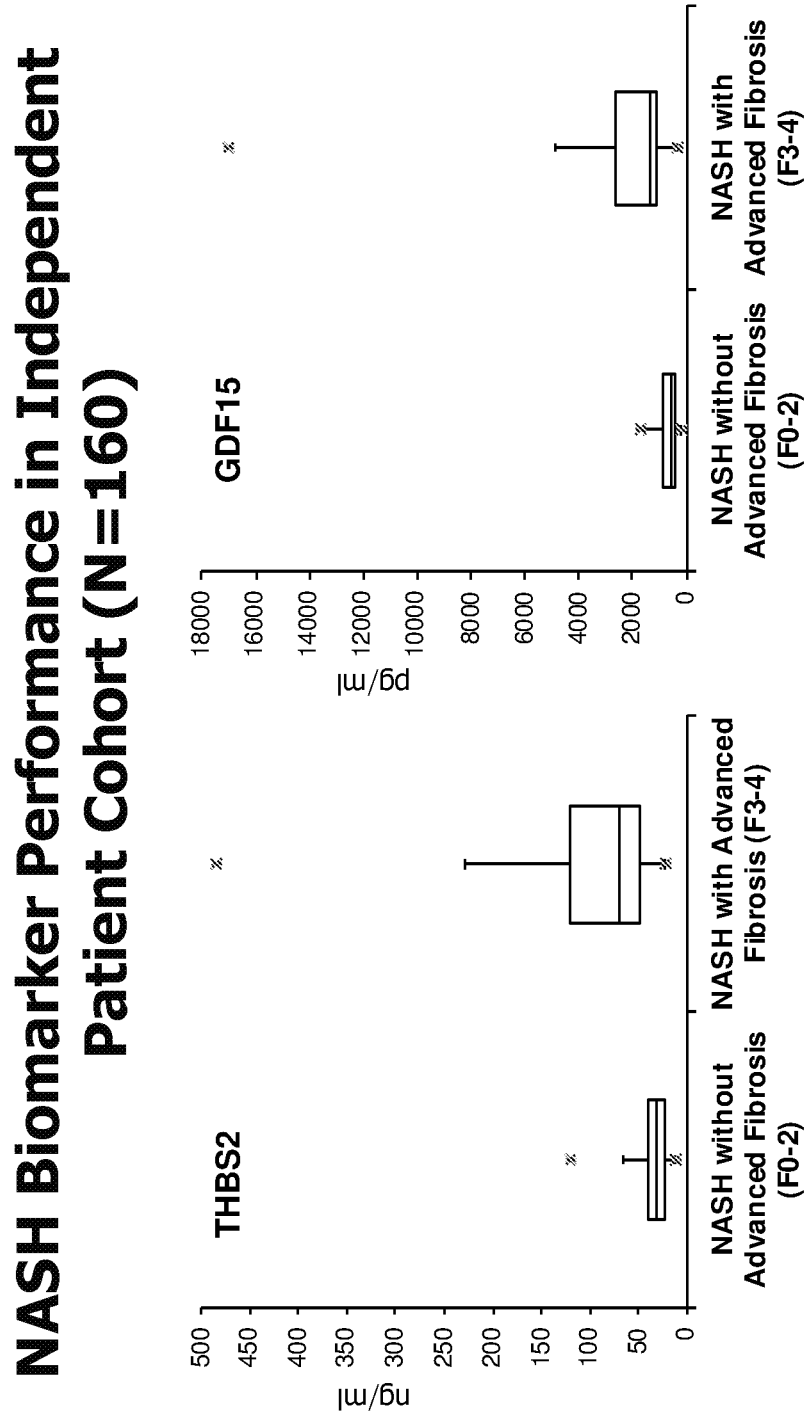
FIG. 19 is a combination of Box and Whisker plots depicting the median protein levels of THBS2 and GDF15 for NASH with advanced fibrosis (F3-4) and NASH without advanced fibrosis (F0-2) as determined by ELISA in an independent validation cohort of 160 patients.

To further confirm whether the NASH and fibrosis biomarkers are accurate, ELISA was performed for THBS2 and GDF15 on an independent validation cohort of 160 patients from another institution. As shown in FIG. 19 by Box and Whisker plots, both THBS2 and GDF15 were significantly increased in NASH with Advanced Fibrosis (F3-4) versus NASH without Advanced Fibrosis (F0-2), further validating that these protein biomarkers are markers of NASH fibrosis progression.

Example 5. Development of a Diagnostic Model for NASH and for Advanced Fibrosis Incorporating ELISA Data and Clinical Variables In order to determine whether incorporating clinical variables further enhances predictive accuracy of the identified biomarkers, similar analytical models as developed for the SOMAscan data were applied to the ELISA data. All combinations of the clinical variables: gender, BMI, age, albumin, alanine aminotransferase (ALT), aspartate aminotransferase (AST), platelet counts, diabetes, hypercholesterolemia, and hypertension were tested with the four proteins THBS2, GDF15, SELE, and COLEC11 to determine the sensitivity, specificity, and accuracy of these different combinations and to assess whether any of the clinical variables or combinations thereof enhance the accuracy of the protein biomarkers.

Predictor Development Strategy

Data consisted of 13 subjects with NASH with advanced fibrosis (AN), 13 subjects with NASH without advanced fibrosis (NN), and 14 subjects with simple steatosis (ST), for a total of 40 subjects. For each subject, ELISA measurements of four proteins were supplemented by measurements of ten clinical variables (gender, BMI, age, albumin, alanine aminotransferase (ALT), aspartate aminotransferase (AST), platelet counts, diabetes, hypercholesterolemia, and hypertension), three of which are dichotomous and six of which are continuous. Prediction was performed for NASH versus Simple Steatosis and NASH with advanced fibrosis (F3-4) versus NASH without advanced fibrosis (F0-2). Data was evaluated using 5-fold cross validation. That is, in each "split," one fifth of the samples in each group were left out as the test set and the remaining samples were used as the training set. Data was split 1,000 times. For each split support vector machine (SVM) prediction based on the principal components analysis (PCA) projections of the samples were used (see, e.g., Huang S, et al. Cancer Genomics Proteomics 2018 January-February; 15(1):41-51; Zhang F, Biomed Res Int. 2013; 2013:781618; C. W. Hsu and C. J. Lin, IEEE Trans Neural Netw., vol. 13, pp. 415-25, 2002; and K. Pearson, Philosophical Magazine, vol. 2, pp. 559-572, 1901). The number of features used for each 1,000 split case were based on all possible combinations of the 14 features (four proteins+ten clinical variables). Hence, $(2^{13})-1=8,191$ feature sets were analyzed for predictive value. The specificity, sensitivity, and accuracy measures are reported below for certain feature combinations based on the 1,000 splits.

PCA is a dimension reduction method that represents high-dimensional data in a few dimensions. Each dimension in the PCA projection space is called a principal component (PC). The projection of a sample on a PC is the linear weighted average of the components of the sample in the high-dimensional space. For example, if, with respect to the proteins in the data set, each sample is represented by a 4-component vector (one value for each of the 4 proteins), the first PC value for a sample would be a weighted average of the 14 feature values for that sample. Same coefficients are used to calculate the first PC value of each sample. For the second PC, another set of weights are used; again, same for each sample.

An example of the method is as follows. When the log 2 transformation of the four ELISA protein measurements is used as the feature set for the prediction, including all 40 samples, the weights to be used to calculate the first PC becomes: [0.5172, 0.6587, 0.1372, 0.5290]. The logged ELISA measurements for one of the samples is [6.9588, 7.2288, 15.6052, 11.5507]. Prior to application of PCA, each feature is "centered," i.e., the mean of the feature across all samples is subtracted from the feature value. When each feature is centered, the aforementioned logged ELISA measurements for that sample becomes [1.2236, 2.0769, 1.0131, 1.9924]. Now, the first PC component for this sample is simply the inner product (i.e., weighted average) of the coefficient vector and the signal vector: 0.5172*1.2236+ 0.6587*2.0769+0.1372*1.0131+0.5290*1.9924=3.1938. This way, PC1 and PC2 coordinates for all samples are obtained. Therefore, each sample is now a point in 2D space. SVM identifies the best separating line (decision line) between the two groups, after the samples are projected on the 2D PCA space. If a new sample is to be predicted, first the PC1 and PC2 component values for this new sample are calculated based on the sample's ELISA measurement values. These values are first log 2 transformed, then centered by subtracting the mean feature value coming from the training set. The inner product (i.e., linear weighted average) of this transformed, centered vector with the coefficients of first PC ([0.5172, 0.6587, 0.1372, 0.5290]) results in PC1 component for the sample to be predicted. Similarly, PC2 component for the sample to be predicted is calculated. Now, this new sample is a point in the 2D PCA space. Based on the SVM decision rule line obtained using the training samples, depending on which region on the 2D space this sample to be predicted falls in, it is predicted as "NASH" or "Simple Steatosis," for example.

Results

Applying linear Support Vector Machine (SVM) to the ELISA data for comparing NASH versus simple steatosis and evaluating all different combinations of the four proteins identified the combination of THBS2, COLEC11, and GDF15 as the predictor with an accuracy of 0.775 and an area under the ROC curve (AUROC) of 0.876. When combining the ELISA data for the four proteins with multiple clinical variables such as gender, BMI, age, albumin, alanine aminotransferase (ALT), aspartate aminotransferase (AST), platelet counts, diabetes, hypercholesterolemia, hypertension, and performing the same linear SVM analysis, the best predictor for NASH versus simple steatosis included COLEC11, GDF15, albumin, and AST, which achieved an accuracy of 0.897. A similar accuracy of 0.892 was achieved with the combination of SELE, COLEC11, BMI, ALT, albumin, and platelet counts.

Similar analysis for NASH with Advanced Fibrosis (F3-4) versus NASH without Advanced Fibrosis (F0-2) determined as the best predictor a combination of SELE, COLEC11, GDF15, and BMI with an accuracy of 0.962.

Tables 7 and 8 list the top 10 predictors, including clinical variables, for NASH versus simple steatosis (Table 7), and NASH with advanced fibrosis versus NASH without advanced fibrosis (Table 8).

Table 9 lists additional markers for NASH versus simple steatosis and Table 10 lists additional markers for NASH with advanced fibrosis versus NASH without advanced fibrosis. Tables 9 and 10 also include protein markers and clinical variables.

TABLE 7

Top Ten Predictors for Models for NASH vs. Simple Steatosis

| Models for NASH vs Simple Steatosis | Components | Accuracy |
|---|---|---|
| Model 1 | THBS2, COLEC11, GDF15 | 0.775 |
| Model 2 | COLEC11, GDF15, albumin, AST | 0.897 |
| Model 3 | SELE, COLEC11, BMI, ALT, albumin, platelet counts | 0.892 |
| Model 4 | SELE THBS2 COLEC11 GDF15 | 0.733 |
| Model 5 | GDF15 | 0.738 |
| Model 6 | COLEC11 GDF15 Age BMI ALT Albumin Platelets | 0.853 |
| Model 7 | COLEC11 GDF15 Age ALT | 0.852 |
| Model 8 | COLEC11 GDF15 BMI ALT Albumin Diabetes | 0.852 |
| Model 9 | COLEC11 GDF15 BMI ALT Albumin Platelets | 0.851 |
| Model 10 | COLEC11 GDF15 BMI ALT | 0.85 |

TABLE 8

Top Ten Predictors for Models for NASH without Advanced Fibrosis (F0-2) versus NASH with Advanced Fibrosis (F3-4)

| Models for NASH with F3-4 vs NASH with F0-2 | | |
|---|---|---|
| Model 1 | SELE, COLEC11, GDF15, BMI | 0.962 |
| Model 2 | SELE, COLEC11 | 0.95 |
| Model 3 | SELE COLEC11 GDF15 | 0.874 |
| Model 4 | SELE THBS2 COLEC11 | 0.86 |
| Model 5 | THBS2 COLEC11 | 0.837 |
| Model 6 | SELE COLEC11 Age BMI | 0.896 |
| Model 7 | SELE COLEC11 GDF15 BMI Albumin | 0.893 |
| Model 8 | SELE COLEC11 BMI ALT Albumin | 0.892 |
| Model 9 | SELE COLEC11 BMI ALT | 0.891 |
| Model 10 | SELE COLEC11 Age BMI Albumin | 0.886 |

TABLE 9

Markers Including Clinical Variables For NASH and Simple Steatosis Based On Average Accuracy, Sensitivity and Specificity

| Models with Proteins Only | Avg Acc (%) | Avg Sen (%) | Avg Spec (%) |
|---|---|---|---|
| THBS2, COLEC11, GDF15 | 77.5 | | |
| GDF15 | 73.825 | 77.44 | 67.8 |
| SELE THBS2 COLEC11 GDF15 | 73.275 | 68.48 | 81.267 |
| COLEC11 GDF15 | 73.05 | 71.16 | 76.2 |
| SELE GDF15 | 72.125 | 75.08 | 67.2 |
| THBS2 GDF15 | 71.9125 | 77.7 | 62.267 |

| Models with Proteins and Clinical Variables | Average Accuracy (%) | Average Sensitivity (%) | Average Specificity (%) |
|---|---|---|---|
| COLEC11, GDF15, albumin, AST | 89.7 | | |
| SELE, COLEC11, BMI, ALT, albumin, platelet counts | 89.2 | | |
| COLEC11 GDF15 Age BMI ALT Albumin Platelets | 85.25 | 90.52 | 76.467 |
| COLEC11 GDF15 Age ALT | 85.175 | 90.14 | 76.9 |
| COLEC11 GDF15 BMI ALT Albumin Diabetes | 85.125 | 90.16 | 76.733 |
| COLEC11 GDF15 BMI ALT Albumin Platelets | 85.075 | 90.36 | 76.267 |
| COLEC11 GDF15 BMI ALT | 85.025 | 90.76 | 75.467 |
| COLEC11 GDF15 Age ALT Albumin Diabetes | 85 | 90.44 | 75.933 |
| COLEC11 GDF15 ALT Albumin Diabetes | 84.925 | 90.48 | 75.667 |
| COLEC11 GDF15 Age BMI ALT Albumin Platelets Diabetes | 84.9125 | 89.88 | 76.633 |
| COLEC11 GDF15 Age ALT Platelets | 84.8875 | 89.7 | 76.867 |
| COLEC11 GDF15 ALT | 84.8875 | 90.56 | 75.433 |
| COLEC11 GDF15 Age BMI ALT Albumin | 84.875 | 90.12 | 76.133 |
| COLEC11 GDF15 BMI ALT Platelets | 84.875 | 90.16 | 76.067 |
| COLEC11 GDF15 BMI ALT Diabetes | 84.8625 | 90.06 | 76.2 |
| COLEC11 GDF15 ALT Platelets | 84.775 | 89.84 | 76.333 |
| COLEC11 GDF15 BMI ALT Albumin | 84.7625 | 90.82 | 74.667 |
| COLEC11 GDF15 Age ALT Albumin | 84.75 | 90.04 | 75.933 |
| COLEC11 GDF15 Age BMI ALT | 84.75 | 89.86 | 76.233 |
| COLEC11 GDF15 Age BMI ALT Albumin Diabetes | 84.7375 | 90.06 | 75.867 |
| COLEC11 GDF15 Age BMI ALT Diabetes | 84.725 | 89.66 | 76.5 |
| COLEC11 GDF15 ALT Albumin | 84.65 | 89.76 | 76.133 |
| COLEC11 GDF15 ALT Albumin Platelets | 84.625 | 90.04 | 75.6 |
| COLEC11 GDF15 BMI ALT Platelets Diabetes | 84.6125 | 90.34 | 75.067 |

TABLE 9-continued

Markers Including Clinical Variables For NASH
and Simple Steatosis Based On
Average Accuracy, Sensitivity and Specificity

| | | | |
|---|---|---|---|
| COLEC11 GDF15 ALT Diabetes | 84.6 | 89.52 | 76.4 |
| COLEC11 GDF15 Age ALT Albumin Platelets | 84.525 | 90.06 | 75.3 |
| COLEC11 GDF15 Age BMI ALT AST Platelets Diabetes | 84.4875 | 93.12 | 70.1 |
| COLEC11 GDF15 BMI ALT Albumin Platelets Diabetes | 84.4875 | 89.86 | 75.533 |
| COLEC11 GDF15 BMI ALT AST Platelets Diabetes | 84.4875 | 93.14 | 70.067 |
| COLEC11 GDF15 Age BMI ALT Platelets | 84.45 | 89.4 | 76.2 |
| COLEC11 GDF15 ALT Albumin Platelets Diabetes | 84.4 | 89.54 | 75.833 |
| COLEC11 GDF15 Age BMI ALT Platelets Diabetes | 84.3875 | 89.8 | 75.367 |
| COLEC11 GDF15 ALT AST Platelets Diabetes | 84.3375 | 92.92 | 70.033 |
| COLEC11 GDF15 Age BMI ALT AST Albumin Platelets Diabetes | 84.325 | 92.42 | 70.833 |
| COLEC11 GDF15 Age BMI AST Platelets Diabetes | 84.3125 | 93.46 | 69.067 |
| COLEC11 GDF15 Age ALT Platelets Diabetes | 84.2875 | 89.26 | 76 |
| COLEC11 GDF15 ALT Platelets Diabetes | 84.2875 | 89.56 | 75.5 |
| COLEC11 GDF15 Age BMI ALT AST Diabetes | 84.2625 | 93.2 | 69.367 |
| COLEC11 GDF15 Age ALT AST Platelets Diabetes | 84.1375 | 93.1 | 69.2 |
| COLEC11 GDF15 Age ALT AST Platelets | 84.0375 | 92.78 | 69.467 |
| COLEC11 GDF15 ALT AST Albumin Platelets Diabetes | 84.0375 | 93.18 | 68.8 |
| COLEC11 GDF15 Age ALT AST Albumin Platelets | 84.0125 | 92.6 | 69.7 |

TABLE 10

Markers Including Clinical Variables For NASH With Advanced
Liver Fibrosis Versus NASH Without Advanced Liver Fibrosis
Based On Average Accuracy, Sensitivity and Specificity

| Models with Proteins only | Avg Acc (%) | Avg Sen (%) | Avg Spec (%) |
|---|---|---|---|
| SELE, COLEC11, GDF15, BMI | 96.2 | | |
| SELE, COLEC11 | 95 | | |
| SELE COLEC11 GDF15 | 87.383 | 86.9 | 87.867 |
| SELE THBS2 COLEC11 | 86.033 | 81.467 | 90.6 |
| SELE COLEC11 | 83.983 | 82.6 | 85.367 |
| THBS2 COLEC11 | 83.7 | 80.733 | 86.667 |
| SELE | 82.033 | 79.867 | 84.2 |
| SELE THBS2 | 80.717 | 78 | 83.433 |

| Models with Proteins and Clinical Variables | Average Accuracy (%) | Average Sensitivity (%) | Average Specificity (%) |
|---|---|---|---|
| SELE COLEC11 Age BMI | 89.6 | 91.2 | 88 |
| SELE COLEC11 GDF15 BMI Albumin | 89.267 | 89.533 | 89 |
| SELE COLEC11 BMI ALT Albumin | 89.217 | 93.567 | 84.867 |
| SELE COLEC11 BMI ALT | 89.133 | 93.033 | 85.233 |
| SELE COLEC11 GDF15 BMI | 88.75 | 89.5 | 88 |
| SELE COLEC11 Age BMI Albumin | 88.633 | 89.667 | 87.6 |
| SELE COLEC11 BMI | 88.617 | 89.8 | 87.433 |
| SELE COLEC11 GDF15 Age BMI | 88.583 | 87.5 | 89.667 |
| SELE COLEC11 Age BMI ALT | 88.3 | 90.633 | 85.967 |
| SELE COLEC11 GDF15 Age Diabetes Hypercholesteroloemia | 88.3 | 81.233 | 95.367 |
| SELE COLEC11 GDF15 Age BMI Albumin | 88.283 | 87.533 | 89.033 |
| SELE COLEC11 GDF15 Albumin | 88.217 | 87.967 | 88.467 |
| SELE COLEC11 GDF15 Diabetes Hypercholesteroloemia | 88.167 | 81.233 | 95.1 |
| SELE COLEC11 GDF15 Age BMI Albumin Diabetes Hypercholesteroloemia | 88.15 | 81.533 | 94.767 |
| SELE COLEC11 BMI Albumin | 88.067 | 88.767 | 87.367 |
| SELE COLEC11 GDF15 BMI Albumin Platelets | 88.05 | 87.033 | 89.067 |
| SELE COLEC11 GDF15 BMI Diabetes Hypercholesteroloemia | 88 | 80.167 | 95.833 |

TABLE 10-continued

Markers Including Clinical Variables For NASH With Advanced
Liver Fibrosis Versus NASH Without Advanced Liver Fibrosis
Based On Average Accuracy, Sensitivity and Specificity

| Markers | Accuracy | Sensitivity | Specificity |
|---|---|---|---|
| SELE COLEC11 ALT Albumin | 87.817 | 90.2 | 85.433 |
| SELE COLEC11 GDF15 BMI Albumin Diabetes Hypercholesteroloemia | 87.783 | 80.267 | 95.3 |
| SELE COLEC11 GDF15 Age BMI Diabetes Hypercholesteroloemia | 87.767 | 80.767 | 94.767 |
| SELE COLEC11 Age BMI ALT Albumin | 87.667 | 90.667 | 84.667 |
| SELE COLEC11 GDF15 BMI Platelets Diabetes Hypercholesteroloemia | 87.517 | 80.533 | 94.5 |
| SELE COLEC11 GDF15 Platelets | 87.517 | 86.733 | 88.3 |
| SELE COLEC11 GDF15 Albumin Diabetes Hypercholesteroloemia | 87.45 | 79.8 | 95.1 |
| SELE COLEC11 BMI Platelets | 87.417 | 88.3 | 86.533 |
| SELE COLEC11 GDF15 Age BMI Albumin Hypercholesteroloemia | 87.4 | 82 | 92.8 |
| SELE COLEC11 GDF15 | 87.383 | 86.9 | 87.867 |
| SELE COLEC11 GDF15 Age Albumin Diabetes Hypercholesteroloemia | 87.333 | 79.867 | 94.8 |
| SELE COLEC11 BMI ALT AST | 87.3 | 88.4 | 86.2 |
| SELE COLEC11 BMI ALT AST Hypercholesteroloemia | 87.267 | 85.533 | 89 |
| SELE COLEC11 GDF15 Age BMI Albumin Platelets Diabetes Hypercholesteroloemia | 87.25 | 79.5 | 95 |
| SELE COLEC11 BMI Hypercholesteroloemia | 87.217 | 89.6 | 84.833 |
| SELE THBS2 COLEC11 Age BMI | 87.217 | 83.4 | 91.033 |
| SELE COLEC11 GDF15 BMI Albumin Hypercholesteroloemia | 87.2 | 80 | 94.4 |
| SELE THBS2 COLEC11 BMI | 87.167 | 83.6 | 90.733 |
| SELE COLEC11 GDF15 Age BMI Hypercholesteroloemia | 87.117 | 81.433 | 92.8 |
| SELE COLEC11 GDF15 Albumin Platelets Diabetes Hypercholesteroloemia | 87.017 | 79.767 | 94.267 |
| SELE COLEC11 GDF15 BMI Albumin Platelets Diabetes Hypercholesteroloemia | 87.017 | 79 | 95.033 |
| SELE THBS2 COLEC11 BMI Albumin | 87 | 82.767 | 91.233 |
| SELE COLEC11 BMI ALT Albumin Hypercholesteroloemia | 87 | 87.867 | 86.133 |
| SELE COLEC11 BMI ALT AST Albumin | 86.967 | 87.6 | 86.33 |
| SELE COLEC11 GDF15 BMI Platelets | 86.9 | 85.967 | 87.833 |
| SELE THBS2 COLEC11 Albumin | 86.867 | 83.133 | 90.6 |
| SELE THBS2 COLEC11 Age BMI Albumin | 86.85 | 83.167 | 90.533 |
| SELE COLEC11 ALT | 86.817 | 91.833 | 81.8 |
| SELE COLEC11 Age BMI ALT Hypertension Hypercholesteroloemia | 86.767 | 75.267 | 98.267 |
| SELE COLEC11 GDF15 Platelets Diabetes Hypercholesteroloemia | 86.7 | 79.867 | 93.533 |
| SELE COLEC11 BMI Hypertension | 86.65 | 80.667 | 92.633 |
| SELE THBS2 COLEC11 Age Diabetes | 86.567 | 80.6 | 92.533 |
| SELE COLEC11 BMI Albumin Hypertension | 86.567 | 80.567 | 92.567 |
| SELE COLEC11 Age BMI Albumin Platelets | 86.567 | 86.833 | 86.3 |
| SELE COLEC11 GDF15 Albumin Platelets | 86.55 | 85.833 | 87.267 |
| SELE THBS2 COLEC11 Hypertension Hypercholesteroloemia | 86.517 | 80.267 | 92.767 |
| SELE COLEC11 GDF15 Age Hypercholesteroloemia | 86.5 | 80.967 | 92.033 |
| SELE THBS2 COLEC11 Age | 86.483 | 81.567 | 91.4 |
| SELE COLEC11 BMI ALT AST Albumin Hypertension Hypercholesteroloemia | 86.467 | 75.767 | 97.167 |
| SELE COLEC11 GDF15 Age BMI Albumin Platelets Hypercholesteroloemia | 86.45 | 78.467 | 94.433 |
| SELE THBS2 COLEC11 Age Diabetes Hypertension Hypercholesteroloemia | 86.433 | 80.967 | 91.9 |
| SELE COLEC11 Age BMI Platelets | 86.433 | 86.833 | 86.033 |
| SELE THBS2 COLEC11 BMI Diabetes Hypertension | 86.417 | 80.033 | 92.8 |
| SELE THBS2 COLEC11 Hypercholesteroloemia | 86.417 | 80.933 | 91.9 |
| SELE COLEC11 GDF15 Age Albumin | 86.417 | 85.133 | 87.7 |
| SELE COLEC11 GDF15 Age Platelets Diabetes Hypercholesteroloemia | 86.4 | 77.867 | 94.933 |
| SELE COLEC11 BMI ALT Albumin Hypertension Hypercholesteroloemia | 86.367 | 75.5 | 97.233 |
| SELE THBS2 COLEC11 Age BMI Hypercholesteroloemia | 86.367 | 80.033 | 92.7 |
| SELE COLEC11 BMI ALT AST Albumin Hypercholesteroloemia | 86.35 | 84.833 | 87.867 |
| SELE COLEC11BMIALT Hypercholesteroloemia | 86.35 | 86.7 | 86 |

TABLE 10-continued

Markers Including Clinical Variables For NASH With Advanced
Liver Fibrosis Versus NASH Without Advanced Liver Fibrosis
Based On Average Accuracy, Sensitivity and Specificity

| Markers | Accuracy | Sensitivity | Specificity |
|---|---|---|---|
| SELE COLEC11 Age ALT Albumin Hypertension Hypercholesteroloemia | 86.35 | 75.433 | 97.267 |
| SELE COLEC11 GDF15 Age BMI Platelets Hypercholesteroloemia | 86.333 | 80.033 | 92.633 |
| SELE COLEC11 BMI Albumin Platelets | 86.3 | 86.933 | 85.667 |
| SELE THBS2 COLEC11 Age BMI Hypertension | 86.3 | 80.167 | 92.433 |
| SELE COLEC11 Age ALT Hypertension Hypercholesteroloemia | 86.283 | 75.933 | 96.633 |
| SELE THBS2 COLEC11 Age Albumin | 86.283 | 82.8 | 89.767 |
| SELE COLEC11 GDF15 BMI Hypercholesteroloemia | 86.283 | 79.633 | 92.933 |
| SELE COLEC11 Age BMI ALT Albumin Hypertension Hypercholesteroloemia | 86.25 | 75.233 | 97.267 |
| SELE COLEC11 GDF15 Age BMI Albumin Platelets | 86.233 | 83.4 | 89.067 |
| SELE THBS2 COLEC11 BMI Albumin Hypertension Hypercholesteroloemia | 86.217 | 79.633 | 92.8 |
| SELE COLEC11 GDF15 Age Albumin Platelets Diabetes Hypercholesteroloemia | 86.167 | 77.333 | 95 |
| SELE THBS2 COLEC11 Age BMI Diabetes Hypertension | 86.133 | 79.733 | 92.533 |
| SELE COLEC11 GDF15 Age BMI Platelets Diabetes Hypercholesteroloemia | 86.117 | 77.967 | 94.267 |
| SELE THBS2 COLEC11 BMI Hypertension | 86.083 | 79.833 | 92.333 |
| SELE COLEC11 Age BMI ALT Platelets Hypertension Hypercholesteroloemia | 86.083 | 76.567 | 95.6 |
| SELE THBS2 COLEC11 Age Hypercholesteroloemia | 86.067 | 80.167 | 91.967 |
| SELE THBS2 COLEC11 Albumin Hypertension | 86.067 | 79.667 | 92.467 |
| SELE COLEC11 BMI ALT Platelets Hypertension Hypercholesteroloemia | 86.05 | 76.6 | 95.5 |
| SELE THBS2 COLEC11 Age Albumin Hypertension | 86.05 | 79.667 | 92.433 |
| SELE THBS2 COLEC11 | 86.033 | 81.467 | 90.6 |
| SELE COLEC11 BMI Albumin Hypercholesteroloemia | 86.017 | 87.633 | 84.4 |
| SELE COLEC11 GDF15 Age BMI Platelets | 86.017 | 83.467 | 88.567 |
| SELE COLEC11 BMI Albumin Hypertension Hypercholesteroloemia | 86.017 | 79.4 | 92.633 |
| SELE COLEC11 BMI ALT Hypertension Hypercholesteroloemia | 86.017 | 75.1 | 96.933 |
| SELE THBS2 COLEC11 BMI Albumin Hypercholesteroloemia | 86.017 | 79.033 | 93 |
| SELE THBS2 COLEC11 Age BMI Albumin Hypertension | 86.017 | 79.533 | 92.5 |
| SELE COLEC11 GDF15 Age | 86 | 84.067 | 87.933 |
| SELE COLEC11 Age ALT Albumin | 85.983 | 86.967 | 85 |
| SELE THBS2 COLEC11 Age Hypertension Hypercholesteroloemia | 85.933 | 79.133 | 92.733 |
| SELE COLEC11 BMI Hypertension Hypercholesteroloemia | 85.883 | 78.5 | 93.267 |
| SELE THBS2 COLEC11 BMI Diabetes | 85.867 | 79.133 | 92.6 |
| SELE COLEC11 GDF15 BMI Platelets Hypercholesteroloemia | 85.867 | 78.967 | 92.767 |
| SELE COLEC11 GDF15 BMI Albumin Platelets Hypercholesteroloemia | 85.867 | 78.067 | 93.667 |
| SELE THBS2 COLEC11 BMI Albumin Diabetes Hypertension | 85.85 | 79.467 | 92.233 |
| SELE COLEC11 ALT Hypercholesteroloemia | 85.833 | 86.2 | 85.467 |
| SELE THBS2 COLEC11 Age Albumin Diabetes Hypertension Hypercholesteroloemia | 85.817 | 79.8 | 91.833 |
| SELE THBS2 COLEC11 BMI Hypercholesteroloemia | 85.8 | 79.633 | 91.967 |
| SELE THBS2 COLEC11 Age Albumin Hypertension Hypercholesteroloemia | 85.8 | 79.433 | 92.167 |
| SELE COLEC11 GDF15 Albumin Hypercholesteroloemia | 85.8 | 78.933 | 92.667 |
| SELE COLEC11 ALT Albumin Hypertension Hypercholesteroloemia | 85.783 | 76.167 | 95.4 |
| SELE THBS2 COLEC11 Age BMI Diabetes Hypercholesteroloemia | 85.783 | 78.633 | 92.933 |
| SELE COLEC11 BMI ALT AST Platelets Hypertension Hypercholesteroloemia | 85.767 | 74.567 | 96.967 |

Example 6. Systems Biology Analysis for Predictors Between NASH with Advanced Liver Fibrosis and NASH without Advanced Liver Fibrosis Systems biology analysis of the top proteins differentially expressed between NASH with advanced liver fibrosis and NASH without advanced liver fibrosis were performed. These analyses revealed various biomarkers as high priority therapeutic targets for development of biologics, since most of these proteins are secreted, shed or transmembrane. Various pathways were identified where a significant number of proteins were dysregulated in NASH with advanced liver fibrosis.

For example, Hepatic Fibrosis signaling is enhanced in patients with NASH with advanced liver fibrosis as seen by increased expression of multiple proteins, fitting with the expected effect of advanced liver fibrosis.

Similarly, metalloproteinase signaling was enhanced in NASH with advanced liver fibrosis compared to NASH without advanced liver fibrosis.

Network analysis identified a number of networks of interacting proteins for a network of proteins overexpressed or reduced in serum of NASH with advanced liver fibrosis patients. Systems biology analysis demonstrated that the advanced liver fibrosis biomarkers are closely connected in interactive networks, and are likely high priority therapeutic targets for biologics.

Upstream regulator analysis using Ingenuity Pathway Analysis identified IL-13, TNFα, IL-6, IL-4, TGF-β1, MGEA5, CEACAM1, IL17A and AGT as key upstream regulators of many of the genes/proteins differentially regulated in advanced liver fibrosis in NASH patients.

Using the data for the advanced liver fibrosis specific proteins, prediction models were developed for the potential function of the advanced liver fibrosis serum biomarkers using Ingenuity Pathway Analysis tools. Based on the analysis, movement of endothelial cells, leukocyte infiltration, cell branching, and activation of antigen presenting cells emerged as a plausible model for advanced liver fibrosis, mostly driven by proteins increased in NASH with advanced liver fibrosis versus NASH without advanced liver fibrosis.

Prediction models for the potential link of the advanced liver fibrosis serum biomarkers with liver disease and liver functions were also developed using Ingenuity Pathway Analysis tools. Based on the analysis, various advanced liver fibrosis-specific markers emerged as directly associated with liver disease functions.

Thus, a whole set of advanced liver fibrosis-specific biomarkers that are functionally related and involved in the pathophysiology of advanced liver fibrosis, as well as the pathophysiology of liver disease and function, was identified. These mostly secreted and transmembrane biomarkers, are not only relevant for diagnostics, but are also candidate therapeutic targets for biologics development.

Example 7. Systems Biology Analysis for Predictors Between NASH with Advanced Liver Fibrosis and Simple Steatosis Systems biology analysis was also performed with the top proteins differentially expressed between NASH with advanced liver fibrosis and Simple Steatosis. These analyses have revealed various of the biomarkers as high priority therapeutic targets for development of biologics, since most of these proteins are secreted, shed or transmembrane. Various pathways were identified where a significant number of proteins were dysregulated in NASH with advanced liver fibrosis versus Simple Steatosis.

For example, Angiopoietin signaling is clearly enhanced in patients with NASH with advanced liver fibrosis as seen by increased expression of multiple proteins, generating an interesting new hypothesis about NASH and the link to angiogenic pathways.

Similarly, metalloproteinase signaling was also enhanced in NASH with advanced liver fibrosis compared to Simple Steatosis.

Network analysis identified a number of networks of interacting proteins for a network of proteins overexpressed or reduced in serum of NASH with advanced liver fibrosis compared to Simple Steatosis patients. Systems biology analysis demonstrated that the NASH biomarkers are closely connected in interactive networks and are likely high priority therapeutic targets for biologics.

Upstream regulator analysis using Ingenuity Pathway Analysis identified IL-13, TNFα, IFNγ, TGF-β1, Alpha catenin, ERBB2, IL-4, SPHK2 and ANGPT2 as key upstream regulators of many of the proteins differentially regulated in NASH patients.

Using the data for the NASH with advanced liver fibrosis specific proteins, prediction models for the potential function of the NASH with advanced liver fibrosis serum biomarkers were developed using Ingenuity Pathway Analysis tools. Based on the analysis, leukocyte infiltration and lymphocyte adhesion emerged as a plausible model for NASH with advanced liver fibrosis, mostly driven by proteins increased in NASH with advanced liver fibrosis versus Simple Steatosis.

Prediction models for the potential link of the NASH with advanced liver fibrosis serum biomarkers with liver disease and liver functions were also developed using Ingenuity Pathway Analysis tools. Based on the analysis, NASH with advanced liver fibrosis-specific proteins were directly associated with liver disease functions.

Thus, a whole set of NASH with advanced liver fibrosis-specific biomarkers that are functionally related and involved in the pathophysiology of NASH, as well as the pathophysiology of liver disease and function, was identified. These mostly secreted and transmembrane biomarkers are not only relevant for diagnostics, but are also candidate therapeutic targets for biologics development.

Using the data for the NASH with and without advanced liver fibrosis versus Simple Steatosis specific proteins, similar prediction models for the potential link of the overall NASH serum biomarkers with liver disease and liver functions were also developed using Ingenuity Pathway Analysis tools. NASH-specific proteins were directly associated with liver disease functions. Thus, a whole set of NASH-specific biomarkers that are functionally related and involved in the pathophysiology of liver disease and function, has been identified. These mostly secreted, shed and transmembrane biomarkers are also candidate therapeutic targets for biologics development. Various additional highly significant pathway associations and candidate therapeutic targets for biologics were also identified.

Example 8. Systems Biology Analysis for Predictors Between NASH without Advanced Liver Fibrosis and Simple Steatosis Systems biology analysis of the top proteins differentially expressed between NASH without advanced liver fibrosis and Simple Steatosis was performed. These analyses have revealed various of the biomarkers as high priority therapeutic targets for development of biologics, since most of these proteins are secreted or transmembrane. Various pathways were identified where a significant number of proteins were dysregulated in NASH without advanced liver fibrosis versus Simple Steatosis.

For example, T Helper cell signaling is clearly impacted in patients with NASH without advanced liver fibrosis as seen by increased expression of multiple proteins in TH1, TH17 and TReg cells, but reduced expression of TH2 specific proteins, suggesting a shift from TH2 to TH1 during NASH development, generating an interesting new hypothesis about NASH and the link to T Helper cell pathways.

Network analysis identified a number of networks of interacting proteins for a network of proteins overexpressed or reduced in serum of NASH without advanced liver fibrosis compared to Simple Steatosis patients. Systems biology analysis demonstrated that the NASH biomarkers are closely connected in interactive networks and are likely high priority therapeutic targets for biologics.

Upstream regulator analysis using Ingenuity Pathway Analysis identified IL-13, TNFα, IFNγ, TGF-β1, IL-18, CEBPB, and HGF as key upstream regulators of many of the proteins differentially regulated in NASH without advanced liver fibrosis patients.

Using the data for the NASH without advanced liver fibrosis specific proteins, prediction models for the potential link of the NASH without advanced liver fibrosis serum biomarkers with liver disease and liver functions were also developed using Ingenuity Pathway Analysis tools.

NASH without advanced liver fibrosis-specific proteins were directly associated with liver disease functions. Thus, a whole set of NASH without advanced liver fibrosis-specific biomarkers that are functionally related and involved in the pathophysiology of liver disease and function has been identified. These mostly secreted, shed and transmembrane biomarkers are also candidate therapeutic targets for biologics development. Various additional highly significant pathway associations and candidate therapeutic targets for biologics were also identified.

In conclusion, the present invention successfully identified various sets of new high accuracy diagnostic biomarkers that are linked to NASH and to advanced liver fibrosis pathogenesis, including low abundance proteins. The biomarkers of the invention can predict the risk of NASH or advanced liver fibrosis development or differentially diagnose with high accuracy and are therefore of high clinical utility, can cut costs to the healthcare system and most importantly be of major benefit to the patients. The biomarker assays can help to monitor resolution of fibrosis or NASH altogether during therapy and to stratify patients with regard to therapies or with regard to undergoing biopsy. The unbiased proteomics strategy for identifying candidate biomarkers for NASH and for advanced liver fibrosis identified a significant number of serum proteins that are differentially expressed in patients who develop NASH or who develop advanced liver fibrosis. The biomarkers disclosed herein also yielded new insights into NASH and advanced liver fibrosis pathogenesis and the pathophysiological pathways associated with it that allows prioritization of novel therapeutic targets encoding secreted and transmembrane proteins for biologics development.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

We claim:

1. A method of diagnosing non-alcoholic steatohepatitis (NASH) versus simple steatosis in a subject, comprising:
    (a) detecting the level of a NASH marker in a biological sample from the subject, wherein the NASH marker comprises a panel of markers selected from the group consisting of: GDF15 and THBS2; GDF15 and IGFBP7; and THBS2, IGFBP7 and GDF15; and
    (b) comparing the level of the NASH marker in the biological sample with a predetermined threshold value;
    wherein the level of the NASH marker above the predetermined threshold value indicates a diagnosis of NASH in the subject, wherein the NASH comprises NASH without advanced liver fibrosis; and
    wherein, when the method indicates the presence of NASH in the subject, the subject is treated with one or more therapeutic agents selected from the group consisting of stearoyl CoA desaturase-1 inhibitor, farnesoid X receptor agonist, CCR2 and CCR5 chemokine antagonist, PPAR alpha and delta agonist, caspase inhibitor, Galectin-3 inhibitor, acetyl COA carboxylase inhibitor, PDE-5 inhibitor, deacetylase sirtuin stimulator, ileal sodium bile acid co-transporter inhibitor, lysyl oxidase-like 2 (LOXL2) inhibitor, ASK-1 inhibitor, DPP4 inhibitor, FGF21 agonist, ASBT inhibitor, niacin analogue, SGLT2 inhibitor, GLP1R agonist, HSP47 inhibitor, MAPK5 inhibitor, thyroid receptor β agonist, LTD receptor antagonist, semicarbazide sensitive amine oxidase inhibitor, and an immunomodulatory agent.

2. The method of claim 1, wherein the subject has or has been diagnosed with non-alcoholic fatty liver disease (NAFLD).

3. The method of claim 1, further comprising evaluating one or more clinical variables selected from the group consisting of: gender, body mass index (BMI), age, albumin, alanine aminotransferase (ALT), aspartate aminotransferase (AST), platelet counts, diabetes, hypercholesterolemia, and hypertension.

4. The method of claim 1, wherein the NASH marker further comprises one or more markers selected from the group consisting of THBS2, BCL2A1, YES1, COLEC11, IGFBP7, N6AMT1, C7, ITGA1, ITGB1, AKT2, SELE, ACY1, TGFB1, TIMP1, DCN, LTBP4, NAGK, IGFBP5, IL19, APOM, MMP7, ANGPT2, and POR.

5. The method of claim 4, wherein the NASH marker comprises one or more markers with an increased level when compared to the predetermined threshold value in the subject, and/or one or more markers with a decreased level when compared to the predetermined threshold value in the subject;
  wherein the NASH marker having an increased level when compared to the predetermined threshold value in the subject is selected from the group consisting of THBS2, YES1, COLEC11, IGFBP7, GDF15, C7, ITGA1, ITGB1, SELE, ACY1, TGFB1, TIMP1, DCN, LTBP4, NAGK, IL19, MMP7, ANGPT2, and POR; or
  wherein the NASH marker having a decreased level when compared to the predetermined threshold value in the subject is selected from the group consisting of BCL2A1, N6AMT1, IGFBP5, APOM, and AKT2.

6. The method of claim 1, wherein the subject has a non-alcoholic fatty liver disease (NAFLD) comorbidity selected from obesity, abdominal obesity, metabolic syndrome, cardiovascular disease, and diabetes.

7. The method of claim 1, wherein the one or more NASH markers are detected by enzymatic analysis, mass spectrometry, NMR, immunoassay, ELISA, aptamers, nanopores, microfluidics, sequencing or any combination thereof, or by determining the level of their corresponding mRNA in the biological sample.

8. The method of claim 1, wherein the biological sample is selected from the group consisting of a serum sample, a plasma sample, a saliva sample, a tear sample, a urine sample, and a tissue sample.

9. The method of claim 5, wherein the NASH marker comprises THBS2, GDF15, SELE and IGFBP7.

10. The method of claim 1, wherein the NASH marker comprises a marker or a panel of markers selected from the following makers and panels of markers: THBS2, COLEC11, and GDF15; COLEC11, GDF15, albumin, and AST; SELE, THBS2, COLEC11 and GDF15; GDF15; COLEC11, GDF15, age, BMI, ALT, albumin, and platelet count; COLEC11, GDF15, age, and ALT; COLEC11, GDF15, BMI, ALT, albumin, and diabetes; COLEC11, GDF15, BMI, ALT, albumin, and platelet count; and COLEC11, GDF15, BMI, and ALT.

11. The method of claim 1, further comprising evaluating one or more clinical variables selected from the group consisting of: body mass index (BMI), age, alanine aminotransferase (ALT), diabetes, and hypertension.

12. The method of claim 9, further comprising evaluating one or more clinical variables selected from the group consisting of: body mass index (BMI), age, alanine aminotransferase (ALT), diabetes, and hypertension.

* * * * *